United States Patent
Biftu et al.

(10) Patent No.: US 10,000,454 B2
(45) Date of Patent: Jun. 19, 2018

(54) ANTIDIABETIC TRICYCLIC COMPOUNDS

(71) Applicant: Merck Sharp & Dohme Corp., Rahway, NJ (US)

(72) Inventors: Tesfaye Biftu, Freehold, NJ (US); Purakkattle Biju, Westwood, MA (US); Timothy A. Blizzard, Princeton, NJ (US); Zhengxia Chen, Shanghai (CN); Matthew J. Clements, Old Bridge, NJ (US); Mingxiang Cui, Shanghai (CN); Jessica L. Frie, Harleysville, PA (US); William K. Hagmann, Westfield, NJ (US); Bin Hu, Shanghai (CN); Hubert Josien, Jersey City, NJ (US); Anilkumar G. Nair, Edison, NJ (US); Christopher W. Plummer, Hoboken, NJ (US); Cheng Zhu, Edison, NJ (US)

(73) Assignee: Merck Sharp & Dohme, Rahway, NJ (US)

( * ) Notice: Subject to any disclaimer, the term of this patent is extended or adjusted under 35 U.S.C. 154(b) by 0 days. days.

(21) Appl. No.: 15/310,488

(22) PCT Filed: May 19, 2015

(86) PCT No.: PCT/CN2015/079262
§ 371 (c)(1),
(2) Date: Nov. 11, 2016

(87) PCT Pub. No.: WO2015/176640
PCT Pub. Date: Nov. 26, 2015

(65) Prior Publication Data
US 2017/0081287 A1 Mar. 23, 2017

(30) Foreign Application Priority Data

May 22, 2014 (CN) ................. PCT/CN2014/078104

(51) Int. Cl.
| | |
|---|---|
| C07D 221/16 | (2006.01) |
| A61K 31/435 | (2006.01) |
| A61K 31/444 | (2006.01) |
| C07D 401/12 | (2006.01) |
| C07D 405/12 | (2006.01) |
| A61K 31/192 | (2006.01) |
| A61K 31/438 | (2006.01) |
| A61K 31/47 | (2006.01) |
| A61K 31/4709 | (2006.01) |
| A61K 31/4725 | (2006.01) |

(Continued)

(52) U.S. Cl.
CPC .......... *C07D 221/16* (2013.01); *A61K 31/192* (2013.01); *A61K 31/435* (2013.01); *A61K 31/438* (2013.01); *A61K 31/444* (2013.01); *A61K 31/47* (2013.01); *A61K 31/4709* (2013.01); *A61K 31/4725* (2013.01); *A61K 31/538* (2013.01); *A61K 31/55* (2013.01); *A61K 45/06* (2013.01); *C07C 61/39* (2013.01); *C07D 215/14* (2013.01); *C07D 401/04* (2013.01); *C07D 401/12* (2013.01); *C07D 405/12* (2013.01); *C07D 413/12* (2013.01); *C07C 2602/08* (2017.05); *C07C 2603/12* (2017.05)

(58) Field of Classification Search
CPC .................................................. C07D 211/16
See application file for complete search history.

(56) References Cited

U.S. PATENT DOCUMENTS

| | | | |
|---|---|---|---|
| 7,442,808 B2 * | 10/2008 | Ge ......................... C07C 62/34 |
| | | | 548/439 |
| 2007/0213364 A1 | 9/2007 | Yasuma et al. | |
| 2014/0045746 A1 | 2/2014 | Hagmann et al. | |

FOREIGN PATENT DOCUMENTS

| | | |
|---|---|---|
| GB | 2498976 A | 7/2013 |
| WO | WO2004022551 A1 | 3/2004 |

(Continued)

OTHER PUBLICATIONS

Wermuth, Camille G. "Molecular Variation Based on Isosteric Replacements" in Chapter 13, The Practice of Medicinal Chemistry, Academic: 1996.*
Nakamura "Imidazole derivatives as new potent and selective 20-HETE synthase inhibitors." Bioorganic & Medicinal Chemistry Letters 2004, 14, 333-336.*
Patani "Bioisosterism: A Rational Approach in Drug Design" Chemical Reviews 1996, 96, 3147-3176.*

(Continued)

*Primary Examiner* — David K O'Dell
(74) *Attorney, Agent, or Firm* — Baerbel R. Brown; Catherine D. Fitch

(57) ABSTRACT

Novel compounds of the structural formula (I), and the pharmaceutically acceptable salts thereof, are agonists of G-protein coupled receptor 40 (GPR40) and may be useful in the treatment, prevention and suppression of diseases mediated by the G-protein-coupled receptor 40. The compounds of the present invention may be useful in the treatment of Type 2 diabetes mellitus, and of conditions that are often associated with this disease, including obesity and lipid disorders, such as mixed or diabetic dyslipidemia, hyperlipidemia, hypercholesterolemia, and hypertriglyceridemia.

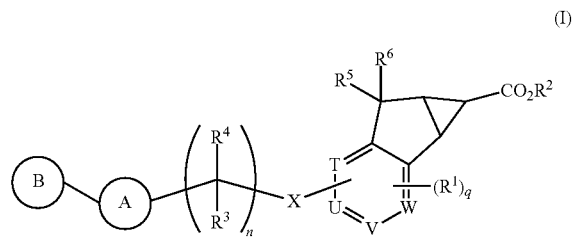

(I)

22 Claims, No Drawings

(51) Int. Cl.
- A61K 31/538 (2006.01)
- A61K 31/55 (2006.01)
- A61K 45/06 (2006.01)
- C07C 61/39 (2006.01)
- C07D 215/14 (2006.01)
- C07D 401/04 (2006.01)
- C07D 413/12 (2006.01)

(56) References Cited

FOREIGN PATENT DOCUMENTS

| | | | |
|---|---|---|---|
| WO | WO2004041266 A1 | 5/2004 | |
| WO | WO2005051373 A1 | 6/2005 | |
| WO | WO2005051890 A1 | 6/2005 | |
| WO | WO2005063729 A1 | 7/2005 | |
| WO | WO2005086661 A2 | 9/2005 | |
| WO | WO2005087710 A1 | 9/2005 | |
| WO | WO2006038738 A1 | 4/2006 | |
| WO | WO2006083612 A1 | 8/2006 | |
| WO | WO2006083781 A1 | 8/2006 | |
| WO | WO2006127503 A2 | 11/2006 | |
| WO | WO2007033002 A1 | 3/2007 | |
| WO | WO2007106469 A2 | 9/2007 | |
| WO | WO2007123225 A1 | 11/2007 | |
| WO | WO2007136572 A2 | 11/2007 | |
| WO | WO2007136573 A2 | 11/2007 | |
| WO | WO2008001931 A2 | 1/2008 | |
| WO | WO2008030520 A1 | 3/2008 | |
| WO | WO2008030618 A1 | 3/2008 | |
| WO | WO2008054674 A2 | 5/2008 | |
| WO | WO2008054675 A2 | 5/2008 | |
| WO | WO2008066097 A1 | 6/2008 | |
| WO | WO2008130514 A1 | 10/2008 | |
| WO | WO2009048527 A1 | 4/2009 | |
| WO | WO2009058237 A1 | 5/2009 | |
| WO | WO2009111056 A1 | 9/2009 | |
| WO | WO2010004347 A1 | 1/2010 | |
| WO | WO2010045258 A1 | 4/2010 | |
| WO | WO2010085522 A1 | 7/2010 | |
| WO | WO2010085525 A1 | 7/2010 | |
| WO | WO2010085528 A1 | 7/2010 | |
| WO | WO2010091176 A1 | 8/2010 | |
| WO | WO2010143733 A1 | 12/2010 | |
| WO | WO2012072691 A1 | 6/2012 | |
| WO | WO 2013097224 A1 * | 7/2013 | ........... C07D 471/04 |
| WO | WO2013122028 A1 | 8/2013 | |
| WO | WO2013122029 A1 | 8/2013 | |
| WO | WO2014019186 A1 | 2/2014 | |
| WO | WO2014022528 A1 | 2/2014 | |
| WO | WO2015051725 A1 | 4/2015 | |

OTHER PUBLICATIONS

Li "N-(Arylacetyl)-biphenylalanines as Potent VLA-4 Antagonists" Bioorganic & Medicinal Chemistry Letters 2002, 12, 2141-2144.*
Briscoe, C. P. et al., The Orphan G Protein-coupled Receptor GPR40 Is Activated by Medium and Long Chain Fatty Acids, The Journal of Biological Chemistry, 2003, 11303-11311, No. 13, 278.
Brown, S. P. et al., Discovery of AM-1638: A Potent and Orally Bioavailable GPR40/FFA1 Full Agonist, American Chemical Society, 2012, p. 726-730, vol. 3.
Executive Summary, Detection, Evaluation, and Treatment of High Blood Cholesterol in Adults (Adult Treatment Panel III), National Institutes of Health, 2001, pp. 1-40, NIH Publication No. 01-3670.
Houze, J. B. et al., 265—AMG 837: A potent, orally bioavailable, partial allosteric agonist of GPR40, MEDI, 2012, p. 1, Abstracts of Papers, 243rd ACS National Meeting & Exposition, San Diego, CA, Mar. 25-29, 2012.
Houze, J. B. et al., AMG 837: A potent, orally bioavailable GPR40 agonist, Bioorganic & Medicinal Chemistry Letters, 2012, p. 1267-1270, vol. 22.
Itoh, Y. et al., Free fatty acids regulate insulin secretion from pancreatic B cells through GPR40, Nature, 2003, 173-176, 422.
Kotarsky, K. et al., A human cell surface receptor activated by free fatty acids and thiazolidinedione drugs, Biochemical and Biophysical Research Communications, 2003, 406-410, 301.
Lin, D. C. H. et al., Identification and Pharmacological Characterization of Multiple Allosteric Binding Sites on the Free Fatty Acid 1 Receptor, Molecular Pharmacology, 2012, p. 843-859, vol. 82, No. 5.
Lin, D. D. H. et al., AMG 837: A Novel GPR40/FFA1 Agonist that Enhances Insulin Secretion and Lowers Glucose Levels in Rodents, PLoS One, 2011, p. 1-10, vol. 6, No. 11.
Lou, J. et al., A Potent Class of GPR40 Full Agonist Engages the EnteroInsular Axis to Promote Glucose Control in Rodents, PLOS One, 2012, p. 6-12, vol. 7, Issue 10.
Tan, C. P. et al., Selective Small-Molecule Agonists of G Protein-Coupled Receptor 40 Promote Glucose-Dependent Insulin Secretion and Reduce Blood Glucose in Mice, Diabetes, 2008, p. 2211-2219, vol. 57.
Walsh, S. P. et al., 3-Substituted 3-(4-aryloxyaryl)-propanoic acids as GPR40 agonists, Bioorganic & Medicinal Chemistry Letters, 2011, p. 3390-3394, vol. 21.
Yang, L., 313—Discovery of selective small molecule GPR40 agonists as antidiabetic compounds, MEDI, 2010, p. 1, Abstracts of Papers, 239th ACS Meeting, San Francisco, CA, Mar. 21-25.
Zhou, C. et al., Discovery of 5-aryloxy-2,4-thiazolidinediones as potent GPR40 agonists, Bioorganic & Medicinal Chemistry Letters, 2010, p. 1298-1301, vol. 20.

* cited by examiner

ANTIDIABETIC TRICYCLIC COMPOUNDS

CROSS-REFERENCE TO RELATED APPLICATIONS

This application is a U.S. National Phase application under 35 U.S.C. § 371 of PCT Application No. PCT/CN2015/079262, filed on May 19, 2015, which claims priority from and the benefit of PCT Application No. PCT/CN2014/078104, filed on May 22, 2014.

BACKGROUND OF THE INVENTION

Diabetes mellitus is a disease derived from multiple causative factors and characterized by elevated levels of plasma glucose (hyperglycemia) in the fasting state or after administration of glucose during an oral glucose tolerance test. There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced in the body, however patients have a resistance to the effects of insulin in stimulating glucose and lipid metabolism in the insulin-sensitive muscle, liver and adipose tissues. Type 2 diabetes patients often have normal levels of insulin, and may have hyperinsulinemia (elevated plasma insulin levels), as they compensate for the reduced effectiveness of insulin by secreting increased amounts of insulin. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver.

Persistent or uncontrolled hyperglycemia is associated with increased and premature morbidity and mortality. Abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have Metabolic Syndrome (as defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670). Patients with Metabolic Syndrome have an increased risk of developing the macrovascular and microvascular complications that occur with Type 2 diabetes, such as atherosclerosis and coronary heart disease.

There are several available treatments for Type 2 diabetes. Physical exercise and a reduction in dietary intake of calories are the recommended first-line treatment of Type 2 diabetes and of pre-diabetic conditions associated with insulin resistance, however compliance is generally poor. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, and pioglitazone), (3) insulin secretion (sulfonylureas, such as tolbutamide, glipizide and glimipiride); (4) incretin hormone mimetics (GLP-1 derivatives and analogs, such as exenatide, liraglutide, dulaglutide, semaglutide, lixisenatide, albiglutide and taspoglutide); and (5) inhibitors of incretin hormone degradation (DPP-4 inhibitors, such as sitagliptin, alogliptin, vildagliptin, linagliptin, denagliptin and saxagliptin).

The two best known biguanides, phenformin and metformin, cause some correction of hyperglycemia, but can also induce lactic acidosis and nausea/diarrhea. PPAR gamma agonists, such as rosiglitazone and pioglitazone, are modestly effective in reducing plasma glucose and Hemoglobin A1C. However, the currently marketed glitazones do not greatly improve lipid metabolism and may negatively effect on the lipid profile. The administration of insulin secretagogues, such as the sulfonylureas (e.g. tolbutamide, glipizide, and glimepiride) can result in hypoglycemia; their administration must therefore be carefully controlled.

There has been a renewed focus on pancreatic islet-based insulin secretion that is controlled by glucose-dependent insulin secretion. This approach has the potential for stabilization and restoration of β-cell function. Several orphan G-protein coupled receptors (GPCR's) have been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 [Itoh, Y. et al., *Nature*, 422: 173 (2003); Briscoe, C. P. et al., *J. Biol. Chem.*, 278: 11303 (2003); Kotarsky, K. et al., *Biochem. Biophys. Res. Comm.*, 301: 406 (2003)]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion. There are several potential advantages of GPR40 as a target for the treatment of Type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be advantageous, because long term diabetes therapy often leads to the gradual diminution of islet activity; after extended periods of treatment, it is often necessary to treat Type 2 diabetic patients with daily insulin injections. By restoring or preserving islet function, GPR40 agonists may delay or prevent the diminution and loss of islet function in a Type 2 diabetic patient.

Compounds that are agonists of G-protein-coupled receptor 40 (GPR40) may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight. There is a need for potent GPR40 agonists that have pharmacokinetic and pharmacodynamic properties suitable for use as human pharmaceuticals.

G-protein-coupled receptor 40 (GPR40) agonists are disclosed in WO 2007/136572, WO 2007/136573, WO 2009/058237, WO 2006/083612, WO 2006/083781, WO 2010/085522, WO 2010/085525, WO 2010/085528, WO 2010/091176, WO 2004/041266, EP 2004/1630152, WO 2004/022551, WO 2005/051890, WO 2005/051373, EP 2004/1698624, WO 2005/086661, WO 2007/213364, WO 2005/063729, WO 2005/087710, WO 2006/127503, WO 2007/1013689, WO 2006/038738, WO 2007/033002, WO 2007/106469, WO 2007/123225, WO 2008/001931, WO 2008/030520, WO 2008/030618, WO 2008/054674, WO 2008/054675, WO 2008/066097, WO 2008/130514, WO 2009/048527, WO 2009/058237, WO 2009/111056, WO 2010/004347, WO y2010/045258, WO 2010/085522, WO 2010/085525, WO 2010/085528, WO 2010/091176, WO 2010/143733, WO 2012/0004187, WO 2012/072691, WO 2013/122028, WO2013/122029, WO2014/022528, and GB 2498976.

GPR40 agonists are also disclosed in Walsh et al., Bioorganic & Medicinal Chemistry Letters (2011), 21(11), 3390-3394; Zhou et al., Bioorganic & Medicinal Chemistry Letters (2010), 20(3), 1298-1301; Tan et al., Diabetes (2008), 57(8), 2211-2219; Houze et al., Bioorganic & Medicinal Chemistry Letters (2012), 22(2), 1267-1270; Brown et al., ACS Medicinal Chemistry Letters (2012), 3(9), 726-730; Lin et al., PloS One (2011), 6(11), e27270; Lou et al., PloS One (2012), 7(10), e46300; Lin et al., Molecular Pharmacology (2012), 82(5), 843-859; Yang, Lihu, Abstracts of Papers, 239th ACS Meeting, San Francisco, Calif., USA Mar. 21-25, 2010 MEDI-313; and Houze et al., Abstracts of Papers, 243rd ACS National Meeting & Exposition, San Diego, Calif., USA Mar. 25-29, 2012, MEDI-265.

SUMMARY OF THE INVENTION

The present invention relates to novel substituted compounds of structural formula I:

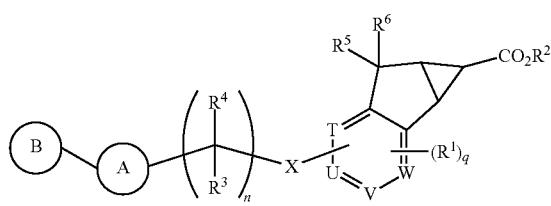

I and pharmaceutically acceptable salts thereof. The compounds of structural formula I, and embodiments thereof, are agonists of G-protein-coupled receptor 40 (GPR40) and may be useful in the treatment, prevention and suppression of diseases, disorders and conditions mediated by agonism of the G-protein-coupled receptor 40, such as Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions that may be responsive to agonism of the G-protein-coupled receptor 40 in a subject in need thereof by administering the compounds and pharmaceutical compositions of the present invention. The present invention also relates to the use of compounds of the present invention for manufacture of a medicament useful in treating diseases, disorders and conditions that may be responsive to the agonism of the G-protein-coupled receptor 40. The present invention is also concerned with treatment of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

The present invention is concerned with novel compounds of structural Formula II:

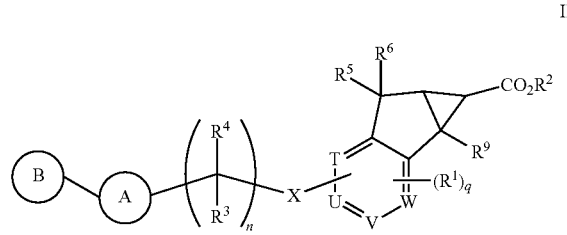

II or a pharmaceutically acceptable salt thereof; wherein
X is selected from the group consisting of:
  (1) oxygen, and
  (2) $NR^7$;
T is selected from the group consisting of: CH, N and N-oxide;
U is selected from the group consisting of: CH, N and N-oxide;
V is selected from the group consisting of: CH, N and N-oxide;
W is selected from the group consisting of: CH, N and N-oxide,
provided that no more than two of T, U, V and W are N or N-oxide;
A is selected from the group consisting of:
  (1) bicyclic aryl ring, and
  (2) bicyclic heteroaryl ring,
wherein each bicyclic aryl ring and bicyclic heteroaryl ring is unsubstituted or substituted with one to six substituents selected from $R^a$, and wherein two $R^a$ substituents together with the carbon atom to which they are attached may form a 3-6 membered cycloalkyl ring, or a 3-6 membered cycloheteroalkyl ring containing 0 to 3 heteroatoms independently selected from oxygen, sulfur, and $NR^8$, and wherein each 3-6 membered cycloalkyl and each 3-6 membered cycloheteroalkyl ring is unsubstituted or substituted with 1 to 4 substituents selected from:
—$C_{1-6}$alkyl, —O—$C_{1-6}$alkyl, halogen and OH;
B is selected from the group consisting of:
  (1) $C_{1-6}$alkyl,
  (2) aryl,
  (3) aryl-O—,
  (4) $C_{3-6}$cycloalkyl-, (5) $C_{3-6}$cycloalkyl-$C_{1-10}$alkyl-,
(6) $C_{3-6}$cycloalkyl-$C_{1-10}$alkyl-O—,
(7) $C_{2-5}$cycloheteroalkyl-,
(8) $C_{3-6}$cycloheteroalkyl-$C_{1-10}$alkyl-,
(9) $C_{3-6}$cycloheteroalkyl-$C_{1-10}$alkyl-O—,
(10) heteroaryl,
(11) heteroaryl-O—,
(12) aryl-$C_{1-10}$ alkyl-, and
(13) heteroaryl-$C_{1-10}$ alkyl-;
wherein B is unsubstituted or substituted with one to six substituents selected from $R^b$;
each $R^1$ is independently selected from the group consisting of:
(1) hydrogen,
(2) halogen,
(3) —$OR^e$,
(4) —CN,
(5) —$C_{1-6}$alkyl, and
(6) —$C_{3-6}$cycloalkyl,
wherein each alkyl and cycloalkyl is unsubstituted or substituted with one to three substituents selected from $R^i$;
$R^2$ is selected from the group consisting of:
(1) hydrogen,
(2) —$C_{1-6}$alkyl, and
(3) —$C_{3-6}$cycloalkyl,
wherein each alkyl and cycloalkyl is unsubstituted or substituted with one to three substituents selected from $R^j$;
each $R^3$ is independently selected from the group consisting of:
(1) hydrogen,
(2) halogen,
(3) —$OR^e$,
(4) —$C_{1-6}$alkyl,
(5) —$C_{2-6}$alkenyl,
(6) —$C_{2-6}$alkynyl,
(7) —$C_{3-6}$cycloalkyl, and
(8) —$C_{2-6}$cycloheteroalkyl,
wherein each alkyl, alkenyl, alkynyl, cycloalkyl and cycloheteroalkyl is unsubstituted or substituted with one to three substituents selected from $R^L$;
each $R^4$ is independently selected from the group consisting of:
(1) hydrogen,
(2) halogen,
(3) —$OR^e$,
(4) —$C_{1-6}$alkyl,
(5) —$C_{2-6}$alkenyl,
(6) —$C_{2-6}$alkynyl,
(7) —$C_{3-6}$cycloalkyl, and
(8) —$C_{2-6}$cycloheteroalkyl,
wherein each alkyl, alkenyl, alkynyl, and cycloalkyl is unsubstituted or substituted with one to three substituents selected from $R^L$;
$R^5$ is selected from the group consisting of:
(1) hydrogen,
(2) —$C_{1-3}$alkyl, and
(3) halogen;
$R^6$ is selected from the group consisting of:
(1) hydrogen,
(2) —$C_{1-3}$alkyl, and
(3) halogen, or
$R^5$ and $R^6$ can together form oxo;
$R^7$ is selected from the group consisting of:
(1) hydrogen,
(2) —C(O)$R^e$, and
(3) —$C_{1-10}$alkyl,
wherein —$C_{1-10}$alkyl is unsubstituted or substituted with one to five fluorines;
each $R^8$ is selected from the group consisting of:
(1) hydrogen,
(2) —C(O)$R^e$, and
(3) —$C_{1-10}$alkyl,
wherein —$C_{1-10}$alkyl is unsubstituted or substituted with one to five fluorines;
each $R^9$ is selected from the group consisting of:
(1) hydrogen, and
(2) —$C_{1-6}$alkyl,
wherein —$C_{1-6}$alkyl is unsubstituted or substituted with one to five fluorines;
each $R^a$ is independently selected from the group consisting of:
(1) —$C_{1-6}$alkyl,
(2) —O—$C_{1-6}$alkyl,
(3) halogen,
(4) oxo,
(5) —$OR^e$,
(6) —N($R^c$)S(O)$_m R^e$,
(7) —S(O)$_m R^e$,
(8) —S(O)$_m NR^c R^d$,
(9) —$NR^c R^d$,
(10) —C(O)$R^e$,
(11) —OC(O)$R^e$,
(12) —$CO_2 R^e$,
(13) —CN,
(14) —C(O)$NR^c R^d$,
(15) —N($R^c$)C(O)$R^e$,
(16) —N($R^c$)C(O)$OR^e$,
(17) —N($R^c$)C(O)$NR^c R^d$,
(18) —$CF_3$,
(19) —$OCF_3$,
(20) —$OCHF_2$,
(21) —$(CH_2)_p$—$C_{3-6}$cycloalkyl,
(22) —$(CH_2)_p$—$C_{2-10}$cycloheteroalkyl,
(23) —$(CH_2)_p$-aryl, and
(24) —$(CH_2)_p$-heteroaryl,
wherein $R^a$ is unsubstituted or substituted with one to three substituents selected from $R^m$;
each $R^b$ is independently selected from the group consisting of:
(1) —$C_{1-10}$alkyl,
(2) —O—$C_{1-10}$alkyl,
(3) —$C_{2-10}$alkenyl,
(4) halogen,
(5) —OH,
(6) —$OC_{2-10}$ alkenyl,
(7) —O($CH_2$)pO$C_{1-10}$alkyl,
(8) —O($CH_2$)p$C_{3-6}$cycloalkyl,
(9) —O($CH_2$)p$C_{2-10}$cycloheteroalkyl,
(10) —O($CH_2$)p-aryl,
(11) —O($CH_2$)p-heteroaryl,
(12) —N($R^c$)S(O)$_m R^e$,
(13) —S(O)$_m R^e$,
(14) —O($CH_2$)p-S(O)$_m R^e$,
(15) —S(O)$_m NR^c R^d$,
(16) —$NR^c R^d$,
(17) —C(O)$R^e$,
(18) —OC(O)$R^e$,
(19) —$CO_2 R^e$,
(20) —CN,
(21) —C(O)$NR^c R^d$,
(22) —N($R^c$)C(O)$R^e$,
(23) —N($R^c$)C(O)$OR^e$,
(24) —N($R^c$)C(O)$NR^c R^d$,

(25) —O(CH$_2$)pO—C$_{3-6}$cycloalkyl,
(26) —O(CH$_2$)pO—C$_{2-10}$cycloheteroalkyl,
(27) —CF$_3$,
(28) —OCF$_3$,
(29) —OCHF$_2$,
(30) —(CH$_2$)p-C$_{3-6}$cycloalkyl,
(31) —(CH$_2$)p-C$_{2-10}$cycloheteroalkyl,
(32) —(CH$_2$)p-aryl, and
(33) —(CH$_2$)p-heteroaryl,
wherein each R$^b$ is unsubstituted or substituted with one to five substituents selected from R$^k$;
each R$^c$ and R$^d$ is independently selected from the group consisting of:
(1) hydrogen,
(2) —C$_{1-10}$alkyl,
(3) —C$_{2-10}$alkenyl,
(4) —C$_{3-6}$cycloalkyl,
(5) C$_{3-6}$ cycloalkyl-C$_{1-10}$alkyl-,
(6) —C$_{2-6}$cycloheteroalkyl,
(7) C$_{2-6}$cycloheteroalkyl-C$_{1-10}$alkyl-,
(8) aryl,
(9) heteroaryl,
(10) aryl-C$_{1-10}$alkyl-, and
(11) heteroaryl-C$_{1-10}$alkyl-, or
R$^c$ and R$^d$ together with the atom(s) to which they are attached form a cycloheteroalkyl ring of 4 to 7 members containing 0-2 additional heteroatoms independently selected from oxygen, sulfur and N—R$^g$, and wherein each R$^c$ and R$^d$ is unsubstituted or substituted with one to three substituents independently selected from R$^f$;
each R$^e$ is independently selected from the group consisting of:
(1) hydrogen,
(2) —C$_{1-10}$alkyl,
(3) —C$_{2-10}$ alkenyl,
(4) —C$_{3-6}$ cycloalkyl,
(5) —C$_{3-6}$ cycloalkyl-C$_{1-10}$alkyl-,
(6) —C$_{2-5}$cycloheteroalkyl,
(7) —C$_{2-5}$cycloheteroalkyl-C$_{1-10}$alkyl-,
(8) aryl,
(9) heteroaryl,
(10) aryl-C$_{1-10}$alkyl-, and
(11) heteroaryl-C$_{1-10}$alkyl-,
wherein each R$^e$ is unsubstituted or substituted with one to three substituents selected from R$^h$;
each R$^f$ is selected from the group consisting of:
(1) halogen,
(2) —C$_{1-10}$alkyl,
(3) —OH,
(4) —OC$_{1-6}$alkyl,
(5) —S(O)$_m$—C$_{1-4}$alkyl,
(6) —CN,
(7) —CF$_3$,
(8) —OCHF$_2$, and
(9) —OCF$_3$,
wherein each alkyl is unsubstituted or substituted with one to three substituents independently selected from: —OH, halogen, cyano, and —S(O)$_2$CH$_3$;
each R$^g$ is selected from the group consisting of:
(1) hydrogen,
(2) —C(O)R$^e$, and
(3) —C$_{1-10}$alkyl,
wherein alkyl is unsubstituted or substituted with one to five fluorines;
each R$^h$ is selected from the group consisting of:
(1) halogen,
(2) —C$_{1-10}$alkyl,
(3) —OH,
(4) —O—C$_{1-4}$alkyl,
(5) —S(O)$_m$—C$_{1-4}$alkyl,
(6) —CN,
(7) —CF$_3$,
(8) —OCHF$_2$, and
(9) —OCF$_3$,
wherein each alkyl is unsubstituted or substituted with one to three substituents independently selected from: —OH, halogen, cyano, and —S(O)$_2$CH$_3$;
R$^i$ is independently selected from the group consisting of:
(1) —C$_{1-6}$alkyl,
(2) —OR$^e$,
(3) —N(R$^c$)S(O)$_m$R$^e$,
(4) halogen,
(5) —S(O)$_m$R$^e$,
(6) —S(O)$_m$NR$^c$R$^d$,
(7) —NR$^c$R$^d$,
(8) —C(O)R$^e$,
(9) —OC(O)R$^e$,
(10) —CO$_2$R$^e$,
(11) —CN,
(12) —C(O)NR$^c$R$^d$,
(13) —N(R$^c$)C(O)R$^e$,
(14) —N(R$^c$)C(O)OR$^e$,
(15) —N(R$^c$)C(O)NR$^c$R$^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;
R$^i$ is independently selected from the group consisting of:
(1) —C$_{1-6}$alkyl,
(2) —OR$^e$,
(3) —N(R$^c$)S(O)$_m$R$^e$,
(4) halogen,
(5) —S(O)$_m$R$^e$,
(6) —S(O)$_m$NR$^c$R$^d$,
(7) —NR$^c$R$^d$,
(8) —C(O)R$^e$,
(9) —OC(O)R$^e$,
(10) —CO$_2$R$^e$,
(11) —CN,
(12) —C(O)NR$^c$R$^d$,
(13) —N(R$^c$)C(O)R$^e$,
(14) —N(R$^c$)C(O)OR$^e$,
(15) —N(R$^c$)C(O)NR$^c$R$^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;
each R$^k$ is independently selected from the group consisting of:
(1) halogen,
(2) —C$_{1-6}$alkyl,
(3) —OH,
(4) oxo,
(5) —OC$_{1-6}$alkyl,
(6) —SO$_2$—C$_{1-6}$ alkyl,
(7) —C$_{1-6}$alkyl-SO$_2$C$_{1-6}$alkyl,
(8) —CN,
(9) —CF$_3$,
(10) —OCHF$_2$,
(11) —OCF$_3$,
(12) —NH$_2$,
(13) —NHSO$_2$C$_{1-6}$alkyl,

(14) —NHC(O)C$_{1-6}$alkyl,
(15) =N(OCH$_3$),
(16) —P(O)(OH)$_2$, and
(17) —P(O)(OC$_{1-6}$alkyl)$_2$,
wherein each alkyl is unsubstituted or substituted with one to three substituents independently selected from: —OH, —OC$_{1-6}$alkyl, halogen, cyano, and —S(O)$_2$C$_{1-6}$alkyl;

R$^L$ is selected from the group consisting of:
(1) C$_{1-6}$alkyl,
(2) halogen,
(3) —OR$^e$,
(4) —N(R$^c$)S(O)$_m$R$^e$,
(5) —S(O)$_m$R$^e$,
(6) —S(O)$_m$NR$^c$R$^d$,
(7) —NR$^c$R$^d$,
(8) —C(O)R$^e$,
(9) —OC(O)R$^e$,
(10) —CO$_2$R$^e$,
(11) —CN,
(12) —C(O)NR$^c$R$^d$,
(13) —N(R$^c$)C(O)R$^e$,
(14) —N(R$^c$)C(O)OR$^e$,
(15) —N(R$^c$)C(O)NR$^c$R$^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;

each R$^m$ is independently selected from the group consisting of:
(1) halogen,
(2) —C$_{1-6}$ alkyl,
(3) —OH,
(4) oxo,
(5) —OC$_{1-6}$alkyl,
(6) —SO$_2$—C$_{1-6}$ alkyl,
(7) —C$_{1-6}$alkyl-SO$_2$C$_{1-6}$alkyl,
(8) —CN,
(9) —CF$_3$,
(10) —OCHF$_2$,
(11) —OCF$_3$,
(12) —NH$_2$,
(13) —NHSO$_2$C$_{1-6}$alkyl,
(14) —NHC(O)C$_{1-6}$alkyl,
(15) =N(OCH$_3$),
(16) —P(O)(OH)$_2$, and
(17) —P(O)(OC$_{1-6}$alkyl)$_2$,
wherein each C$_{1-10}$ alkyl is unsubstituted or substituted with one to three substituents independently selected from: —OH, —OC$_{1-6}$alkyl, halogen, cyano, and —S(O)$_2$C$_{1-6}$alkyl;

n is independently 0, 1, 2 or 3;
each m is independently 0, 1 or 2;
each p is independently selected from: 0, 1, 2, 3, 4, 5, 6, 7, 8, 9 or 10; and
q is independently selected from: 1, 2 or 3.

In another embodiment, the present invention is concerned with novel compounds of structural Formula I:

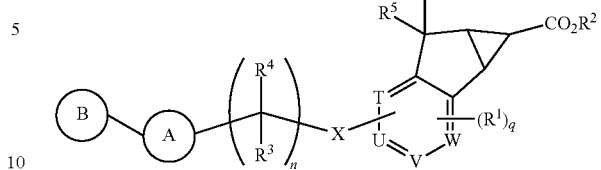

I or a pharmaceutically acceptable salt thereof; wherein
X is selected from the group consisting of:
(1) oxygen, and
(2) NR$^7$;
T is selected from the group consisting of: CH, N and N-oxide;
U is selected from the group consisting of: CH, N and N-oxide;
V is selected from the group consisting of: CH, N and N-oxide;
W is selected from the group consisting of: CH, N and N-oxide,
provided that no more than two of T, U, V and W are N or N-oxide;
A is selected from the group consisting of:
(1) bicyclic aryl ring, and
(2) bicyclic heteroaryl ring,
wherein each bicyclic aryl ring and bicyclic heteroaryl ring is unsubstituted or substituted with one to six substituents selected from R$^a$, and wherein two R$^a$ substituents together with the carbon atom to which they are attached may form a 3-6 membered cycloalkyl ring, or a 3-6 membered cycloheteroalkyl ring containing 0 to 3 heteroatoms independently selected from oxygen, sulfur, and NR$^8$, and wherein each 3-6 membered cycloalkyl and each 3-6 membered cycloheteroalkyl ring is unsubstituted or substituted with 1 to 4 substituents selected from: —C$_{1-6}$alkyl, —O—C$_{1-6}$alkyl, halogen and OH;
B is selected from the group consisting of:
(1) aryl,
(2) aryl-O—,
(3) C$_{3-6}$cycloalkyl-,
(4) C$_{3-6}$cycloalkyl-C$_{1-10}$alkyl-,
(5) C$_{3-6}$cycloalkyl-C$_{1-10}$alkyl-O—,
(6) C$_{2-5}$cycloheteroalkyl-,
(7) C$_{3-6}$cycloheteroalkyl-C$_{1-10}$alkyl-,
(8) C$_{3-6}$cycloheteroalkyl-C$_{1-10}$alkyl-O—,
(9) heteroaryl,
(10) heteroaryl-O—,
(11) aryl-C$_{1-10}$ alkyl-, and
(12) heteroaryl-C$_{1-10}$ alkyl-;
wherein B is unsubstituted or substituted with one to six substituents selected from R$^b$;
each R$^1$ is independently selected from the group consisting of:
(1) hydrogen,
(2) halogen,
(1) —OR$^e$,
(2) —CN,
(3) —C$_{1-6}$alkyl, and
(4) —C$_{3-6}$cycloalkyl,
wherein each alkyl and cycloalkyl is unsubstituted or substituted with one to three substituents selected from R$^i$;

$R^2$ is selected from the group consisting of:
(1) hydrogen,
(2) —$C_{1-6}$alkyl, and
(3) —$C_{3-6}$cycloalkyl,
wherein each alkyl and cycloalkyl is unsubstituted or substituted with one to three substituents selected from $R^j$;
each $R^3$ is independently selected from the group consisting of:
(1) hydrogen,
(2) halogen,
(3) —$OR^e$,
(4) —$C_{1-6}$alkyl,
(5) —$C_{2-6}$alkenyl,
(6) —$C_{2-6}$alkynyl,
(7) —$C_{3-6}$cycloalkyl, and
(8) —$C_{2-6}$cycloheteroalkyl,
wherein each alkyl, alkenyl, alkynyl, cycloalkyl and cycloheteroalkyl is unsubstituted or substituted with one to three substituents selected from $R^L$;
each $R^4$ is independently selected from the group consisting of:
(1) hydrogen,
(2) halogen,
(3) —$OR^e$,
(4) —$C_{1-6}$alkyl,
(5) —$C_{2-6}$alkenyl,
(6) —$C_{2-6}$alkynyl,
(7) —$C_{3-6}$cycloalkyl, and
(8) —$C_{2-6}$cycloheteroalkyl,
wherein each alkyl, alkenyl, alkynyl, and cycloalkyl is unsubstituted or substituted with one to three substituents selected from $R^L$;
$R^5$ is selected from the group consisting of:
(1) hydrogen,
(2) —$C_{1-3}$alkyl, and
(3) halogen;
$R^6$ is selected from the group consisting of:
(1) hydrogen,
(2) —$C_{1-3}$alkyl, and
(3) halogen, or
$R^5$ and $R^6$ can together form oxo;
$R^7$ is selected from the group consisting of:
(1) hydrogen,
(2) —$C(O)R^e$, and
(3) —$C_{1-10}$alkyl,
wherein —$C_{1-10}$alkyl is unsubstituted or substituted with one to five fluorines;
each $R^8$ is selected from the group consisting of:
(1) hydrogen,
(2) —$C(O)R^e$, and
(3) —$C_{1-10}$alkyl,
wherein —$C_{1-10}$alkyl is unsubstituted or substituted with one to five fluorines;
each $R^a$ is independently selected from the group consisting of:
(1) —$C_{1-6}$alkyl,
(2) —O—$C_{1-6}$alkyl,
(3) halogen,
(4) oxo,
(5) —$OR^e$,
(6) —$N(R^c)S(O)_mR^e$,
(7) —$S(O)_mR^e$,
(8) —$S(O)_mNR^cR^d$,
(9) —$NR^cR^d$,
(10) —$C(O)R^e$,
(11) —$OC(O)R^e$,
(12) —$CO_2R^e$,
(13) —CN,
(14) —$C(O)NR^cR^d$,
(15) —$N(R^c)C(O)R^e$,
(16) —$N(R^c)C(O)OR^e$,
(17) —$N(R^c)C(O)NR^cR^d$,
(18) —$CF_3$,
(19) —$OCF_3$,
(20) —$OCHF_2$,
(21) —$(CH_2)_p$—$C_{3-6}$cycloalkyl,
(22) —$(CH_2)_p$—$C_{2-10}$cycloheteroalkyl,
(23) —$(CH_2)_p$-aryl, and
(24) —$(CH_2)_p$-heteroaryl,
wherein $R^a$ is unsubstituted or substituted with one to three substituents selected from $R^m$;
each $R^b$ is independently selected from the group consisting of:
(1) —$C_{1-10}$alkyl,
(2) —O—$C_{1-10}$alkyl,
(3) —$C_{2-10}$ alkenyl,
(4) halogen,
(5) —OH,
(6) —$OC_{2-10}$ alkenyl,
(7) —$O(CH_2)pOC_{1-10}$alkyl,
(8) —$O(CH_2)pC_{3-6}$cycloalkyl,
(9) —$O(CH_2)pC_{2-10}$cycloheteroalkyl,
(10) —$O(CH_2)$p-aryl,
(11) —$O(CH_2)$p-heteroaryl,
(12) —$N(R^c)S(O)_mR^e$,
(13) —$S(O)_mR^e$,
(14) —$O(CH_2)$p-$S(O)_mR^e$,
(15) —$S(O)_mNR^cR^d$,
(16) —$NR^cR^d$,
(17) —$C(O)R^e$,
(18) —$OC(O)R^e$,
(19) —$CO_2R^e$,
(20) —CN,
(21) —$C(O)NR^cR^d$,
(22) —$N(R^c)C(O)R^e$,
(23) —$N(R^c)C(O)OR^e$,
(24) —$N(R^c)C(O)NR^cR^d$,
(25) —$O(CH_2)pO$—$C_{3-6}$cycloalkyl,
(26) —$O(CH_2)pO$—$C_{2-10}$cycloheteroalkyl,
(27) —$CF_3$,
(28) —$OCF_3$,
(29) —$OCHF_2$,
(30) —$(CH_2)$p-$C_{3-6}$cycloalkyl,
(31) —$(CH_2)$p-$C_{2-10}$cycloheteroalkyl,
(32) —$(CH_2)$p-aryl, and
(33) —$(CH_2)$p-heteroaryl,
wherein each $R^b$ is unsubstituted or substituted with one to five substituents selected from $R^k$;
each $R^c$ and $R^d$ is independently selected from the group consisting of:
(1) hydrogen,
(2) —$C_{1-10}$alkyl,
(3) —$C_{2-10}$alkenyl,
(4) —$C_{3-6}$cycloalkyl,
(5) $C_{3-6}$ cycloalkyl-$C_{1-10}$alkyl-,
(6) —$C_{2-6}$cycloheteroalkyl,
(7) $C_{2-6}$cycloheteroalkyl-$C_{1-10}$alkyl-,
(8) aryl,
(9) heteroaryl,
(10) aryl-$C_{1-10}$alkyl-, and
(11) heteroaryl-$C_{1-10}$alkyl-, or
$R^c$ and $R^d$ together with the atom(s) to which they are attached form a cycloheteroalkyl ring of 4 to 7 members containing 0-2 additional heteroatoms independently selected from oxygen, sulfur and N—$R^g$, and wherein each $R^c$ and $R^d$ is unsubstituted or substituted with one to three substituents independently selected from $R^f$;

each $R^e$ is independently selected from the group consisting of:
(1) hydrogen,
(2) —$C_{1-10}$alkyl,
(3) —$C_{2-10}$ alkenyl,
(4) —$C_{3-6}$ cycloalkyl,
(5) —$C_{3-6}$ cycloalkyl-$C_{1-10}$alkyl-,
(6) —$C_{2-5}$cycloheteroalkyl,
(7) —$C_{2-5}$cycloheteroalkyl-$C_{1-10}$alkyl-,
(8) aryl,
(9) heteroaryl,
(10) aryl-$C_{1-10}$alkyl-, and
(11) heteroaryl-$C_{1-10}$alkyl-, wherein each $R^e$ is unsubstituted or substituted with one to three substituents selected from $R^h$;

each $R^f$ is selected from the group consisting of:
(1) halogen,
(2) —$C_{1-10}$alkyl,
(3) —OH,
(4) —O$C_{1-6}$alkyl,
(5) —S(O)$_m$—$C_{1-4}$alkyl,
(6) —CN,
(7) —$CF_3$,
(8) —$OCHF_2$, and
(9) —$OCF_3$, wherein each alkyl is unsubstituted or substituted with one to three substituents independently selected from: —OH, halogen, cyano, and —S(O)$_2$CH$_3$;

each $R^g$ is selected from the group consisting of:
(1) hydrogen,
(2) —C(O)$R^e$, and
(3) —$C_{1-10}$alkyl, wherein alkyl is unsubstituted or substituted with one to five fluorines;

each $R^h$ is selected from the group consisting of:
(1) halogen,
(2) —$C_{1-10}$alkyl,
(3) —OH,
(4) —O—$C_{1-4}$alkyl,
(5) —S(O)$_m$—$C_{1-4}$alkyl,
(6) —CN,
(7) —$CF_3$,
(8) —$OCHF_2$, and
(9) —$OCF_3$, wherein each alkyl is unsubstituted or substituted with one to three substituents independently selected from: —OH, halogen, cyano, and —S(O)$_2$CH$_3$;

$R^i$ is independently selected from the group consisting of:
(1) —$C_{1-6}$alkyl,
(2) —$OR^e$,
(3) —$N(R^c)S(O)_mR^e$,
(4) halogen,
(5) —S(O)$_m R^e$,
(6) —S(O)$_m NR^c R^d$,
(7) —$NR^c R^d$,
(8) —C(O)$R^e$,
(9) —OC(O)$R^e$,
(10) —CO$_2 R^e$,
(11) —CN,
(12) —C(O)$NR^c R^d$,
(13) —$N(R^c)C(O)R^e$,
(14) —$N(R^c)C(O)OR^e$,
(15) —$N(R^c)C(O)NR^c R^d$,
(16) —$CF_3$,
(17) —$OCF_3$,
(18) —$OCHF_2$,
(19) —$C_{3-6}$cycloalkyl, and
(20) —$C_{2-5}$cycloheteroalkyl;

$R^j$ is independently selected from the group consisting of:
(1) —$C_{1-6}$alkyl,
(2) —$OR^e$,
(3) —$N(R^c)S(O)_mR^e$,
(4) halogen,
(5) —S(O)$_m R^e$,
(6) —S(O)$_m NR^c R^d$,
(7) —$NR^c R^d$,
(8) —C(O)$R^e$,
(9) —OC(O)$R^e$,
(10) —CO$_2 R^e$,
(11) —CN,
(12) —C(O)$NR^c R^d$,
(13) —$N(R^c)C(O)R^e$,
(14) —$N(R^c)C(O)OR^e$,
(15) —$N(R^c)C(O)NR^c R^d$,
(16) —$CF_3$,
(17) —$OCF_3$,
(18) —$OCHF_2$,
(19) —$C_{3-6}$cycloalkyl, and
(20) —$C_{2-5}$cycloheteroalkyl;

each $R^k$ is independently selected from the group consisting of:
(1) halogen,
(2) —$C_{1-6}$alkyl,
(3) —OH,
(4) oxo,
(5) —O$C_{1-6}$alkyl,
(6) —SO$_2$—$C_{1-6}$ alkyl,
(7) —$C_{1-6}$alkyl-SO$_2 C_{1-6}$alkyl,
(8) —CN,
(9) —$CF_3$,
(10) —$OCHF_2$,
(11) —$OCF_3$,
(12) —$NH_2$,
(13) —NHSO$_2 C_{1-6}$alkyl,
(14) —NHC(O)$C_{1-6}$alkyl,
(15) =N(OCH$_3$),
(16) —P(O)(OH)$_2$, and
(17) —P(O)(O$C_{1-6}$alkyl)$_2$, wherein each alkyl is unsubstituted or substituted with one to three substituents independently selected from: —OH, —O$C_{1-6}$alkyl, halogen, cyano, and —S(O)$_2 C_{1-6}$alkyl;

$R^L$ is selected from the group consisting of:
(1) $C_{1-6}$alkyl,
(2) halogen,
(3) —$OR^e$,
(4) —$N(R^c)S(O)_mR^e$,
(5) —S(O)$_m R^e$,
(6) —S(O)$_m NR^c R^d$,
(7) —$NR^c R^d$,
(8) —C(O)$R^e$,
(9) —OC(O)$R^e$,
(10) —CO$_2 R^e$,
(11) —CN,
(12) —C(O)$NR^c R^d$,
(13) —$N(R^c)C(O)R^e$,
(14) —$N(R^c)C(O)OR^e$,
(15) —$N(R^c)C(O)NR^c R^d$,
(16) —$CF_3$,
(17) —$OCF_3$,

(18) —OCHF$_2$,
(19) —C$_{3-6}$cycloalkyl, and
(20) —C$_{2-5}$cycloheteroalkyl;

each R$^m$ is independently selected from the group consisting of:
(1) halogen,
(2) —C$_{1-6}$ alkyl,
(3) —OH,
(4) oxo,
(5) —OC$_{1-6}$alkyl,
(6) —SO$_2$—C$_{1-6}$ alkyl,
(7) —C$_{1-6}$alkyl-SO$_2$C$_{1-6}$alkyl,
(8) —CN,
(9) —CF$_3$,
(10) —OCHF$_2$,
(11) —OCF$_3$,
(12) —NH$_2$,
(13) —NHSO$_2$C$_{1-6}$alkyl,
(14) —NHC(O)C$_{1-6}$alkyl,
(15) =N(OCH$_3$),
(16) —P(O)(OH)$_2$, and
(17) —P(O)(OC$_{1-6}$alkyl)$_2$, wherein each C$_{1-10}$ alkyl is unsubstituted or substituted with one to three substituents independently selected from: —OH, —OC$_{1-6}$alkyl, halogen, cyano, and —S(O)$_2$C$_{1-6}$ alkyl;

n is independently 0, 1, 2 or 3;
each m is independently 0, 1 or 2;
each p is independently selected from: 0, 1, 2, 3, 4, 5, 6, 7, 8, 9 or 10; and
q is independently selected from: 1, 2 or 3.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In one embodiment of the present invention, X is oxygen. In another embodiment of the present invention, X is NR$^7$. In a class of this embodiment, X is NH.

In another embodiment of the present invention, T is selected from the group consisting of: CH and N; U is selected from the group consisting of: CH and N; V is selected from the group consisting of: CH and N; and W is selected from the group consisting of: CH and N, provided that one or two of T, U, V and W are N. In another embodiment of the present invention, T is selected from the group consisting of: CH and N; U is selected from the group consisting of: CH and N; V is selected from the group consisting of: CH and N; and W is selected from the group consisting of: CH and N, provided that one or none of T, U, V and W is N. In another embodiment of the present invention, T is selected from the group consisting of: CH and N; U is selected from the group consisting of: CH and N; V is selected from the group consisting of: CH and N; and W is selected from the group consisting of: CH and N, provided that one of T, U, V and W is N. In another embodiment of the present invention, T is selected from the group consisting of: CH and N; U is selected from the group consisting of: CH and N; V is selected from the group consisting of: CH and N; and W is selected from the group consisting of: CH and N, provided that two of T, U, V and W are N.

In another embodiment of the present invention, T is CH, U is CH; V is N or N-oxide; and W is CH. In a class of this embodiment, T is CH, U is CH; V is N; and W is CH. In another embodiment of the present invention, T is selected from the group consisting of: CH, N and N-oxide. In a class of this embodiment, T is selected from the group consisting of: CH and N. In another class of this embodiment, T is CH. In another class of this embodiment, T is N or N-oxide. In another class of this embodiment, T is N.

In another embodiment of the present invention, U is selected from the group consisting of: CH, N and N-oxide. In a class of this embodiment, U is selected from the group consisting of: CH and N. In another class of this embodiment, U is CH. In another class of this embodiment, U is N or N-oxide. In another class of this embodiment, U is N.

In another embodiment of the present invention, V is selected from the group consisting of: CH, N and N-oxide. In a class of this embodiment, V is selected from the group consisting of: CH and N. In another class of this embodiment, V is CH. In another class of this embodiment, V is N or N-oxide. In another class of this embodiment, V is N.

In another embodiment of the present invention, W is selected from the group consisting of: CH, N and N-oxide. In a class of this embodiment, W is selected from the group consisting of: CH and N. In another class of this embodiment, W is CH. In another class of this embodiment, W is N or N-oxide. In another class of this embodiment, W is N.

In another embodiment of the present invention, T is CH, U is CH, V is N or N-oxide, and W is CH. In a class of this embodiment, T is CH, U is CH, V is N, and W is CH. In another class of this embodiment, T is CH, V is N or N-oxide, and W is CH. In another class of this embodiment, T is CH, V is N, and W is CH. In another class of this embodiment, U is CH, V is N or N-oxide, and W is CH. In another class of this embodiment, U is CH, V is N, and W is CH. In another class of this embodiment, T is CH, U is CH, and V is N or N-oxide. In another class of this embodiment, T is CH, U is CH, and V is N.

In another embodiment of the present invention, T is CH, U is N or N-oxide, V is CH, and W is CH. In a class of this embodiment, T is CH, U is N, V is CH, and W is CH. In another class of this embodiment, T is CH, U is N or N-oxide, and W is CH. In another class of this embodiment, T is CH, U is N, and W is CH. In another class of this embodiment, U is N or N-oxide, V is CH, and W is CH. In another class of this embodiment, U is N, V is CH, and W is CH. In another class of this embodiment, T is CH, U is N or N-oxide, and V is CH. In another class of this embodiment, T is CH, U is N, and V is CH.

In another embodiment of the present invention, T is N or N-oxide, U is CH, V is CH, and W is CH. In a class of this embodiment, T is N, U is CH, V is CH, and W is CH. In another class of this embodiment, T is N or N-oxide, V is CH, and W is CH. In another class of this embodiment, T is N, V is CH, and W is CH. In another class of this embodiment, T is N or N-oxide, U is CH, and W is CH. In another class of this embodiment, T is N, U is CH, and W is CH. In another class of this embodiment, T is N or N-oxide, U is CH, and V is CH. In another class of this embodiment, T is N, U is CH, and V is CH.

In another embodiment of the present invention, T is CH, U is CH, V is CH, and W is N or N-oxide. In a class of this embodiment, T is CH, U is CH, V is CH, and W is N. In another class of this embodiment, T is CH, V is CH, and W is N or N-oxide. In another class of this embodiment, T is CH, V is CH, and W is N. In another class of this embodiment, T is CH, U is CH, and W is N or N-oxide. In another class of this embodiment, T is CH, U is CH, and W is N. In another class of this embodiment, U is CH, V is CH, and W is N or N-oxide. In another class of this embodiment, U is CH, V is CH, and W is N.

In another embodiment of the present invention, A is a bicyclic aryl ring, wherein each bicyclic aryl ring is unsubstituted or substituted with one to six substituents selected from $R^a$, and wherein two $R^a$ substituents together with the carbon atom to which they are attached may form a 3-6 membered cycloalkyl ring, or a 3-6 membered cycloheteroalkyl ring containing 0 to 3 heteroatoms independently selected from oxygen, sulfur, and $NR^8$, and wherein each 3-6 membered cycloalkyl and each 3-6 membered cycloheteroalkyl ring is unsubstituted or substituted with 1 to 4 substituents selected from: —$C_{1-6}$alkyl, —O—$C_{1-6}$alkyl, halogen and OH.

In another embodiment of the present invention, A is a bicyclic heteroaryl ring, wherein each bicyclic heteroaryl ring is unsubstituted or substituted with one to six substituents selected from $R^a$, and wherein two $R^a$ substituents together with the carbon atom to which they are attached may form a 3-6 membered cycloalkyl ring, or a 3-6 membered cycloheteroalkyl ring containing 0 to 3 heteroatoms independently selected from oxygen, sulfur, and $NR^8$, and wherein each 3-6 membered cycloalkyl and each 3-6 membered cycloheteroalkyl ring is unsubstituted or substituted with 1 to 4 substituents selected from: —$C_{1-6}$alkyl, —O—$C_{1-6}$alkyl, halogen and OH.

In another embodiment of the present invention, A is selected from the group consisting of:

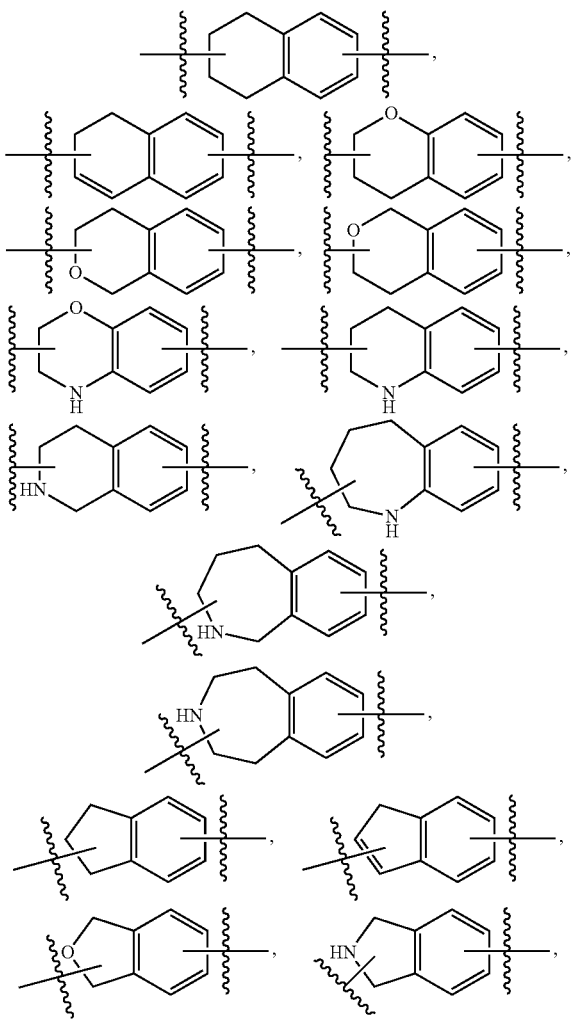

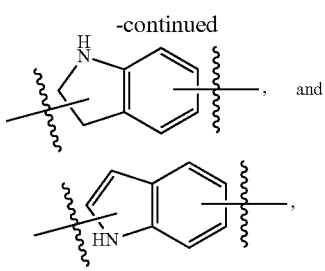

wherein A is unsubstituted or substituted with one to six substituents selected from $R^a$, and wherein two $R^a$ substituents together with the carbon atom to which they are attached may form a 3-6 membered cycloalkyl ring or a 3-6 membered cycloheteroalkyl ring containing 0 to 3 heteroatoms independently selected from oxygen, sulfur, and $NR^8$, and wherein each 3-6 membered cycloalkyl and each 3-6 membered cycloheteroalkyl ring is unsubstituted or substituted with 1 to 4 substituents selected from: —$C_{1-6}$alkyl, —O—$C_{1-6}$alkyl, halogen and OH. In a class of this embodiment, A is unsubstituted or substituted with one to four substituents selected from $R^a$, and wherein two $R^a$ substituents together with the carbon atom to which they are attached may form a 3-6 membered cycloalkyl ring or a 3-6 membered cycloheteroalkyl ring containing 0 to 3 heteroatoms independently selected from oxygen, sulfur, and $NR^8$, and wherein each 3-6 membered cycloalkyl ring and each 3-6 membered cycloheteroalkyl ring is unsubstituted or substituted with 1 to 4 substituents selected from: —$C_{1-6}$alkyl, —O—$C_{1-6}$alkyl, halogen and OH.

In another class of this embodiment, A is unsubstituted or substituted with one to three substituents selected from $R^a$, and wherein two $R^a$ substituents together with the carbon atom to which they are attached may form a 3-6 membered cycloalkyl ring or a 3-6 membered cycloheteroalkyl ring containing 0 to 3 heteroatoms independently selected from oxygen, sulfur, and $NR^8$, and wherein each 3-6 membered cycloalkyl ring and each 3-6 membered cycloheteroalkyl ring is unsubstituted or substituted with 1 to 4 substituents selected from: —$C_{1-6}$alkyl, —O—$C_{1-6}$alkyl, halogen and OH. In another class of this embodiment, the 3-6 membered cycloalkyl ring and the 3-6 membered cycloheteroalkyl ring formed by two $R^a$ substituents on A together with the carbon atom to which they are attached is selected from: cyclopropyl, cyclobutyl, oxetane and dioxane. In subclass of this class, the 3-6 membered cycloalkyl ring and the 3-6 membered cycloheteroalkyl ring formed by two $R^a$ substituents on A together with the carbon atom to which they are attached is selected from: cyclopropyl, cyclobutyl, oxetane and 1,3 dioxane. In another class of this embodiment, A is unsubstituted or substituted with one to six substituents selected from $R^a$, and wherein two $R^a$ substituents together with the carbon atom to which they are attached may form a 3-6 membered cycloalkyl ring, and wherein each 3-6 membered cycloalkyl ring is unsubstituted or substituted with 1 to 4 substituents selected from: —$C_{1-6}$alkyl, —O—$C_{1-6}$alkyl, halogen and OH. In a subclass of this class, the 3-6 membered cycloalkyl ring formed by two $R^a$ substituents on A together with the carbon atom to which they are attached is selected from: cyclopropyl, and cyclobutyl. In another class of this embodiment, A is unsubstituted or substituted with one to six substituents selected from $R^a$, and wherein two $R^a$ substituents together with the carbon atom to which they are attached may form a 3-6 membered cycloheteroalkyl ring containing 0 to 3 heteroatoms independently selected from oxygen, sulfur, and NR⁸, and wherein each 3-6 membered cycloheteroalkyl ring is unsubstituted or substituted with 1 to 4 substituents selected from: —C$_{1-6}$alkyl, —O—C$_{1-6}$alkyl, halogen and OH. In a subclass of this class, the 3-6 membered cycloheteroalkyl ring formed by two R$^a$ substituents on A together with the carbon atom to which they are attached is selected from: oxetane and dioxane. In another subclass of this class, the 3-6 membered cycloheteroalkyl ring formed by two R$^a$ substituents on A together with the carbon atom to which they are attached is selected from: oxetane and 1,3 dioxane.

In another embodiment of the present invention, A is selected from the group consisting of:

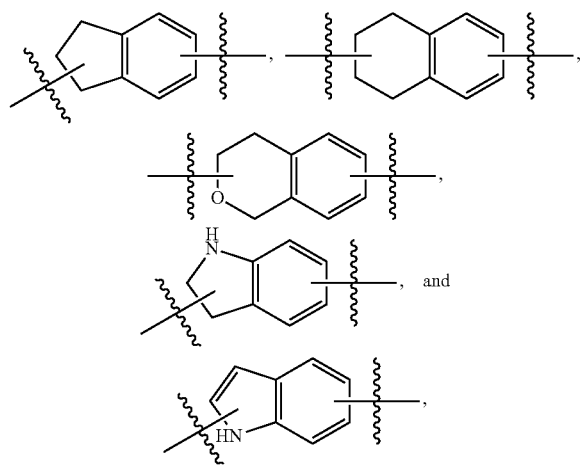

wherein A is unsubstituted or substituted with one to six substituents selected from R$^a$, and wherein two R$^a$ substituents together with the carbon atom to which they are attached may form a 3-6 membered cycloalkyl ring or a 3-6 membered cycloheteroalkyl ring containing 0 to 3 heteroatoms independently selected from oxygen, sulfur, and NR⁸, and wherein each 3-6 membered cycloalkyl ring and each 3-6 membered cycloheteroalkyl ring is unsubstituted or substituted with 1 to 4 substituents selected from: —C$_{1-6}$alkyl, —O—C$_{1-6}$alkyl, halogen and OH. In another class, A is unsubstituted or substituted with one to four substituents selected from R$^a$, and wherein two R$^a$ substituents together with the carbon atom to which they are attached may form a 3-6 membered cycloalkyl ring or a 3-6 membered cycloheteroalkyl ring containing 0 to 3 heteroatoms independently selected from oxygen, sulfur, and NR⁸, and wherein each 3-6 membered cycloalkyl ring and each 3-6 membered cycloheteroalkyl ring is unsubstituted or substituted with 1 to 4 substituents selected from: —C$_{1-6}$alkyl, —O—C$_{1-6}$alkyl, halogen and OH. In another class, A is unsubstituted or substituted with one to three substituents selected from R$^a$, and wherein two R$^a$ substituents together with the carbon atom to which they are attached may form a 3-6 membered cycloalkyl ring or a 3-6 membered cycloheteroalkyl ring containing 0 to 3 heteroatoms independently selected from oxygen, sulfur, and NR⁸, and wherein each 3-6 membered cycloalkyl ring and each 3-6 membered cycloheteroalkyl ring is unsubstituted or substituted with 1 to 4 substituents selected from: —C$_{1-6}$alkyl, —O—C$_{1-6}$alkyl, halogen and OH. In another class of this embodiment, the 3-6 membered cycloalkyl ring and the 3-6 membered cycloheteroalkyl ring formed by two R$^a$ substituents on A together with the carbon atom to which they are attached is selected from: cyclopropyl, cyclobutyl, oxetane and dioxane. In subclass of this class, the 3-6 membered cycloalkyl ring and the 3-6 membered cycloheteroalkyl ring formed by two R$^a$ substituents on A together with the carbon atom to which they are attached is selected from: cyclopropyl, cyclobutyl, oxetane and 1,3 dioxane. In another class of this embodiment, A is unsubstituted or substituted with one to six substituents selected from R$^a$, and wherein two R$^a$ substituents together with the carbon atom to which they are attached may form a 3-6 membered cycloalkyl ring, and wherein each 3-6 membered cycloalkyl ring is unsubstituted or substituted with 1 to 4 substituents selected from: —C$_{1-6}$alkyl, —O—C$_{1-6}$alkyl, halogen and OH. In a subclass of this class, the 3-6 membered cycloalkyl ring formed by two R$^a$ substituents on A together with the carbon atom to which they are attached is selected from: cyclopropyl, and cyclobutyl. In another class of this embodiment, A is unsubstituted or substituted with one to six substituents selected from R$^a$, and wherein two R$^a$ substituents together with the carbon atom to which they are attached may form a 3-6 membered cycloheteroalkyl ring containing 0 to 3 heteroatoms independently selected from oxygen, sulfur, and NR⁸, and wherein each 3-6 membered cycloheteroalkyl ring is unsubstituted or substituted with 1 to 4 substituents selected from: —C$_{1-6}$alkyl, —O—C$_{1-6}$alkyl, halogen and OH. In a subclass of this class, the 3-6 membered cycloheteroalkyl ring formed by two R$^a$ substituents on A together with the carbon atom to which they are attached is selected from: oxetane and dioxane.

In another embodiment of the present invention, A is selected from the group consisting of:

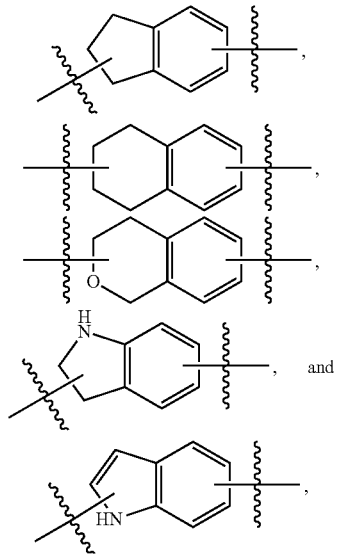

wherein A is unsubstituted or substituted with one to six substituents selected from R$^a$, and wherein two R$^a$ substituents together with the carbon atom to which they are attached may form a 3-6 membered cycloalkyl ring, which is unsubstituted or substituted with 1 to 4 substituents selected from: —C$_{1-6}$alkyl, —O—C$_{1-6}$alkyl, halogen and OH. In a class of this embodiment, A is unsubstituted or substituted with one to four substituents selected from R$^a$, and wherein two R$^a$ substituents together with the carbon atom to which they are attached may form a 3-6 membered cycloalkyl ring, which is unsubstituted or substituted with 1 to 4 substituents selected from: —$C_{1-6}$alkyl, —O—$C_{1-6}$alkyl, halogen and OH. In another class of this embodiment, A is unsubstituted or substituted with one to three substituents selected from $R^a$, and wherein two $R^a$ substituents together with the carbon atom to which they are attached may form a 3-6 membered cycloalkyl ring, which is unsubstituted or substituted with 1 to 4 substituents selected from: —$C_{1-6}$alkyl, —O—$C_{1-6}$alkyl, halogen and OH. In another class of this embodiment, the 3-6 membered cycloalkyl ring formed by two $R^a$ substituents on A together with the carbon atom to which they are attached is selected from: cyclopropyl, and cyclobutyl.

In another embodiment of the present invention, A is selected from the group consisting of:

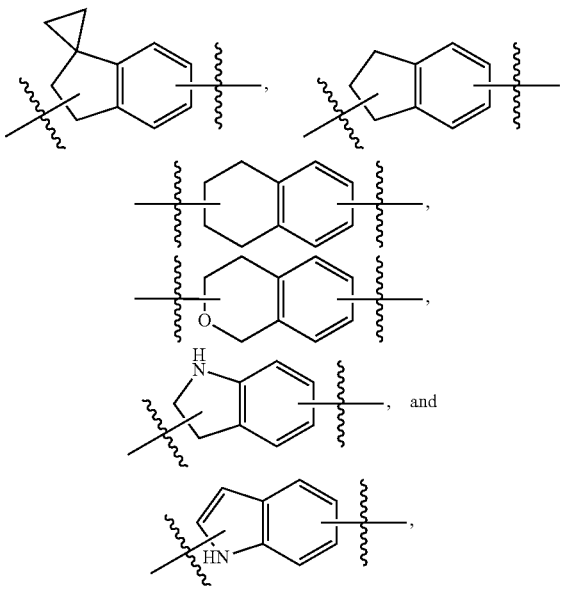

wherein A is unsubstituted or substituted with one to six substituents selected from $R^a$.

In certain embodiments of the invention, A is bonded to the carbon substituted with $R^3$ and $R^4$, or when n is 0 A is bonded to X.

In another embodiment of the present invention, B is selected from the group consisting of: aryl, aryl-O—, $C_{3-6}$cycloalkyl-, $C_{3-6}$cycloalkyl-$C_{1-10}$alkyl-, $C_{3-6}$cycloalkyl-$C_{1-10}$alkyl-O—, $C_{2-5}$cycloheteroalkyl-, heteroaryl, heteroaryl-O—, aryl-$C_{1-10}$ alkyl-, and heteroaryl-$C_{1-10}$ alkyl-; wherein B is unsubstituted or substituted with one to six substituents selected from $R^b$. In another embodiment of the present invention, B is selected from the group consisting of: aryl, aryl-O—, heteroaryl, heteroaryl-O—, aryl-$C_{1-10}$ alkyl-, and heteroaryl-$C_{1-10}$ alkyl-; wherein B is unsubstituted or substituted with one to six substituents selected from $R^b$. In another embodiment of the present invention, B is selected from the group consisting of: aryl, heteroaryl, aryl-$C_{1-10}$ alkyl- and heteroaryl-$C_{1-10}$ alkyl-; wherein B is unsubstituted or substituted with one to six substituents selected from $R^b$.

In another embodiment of the present invention, B is selected from the group consisting of: aryl, and heteroaryl, wherein each aryl and heteroaryl is unsubstituted or substituted with one to six substituents selected from $R^b$. In a class of this embodiment, B is selected from the group consisting of: phenyl, pyridine and benzimidazole, wherein each phenyl, pyridine and benzimidazole is unsubstituted or substituted with one to six substituents selected from $R^b$. In another class of this embodiment, B is selected from the group consisting of: phenyl and pyridine, wherein each phenyl and pyridine is unsubstituted or substituted with one to six substituents selected from $R^b$. In another class of this embodiment, B is unsubstituted or substituted with one to five substituents selected from $R^b$. In another class of this embodiment, B is unsubstituted or substituted with one to four substituents selected from $R^b$. In another class of this embodiment, B is unsubstituted or substituted with one to three substituents selected from $R^b$. In another class of this embodiment, B is unsubstituted or substituted with one to two substituents selected from $R^b$.

In another embodiment of the present invention, each $R^1$ is independently selected from the group consisting of: hydrogen, halogen, —$OR^e$, —CN, and —$C_{1-6}$alkyl, wherein each alkyl is unsubstituted or substituted with one to three substituents selected from $R^i$. In another embodiment of the present invention, each $R^1$ is independently selected from the group consisting of: hydrogen, halogen, —CN, and —$C_{1-6}$alkyl, wherein each alkyl is unsubstituted or substituted with one to three substituents selected from $R^i$. In another embodiment of the present invention, each $R^1$ is independently selected from the group consisting of: hydrogen, halogen and —$C_{1-6}$alkyl, wherein each alkyl is unsubstituted or substituted with one to three substituents selected from $R^i$. In a class of this embodiment, each $R^1$ is independently selected from the group consisting of: hydrogen, halogen and —$C_{1-6}$alkyl.

In another embodiment of the present invention, each $R^1$ is independently selected from the group consisting of: hydrogen and —$C_{1-6}$alkyl, wherein each alkyl is unsubstituted or substituted with one to three substituents selected from $R^i$. In a class of this embodiment, each $R^1$ is independently selected from the group consisting of: hydrogen and —$C_{1-6}$alkyl. In another embodiment of the present invention, each $R^1$ is halogen. In another embodiment of the present invention, each $R^1$ is —$C_{1-6}$alkyl, wherein each alkyl is unsubstituted or substituted with one to three substituents selected from $R^i$. In another embodiment of the present invention, each $R^1$ is hydrogen.

In another embodiment of the present invention, $R^2$ is selected from the group consisting of: hydrogen and —$C_{1-6}$alkyl, wherein each alkyl is unsubstituted or substituted with one to three substituents selected from $R^j$. In a class of this embodiment, $R^2$ is selected from the group consisting of: hydrogen and —$C_{1-6}$alkyl. In another embodiment of the present invention, $R^2$ is —$C_{1-6}$alkyl, wherein each alkyl is unsubstituted or substituted with one to three substituents selected from $R^j$. In a class of this embodiment, $R^2$ is —$C_{1-6}$alkyl. In another embodiment of the present invention, $R^2$ is hydrogen.

In another embodiment of the present invention, each $R^3$ is independently selected from the group consisting of: hydrogen, halogen, —$OR^e$, —$C_{1-6}$alkyl, —$C_{2-6}$alkenyl and —$C_{2-6}$alkynyl, wherein each alkyl, alkenyl and alkynyl is unsubstituted or substituted with one to three substituents selected from $R^L$. In a class of this embodiment, each $R^3$ is independently selected from the group consisting of: hydrogen, halogen, —$OR^e$, —$C_{1-6}$alkyl, —$C_{2-6}$alkenyl and —$C_{2-6}$ alkynyl. In another embodiment of the present invention, each $R^3$ is independently selected from the group consisting of: hydrogen, halogen, —$OR^e$ and —$C_{1-6}$alkyl, wherein each alkyl is unsubstituted or substituted with one to three substituents selected from $R^L$. In a class of this embodiment, each $R^3$ is independently selected from the group consisting of: hydrogen, halogen, —$OR^e$ and —$C_{1-6}$alkyl.

In another embodiment of the present invention, each $R^3$ is independently selected from the group consisting of: hydrogen, halogen and —$C_{1-6}$alkyl, wherein each alkyl is unsubstituted or substituted with one to three substituents selected from $R^L$. In a class of this embodiment, each $R^3$ is independently selected from the group consisting of: hydrogen, halogen and —$C_{1-6}$alkyl. In another embodiment of the present invention, each $R^3$ is independently selected from the group consisting of: hydrogen and —$C_{1-6}$alkyl, wherein each alkyl is unsubstituted or substituted with one to three substituents selected from $R^L$. In a class of this embodiment, each $R^3$ is independently selected from the group consisting of: hydrogen and —$C_{1-6}$alkyl. In another embodiment of the present invention, each $R^3$ is —$C_{1-6}$alkyl, wherein each alkyl is unsubstituted or substituted with one to three substituents selected from $R^L$. In a class of this embodiment, each $R^3$ is —$C_{1-6}$alkyl. In another embodiment of the present invention, each $R^3$ is hydrogen.

In another embodiment of the present invention, each $R^4$ is independently selected from the group consisting of: hydrogen, halogen, —$OR^e$, —$C_{1-6}$alkyl, —$C_{2-6}$alkenyl and —$C_{2-6}$alkynyl, wherein each alkyl, alkenyl and alkynyl is unsubstituted or substituted with one to three substituents selected from $R^L$. In a class of this embodiment, each $R^4$ is independently selected from the group consisting of: hydrogen, halogen, —$OR^e$, —$C_{1-6}$alkyl, —$C_{2-6}$alkenyl and —$C_{2-6}$alkynyl.

In another embodiment of the present invention, each $R^4$ is independently selected from the group consisting of: hydrogen, halogen, —$OR^e$ and —$C_{1-6}$alkyl, wherein each alkyl is unsubstituted or substituted with one to three substituents selected from $R^L$. In a class of this embodiment, each $R^4$ is independently selected from the group consisting of: hydrogen, halogen, —$OR^e$ and —$C_{1-6}$alkyl. In another embodiment of the present invention, each $R^4$ is independently selected from the group consisting of: hydrogen, halogen and —$C_{1-6}$alkyl, wherein each alkyl is unsubstituted or substituted with one to three substituents selected from $R^L$. In a class of this embodiment, each $R^4$ is independently selected from the group consisting of: hydrogen, halogen and —$C_{1-6}$alkyl.

In another embodiment of the present invention, each $R^4$ is independently selected from the group consisting of: hydrogen and —$C_{1-6}$alkyl, wherein each alkyl is unsubstituted or substituted with one to three substituents selected from $R^L$. In a class of this embodiment, each $R^4$ is independently selected from the group consisting of: hydrogen and —$C_{1-6}$alkyl. In another embodiment of the present invention, each $R^4$ is —$C_{1-6}$alkyl, wherein each alkyl is unsubstituted or substituted with one to three substituents selected from $R^L$. In a class of this embodiment, each $R^4$ is —$C_{1-6}$alkyl. In another embodiment of the present invention, each $R^4$ is hydrogen.

In another embodiment of the present invention, $R^5$ is selected from the group consisting of: hydrogen, and halogen. In a class of this embodiment, $R^5$ is selected from the group consisting of: hydrogen and F. In another embodiment of the present invention, $R^5$ is halogen. In a class of this embodiment, $R^5$ is F. In another embodiment of the present invention, $R^5$ is hydrogen.

In another embodiment of the present invention, $R^6$ is selected from the group consisting of: hydrogen, —$C_{1-3}$alkyl, and halogen. In another embodiment of the present invention, $R^6$ is selected from the group consisting of: hydrogen, and halogen. In a class of this embodiment, $R^6$ is selected from the group consisting of: hydrogen and F. In another embodiment of the present invention, $R^6$ is halogen. In a class of this embodiment, $R^6$ is F. In another embodiment of the present invention, $R^6$ is hydrogen.

In another embodiment of the present invention, $R^7$ is selected from the group consisting of: hydrogen, and —$C_{1-10}$alkyl, wherein —$C_{1-10}$alkyl is unsubstituted or substituted with one to five fluorines. In a class of this embodiment, $R^7$ is selected from the group consisting of: hydrogen and —$C_{1-10}$alkyl. In another embodiment of the present invention, $R^7$ is —$C_{1-10}$alkyl, wherein —$C_{1-10}$alkyl is unsubstituted or substituted with one to five fluorines. In a class of this embodiment, $R^7$ is —$C_{1-10}$alkyl. In another embodiment of the present invention, $R^7$ is hydrogen.

In another embodiment of the present invention, each $R^8$ is selected from the group consisting of: hydrogen, and —$C_{1-10}$alkyl, wherein —$C_{1-10}$alkyl is unsubstituted or substituted with one to five fluorines. In a class of this embodiment, each $R^8$ is selected from the group consisting of: hydrogen and —$C_{1-10}$alkyl.

In another embodiment of the present invention, each $R^8$ is —$C_{1-10}$alkyl, wherein —$C_{1-10}$alkyl is unsubstituted or substituted with one to five fluorines. In a class of this embodiment, each $R^8$ is —$C_{1-10}$alkyl. In another embodiment of the present invention, each $R^8$ is hydrogen.

In another embodiment of the present invention, each $R^9$ is —$C_{1-6}$alkyl, wherein —$C_{1-10}$alkyl is unsubstituted or substituted with one to five fluorines. In a class of this embodiment, each $R^9$ is —$C_{1-6}$alkyl. In a class of this embodiment, each $R^9$ is $CH_3$. In another embodiment of the present invention, $R^9$ is $CH_3$ or hydrogen. In another embodiment of the present invention, each $R^9$ is hydrogen.

In another embodiment of the present invention, each $R^a$ is independently selected from the group consisting of: —$C_{1-6}$alkyl, —O—$C_{1-6}$alkyl, halogen, oxo, —$OR^e$, —$CO_2R^e$, —$(CH_2)_p$—$C_{3-6}$cycloalkyl, —$(CH_2)_p$—$C_{2-5}$cycloheteroalkyl, —$(CH_2)_p$-aryl and —$(CH_2)_p$-heteroaryl, wherein $R^a$ is unsubstituted or substituted with one to three substituents selected from $R^m$. In a class of this embodiment, each $R^a$ is independently selected from the group consisting of: —$C_{1-6}$alkyl, —O—$C_{1-6}$alkyl, halogen, oxo, —$OR^e$, —$CO_2R^e$, —$C_{3-6}$cycloalkyl, —$C_{2-5}$cycloheteroalkyl, aryl, and heteroaryl, wherein $R^a$ is unsubstituted or substituted with one to three substituents selected from $R^m$.

In another embodiment of the present invention, each $R^a$ is independently selected from the group consisting of: —$C_{1-6}$alkyl, —O—$C_{1-6}$alkyl, halogen, oxo, —$OR^e$, —$CO_2R^e$, —$(CH_2)_p$—$C_{3-6}$cycloalkyl, —$(CH_2)_p$-aryl and —$(CH_2)_p$-heteroaryl, wherein $R^a$ is unsubstituted or substituted with one to three substituents selected from $R^m$. In a class of this embodiment of the present invention, each $R^a$ is independently selected from the group consisting of: —$C_{1-6}$alkyl, —O—$C_{1-6}$alkyl, halogen, oxo, —$OR^e$, —$CO_2R^e$, —$C_{3-6}$cycloalkyl, -aryl and -heteroaryl, wherein $R^a$ is unsubstituted or substituted with one to three substituents selected from $R^m$. In another embodiment of the present invention, each $R^a$ is independently selected from the group consisting of: —$C_{1-6}$alkyl, halogen, oxo, —$OR^e$, —$CO_2R^e$, —$(CH_2)_p$—$C_{3-6}$cycloalkyl, —$(CH_2)_p$-aryl and —$(CH_2)_p$-heteroaryl, wherein $R^a$ is unsubstituted or substituted with one to three substituents selected from $R^m$. In a class of this embodiment, each $R^a$ is independently selected from the group consisting of: —$C_{1-6}$alkyl, halogen, oxo, —$OR^e$, —$CO_2R^e$, —$C_{3-6}$cycloalkyl, aryl and heteroaryl, wherein $R^a$ is unsubstituted or substituted with one to three substituents selected from $R^m$. In another class of this embodiment, each $R^a$ is independently selected from the group consisting of:

—CH$_3$, F, Br, oxo, —OH, —CO$_2$C(CH$_3$)$_3$, cyclopropyl, phenyl and pyrazole, wherein R$^a$ is unsubstituted or substituted with one to three substituents selected from R$^m$.

In another embodiment of the present invention, each R$^a$ is independently selected from the group consisting of: —C$_{1-6}$alkyl, halogen, —(CH$_2$)$_p$-aryl, and —(CH$_2$)$_p$-heteroaryl, wherein R$^a$ is unsubstituted or substituted with one to three substituents selected from R$^m$. In a class of this embodiment, each R$^a$ is independently selected from the group consisting of: —C$_{1-6}$alkyl, halogen, aryl, and heteroaryl, wherein R$^a$ is unsubstituted or substituted with one to three substituents selected from R$^m$. In another class of this embodiment, each R$^a$ is independently selected from the group consisting of: —CH$_3$, F, Br, phenyl, and pyrazole, wherein R$^a$ is unsubstituted or substituted with one to three substituents selected from R$^m$. In another embodiment of the present invention, each R$^a$ is independently selected from the group consisting of: —C$_{1-6}$alkyl, —(CH$_2$)$_p$-aryl, and —(CH$_2$)$_p$-heteroaryl, wherein R$^a$ is unsubstituted or substituted with one to three substituents selected from R$^m$. In a class of this embodiment, each R$^a$ is independently selected from the group consisting of: —C$_{1-6}$alkyl, aryl and heteroaryl, wherein R$^a$ is unsubstituted or substituted with one to three substituents selected from R$^m$. In a class of this embodiment, each R$^a$ is independently selected from the group consisting of: —CH$_3$, phenyl, and pyrazole, wherein R$^a$ is unsubstituted or substituted with one to three substituents selected from R$^m$.

In another embodiment of the present invention, each R$^b$ is independently selected from the group consisting of: —C$_{1-10}$ alkyl, —O—C$_{1-10}$alkyl, —C$_{2-10}$ alkenyl, halogen, —OH, —OC$_{2-10}$ alkenyl, —O(CH$_2$)pOC$_{1-10}$alkyl, —N(R$^c$)S(O)$_m$R$^e$, —S(O)$_m$R$^e$, —O(CH$_2$)p-S(O)$_m$R$^e$, —S(O)$_m$NR$^c$R$^d$, —NR$^c$R$^d$, —C(O)R$^e$, —OC(O)R$^e$, —CO$_2$R$^e$, —CN, —C(O)NR$^c$R$^d$, —N(R$^c$)C(O)R$^e$, —N(R$^c$)C(O)OR$^e$, —N(R$^c$)C(O)NR$^c$R$^d$, —CF$_3$, —OCF$_3$, and —OCHF$_2$, wherein each R$^b$ is unsubstituted or substituted with one to five substituents selected from R$^k$. In another embodiment of the present invention, each R$^b$ is independently selected from the group consisting of: —C$_{1-10}$ alkyl, —O—C$_{1-10}$ alkyl, halogen, —OH, —N(R$^c$)S(O)$_m$R$^e$, —S(O)$_m$R$^e$, —O(CH$_2$)$_p$—S(O)$_m$R$^e$, —S(O)$_m$NR$^c$R$^d$, —NR$^c$R$^d$, —C(O)R$^e$, —OC(O)R$^e$, —CO$_2$R$^e$, —CN, —C(O)NR$^c$R$^d$, —N(R$^c$)C(O)R$^e$, —N(R$^c$)C(O)OR$^e$, —N(R$^c$)C(O)NR$^c$R$^d$, —CF$_3$, —OCF$_3$, and —OCHF$_2$, wherein each R$^b$ is unsubstituted or substituted with one to five substituents selected from R$^k$.

In another embodiment of the present invention, each R$^b$ is independently selected from the group consisting of: —C$_{1-10}$ alkyl, —O—C$_{1-10}$alkyl, halogen, —OH, —N(R$^c$)S(O)$_m$R$^e$, —S(O)$_m$R$^e$, —O(CH$_2$)p-S(O)$_m$R$^e$, —S(O)$_m$NR$^c$R$^d$, —NR$^c$R$^d$, —C(O)R$^e$, —OC(O)R$^e$, —CO$_2$R$^e$, —CN, —CF$_3$, —OCF$_3$, and —OCHF$_2$, wherein each R$^b$ is unsubstituted or substituted with one to five substituents selected from R$^k$. In another embodiment of the present invention, each R$^b$ is independently selected from the group consisting of: j—C$_{1-10}$alkyl, —O—C$_{1-10}$alkyl, halogen, —OH, —S(O)$_m$R$^e$, —O(CH$_2$)p-S(O)$_m$R$^e$, —CN, —CF$_3$, —OCF$_3$, and —OCHF$_2$, wherein each R$^b$ is unsubstituted or substituted with one to five substituents selected from R$^k$.

In another embodiment of the present invention, each R$^b$ is independently selected from the group consisting of: —C$_{1-10}$ alkyl, —O—C$_{1-10}$alkyl, halogen, —OH, —S(O)$_m$R$^e$, —O(CH$_2$)p-S(O)$_m$R$^e$, and —CF$_3$, wherein each R$^b$ is unsubstituted or substituted with one to five substituents selected from R$^k$. In a class of this embodiment, each R$^b$ is independently selected from the group consisting of: —CH$_3$, —OCH$_3$, —O(CH$_2$)$_2$C(CH$_3$)$_2$CH$_3$, —O(CH$_2$)$_2$C(CH$_3$)$_3$, —O(CH$_2$)$_2$C(CH$_3$)$_2$OH, —O—CH$_2$(CH$_3$)C(CH$_3$)$_2$OH, F, Cl, —OH, —SO$_2$CH$_3$, —O(CH$_2$)$_3$—SO$_2$CH$_3$, and —CF$_3$.

In another embodiment of the present invention, each R$^b$ is independently selected from the group consisting of: —O—C$_{1-10}$alkyl and —CF$_3$, wherein each R$^b$ is unsubstituted or substituted with one to five substituents selected from R$^k$. In a class of this embodiment, each R$^b$ is independently selected from the group consisting of: —OCH$_3$ and —CF$_3$.

In another embodiment of the present invention, each R$^c$ and R$^d$ is independently selected from the group consisting of: hydrogen, —C$_{1-10}$alkyl, —C$_{2-10}$alkenyl, —C$_{3-6}$cycloalkyl, C$_{3-6}$ cycloalkyl-C$_{1-10}$alkyl-, —C$_{2-6}$cycloheteroalkyl, C$_{2-6}$cycloheteroalkyl-C$_{1-10}$alkyl-, aryl, heteroaryl, aryl-C$_{1-10}$alkyl- and heteroaryl-C$_{1-10}$alkyl-, wherein each R$^c$ and R$^d$ is unsubstituted or substituted with one to three substituents independently selected from R$^f$.

In another embodiment of the present invention, each R$^c$ and R$^d$ is independently selected from the group consisting of: hydrogen, —C$_{1-10}$alkyl, —C$_{2-10}$alkenyl, —C$_{3-6}$cycloalkyl, —C$_{2-6}$cycloheteroalkyl, wherein each R$^c$ and R$^d$ is unsubstituted or substituted with one to three substituents independently selected from R$^f$.

In another embodiment of the present invention, each R$^c$ and R$^d$ is independently selected from the group consisting of: hydrogen, —C$_{1-10}$alkyl, and —C$_{2-10}$alkenyl, wherein each R$^c$ and R$^d$ is unsubstituted or substituted with one to three substituents independently selected from R$^f$. In another embodiment of the present invention, each R$^c$ and R$^d$ is independently selected from the group consisting of: hydrogen, and —C$_{1-10}$alkyl, wherein each R$^c$ and R$^d$ is unsubstituted or substituted with one to three substituents independently selected from R$^f$. In another embodiment of the present invention, each R$^c$ and R$^d$ is hydrogen.

In another embodiment of the present invention, each R$^c$ and R$^d$ is independently selected from the group consisting of: —C$_{1-10}$alkyl, wherein each R$^c$ and R$^d$ is unsubstituted or substituted with one to three substituents independently selected from R$^f$. In another embodiment of the present invention, each R$^c$ and R$^d$ is independently selected from the group consisting of: —C$_{1-10}$alkyl.

In another embodiment of the present invention, each R$^c$ is independently selected from the group consisting of: hydrogen, —C$_{1-10}$alkyl, —C$_{2-10}$alkenyl, —C$_{3-6}$cycloalkyl, C$_{3-6}$ cycloalkyl-C$_{1-10}$alkyl-, —C$_{2-6}$cycloheteroalkyl, C$_{2-6}$cycloheteroalkyl-C$_{1-10}$alkyl-, aryl, heteroaryl, aryl-C$_{1-10}$alkyl- and heteroaryl-C$_{1-10}$alkyl-, wherein each R$^c$ is unsubstituted or substituted with one to three substituents independently selected from R$^f$.

In another embodiment of the present invention, each R$^c$ is independently selected from the group consisting of: hydrogen, —C$_{1-10}$alkyl, —C$_{2-10}$alkenyl, —C$_{3-6}$cycloalkyl, —C$_{2-6}$cycloheteroalkyl, wherein each R$^c$ is unsubstituted or substituted with one to three substituents independently selected from R$^f$. In another embodiment of the present invention, each R$^c$ is independently selected from the group consisting of: hydrogen, —C$_{1-10}$alkyl, and —C$_{2-10}$alkenyl, wherein each R$^c$ is unsubstituted or substituted with one to three substituents independently selected from R$^f$.

In another embodiment of the present invention, each R$^c$ is independently selected from the group consisting of: hydrogen, and —C$_{1-10}$alkyl, wherein each R$^c$ is unsubstituted or substituted with one to three substituents independently selected from R$^f$.

In another embodiment of the present invention, each R$^c$ is hydrogen.

In another embodiment of the present invention, each $R^c$ is independently selected from the group consisting of: —$C_{1-10}$alkyl, wherein each $R^c$ is unsubstituted or substituted with one to three substituents independently selected from $R^f$. In another embodiment of the present invention, each $R^c$ is independently selected from the group consisting of: —$C_{1-10}$alkyl.

In another embodiment of the present invention, each $R^d$ is independently selected from the group consisting of: hydrogen, —$C_{1-10}$alkyl, —$C_{2-10}$alkenyl, —$C_{3-6}$cycloalkyl, $C_{3-6}$ cycloalkyl-$C_{1-10}$alkyl-, —$C_{2-6}$cycloheteroalkyl, $C_{2-6}$cycloheteroalkyl-$C_{1-10}$alkyl-, aryl, heteroaryl, aryl-$C_{1-10}$alkyl and eteroaryl-$C_{1-10}$alkyl-, wherein each $R^d$ is unsubstituted or substituted with one to three substituents independently selected from $R^f$.

In another embodiment of the present invention, each $R^d$ is independently selected from the group consisting of: hydrogen, —$C_{1-10}$alkyl, —$C_{2-10}$alkenyl, —$C_{3-6}$cycloalkyl, —$C_{2-6}$cycloheteroalkyl, wherein each $R^d$ is unsubstituted or substituted with one to three substituents independently selected from $R^f$. In another embodiment of the present invention, each $R^d$ is independently selected from the group consisting of: hydrogen, —$C_{1-10}$alkyl, and —$C_{2-10}$alkenyl, wherein each $R^d$ is unsubstituted or substituted with one to three substituents independently selected from $R^f$. In another embodiment of the present invention, each $R^d$ is independently selected from the group consisting of: hydrogen, and —$C_{1-10}$alkyl, wherein each $R^d$ is unsubstituted or substituted with one to three substituents independently selected from $R^f$.

In another embodiment of the present invention, each $R^d$ is hydrogen.

In another embodiment of the present invention, each $R^d$ is independently selected from the group consisting of: —$C_{1-10}$alkyl, wherein each $R^d$ is unsubstituted or substituted with one to three substituents independently selected from $R^f$. In another embodiment of the present invention, each $R^d$ is independently selected from the group consisting of: —$C_{1-10}$alkyl.

In another embodiment of the present invention, each $R^e$ is independently selected from the group consisting of: hydrogen, —$C_{1-10}$alkyl, —$C_{2-10}$ alkenyl, —$C_{3-6}$ cycloalkyl, —$C_{2-5}$cycloheteroalkyl, aryl, and heteroaryl, wherein each $R^e$ is unsubstituted or substituted with one to three substituents selected from $R^h$.

In another embodiment of the present invention, each $R^e$ is independently selected from the group consisting of: hydrogen, —$C_{1-10}$alkyl, and —$C_{2-10}$ alkenyl, wherein each $R^e$ is unsubstituted or substituted with one to three substituents selected from $R^h$. In another embodiment of the present invention, each $R^e$ is independently selected from the group consisting of: hydrogen, and —$C_{1-10}$alkyl, wherein each $R^e$ is unsubstituted or substituted with one to three substituents selected from $R^h$. In a class of this embodiment, each $R^e$ is independently selected from the group consisting of: hydrogen, —$CH_3$, and —$C(CH_3)_3$.

In another embodiment of the present invention, each $R^e$ is —$C_{1-10}$alkyl, wherein each $R^e$ is unsubstituted or substituted with one to three substituents selected from $R^h$. In a class of this embodiment, each $R^e$ is —$C_{1-10}$alkyl. In a subclass of this class, each $R^e$ is independently selected from the group consisting of: —$CH_3$, and —$C(CH_3)_3$.

In another embodiment of the present invention, each $R^e$ is hydrogen.

In another embodiment of the present invention, each $R^f$ is selected from the group consisting of: halogen, —$C_{1-10}$ alkyl, —OH, —$OC_{1-6}$alkyl, —CN, —$CF_3$, —$OCHF_2$, and —$OCF_3$, wherein each alkyl is unsubstituted or substituted with one to three substituents independently selected from: —OH, halogen, cyano, and —$S(O)_2CH_3$.

In another embodiment of the present invention, each $R^f$ is selected from the group consisting of: halogen, —$C_{1-10}$ lkyl, —CN, —$CF_3$, —$OCHF_2$, and —$OCF_3$, wherein each alkyl is unsubstituted or substituted with one to three substituents independently selected from: —OH, halogen, cyano, and —$S(O)_2CH_3$. In another embodiment of the present invention, each $R^f$ is selected from the group consisting of: halogen, —$C_{1-10}$alkyl, and —$CF_3$, wherein each alkyl is unsubstituted or substituted with one to three substituents independently selected from: —OH, halogen, cyano, and —$S(O)_2CH_3$.

In another embodiment of the present invention, each $R^f$ is selected from the group consisting of: halogen, and —$C_{1-10}$alkyl, wherein each alkyl is unsubstituted or substituted with one to three substituents independently selected from: —OH, halogen, cyano, and —$S(O)_2CH_3$. In a class of this embodiment, each $R^f$ is selected from the group consisting of: halogen, and —$C_{1-10}$alkyl.

In another embodiment of the present invention, each $R^f$ is selected from the group consisting of: halogen. In another embodiment of the present invention, each $R^f$ is —$C_{1-10}$alkyl, wherein each alkyl is unsubstituted or substituted with one to three substituents independently selected from: —OH, halogen, cyano, and —$S(O)_2CH_3$. In a class of this embodiment, each $R^f$ is —$C_{1-10}$alkyl.

In another embodiment of the present invention, each $R^g$ is selected from the group consisting of: hydrogen, and —$C_{1-10}$alkyl, wherein —$C_{1-10}$alkyl is unsubstituted or substituted with one to five fluorines.

In another embodiment of the present invention, each $R^g$ is selected from: —$C_{1-10}$alkyl, wherein —$C_{1-10}$alkyl is unsubstituted or substituted with one to five fluorines. In a class of this embodiment, each $R^g$ is selected from: —$C_{1-10}$alkyl. In another embodiment of the present invention, each $R^g$ is hydrogen.

In another embodiment of the present invention, each $R^h$ is selected from the group consisting of: halogen, —$C_{1-10}$ lkyl, —OH, —O—$C_{1-4}$alkyl, —CN, —$CF_3$, —$OCHF_2$, and —$OCF_3$, wherein each $C_{1-10}$ alkyl is unsubstituted or substituted with one to three substituents independently selected from: —OH, halogen, cyano, and —$S(O)_2CH_3$.

In another embodiment of the present invention, each $R^h$ is selected from the group consisting of: halogen, —$C_{1-10}$ lkyl, —OH, —CN, —$CF_3$, —$OCHF_2$, and —$OCF_3$, wherein each $C_{1-10}$ alkyl is unsubstituted or substituted with one to three substituents independently selected from: —OH, halogen, cyano, and —$S(O)_2CH_3$. In another embodiment of the present invention, each $R^h$ is selected from the group consisting of: halogen, and —$C_{1-10}$alkyl, wherein each $C_{1-10}$ alkyl is unsubstituted or substituted with one to three substituents independently selected from: —OH, halogen, cyano, and —$S(O)_2CH_3$. In a class of this embodiment, each $R^h$ is selected from the group consisting of: halogen, and —$C_{1-10}$alkyl.

In another embodiment of the present invention, each $R^h$ is selected from the group consisting of: —$C_{1-10}$alkyl, wherein each $C_{1-10}$ alkyl is unsubstituted or substituted with one to three substituents independently selected from: —OH, halogen, cyano, and —$S(O)_2CH_3$. In a class of this embodiment, each $R^h$ is selected from the group consisting of: —$C_{1-10}$alkyl. In another embodiment of the present invention, each $R^h$ is selected from the group consisting of halogen.

In another embodiment of the present invention, $R^i$ is selected from the group consisting of: —$C_{1-6}$alkyl, halogen, —$OR^e$, —$NR^cR^d$, —$C(O)R^e$, —$OC(O)R^e$, —$CO_2R^e$, —CN, —$CF_3$, —$OCF_3$, and —$OCHF_2$. In another embodiment of the present invention, $R^i$ is selected from the group consisting of: —$C_{1-6}$alkyl, halogen, —CN, —$CF_3$, —$OCF_3$, and —$OCHF_2$. In another embodiment of the present invention, $R^i$ is selected from the group consisting of: —$C_{1-6}$alkyl, halogen, and —$CF_3$. In a class of this embodiment, $R^i$ is selected from the group consisting of: halogen. In another class of this embodiment, $R^i$ is selected from the group consisting of: —$C_{1-6}$alkyl. In another class of this embodiment, $R^i$ is —$CF_3$.

In another embodiment of the present invention, $R^j$ is selected from the group consisting of: —$C_{1-6}$alkyl, halogen, —$OR^e$, —$NR^cR^d$, —$C(O)R^e$, —$OC(O)R^e$, —$CO_2R^e$, —CN, —$CF_3$, —$OCF_3$, and —$OCHF_2$. In another embodiment of the present invention, $R^j$ is selected from the group consisting of: —$C_{1-6}$alkyl, halogen, —CN, —$CF_3$, —$OCF_3$, and —$OCHF_2$. In another embodiment of the present invention, $R^j$ is selected from the group consisting of: —$C_{1-6}$alkyl, halogen, and —$CF_3$. In a class of this embodiment, $R^j$ is selected from the group consisting of: halogen. In another class of this embodiment, $R^j$ is selected from the group consisting of: —$C_{1-6}$alkyl. In another class of this embodiment, $R^j$ is —$CF_3$.

In another embodiment of the present invention, each $R^k$ is independently selected from the group consisting of: halogen, —$C_{1-6}$alkyl, —OH, oxo, —$OC_{1-6}$alkyl, —$SO_2$—$C_{1-6}$ alkyl, —$C_{1-6}$alkyl-$SO_2C_{1-6}$alkyl, —CN, —$CF_3$, —$OCHF_2$, —$OCF_3$, —$NH_2$, —$NHSO_2C_{1-6}$alkyl, and —$NHC(O)C_{1-6}$alkyl, wherein each alkyl is unsubstituted or substituted with one to three substituents independently selected from: —OH, —$OC_{1-6}$alkyl, halogen, cyano, and —$S(O)_2C_{1-6}$alkyl.

In another embodiment of the present invention, each $R^k$ is independently selected from the group consisting of: halogen, —$C_{1-6}$alkyl, —OH, —$OC_{1-6}$alkyl, —CN, —$CF_3$, —$OCHF_2$, —$OCF_3$, and —$NH_2$, wherein each alkyl is unsubstituted or substituted with one to three substituents independently selected from: —OH, —$OC_{1-6}$alkyl, halogen, cyano, and —$S(O)_2C_{1-6}$alkyl.

In another embodiment of the present invention, each $R^k$ is independently selected from the group consisting of: halogen, —$C_{1-6}$alkyl, —$OC_{1-6}$alkyl, and —OH, wherein each alkyl is unsubstituted or substituted with one to three substituents independently selected from: —OH, —$OC_{1-6}$alkyl, halogen, cyano, and —$S(O)_2C_{1-6}$alkyl. In a class of this embodiment, each $R^k$ is independently selected from the group consisting of: halogen, —$C_{1-6}$alkyl, —$OC_{1-6}$alkyl, and —OH, wherein each alkyl is unsubstituted or substituted with one to three substituents independently selected from: —OH, —$OC_{1-6}$alkyl, halogen, and cyano. In another class of this embodiment, each $R^k$ is independently selected from the group consisting of: halogen, —$C_{1-6}$alkyl, —$OC_{1-6}$alkyl, and —OH. In another class of this embodiment, each $R^k$ is independently selected from the group consisting of: F, —$CH_3$, —$OCH_3$, and —OH.

In another embodiment of the present invention, each $R^k$ is independently selected from the group consisting of: halogen, —$C_{1-6}$alkyl, and —OH, wherein each alkyl is unsubstituted or substituted with one to three substituents independently selected from: —OH, —$OC_{1-6}$alkyl, halogen, cyano, and —$S(O)_2C_{1-6}$alkyl. In a class of this embodiment, each $R^k$ is independently selected from the group consisting of: F, —$CH_3$, and —OH.

In another embodiment of the present invention, each $R^k$ is independently selected from the group consisting of: halogen and —$C_{1-6}$alkyl, wherein each alkyl is unsubstituted or substituted with one to three substituents independently selected from: —OH, —$OC_{1-6}$alkyl, halogen, cyano, and —$S(O)_2C_{1-6}$alkyl. In a class of this embodiment, each $R^k$ is independently selected from the group consisting of: halogen and —$C_{1-6}$alkyl. In another class of this embodiment, each $R^k$ is independently selected from the group consisting of: F and —$CH_3$.

In another embodiment of the present invention, each $R^k$ is independently selected from the group consisting of: —$C_{1-6}$alkyl, wherein each alkyl is unsubstituted or substituted with one to three substituents independently selected from: —OH, —$OC_{1-6}$alkyl, halogen, cyano, and —$S(O)_2C_{1-6}$alkyl. In a class of this embodiment, each $R^k$ is independently selected from the group consisting of: —$C_{1-6}$alkyl. In another class of this embodiment, each $R^k$ is —$CH_3$.

In another embodiment of the present invention, each $R^k$ is independently selected from the group consisting of: halogen. In another class of this embodiment, each $R^k$ is F.

In another embodiment of the present invention, $R^L$ is selected from the group consisting of: —$C_{1-6}$alkyl, halogen, —$OR^e$, —$N(R^c)S(O)_mR^e$, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$N(R^c)C(O)R^e$, —$N(R^c)C(O)OR^e$, —$N(R^c)C(O)NR^cR^d$, —$CF_3$, —$OCF_3$, and —$OCHF_2$.

In another embodiment of the present invention, $R^L$ is selected from the group consisting of: —$C_{1-6}$alkyl, halogen, —$OR^e$, —$S(O)_mR^e$, —$S(O)_mNR^cR^d$, —$NR^cR^d$, —$CO_2R^e$, —CN, —$CF_3$, —$OCF_3$, and —$OCHF_2$. In another embodiment of the present invention, $R^L$ is selected from the group consisting of: —$C_{1-6}$alkyl, halogen, —$OR^e$, —CN, —$CF_3$, —$OCF_3$, and —$OCHF_2$.

In another embodiment of the present invention, $R^L$ is selected from the group consisting of: —$C_{1-6}$alkyl, halogen, —$OR^e$, and —$CF_3$. In another embodiment of the present invention, $R^L$ is selected from the group consisting of: —$C_{1-6}$alkyl, halogen, and —$CF_3$. In another embodiment of the present invention, $R^L$ is selected from the group consisting of: —$C_{1-6}$alkyl, and halogen. In another embodiment of the present invention, $R^L$ is selected from the group consisting of: halogen. In another embodiment of the present invention, $R^L$ is selected from the group consisting of: —$C_{1-6}$alkyl.

In another embodiment of the present invention, each $R^m$ is independently selected from the group consisting of: halogen, —$C_{1-6}$alkyl, —OH, oxo, —$OC_{1-6}$alkyl, —$SO_2$—$C_{1-6}$ alkyl, —$C_{1-6}$alkyl-$SO_2C_{1-6}$alkyl, —CN, —$CF_3$, —$OCHF_2$, —$OCF_3$, —$NH_2$, —$NHSO_2C_{1-6}$alkyl, and —$NHC(O)C_{1-6}$alkyl, wherein each alkyl is unsubstituted or substituted with one to three substituents independently selected from: —OH, —$OC_{1-6}$alkyl, halogen, cyano, and —$S(O)_2C_{1-6}$alkyl.

In another embodiment of the present invention, each $R^m$ is independently selected from the group consisting of: halogen, —$C_{1-6}$alkyl, —OH, —$OC_{1-6}$alkyl, —CN, —$CF_3$, —$OCHF_2$, —$OCF_3$, and —$NH_2$, wherein each alkyl is unsubstituted or substituted with one to three substituents independently selected from: —OH, —$OC_{1-6}$alkyl, halogen, cyano, and —$S(O)_2C_{1-6}$alkyl. In another embodiment of the present invention, each $R^m$ is independently selected from the group consisting of: halogen, —$C_{1-6}$alkyl, —$OC_{1-6}$alkyl, and —OH, wherein each alkyl is unsubstituted or substituted with one to three substituents independently selected from:

—OH, —OC$_{1-6}$alkyl, halogen, cyano, and —S(O)$_2$C$_{1-6}$ alkyl. In a class of this embodiment, each R$^m$ is independently selected from the group consisting of: halogen, —C$_{1-6}$ alkyl, —OC$_{1-6}$alkyl, and —OH, wherein each alkyl is unsubstituted or substituted with one to three substituents independently selected from: —OH, —OC$_{1-6}$alkyl, halogen, and cyano. In another class of this embodiment, each R$^m$ is independently selected from the group consisting of: halogen, —C$_{1-6}$alkyl, —OC$_{1-6}$alkyl, and —OH. In another class of this embodiment, each R$^m$ is independently selected from the group consisting of: F, —CH$_3$, —OCH$_3$, and —OH.

In another embodiment of the present invention, each R$^m$ is independently selected from the group consisting of: halogen, —C$_{1-6}$alkyl, and —OH, wherein each alkyl is unsubstituted or substituted with one to three substituents independently selected from: —OH, —OC$_{1-6}$alkyl, halogen, cyano, and —S(O)$_2$C$_{1-6}$alkyl. In a class of this embodiment, each R$^m$ is independently selected from the group consisting of: halogen, —C$_{1-6}$alkyl, and —OH. In another class of this embodiment, each R$^m$ is independently selected from the group consisting of: F, —CH$_3$, and —OH. In another embodiment of the present invention, each R$^m$ is independently selected from the group consisting of: halogen and —C$_{1-6}$alkyl, wherein each alkyl is unsubstituted or substituted with one to three substituents independently selected from: —OH, —OC$_{1-6}$alkyl, halogen, cyano, and —S(O)$_2$C$_{1-6}$ alkyl. In a class of this embodiment, each R$^m$ is independently selected from the group consisting of: halogen and —C$_{1-6}$alkyl. In another class of this embodiment, each R$^m$ is independently selected from the group consisting of: F and —CH$_3$.

In another embodiment of the present invention, each R$^m$ is independently selected from the group consisting of: —C$_{1-6}$alkyl, wherein each alkyl is unsubstituted or substituted with one to three substituents independently selected from: —OH, —OC$_{1-6}$alkyl, halogen, cyano, and —S(O)$_2$C$_{1-6}$ alkyl. In a class of this embodiment, each R$^m$ is independently selected from the group consisting of: —C$_{1-6}$ alkyl. In another class of this embodiment, each R$^m$ is —CH$_3$. In another embodiment of the present invention, each R$^m$ is independently selected from the group consisting of: halogen. In another class of this embodiment, each R$^m$ is F.

In another embodiment of the present invention, each n is independently selected from: 0, 1, 2 or 3. In a class of this embodiment, each n is independently selected from: 1, 2 or 3. In another class of this embodiment, each n is independently selected from: 0, 1 or 3. In another class of this embodiment, each n is independently selected from: 0, 2 or 3. In another class of this embodiment, each n is independently selected from: 0 or 3. In another class of this embodiment, n is 0, 1 or 2. In a class of this embodiment, n is 0 or 1. In another class of this embodiment, n is 1 or 2. In another class of this embodiment, n is 0 or 2. In another class of this embodiment, n is 0. In another class of this embodiment, n is 1. In another class of this embodiment, n is 2. In another class of this embodiment, n is 3.

In another embodiment of the present invention, m is 0, 1 or 2. In a class of this embodiment, m is 0 or 1. In another class of this embodiment, m is 0 or 2. In another class of this embodiment, m is 1 or 2. In another class of this embodiment, m is 0. In another class of this embodiment, m is 1. In another class of this embodiment, m is 2.

In another embodiment of the present invention, p is 0, 1, 2, 3, 4, 5, 6, 7, 8, 9 or 10. In another embodiment of the present invention, p is 0, 1, 2, 3, 4, 5, 6, 7 or 8. In another embodiment of the present invention, p is 0, 1, 2, 3, 4, 5 or 6. In another embodiment of the present invention, p is 0, 1, 2, 3 or 4. a class of this embodiment, p is 0, 1, 2 or 3. In a class of this embodiment, p is 0, 1 or 2. In another embodiment of the present invention, p is 1, 2, 3, 4, 5, 6, 7, 8, 9 or 10. In another embodiment of the present invention, p is 1, 2, 3, 4, 5, 6, 7 or 8. In another embodiment of the present invention, p is 1, 2, 3, 4, 5 or 6. In another embodiment of the present invention, p is 1, 2, 3 or 4. In a class of this embodiment, p is 1, 2 or 3. In a class of this embodiment, p is 1 or 2. In another class of this embodiment, p is 0 or 1. In another class of this embodiment, p is 0 or 2. In another class of this embodiment, p is 0. In another class of this embodiment, p is 1. In another class of this embodiment, p is 2. In another class of this embodiment, p is 3. In another class of this embodiment, p is 4. In another class of this embodiment, p is 5. In another class of this embodiment, p is 6. In another class of this embodiment, p is 7. In another class of this embodiment, p is 8. In another class of this embodiment, p is 9. In another class of this embodiment, p is 10.

In another embodiment of the present invention, each q is independently selected from: 1, 2 or 3. In another class of this embodiment, each q is independently selected from: 1 or 3. In another class of this embodiment, each q is independently selected from: 2 or 3. In another class of this embodiment, q is 1 or 2. In another class of this embodiment, q is 1. In another class of this embodiment, q is 2. In another class of this embodiment, q is 3.

In another embodiment of the present invention, n is 1; and q is 0

In another embodiment of the present invention, the invention relates to compounds of structural formula Ia:

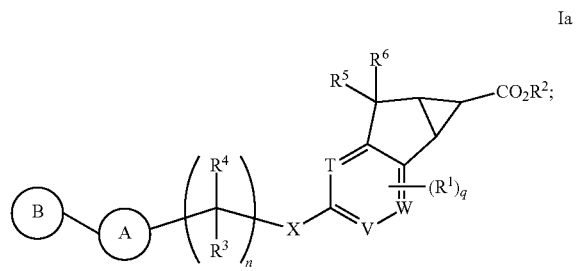

or a pharmaceutically acceptable salt thereof.

In another embodiment of the present invention, the invention relates to compounds of structural formula Ib:

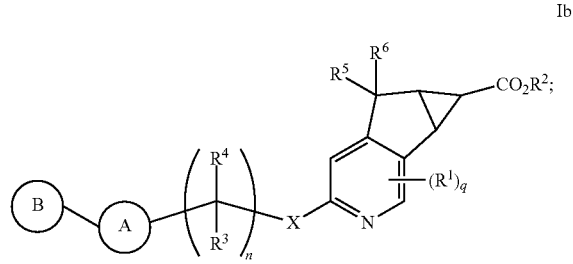

or a pharmaceutically acceptable salt thereof.

In another embodiment of the present invention, the invention relates to compounds of structural formula Ic:

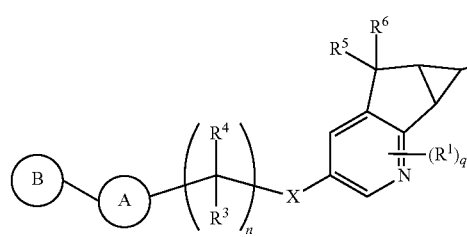

Ib

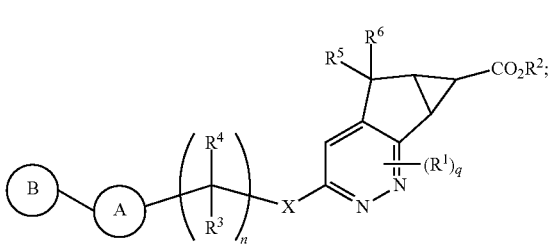

Ig or a pharmaceutically acceptable salt thereof.

In another embodiment of the present invention, the invention relates to compounds of structural formula Id.

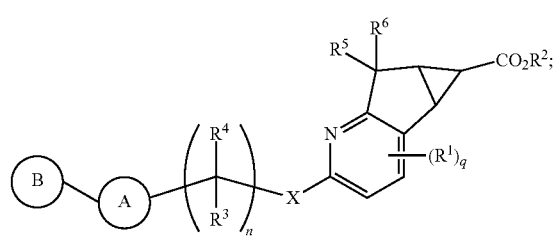

Id or a pharmaceutically acceptable salt thereof.

In another embodiment of the present invention, the invention relates to compounds of structural formula Ie:

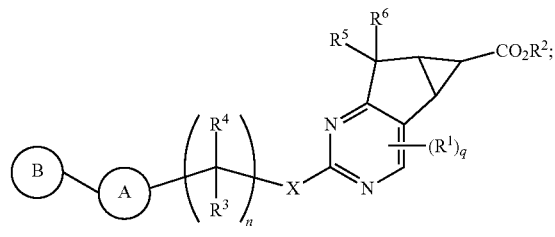

Ie or a pharmaceutically acceptable salt thereof.

In another embodiment of the present invention, the invention relates to compounds of structural formula If:

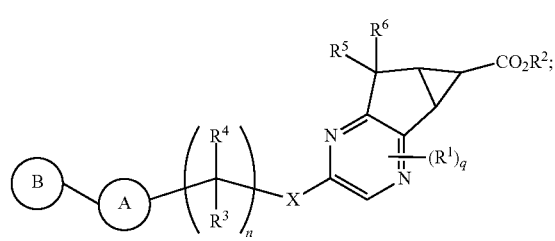

If or a pharmaceutically acceptable salt thereof.

In another embodiment of the present invention, the invention relates to compounds of structural formula Ig:

or a pharmaceutically acceptable salt thereof.

In another embodiment of the present invention, the compounds of formula I have the absolute stereochemistry at the two stereogenic carbon centers as indicated in the compound of structural formula Ih:

Ih

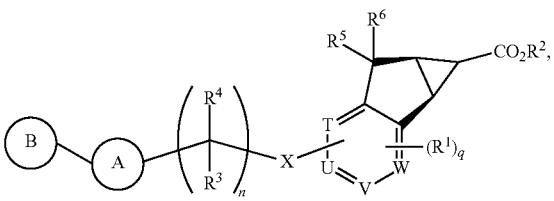

and pharmaceutically acceptable salts thereof.

In another embodiment of the present invention, the compounds of formula I have the absolute stereochemistry at the two stereogenic carbon centers as indicated in the compound of structural formula Ii:

Ii and pharmaceutically acceptable salts thereof.

References to the compound of structural formula I include or apply to the compounds of structural formulas Ia, Ib, Ic, Id, Ie, If, Ig, Ih, Ii, and II, and pharmaceutically acceptable salts, hydrates and solvates thereof.

Another embodiment of the present invention relates to compounds of structural formula Ia

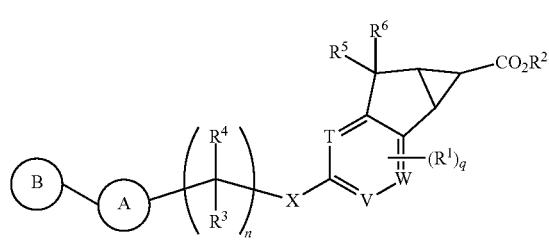

Ia wherein:
X is oxygen;
T is selected from the group consisting of: CH and N;
V is selected from the group consisting of: CH and N;
W is selected from the group consisting of: CH and N, provided that one of T, U, V and W is N;
A is selected from the group consisting of:

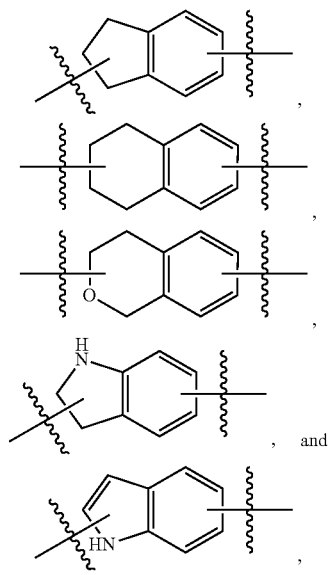

wherein A is unsubstituted or substituted with one to six substituents selected from $R^a$, and wherein two $R^a$ substituents together with the carbon atom to which they are attached may form a 3-6 membered cycloalkyl ring or a 3-6 membered cycloheteroalkyl ring containing 0 to 3 heteroatoms independently selected from oxygen, sulfur, and $NR^8$, and wherein each 3-6 membered cycloalkyl ring and each 3-6 membered cycloheteroalkyl ring is unsubstituted or substituted with 1 to 4 substituents selected from: $-C_{1-6}$alkyl, $-O-C_{1-6}$alkyl, halogen and OH;
B is selected from the group consisting of:
(1) aryl, and
(2) heteroaryl,
wherein each aryl and heteroaryl is unsubstituted or substituted with one to six substituents selected from $R^b$;
$R^1$ and $R^2$ are hydrogen;
$R^3$ and $R^4$ independently selected from the group consisting of:
(1) hydrogen,
(2) halogen, and
(3) $-C_{1-6}$alkyl, wherein each alkyl is unsubstituted or substituted with one to three substituents selected from $R^L$;
$R^5$ and $R^6$ are selected from the group consisting of:
(1) hydrogen, and
(2) halogen; and
n is 1;
or a pharmaceutically acceptable salt thereof.

Another embodiment of the present invention relates to compounds of structural formula Ia

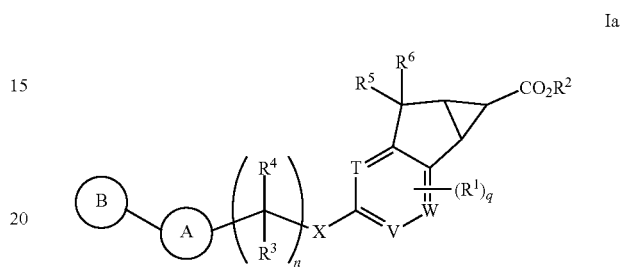

Ia wherein:
X is oxygen;
T is CH;
V is N;
W is CH;
A is selected from the group consisting of:

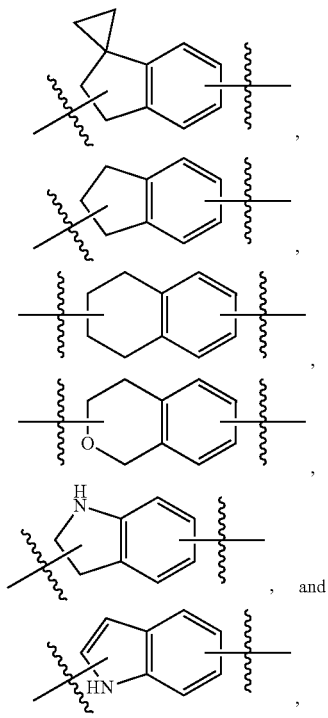

wherein A is unsubstituted or substituted with one to six substituents selected from $R^a$;
B is selected from the group consisting of:
(1) phenyl,
(2) pyridine, and
(3) benzimidazole, wherein each phenyl, pyridine and benzimidazole is unsubstituted or substituted with one to six substituents selected from $R^b$;

$R^1$, $R^2$, $R^3$, $R^4$, $R^5$ and $R^6$ are hydrogen; and n is 1;

or a pharmaceutically acceptable salt thereof.

Illustrative, but non-limiting, examples of the compounds of the present invention that are useful as agonists of G-protein-coupled receptor 40 (GPR40) are the following compounds:

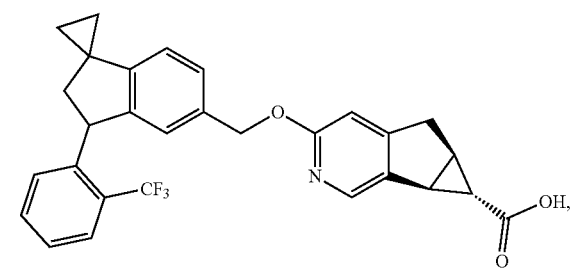

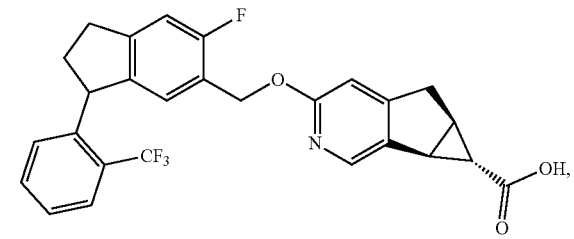

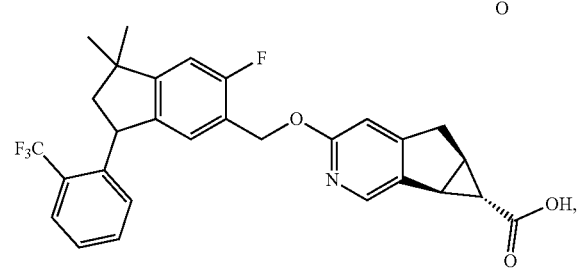

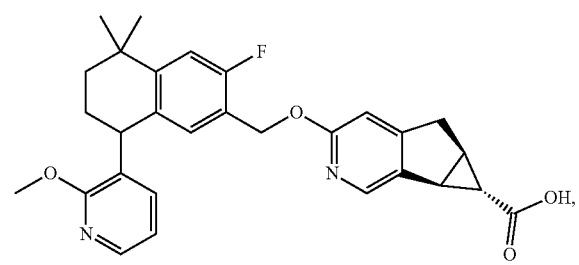

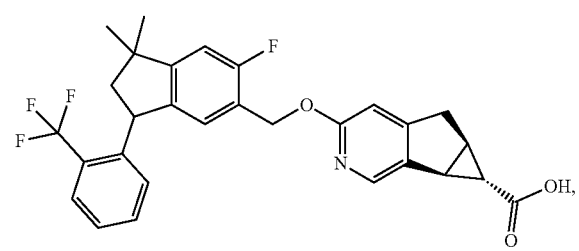

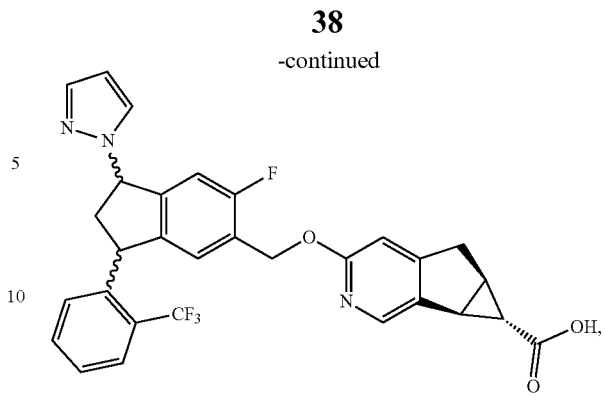

and pharmaceutically acceptable salts thereof.

Although the specific stereochemistries described above are preferred, other stereoisomers, including diastereoisomers, enantiomers, epimers, and mixtures of these may also have utility in treating GPR40 mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

Definitions "Ac" is acetyl, which is CH$_3$C(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like.

"Bicyclic aryl ring" means a bicyclic aromatic ring system containing 5-14 carbon atoms, wherein at least one of the rings is an aryl ring and in which the aryl ring is fused to a C$_{3-6}$cycloalkyl ring, or a C$_{2-6}$ cycloheteroalkyl ring containing at least one ring heteroatom selected from N, NH, S, SO, SO$_2$, and O. Examples of bicyclic aryl rings include but are not limited to, indane, and 1,2,3,4-tetrahydronaphthalene. In one embodiment of the present invention, the bicyclic aryl ring is indane.

"Bicyclic heteroaryl ring" means a bicyclic aromatic ring system containing 5-14 carbon atoms, wherein at least one of the rings is a heteroaryl ring and in which the heteroaryl ring is fused to a C$_{3-6}$cycloalkyl ring, or a C$_{2-6}$cycloheteroalkyl ring containing at least one ring heteroatom selected from N, NH, S, SO, SO$_2$, and O. Examples of bicyclic heteroaryl rings include, but are not limited to, chromane, 1,2,3,4-tetrahydroisoquinoline, 2,3-dihydrobenzofuran, indoline and indole.

"Cycloalkyl" means a saturated monocyclic, bicyclic or bridged carbocyclic ring, having a specified number of carbon atoms. Examples of cycloalkyl include cyclopropyl, cyclopentyl, cyclohexyl, cycloheptyl, and the like. In one embodiment of the present invention, cycloalkyl is selected from: cyclopropane, cyclobutane and cyclohexane. In another embodiment, cycloalkyl is cyclopropyl. In one embodiment of the present invention, a 3-6 membered cycloalkyl ring is selected from: cyclopropyl, and cyclobutyl.

"Cycloalkenyl" means a nonaromatic monocyclic or bicyclic carbocyclic ring containing at least one double bond. Examples of cycloalkenyl include cyclopropenyl, cyclobutenyl, cyclopentenyl, cyclohexenyl, cycloheptenyl, cyclooxtenyl and the like.

"Cycloheteroalkyl" means a saturated or partly unsaturated non-aromatic monocyclic, bicyclic or bridged carbocyclic ring or ring system containing at least one ring heteroatom selected from N, NH, S (including SO and SO$_2$) and O. The cycloheteroalkyl ring may be substituted on the ring carbons and/or the ring nitrogen(s). Examples of cycloheteroalkyl include tetrahydrofuran, pyrrolidine, tetrahydrothiophene, azetidine, piperazine, piperidine, morpholine, oxetane and tetrahydropyran, hexose, pentose, isosorbide and isomannide, dianhydromannitol, 1,4:3,6-dianhydromannitol, 1,4:3,6-dianhydro[D]mannitol, hexahydrofuro[3,2-b]furan, and 2,3,3a,5,6,6a-hexahydrofuro[3,2-b]furan. In one embodiment of the present invention, a 3-6 membered cycloheteroalkyl ring is selected from: oxetane, dioxane and 1,3 dioxane.

"Cycloheteroalkenyl" means a nonaromatic monocyclic, bicyclic or bridged carbocyclic ring or ring system containing at least one double bond and containing at least one heteroatom selected from N, NH, S and O.

"Aryl" means a monocyclic, bicyclic or tricyclic carbocyclic aromatic ring or ring system containing 5-14 carbon atoms, wherein at least one of the rings is aromatic. Examples of aryl include phenyl and naphthyl. In one embodiment of the present invention, aryl is phenyl. "Aryl" includes bicyclic aryl ring.

"Heteroaryl" means a monocyclic, bicyclic or tricyclic ring or ring system containing 1-14 carbon atoms and containing at least one ring heteroatom selected from N, NH, S (including SO and SO$_2$) and O, wherein at least one of the heteroatom containing rings is aromatic. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b)pyridyl, quinolyl, indolyl, isoquinolyl, quinazolinyl, dibenzofuranyl, and the like. In one embodiment of the present invention, heteroaryl is selected from: pyridine and benzimidazole. In another embodiment of the present invention, heteroaryl is pyridine. In another embodiment of the present invention, heteroaryl is benzimidazole. In another embodiment of the present invention, heteroaryl is pyrazole. In another embodiment of the present invention, heteroaryl is indazole. In another embodiment of the present invention, heteroaryl is indole. In another embodiment of the present invention, heteroaryl is 2,3-dihydro-indene. "Heteroaryl" includes bicyclic heteroaryl ring.

"Halogen" includes fluorine, chlorine, bromine and iodine. In one embodiment of the present invention, halogen is bromine, chlorine or fluorine. In another embodiment of the present invention, halogen is chlorine or fluorine. In another embodiment of the present invention, halogen is bromine. In another embodiment of the present invention, halogen is chlorine. In another embodiment of the present invention, halogen is fluorine.

"Me" represents methyl.

"Oxo" means =O.

When any variable (e.g., R$^1$, R$^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a C$_{1-5}$ alkylcarbonylamino C$_{1-6}$ alkyl substituent is equivalent to:

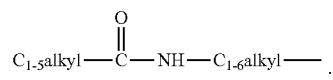

For example, —NR$^c$C(O)R$^e$ is equivalent to —N(R$^c$)C(O)R$^e$.

Unless expressly depicted or described otherwise, substituents depicted in a structural formula with a "floating" bond, such as but not limited to R$^1$ and the sidechain

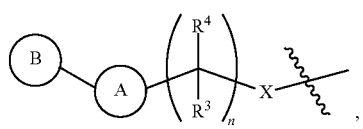

are permitted on any available carbon atom in the ring to which the substituent is attached. In one embodiment of the present invention, R$^1$ and the above sidechain may be substituted on any CH in the ring to which R$^1$ and the above sidechain are attached. In another embodiment of the present invention, U is CH, wherein CH is substituted with the sidechain:

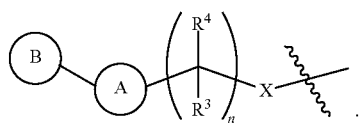

In choosing compounds of the present invention, one of ordinary skill in the art will recognize that the various substituents, i.e. R$^1$, R$^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H), deuterium ($^2$H), and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts:

It will be understood that, as used herein, references to the compounds of the present invention are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of the present invention are included in the present invention as well.

Utilities

The compounds of the present invention are potent agonists of the GPR40 receptor. The compounds, and pharmaceutically acceptable salts thereof, may be efficacious in the treatment of diseases that are modulated by GPR40 ligands, which are generally agonists. Many of these diseases are summarized below.

One or more of these diseases may be treated by the administration of a therapeutically effective amount of a compound of the present invention, or a pharmaceutically acceptable salt thereof, to a patient in need of treatment. Also, the compounds of the present invention may be used for the manufacture of a medicament which may be useful for treating one or more of these diseases: (1) non-insulin dependent diabetes mellitus (Type 2 diabetes); (2) hyperglycemia; (3) insulin resistance; (4) Metabolic Syndrome; (5) obesity; (6) hypercholesterolemia; (7) hypertriglyceridemia (elevated levels of triglyceride-rich-lipoproteins); (8) mixed or diabetic dyslipidemia; (9) low HDL cholesterol; (10) high LDL cholesterol; (11) hyperapo-B liproteinemia; and (12) atherosclerosis.

Preferred uses of the compounds may be for the treatment of one or more of the following diseases by administering a therapeutically effective amount to a patient in need of treatment. The compounds may be used for manufacturing a medicament for the treatment of one or more of these diseases: (1) Type 2 diabetes, and specifically hyperglycemia associated with Type 2 diabetes; (2) Metabolic Syndrome; (3) obesity; and (4) hypercholesterolemia.

The compounds may be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds may also be effective in treating or preventing lipid disorders. The compounds may be effective in treating or preventing diabetes related disorders. The compounds may also be effective in treating or preventing obesity related disorders.

The compounds of this invention may also have utility in improving or restoring β-cell function, so that they may be useful in treating Type 1 diabetes or in delaying or preventing a patient with Type 2 diabetes from needing insulin therapy.

The invention also includes pharmaceutically acceptable salts of the compounds, and pharmaceutical compositions comprising the compounds and a pharmaceutically acceptable carrier. The compounds may be useful in treating insulin resistance, Type 2 diabetes, hyperglycemia, and dyslipidemia that is associated with Type 2 diabetes and insulin resistance. The compounds may also be useful for the treatment of obesity.

A compound of the present invention, or a pharmaceutically acceptable salt thereof, may be used in the manufacture of a medicament for the treatment of Type 2 diabetes in a human or other mammalian patient.

A method of treating Type 2 diabetes comprises the administration of a therapeutically effective amount of a compound of the present invention, or a pharmaceutically acceptable salt thereof, or a pharmaceutical composition comprising the compound, to a human or other mammal subject or patient in need of treatment. Other medical uses of the compounds of the present invention are described herein.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of ≥140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensitivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHID death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated (≥140 mmHg/≥90 mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dylipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. An overweight subject is a subject at risk of obesity. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

The terms "administration of" and or "administering a" compound should be understood to mean providing a compound of the invention or a prodrug of a compound of the invention to a human or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of conditions which require agonism of GPR40 receptor activity, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Combination Therapy

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds of formula I or the other drugs may have utility, where the combination of the drugs together are safer or more effective than either drug alone.

Such other drug(s) may be administered, by a route and in an amount commonly used therefore, contemporaneously or sequentially with a compound of formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I.

Examples of other active ingredients that may be administered separately or in the same pharmaceutical composition in combination with a compound of the formulas described herein include, but are not limited to: (1) dipeptidyl peptidase-IV (DPP-4) inhibitors (e.g., sitagliptin, alogliptin, omarigliptin, linagliptin, vildagliptin, saxagliptin, tenegliptin); (2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814); (3) insulin or insulin analogs (e.g., insulin detemir, insulin glulisine, insulin degludec, insulin glargine, insulin lispro and inhalable formulations of each); (4) leptin and leptin derivatives and agonists; (5) amylin and amylin analogs (e.g., pramlintide); (6) sulfonylurea and non-sulfonylurea insulin secretagogues (e.g., tolbutamide, glyburide, glipizide, glimepiride, mitiglinide, meglitinides, nateglinide and repaglinide); (7) α-glucosidase inhibitors (e.g., acarbose, voglibose and miglitol); (8) glucagon receptor antagonists (e.g., MK-3577, MK-0893, LY-2409021 and KT6-971); (9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); (10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA: cholesterol acyltransferase inhibitors (e.g., avasimibe); (11) HDL-raising drugs, (e.g., niacin and nicotinic acid receptor agonists, and extended-release versions thereof; MK-524A, which is a combination of niacin extended-release and the DP-1 antagonist MK-524); (12) antiobesity compounds; (13) agents intended for use in inflammatory conditions, such as aspirin, non-steroidal anti-inflammatory drugs or NSAIDs, glucocorticoids, and selective cyclooxygenase-2 or COX-2 inhibitors; (14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers; (15) glucokinase activators (GKAs) (e.g., AZD6370); (16) inhibitors of 11β-hydroxysteroid dehydrogenase type 1, (e.g., such as those disclosed in U.S. Pat. No. 6,730,690, and LY-2523199); (17) CETP inhibitors (e.g., anacetrapib, torcetrapib, and AT-03); (18) inhibitors of fructose 1,6-bisphosphatase, (e.g., MB-07803, and such as those disclosed in U.S. Pat. Nos. 6,054,587; 6,110,903; 6,284,748; 6,399,782; and 6,489,476); (19) inhibitors of acetyl CoA carboxylase-1 or 2 (ACC1 or ACC2); (20) AMP-activated Protein Kinase (AMPK) activators (e.g., MB-11055); (21) other agonists of the G-protein-coupled receptors: (i) GPR-109, (ii) GPR-119 (e.g., MBX2982 and PSN821), (iii) GPR-40 (e.g., fasiglifam, JTT-851, P-11187, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2, 6-dimethyl-4-(3-(methylsulfonyl)propoxy)-phenyl)phenyl) methoxy)phenyl)isothiazole-3-ol 1-oxide, 5-(4-((3-(2-methyl-6-(3-hydroxypropoxy)pyridine-3-yl)-2-methylphenyl)methoxy)phenyl)isothiazole-3-ol 1-oxide, and 5-[4-[[3-[4-(3-aminopropoxy)-2,6-dimethylphenyl]phenyl]methoxy]phenyl]isothiazole-3-ol 1-oxide), and (iv) GPR-120 (e.g., KDT-501); (22) SSTR3 antagonists (e.g., pasireotide, and such as those disclosed in WO 2009/011836); (23) neuromedin U receptor agonists (e.g., such as those disclosed in WO 2009/042053, including, but not limited to, neuromedin S (NMS)); (24) SCD inhibitors; (25) GPR-105 antagonists (e.g., such as those disclosed in WO 2009/000087); (26) SGLT inhibitors (e.g., LIK-066, ASP1941, SGLT-3, ertugliflozin, empagliflozin, dapagliflozin, canagliflozin, BI-10773, PF-04971729, remogloflozin, luseogliflozin, tofogliflozin, ipragliflozin, and LX-4211); (27) inhibitors of (i) acyl coenzyme A:diacylglycerol acyltransferase 1, DGAT-1 (e.g., pradigastat, and P-7435) and acyl coenzyme A:diacylglycerol acyltransferase 2, DGAT-2; (28) inhibitors of fatty acid synthase; (29) inhibitors of acyl coenzyme A:monoacylglycerol acyltransferase 1 and 2 (MGAT-1 and MGAT-2); (30) agonists of the TGR5 receptor (also known as GPBAR1, BG37, GPCR19, GPR131, and M-BAR) (eg., sodium taurocholate); (31) ileal bile acid transporter inhibitors (eg., elobixibat); (32) PACAP, PACAP mimetics, and PACAP receptor 3 agonists; (33) PPAR agonists; (34) protein tyrosine phosphatase-1B (PTP-1B) inhibitors; (35) IL-1b antibodies and inhibitors, (e.g., gevokizumab, canakinumab, danazol, AC-201, and BLX-1002); and (36) bromocriptine mesylate and rapid-release formulations thereof.

Of particular interest are dipeptidyl peptidase-IV (DPP-4) inhibitors that can be used in combination with compounds of the present invention. Such inhibitors include, without limitation, sitagliptin (disclosed in U.S. Pat. No. 6,699,871), omarigliptin, trelagliptin, teneligliptin, bisegliptin, anagliptin, LC15-0444, vildagliptin, saxagliptin, alogliptin, melogliptin, linagliptin, gosogliptin, evogliptin, gemigliptin, and pharmaceutically acceptable salts thereof, and fixed-dose combinations of these compounds with metformin hydrochloride, pioglitazone, rosiglitazone, simvastatin, atorvastatin, or a sulfonylurea.

Other GPR-40 agonists that can be used in combination with compounds of the formulas described herein include, but are not limited to: (1) 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide; (2) 5-(4-((3-(2,6-dimethyl-4-(3-(methylsulfonyl)propoxy)phenyl)phenyl)-methoxy)-phenyl)isothiazole-3-ol 1-oxide; (3) 5-(4-((3-(2-methyl-6-(3-hydroxypropoxy)-pyridine-3-yl)-2-methylphenyl)methoxy)phenyl)isothiazole-3-ol 1-oxide; and (4) 5-[4-[[3-[4-(3-aminopropoxy)-2,6-dimethylphenyl]phenyl]methoxy]phenyl]isothiazole-3-ol 1-oxide, and pharmaceutically acceptable salts thereof.

Other dipeptidyl peptidase-IV (DPP-4) inhibitors that can be used in combination with compounds of the formulas described herein include, but are not limited to: (1) (2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine; (2) (2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine; (3) (2R,3S,5R)-2-(2,5-difluorophenyl)tetrahydro)-5-(4,6-dihydropyrrolo[3,4-c]pyrazol-5(1H)-yl)tetrahydro-2H-pyran-3-amine; (4) (3R)-4-[(3R)-3-amino-4-(2,4,5-trifluorophenyl)butanoyl]-hexahydro-3-methyl-2H-1,4-diazepin-2-one; (5) 4-[(3R)-3-amino-4-(2,5-difluorophenyl)butanoyl]hexahydro-1-methyl-2H-1,4-diazepin-2-one hydrochloride; and (6) (3R)-4-[(3R)-3-amino-4-(2,4,5-trifluorophenyl)butanoyl]-hexahydro-3-(2,2,2-trifluoroethyl)-2H-1,4-diazepin-2-one; and pharmaceutically acceptable salts thereof.

Antiobesity compounds that can be combined with compounds of formula I include topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); CB1 receptor inverse agonists and antagonists (such as rimonabant); $\beta_3$ adrenergic receptor agonists; ghrelin antagonists; bombesin receptor agonists (such as bombesin receptor subtype-3 agonists); and 5-hydroxytryptamine-2c (5-HT2c) agonists, such as lorcaserin. For a review of anti-obesity compounds that can be combined with compounds of the present invention, see S. Chaki et al., "Recent advances in feeding suppressing agents: potential therapeutic strategy for the treatment of obesity," *Expert Opin. Ther. Patients*, 11: 1677-1692 (2001); D. Spanswick and K. Lee, "Emerging antiobesity drugs," *Expert Opin. Emerging Drugs*, 8: 217-237 (2003); J. A. Fernandez-Lopez, et al., "Pharmacological Approaches for the Treatment of Obesity," *Drugs*, 62: 915-944 (2002); and K. M. Gadde, et al., "Combination pharmaceutical therapies for obesity," *Exp. Opin. Pharmacother.*, 10: 921-925 (2009).

Glucagon receptor antagonists that can be used in combination with the compounds of formula I include, but are not limited to: (1) N-[4-((1S)-1-{3-(3,5-dichlorophenyl)-5-[6-(trifluoromethoxy)-2-naphthyl]-1H-pyrazol-1-yl}ethyl)benzoyl]-β-alanine; (2) N-[4-((1R)-1-{3-(3,5-dichlorophenyl)-5-[6-(trifluoromethoxy)-2-naphthyl]-1H-pyrazol-1-yl}ethyl)benzoyl]-β-alanine; (3) N-(4-{1-[3-(2,5-dichlorophenyl)-5-(6-methoxy-2-naphthyl)-1H-pyrazol-1-yl]ethyl}benzoyl)-β-alanine; (4) N-(4-{(1S)-1-[3-(3,5-dichlorophenyl)-5-(6-methoxy-2-naphthyl)-1H-pyrazol-1-yl]ethyl}benzoyl)-β-alanine; (5) N-(4-{(1S)-1-[(R)-(4-chlorophenyl)(7-fluoro-5-methyl-1H-indol-3-yl)methyl]butyl}benzoyl)-β-alanine; and (6) N-(4-{(1S)-1-[(4-chlorophenyl)(6-chloro-8-methylquinolin-4-yl)methyl]butyl}benzoyl)-β-alanine; and pharmaceutically acceptable salts thereof.

Another embodiment of the present invention relates to a pharmaceutical composition comprising one or more of the following agents: (a) a compound of structural formula I; (b) one or more compounds selected from the group consisting of: (1) dipeptidyl peptidase-IV (DPP-4) inhibitors; (2) insulin sensitizers, including (i) PPARγ agonists, such as the glitazones (e.g. AMG 131, MBX2044, mitoglitazone, lobeglitazone, IDR-105, pioglitazone, rosiglitazone, and balaglitazone) and other PPAR ligands, including (1) PPARα/γ dual agonists, such as ZYH1, YYH2, chiglitazar, GFT505, muraglitazar, aleglitazar, sodelglitazar, and naveglitazar, (2) PPARα agonists, such as fenofibric acid derivatives (e.g., gemfibrozil, clofibrate, ciprofibrate, fenofibrate and bezafibrate), (3) selective PPARγ modulators (SPPARγM's), and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors, such as ISI-113715, and TTP814; (3) sulfonylurea and non-sulfonylurea insulin secretagogues, (e.g., tolbutamide, glyburide, glipizide, glimepiride, mitiglinide, and meglitinides, such as nateglinide and repaglinide); (4) α-glucosidase inhibitors (e.g., acarbose, voglibose and miglitol); (5) glucagon receptor antagonists; (6) LDL cholesterol lowering agents such as (i) HMG-CoA reductase inhibitors (e.g., lovastatin, simvastatin, pravastatin, cerivastatin, fluvastatin, atorvastatin, pitavastatin, and rosuvastatin), (ii) bile acid sequestering agents (e.g., colestilan, cholestyramine, colestimide, colesevelam hydrochloride, colestipol, and dialkylaminoalkyl derivatives of a cross-linked dextran), (iii) inhibitors of cholesterol absorption, (e.g., ezetimibe), and (iv) acyl CoA:cholesterol acyltransferase inhibitors (e.g., avasimibe); (7) HDL-raising drugs, such as niacin or a salt thereof and extended-release versions thereof; MK-524A, which is a combination of niacin extended-release and the DP-1 antagonist MK-524; and nicotinic acid receptor agonists; (8) antiobesity compounds; (9) agents intended for use in inflammatory conditions, such as aspirin, non-steroidal anti-inflammatory drugs (NSAIDs), glucocorticoids, and selective cyclooxygenase-2 (COX-2) inhibitors; (10) antihypertensive agents, such as ACE inhibitors (e.g., enalapril, lisinopril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers (e.g., calcium channel blockers); (11) glucokinase activators (GKAs) (e.g., AZD6370, GKM-001, TMG-123, HMS-5552, DS-7309, PF-04937319, TTP-399, ZYGK-1); (12) inhibitors of 11β-hydroxysteroid dehydrogenase type 1 (e.g., such as those disclosed in U.S. Pat. No. 6,730,690; WO 03/104207; and WO 04/058741); (13) inhibitors of cholesteryl ester transfer protein (CETP), (e.g., torcetrapib, anacetrapib, and AT-03); (14) inhibitors of fructose 1,6-bisphosphatase (e.g., MB-07803, and such as those disclosed in U.S. Pat. Nos. 6,054,587; 6,110,903; 6,284,748; 6,399,782; and 6,489,476); (15) inhibitors of acetyl CoA carboxylase-1 or 2 (ACC1 or ACC2); (16) AMP-activated Protein Kinase (AMPK) activators (e.g., MB-11055); (17) agonists of the G-protein-coupled receptors: (i) GPR-109, (ii) GPR-119 (e.g., MBX2982, and PSN821), (iii) GPR-40 (e.g., fasiglifam, JTT-851, P-11187, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl)methoxy)phenyl)isothiazole-3-ol 1-oxide, 5-(4-((3-(2-methyl-6-(3-hydroxypropoxy)pyridine-3-yl)-2-methylphenyl)methoxy)phenyl)-isothiazole-3-ol 1-oxide, and 5-[4-[[3-[4-(3-aminopropoxy)-2,6-dimethylphenyl]phenyl]methoxy]phenyl]isothiazole-3-ol 1-oxide), and (iv) GPR-120 (e.g., KDT-501); (18) SSTR3 antagonists (e.g., pasireotide, and such as those disclosed in WO 2009/011836); (19) neuromedin U receptor agonists (e.g., such as those disclosed in WO2009/042053, including, but not limited to, neuromedin S (NMS)); (20) inhibitors of stearoyl-coenzyme A delta-9 desaturase (SCD); (21) GPR-105 antagonists (e.g., such as those disclosed in WO 2009/000087); (22) inhibitors of glucose uptake, such as sodium-glucose transporter (SGLT) inhibitors and its various isoforms, such as SGLT-1; SGLT-2 (e.g., LIK-066, ertuglifozin, ASP1941, luseogliflozin, BI10773, tofogliflozin, LX4211, canagliflozin, dapagliflozin and remogliflozin; and SGLT-3); (23) inhibitors of (i) acyl coenzyme A:diacylglycerol acyltransferase 1, DGAT-1 (e.g., pradigastat, and P-7435) and acyl coenzyme A:diacylglycerol acyltransferase 2, DGAT-2; (24) inhibitors of fatty acid synthase; (25) inhibitors of acyl coenzyme A:monoacylglycerol acyltransferase 1 and 2 (MGAT-1 and MGAT-2); (26) agonists of the TGR5 receptor (also known as GPBAR1, BG37, GPCR19, GPR131, and M-BAR) (eg., sodium taurocholate); (28) bromocriptine mesylate and rapid-release formulations thereof, and (29) IL-1b antibodies and inhibitors (e.g., gevokizumab, canakinumab, danazol, AC-201, and BLX-1002); and (c) a pharmaceutically acceptable carrier.

Specific compounds of use in combination with a compound of the present invention include: simvastatin, mevastatin, ezetimibe, atorvastatin, rosuvastatin, sitagliptin, omarigliptin, metformin, sibutramine, orlistat, topiramate, naltrexone, bupriopion, phentermine, losartan, losartan with hydrochlorothiazide, canagliflozin, dapagliflozin, ipragliflozin and ertugliflozin.

The above combinations include combinations of a compound of the present invention not only with one other active compound, but also with two or more other active compounds. Non-limiting examples include combinations of compounds with two or more active compounds selected from biguanides, sulfonylureas, HMG-CoA reductase inhibitors, PPARγ agonists, DPP-4 inhibitors, anti-obesity compounds, and anti-hypertensive agents.

The present invention also provides a method for the treatment or prevention of a G-protein coupled receptor 40 (GPR40) mediated disease, which method comprises administration to a patient in need of such treatment or at risk of developing a GPR40 mediated disease of an amount of a GPR40 agonist and an amount of one or more active ingredients, such that together they give effective relief.

In a further aspect of the present invention, there is provided a pharmaceutical composition comprising a GPR40 agonist and one or more active ingredients, together with at least one pharmaceutically acceptable carrier or excipient.

Thus, according to a further aspect of the present invention there is provided the use of a GPR40 agonist and one or more active ingredients for the manufacture of a medicament for the treatment or prevention of a GPR40 mediated disease. In a further or alternative aspect of the present invention, there is therefore provided a product comprising a GPR40 agonist and one or more active ingredients as a combined preparation for simultaneous, separate or sequential use in the treatment or prevention of a GPR40 mediated disease. Such a combined preparation may be, for example, in the form of a twin pack.

It will be appreciated that for the treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent effective to threat that disorder, such that together they give effective relief.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Methods of Synthesis of the Compounds of the Present Invention:

The following reaction schemes and Examples illustrate methods which may be employed for the synthesis of the compounds of structural formula I described in this invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI). All temperatures are degrees Celsius unless otherwise noted.

List of Abbreviations

Ac is acetyl; AcO is acetoxy; AcOK is potassium acetate; AcONa is sodium acetate; HOAc or AcOH is acetic acid; aq or aq. is aqueous; Alk is alkyl; APCI is atmospheric pressure chemical ionization; AgNO$_3$ is silver nitrate; aq or aq. is aqueous; Ar is aryl; atm is atmosphere; BH$_3$ DMS is borane dimethylsulfide complex; BINAP is 2,2'-bis(diphenylphosphino)-1,1'-binaphthyl; Boc is tert-butoxycarbonyl; Boc$_2$O is di-tert-butylcarbonate; br is broad; n-BuLi is n-butyl lithium; s-Bu is sec-butyl; t-Bu is tert-butyl; t-BuO is tert-butoxide; t-BuOK is potassium tert-butoxide; t-BuOH is tert-butyl alcohol; t-BuONa is sodium tert-butoxide; Brett-Phos Palladacycle is chloro[2-(dicyclohexylphosphino)-3,6-dimethoxy-2',4',6'-tri-i-propyl-1,1'-biphenyl][2-(2-amino-ethyl)phenyl]palladium(II); ° C. is degrees celsius; CO is carbon monoxide; conc or conc. is concentrated; Cu(OTf)$_2$ is copper triflate; d is doublet; DAST is (diethylamino)sulfur trifluoride; DCM is dichloromethane; DEA is diethylamine; DIAD is diisopropyl azodicarboxylate; DIBAL-H is diisobutylaluminum hydride; DIPEA is N,N-diisopropylethylamine; DMAP is 4-dimethylaminopyridine; DMF is N,N-dimethylformamide; DMSO is dimethylsulfoxide; DMP is N-methyl-2-pyrrolidone; DPPA is diphenylphosphoryl-azide; dppf is 1,1'-bis(diphenyl-phosphino)ferrocene; DTBPF-PdCl$_2$ is [1,1'-Bis(di-tert-butylphosphino)ferrocene] dichloropalladium(II); ESI is electrospray ionization; EA or EtOAc is ethyl acetate; Et is ethyl; EtOH is ethanol; Et$_3$N is triethylamine; Et$_3$SiH is triethylsilane; g or gm is gram(s); h or hr or hrs is hour(s); RMPA is hexamethylphosphoramide; HPLC is high pressure liquid chromatography; kg is kilogram(s); KHMDS is potassium bis(trimethylsilyl)amide; L is liter; LC-MS is liquid chromatography-mass spectroscopy; LAH is lithium aluminum hydride; LDA is lithium diisopropyl amide; LHMDS and LiHMDS is lithium bis (trimethylsilyl)amide; MeMgBr is methylmagnesium bromide; m is multiplet; mL or ml is milliliter; m-CPBA, MCPBA, or mCPBA is meta chloroperbenzoic acid; mg is milligram(s); min or mins is minute(s); mol is mole(s); mmol is mmole(s); MeI is methyl iodide; MeOH is methyl alcohol; Me$_2$S is dimethylsulfide; MS is mass spectroscopy; MsCl or Ms-Cl is methane sulfonyl chloride; MOMCl is methoxymethyl chloride; MTBE is methyl tert-butyl ether; N is normal; NaHMDS is sodium hexamethyldisilazide; NBS is N-bromo succinamide; NFSI is N-fluorobenzenesulfonimide; MS is N-iodo succinamide; NMP is 1-methyl-2-pyrrolidinone; NMR is nuclear magnetic resonance spectroscopy; PCC is pyridinium chlorochromate; PE is petroleum ether; Pd(OAc)$_2$ is palladium (II)acetate; P(Cy)$_3$ is tricyclohexyl phosphine; Pd$_2$(dba)$_3$ is tris(dibenzylideneacetone)dipalladium(0); Pd(dppf)Cl$_2$ is [1,1'-bis(diphenylphosphino)-ferrocene]dichloro-palladium (II); PdCl$_2$(dffp) is 1,1'-Bis(diphenylphosphino)ferrocene-palladium(II)dichloride dichloromethane complex; Pd(dtbpf)Cl$_2$ is [1,1'-bis (di-tert-butylphosphino)-ferrocene]dichloro-palladium (II); Pd(PPh$_3$)$_4$ is tetrakis(triphenylphosphine)-palladium(0); PG is protecting group; Tf$_2$NPh and PhNTf$_2$ and PhN(Tf)$_2$ is N-phenylbis(trifluoromethanesulfonimide; PMB is para-methoxybenzyl; PMBCl is para-methoxybenzyl chloride; PPh$_3$ is triphenyl phosphine; PPA is polyphosphoric acid; PPTS is pyridinium p-toluenesulfonate; Rh(PPh$_3$)$_3$Cl is chlorotris(triphenylphosphine)-rhodium(I); Rh(OAc)$_2$ is rhodium (II) acetate; prep. TLC or preparative TLC is preparative thin layer chromatography; RBF is round bottom flask; RCM is ring closing metathesis reaction; rt or rt. or r.t. or RT is room temperature; s is singlet; SFC is supercritical fluid chromatography; s-phos is 2-dicyclohexylphosphino-2',6'-dimethoxybiphenyl; t is triplet; T3P is propylphosphonic anhydride; TEA is triethyl amine; THF is tetrahydrofuran; TFA is trifluoroacetic acid; TFAA is trifluoroacetic anhydride; Tf$_2$O is trifluoromethanesulfonic anhydride; Tf$_2$NPh is N-Phenylbis(trifluoromethanesulfonimide; TIPS is triisopropylsilyl; TIPSCl is chloro triisopropylsilane; TLC is thin-layer chromatography; TMSCl is trimethyl silyl chloride TMSCN is trimethylsilyl cyanide; tol is toluene; TosCl is p-toluene sulfonyl chloride; p-TsOH is p-toluenesulfonic acid, Xant-phos is 4,5-Bis(diphenylphosphino)-9,9-dimethylxanthene, and xphos is 2-Dicyclohexylphosphino-2',4',6'-triisopropylbiphenyl.

Several methods for preparing the compounds of this invention are illustrated in the following Schemes and Examples. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products. The following Examples are provided to illustrate the invention and are not to be construed as limiting the invention in any manner. The scope of the invention is defined by the appended claims.

Intermediate 1-9

4-Hydroxy-1,1a,6,6a-tetrahydro-3-aza-cyclopropa[a]indene-1-carboxylic acid ethyl ester (1-9)

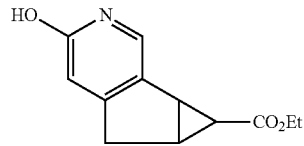 [SMILES: CCOC(=O)C1C2Cc3cc(O)ncc3C21]

Step A: (4-Bromo-pyridin-2-yl)-bis-(4-methoxy-benzyl)-amine (1-2)

To a suspension of sodium hydride (60% in oil, 93 g, 2.32 mol) in DMF (1.8 L), was added 4-bromo-2-aminopyridine 1-1 (100 g, 0.58 mol) in DMF (500 mL) slowly at 0° C. Then the resulting mixture was allowed to stir at r.t. for 0.5 h under N$_2$ protection. PMBCl (227 g, 1.45 mol) was added to the above mixture and the temperature was kept between 0-10° C. After addition, the mixture was allowed to stir at room temperature for 2 h. Then the mixture was carefully poured into ice water, and the resulting solid precipitate was collected, filtered and washed with PE (150 mL×3). The resulting filtrate was concentrated to afford compound 1-2. MS (ESI) m/e (M+H$^+$): 414.1/416.1.

Step B: (4-Bromo-5-iodo-pyridin-2-yl-bis-(4-methoxy-benzyl)-amine (1-3)

To a stirred solution of compound 1-2 (140 g, 0.34 mol) in DMF (2.8 L) was added NIS (115 g, 0.51 mmol) in portions. Then the resulting mixture was heated to 40° C. and stirred for 24 h. The mixture was cooled, poured into ice water and stirred constantly. The resulting solid precipitate was collected, filtered and washed with PE (100 mL×3). The resulting filtrate was concentrated in vacuo to afford compound 1-3. MS (ESI) m/e (M+H⁺): 540,541 (M+H⁺).

Step C: (4-Bromo-5-vinyl-pyridin-2-yl)-bis-(4-methoxy-benzyl)-amine (1-4)

To a stirred solution of compound 1-3 (144 g, 267 mmol) in toluene (2 L) was added tributyl (vinyl) tin (85 g, 267 mmol), Pd(PPh₃)₄ (15.4 g, 13.4 mmol), and KF (31 g, 534 mmol). The resulting mixture was heated to reflux for 18 h under N₂. The mixture was then cooled, KF (300 mL, 2 mol/L) was added and the mixture was stirred for 20 minutes. The mixture was then filtered and the filtrate layers were separated. The organic layer was collected and evaporated in vacuo to give a residue, which was purified by column chromatography on silica gel (eluting with PE:EA=20:1) to give compound 1-4. MS (ESI) m/e (M+H⁺): 439.8/441 8.

Step D: (4-Allyl-5-vinyl-pyridin-2-yl)-bis-(4-methoxy-benzyl)-amine (1-5)

To a stirred solution of compound 1-4 (90 g, 205 mmol) in THF (2 L), was added Cs₂CO₃ (134 g, 410 mmol), Pd(dppf)Cl₂ (7.5 g, 10.3 mmol), and allyltributyltin (136 g, 410 mmol). The resulting mixture was heated to reflux for 18 h under N₂. Then the mixture was cooled, KF (300 mL, 2 mol/L) was added and the mixture was stirred for 20 min. The mixture was then filtered and the filtrate layers were separated. The organic layer was collected and evaporated in vacuo to give a residue, which was purified by column chromatography on silica gel (eluting with PE:EA=30:1) to give compound 1-5. MS (ESI) m/e (M+H⁺): 440.1.

Step E: Bis-(4-methoxy-benzyl)-(5H-[2]pyrindin-3-yl)-amine (1-6)

To a stirred solution of compound 1-5 (55 g, 138 mmol) in DCM (700 mL), was added Grubbs reagent (II) (3.5 g, 4.14 mmol) in one portion. The resulting mixture was heated at reflux for 3 h under N₂. The mixture was then cooled and the crude compound 1-6 as solution was used directly in the next step. MS (ESI) m/e (M+H⁺): 373.2.

Step F: 4-[Bis-(4-methoxy-benzyl)-amino]-1,1a,6,6a-tetrahydro-3-aza-cyclopropara[a]-indene-1-carboxylic acid ethyl ester (1-7)

To a stirred solution of crude compound 1-6 (52 g, 138 mmol) in DCM (0.7 L) was added Rh(OAc)₂ (1.6 g, 6.9 mmol) in one portion. The mixture was stirred for 15 min, then ethyl diazoacetate (126 g, 1.1 mol) was added slowly to the mixture under gentle reflux over 3 h. The resulting mixture was allowed to stir at r.t for 1 h. Then the mixture evaporated in vacuo to give the crude product, which was purified by column chromatography on silica gel (eluting with PE:EA=10:1) to give a trans-isomeric mixture of 1-7. The trans-isomeric mixture of 1-7 was separated by chiral column chromatography (SFC resolution conditions: Instrument: Thar 200; Column: AD 250 mm×50 mm, 10 um; Mobile Phase: A Supercritical CO₂, B EtOH (0.05% NH₃.H₂O), A/B=60/40 at 200 mL/min; Column Temp: 38° C.; Nozzle Pressure: 100 bar; Nozzle Temp: 60° C.; Evaporator Temp: 20° C.; Trimmer Temp: 25° C.; Wavelength: 220 nm) to give the desired enantiomer 1-7. MS (ESI) m/e (M+H⁺): 459.1.

Step G: 4-Amino-1,1a,6,6a-tetrahydro-3-aza-cyclopropa[a]indene-1-carboxylic acid ethyl ester (1-8)

To a stirred solution of compound 1-7 (19 g, 41.4 mmol) in DCM (130 mL) was added TFA (130 mL) in one portion. The resulting mixture was stirred at r.t overnight. The mixture was then evaporated in vacuo to give compound 1-8, which was used directly in the next step. MS (ESI) m/e (M+H⁺): 219.1.

Step H: 4-Hydroxy-1,1a,6,6a-tetrahydro-3-aza-cyclopropa[a]indene-1-carboxylic acid ethyl ester (1-9)

To a stirred solution of compound 1-8 (23 g, crude) in H₂SO₄ (200 mL, 15%) was added NaNO₂ (14.4 g, 209 mmol) in several portions at 0° C. The resulting mixture was allowed to stir at r.t for 2 h. The mixture was then basified with 2N NaOH to pH=5-6, and aqueous NaHCO₃ was added to adjust the filtrate to pH=7. The resulting suspension was extracted with DCM (300 mL×3), and the combined organic layers were washed with brine, dried over Na₂SO₄, and concentrated in vacuo. The resulting residue was purified by column chromatography over silica gel (eluting with DCM: MeOH=50:1 to 20:1) to afford intermediate 1-9. MS (ESI) m/e (M+H⁺): 220 (M+H⁺). ¹H-NMR (400 MHz, CDCl₃) δ: 12.52 (s, 1H), 7.28 (s, 1H), 6.38. (s, 1H), 4.14 (dd, 2H, J=7.2 and 14.4 Hz), 3.18 (dd, 1H, J=6.0 and 12.0 Hz), 2.94 (d, 1H, J=8.8 Hz), 2.77 (dd, 1H, J=2.4 and 6.4 Hz), 2.43-2.39 (m, 1H), 1.28-1.25 (m, 4H).

Intermediate 1-10

(5aR,6S,6aS)-ethyl 3-chloro-5,5a,6,6a-tetrahydrocyclopropa[4,5]cyclopenta[1,2-c]pyridine-6-carboxylate (1-10)

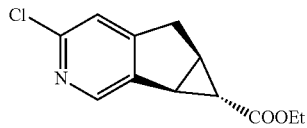 [SMILES: CCOC(=O)[C@H]1[C@@H]2Cc3cc(Cl)ncc3[C@@H]21]

Step A: (5aR,5S,6aS)-ethyl 3-chloro-5,5a,6,6a-tetrahydrocyclopropa[4,5]cyclopenta[1,2-c]pyridine-6-carboxylate (1-10)

A mixture of intermediate 1-9 (5.0 g, 22.8 mmol) in POCl₃ (50 mL) was stirred at 110° C. for 18 h. After cooling to the room temperature, the excess POCl₃ was removed under reduced pressure. The resulting crude residue was diluted with EA, washed with saturated aqueous NaHCO₃ and brine, dried over anhydrous Na₂SO₄, filtered and the filtrate was concentrated in vacuo to provide a residue, which was purified by chromatography over silica gel (eluting with EA:PE=15:85) to afford intermediate 1-10. MS (ESI) m/e (M+H⁺): 238.5.

Intermediate 1-11

(5aR,6S,6aS)-tert-butyl 3-chloro-5,5a,6,6a-tetrahydrocyclopropa[4,5]cyclopenta[1,2-c]pyridine-6-carboxylate (1-11)

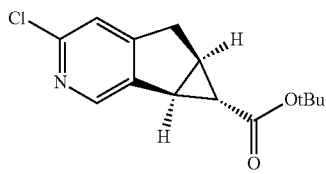 [SMILES: CC(C)(C)OC(=O)[C@H]1[C@@H]2Cc3cc(Cl)ncc3[C@@H]21]

Step A: (E)-methyl 5-(3-(tert-butoxy)-3-oxoprop-1-en-1-yl)-2-chloroisonicotinate (1-11b)

To a solution of 5-bromo-2-chloroisonicotinic acid 1-11a (Combi-Blocks, 100 g, 423 mmol) in THF (200 mL) and toluene (800 mL) was added DMF (1.6 mL, 21.15 mmol). To the resulting slurry was added slowly oxalyl chloride (47 mL, 529 mmol). The reaction was stirred over the weekend at room temperature. Then MeOH (100 mL) was added slowly while cooling in a water bath. After 2 h at room temperature, aqueous $K_2HPO_4$ (1 M, 423 mL, 423 mmol) was added slowly while still cooling in a water bath. The layers were separated and the aqueous layer was extracted with toluene (1×250 mL). The combined organic layers were filtered through Solka-Floc cellulose, then washed with water (1×200 mL), dried over $MgSO_4$ and concentrated in vacuo to give the crude methyl ester intermediate. To the methyl ester intermediate in toluene (2 L) was added chloro[tris(2-methylphenyl)phosphine] [2-(2'-amino-1,1'-biphenyl)]palladium(II) (2.6 g, 4.23 mmol, 1%) and N,N-dicyclohexylmethylamine (226 mL, 1057 mmol). The reaction was degassed for 1 h, then t-Butyl acrylate was added in a single portion and the reaction mixture was heated to 80° C. overnight. Then additional chloro[tris(2-methylphenyl)phosphine] [2-(2'-amino-1,1'-biphenyl)]palladium(II) (1.3 g, 2.12 mmol, 0.5%) was added and the reaction was heated at 80° C. for 3 h. The reaction mixture was then cooled to room temperature and quenched with water (500 ml). The layers were separated. The organic layer was washed with saturated brine (1×500 ml), then filtered through a plug of silica gel (150 g) and rinsed with 20% EtOAc in hexanes. The filtrate was concentrated in vacuo to give a crude oil, which was recrystallized from EtOAc in hexane (1:1) at −10° C. to provide compound 1-11b. MS (ESI) m/e (M+H$^+$): 242.2.

Step B: (E)-5-(3-(tert-butoxy)-3-oxoprop-1-en-1-yl)-2-chloroisonicotinic acid (1-11c)

To a solution of compound 1-11b (1 g, 3.36 mmol) in THF (10 ml) was added a solution of lithium hydroxide hydrate (0.155 g, 3.69 mmol) in water (2 ml), and the reaction was stirred overnight at room temperature. The reaction was then concentrated in vacuo and the resulting residue was diluted with 5 mL water, and slowly acidified with ice-cold 1N HCl solution (4.03 mL). The resulting white solid was filtered and dried under high vacuum to provide compound 1-11c. MS (ESI) m/e (M+H$^+$): 284.2.

Step C: (E)-tert-butyl 3-(6-chloro-4-((E)-2-chloro-2-hydrazonoacetyl)pyridin-3-yl)acrylate (1-11d)

DMF (25 μl, 0.323 mmol) was added to a suspension of compound 1-11c (1.73 g, 6.10 mmol) in dichloromethane (55 mL) and the reaction mixture was stirred at room temperature for 1 hour. The reaction mixture was then concentrated in vacuo, and co-evaporated with 1,2-dichloroethane. Then DCM (24 ml) was added to the residue, and the resulting solution was added to a solution of (isocyanoimino)triphenylphorphorante (2.77 g, 9.15 mmol) in DCM (14 mL) over 10 min. The reaction mixture was stirred at room temperature for 2 hours. Then water (6.6 ml, 366 mmol) was added and the mixture was stirred at room temperature overnight. Then the organic layer was separated, dried over $MgSO_4$ and concentrated in vacuo to provide a residue, which was purified by column chromatography over silica gel (eluting with EA:hexanes=0:100 to 30:70) to give compound 1-11d. MS (ESI) m/e (M+H$^+$): 344, 346, 348.

Step D: (E)-tert-butyl 3-(6-chloro-4-(2-diazoacetyl)pyridin-3-yl)acrylate (1-11e)

Anhydrous zinc bromide (325 mg, 1.443 mmol) was added to a solution of compound 1-11d (2.09 g, 6.07 mmol) in DCM (20 ml), followed by the dropwise addition of diisopropylethylamine (1.2 ml, 8.42 mmol). The reaction was stirred at room temperature for 1 hour, and then diluted with EtOAc. The organic layer was washed with 1% ethylenediamine tetraacetic acid tetrasodium salt, dried over anhydrous $MgSO_4$, and concentrated in vacuo. The resulting crude residue was purified by column chromatography over silica gel (eluting with EA:hexanes=0:100 to 30:70) to give compound 1-11e. MS (ESI) m/e (M+H$^+$): 308, 310.

Step E: (5aR,6R,6aS)-tert-butyl 3-chloro-5-oxo-5,5a,6,6a-tetrahydrocyclopropa[4,5]cyclopenta-[1,2-c]pyridine-6-carboxylate (1-11f)

A solution of 2,2-bis((S)-4-phenyl-4,5-dihydrooxazol-2-yl)acetonitrile (5.17 mg, 0.016 mmol), copper(I)trifluoromethanesulfonate toluene complex (3.36 mg, 6.50 μmol) and 2,6-di-tert-butylpyridine (29.2 μl, 0.130 mmol) in THF (1 mL) was warmed to 25° C., then compound 1-11e (400 mg, 1.300 mmol) in THF (3 mL) was added dropwise over 5 min. After 2.5 hours, the reaction mixture was diluted with EtOAc (3 mL) and MTBE (3 mL), washed with 0.5 M aqueous citric acid (6 mL), and concentrated in vacuo to provide a residue. The residue was purified by chromatography over silica gel (eluting with EA:hexanes=0:100 to 30:70) to provide compound 1-11f. The ee was upgraded to 95% by dissolution in EtOAc (6 mL/g) and removal of the racemate by filtration. MS (ESI) m/e (M+H$^+$): 267.1.

Step F: (5aR,5S,6aS)-tert-butyl 3-chloro-5,5a,6,6a-tetrahydrocyclopropa[4,5]cyclopenta[1,2-c]pyridine-6-carboxylate (1-11)

Sodium borohydride (1.6 mg, 0.071 mmol) was added to a solution of compound 1-11e (20 mg, 0.071 mmol) in MeOH (0.4 mL) at 0° C. After 30 minutes, the reaction was quenched with saturated aqueous $NH_4Cl$ and concentrated in vacuo. The resulting residue was re-dissolved in MTBE and washed once with water. The organic layer was separated, dried over $MgSO_4$ and concentrated in vacuo to give an alcohol intermediate. The alcohol intermediate was dissolved in THF (400 μL) and treated with trifluoroacetic anhydride (2 equiv, 0.142 mmol) for 30 minutes. The reaction was then cooled to 0° C., and concentrated aqueous HCl (5 equiv, 0.355 mmol) was added, followed by the portion wise addition of zinc dust (9.3 mg, 0.142 mmol) over 5 minutes. After stirring for 15 minutes, the reaction was diluted with water and extracted with MTBE twice. The combined organic layers were dried over MgSO$_4$ and concentrated in vacuo to give a residue, which was purified by column chromatography over silica gel (eluting with EA:hexanes=10:90 to 20:80) to provide intermediate 1-11. $^1$H NMR (400 MHz, CDCl$_3$): δ 8.27 (s, 1H), 7.05 (s, 1H), 3.18 (dd, J=6.35 Hz, 12.2 Hz, 1H), 2.97 (d, J=18.5 Hz, 1H), 2.83 (d, J=6.35 Hz, 1H), 2.37 (m, 1H), 1.39 (s, 9H), 1.09 (br.s, 1H). MS (ESI) m/e (M+H$^+$): 280.1.

Intermediate 1-12

((5aR,6R,6aS)-tert-butyl 3-chloro-5-difluoro-5,5a,6,6a-tetrahydrocyclopropa[4,5]cyclopenta[1,2-c]pyridine-6-carboxylate (1-12)

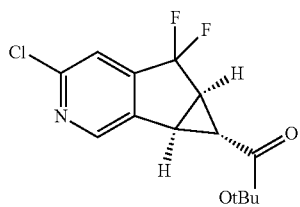

1-12

Step A: (5aR,6R,6aS)-tert-butyl 3-chloro-5-difluoro-5,5a,6,6a-tetrahydrocyclopropa[4,5]-cyclopenta[1,2-c]pyridine-6-carboxylate (1-12)

A solution of compound 1-11f (5 g, 17.88 mmol) in DCM (50 mL) was treated with (diethylamino)difluorosulfonium tetrafluoroborate (16.37 g, 4 eq.), triethylamine trihydrofluoride (17.2 g, 6 eq.) and triethylamine (3.6 g, 2 eq.). The reaction mixture was stirred at room temperature for two days, then diluted with EtOAc (200 mL), and washed with saturated aqueous NaHCO$_3$, water, and brine. The organic layer was separated, dried over Na$_2$SO$_4$ and concentrated in vacuo to give a residue, which was purified by chromatography over silica gel (eluting with EA:hexanes=0:100 to 100:0) to provide intermediate 1-12. MS (ESI) m/e (M+H$^+$): 302.2.

Intermediate 2-7

Ethyl 6-fluoro-1,1-dimethyl-3-oxo-2,3-dihydro-1H-indene-5-carboxylate (2-7)

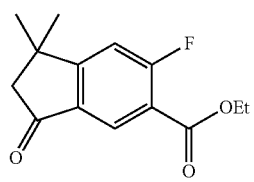

2-7

Step A: (E)-ethyl 3-(4-bromo-3-fluorophenyl)acrylate (2-1)

To a stirring solution of ethyl 2-(diethoxyphosphoryl) acetate (133.00 g, 591 mmol) in anhydrous THF (800 mL) was added sodium hydride (14.19 g, 591 mmol) portion wise at 0° C. After stirring for 90 min at 0° C., 4-bromo-3-fluorobenzaldehyde (80.00 g, 394 mmol) was added dropwise, and the resulting mixture was stirred at 0° C. for 3 hr. The reaction was then quenched with water carefully, and the resulting mixture was acidified with 1N HCl to pH=7. The mixture was partitioned between water and EtOAc, the layers were separated and the aqueous layer was extracted with EA two times. The combined organic layers were concentrated in vacuo to afford a residue, which was purified by column chromatography over silica gel (eluting with PE:EA=50:1) to give compound 2-1.

Step B: ethyl 3-(4-bromo-3-fluorophenyl)propanoate (2-2)

A mixture of compound 2-1 (83.00 g, 304 mmol) and Rh(PPh)$_3$Cl (8.44 g, 9.12 mmol) in THF (400 mL) and t-BuOH (400 mL) was stirred overnight at 40° C. under a H$_2$ atmosphere (50 psi). After filtration, the reaction mixture was concentrated in vacuo and the resulting residue was purified by silica gel column chromatography (eluting with PE:EA=50:1) to give compound 2-2.

Step C: 2-(4-bromophenyl)acetonitrile (2-3)

A mixture of compound 2-2 (45.00 g, 164 mmol) and CF$_3$SO$_3$H (300 mL) was stirred at 100° C. for 16 hr. The reaction mixture was cooled to room temperature, poured into water (500 mL) and the resulting mixture was filtered to give a brown solid, which was purified by column chromatography over silica gel (eluting with PE:EA=10:1 to 5:1) to give compound 2-3.

Step D: ethyl 6-fluoro-3-oxo-2,3-dihydro-1H-indene-5-carboxylate (2-4)

A mixture of compound 2-3 (30.00 g, 131 mmol), sodium acetate (21.49 g, 262 mmol) and PdCl$_2$(dppf) (4.79 g, 6.55 mmol) in EtOH (500 mL) was heated to 80° C. for 16 hr under CO atmosphere (55 psi). After cooling to room temperature, the mixture was filtered and the insoluble part was removed. The filtrate was concentrated to afford a residue, which was partitioned between EtOAc and water. The organic layer was separated and the aqueous layer was extracted with EtOAc twice. The combined organic layers were washed with water, dried over Na$_2$SO$_4$ and concentrated in vacuo to obtain a crude product, which was purified by column chromatography over silica gel (eluting with PE:EA=10:1) to give compound 2-4.

Step E: ethyl 3-((tert-butyldimethylsilyl)oxy)-6-fluoro-1H-indene-5-carboxylate (2-5)

To a solution of compound 2-4 (15.00 g, 67.5 mmol) and triethylamine (20.49 g, 203 mmol) in THF (150 mL) in an ice bath was added tert-butyldimethylsilyl trifluoromethanesulfonate (35.71 g, 135 mmol) dropwise. The mixture was stirred at 0° C. for 2 hours, then aqueous NH$_4$Cl was added to the reaction. The aqueous layer was separated and extracted with EtOAc twice. Then the combined organic layers were concentrated in vacuo to give a residue, which was purified by column chromatography over silica gel (eluting with PE:EA=10:1) to give compound 2-5.

Step F: ethyl 3-((tert-butyldimethylsilyl)oxy)-6-fluoro-1, 1-dimethyl-1H-indene-5-carboxylate (2-6)

To a solution of compound 2-5 (17.05 g, 50.5 mmol) and iodomethane (64.50 g, 455 mmol) in THF (170 mL) and RMPA (17 mL) at −78° C. was added LHMDS (1N in THF, 116 mL, 116 mmol) dropwise under a nitrogen atmosphere. After completion of the addition, the mixture was stirred at −78° C. for 2 hours. Then the reaction mixture was quenched with a saturated aqueous solution of $NH_4Cl$. The resulting mixture was extracted with EtOAc three times. The combined organic layers were washed with brine, dried over $Na_2SO_4$ and concentrated in vacuo to afford crude compound 2-6, which was used in the next step without further purification.

Step G: ethyl 6-fluoro-1,1-dimethyl-3-oxo-2,3-dihydro-1H-indene-5-carboxylate (2-7)

To a solution of compound 2-6 (38.03 g, 31.3 mmol) in DCM (150 mL), was added TFA (10 mL) dropwise at 0° C. The mixture was stirred for 2 hours while warming to room temperature. Then aqueous $NaHCO_3$ was added to the reaction mixture to quench the reaction. The aqueous layer was separated and extracted with EtOAc twice. The organic layer was separated and concentrated to give a residue, which was purified by column chromatography over silica gel (eluting with PE:EA=5:1 to give intermediate 2-7.

Intermediate 3-6

Methyl 3-(2-(trifluoromethyl)phenyl)-2,3-dihydro-1H-indene-5-carboxylate (3-6)

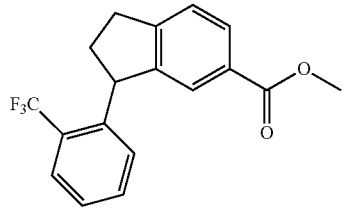

3-6

Step A: 6-bromo-1-(2-(trifluoromethyl)phenyl)-2,3-dihydro-1H-inden-1-ol (3-2)

To a solution of 1-bromo-2-(trifluoromethyl)benzene (495 mg, 2.2 mmol) in dry THF (10 mL) was added n-BuLi (2.5 M in hexane, 0.88 mL, 2.2 mmol) dropwise at −78° C. under a nitrogen atmosphere. After completion of the addition, the mixture was stirred at −78° C. for an hour. Then a solution of 7-bromo-1-indanone 3-1 (422 mg, 2.0 mmol) in dry THF (5 mL) was added dropwise and the reaction mixture was stirred at −78° C. for 3 hr. Then saturated aqueous $NH_4Cl$ was added to the reaction and the mixture was extracted with EtOAc three times. The combined organic layers were washed with brine, dried over $Na_2SO_4$ and concentrated to afford a residue, which was purified by column chromatography over silica gel (eluting with PE:EA=10:1 to 5:1) to give compound 3-2.

Step B: 3-hydroxy-3-(2-(trifluoromethyl)phenyl)-2,3-dihydro-1H-indene-5-carboxylic acid (3-3)

To a stirring solution of compound 3-2 (1.0 g, 2.8 mmol) in dry THF (20 mL) was added n-BuLi (2.5 M in hexane, 3.4 mL, 8.4 mmol) dropwise at −78° C. under a nitrogen atmosphere. After completion of the addition, the mixture was stirred at −78° C. for 2 hours, then carbon dioxide was bubbled into the mixture for 30 min. The mixture was stirred at 78° C. for 1 h, then warmed to −20° C. slowly. The reaction mixture was quenched with water and acidified with diluted HCl (1N) to pH=2. The resulting mixture was extracted with EtOAc three times. The combined organic layers were washed with brine, dried over $Na_2SO_4$ and concentrated to afford a residue, which was purified by column chromatography over silica gel (eluting with PE:EA=10:1 to 5:1) to obtain compound 3-3.

Step C: methyl 3-hydroxy-3-(2-(trifluoromethyl)phenyl)-2,3-dihydro-1H-indene-5-carboxylate (3-4)

To a mixture of compound 3-3 (318 mg, 0.99 mmol) in DMF (6 mL) was added $K_2CO_3$ (178 mg, 1.98 mmol) in one portion at 0° C., followed by MeI (282 mg, 20 mmol) in one portion. The resulting mixture was stirred for 1 h, then warmed to room temperature over 2 h. The mixture was poured into water, and the resulting mixture was extracted with EtOAc (15 mL) three times. The combined organic layers were washed with water, brine, dried over $Na_2SO_4$ and concentrated in vacuo to afford crude compound 3-4, which was used in the next step without purification. MS (ESI) m/e (M+H⁺): 319.3 (−17).

Step D: methyl 3-(2-(trifluoromethyl)phenyl)-1H-indene-5-carboxylate (3-5)

A solution of compound 3-4 (317 mg, 0.94 mmol) and $Et_3SiH$ (274 mg, 2.36 mmol) in dry DCM (5 mL) was stirred at room temperature for 30 min. The mixture was cooled to 0° C. and TFA (2 mL) was added in one portion. The resulting mixture was warmed to room temperature over one hour. Then saturated aqueous $NaHCO_3$ was added to neutralize the reaction and the mixture was extracted with EtOAc three times. The combined organic layers were washed with brine, dried over $Na_2SO_4$ and concentrated in vacuo to afford a residue, which was purified by column chromatography over silica gel (eluting with PE:EA=10:1) to obtain compound 3-5. MS (ESI) m/e (M+H⁺): 319.3.

Step E: methyl 3-(2-(trifluoromethyl)phenyl)-2,3-dihydro-1H-indene-5-carboxylate (3-6)

Palladium (10%) on carbon (20 mg) was added to a solution of compound 3-5 (120 mg) in MeOH (3 mL) and THF (3 mL) and the resulting mixture was stirred at 25° C. under 1 atm of $H_2$ for 16 hr. The reaction was filtered over Celite™ pad and the filtrate was concentrated in vacuo to afford intermediate 3-6, which was used in other steps without purification. MS (ESI) (ESI) m/e (M+H⁺): 321.1.

Intermediate 4-4

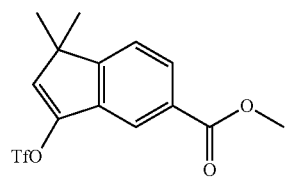

4-4

Step A: 6-bromo-3,3-dimethyl-2,3-dihydro-1H-inden-1-one (4-2)

A mixture of bromobenzene (15 g, 0.1 mol) and 3-methylbut-2-enoic acid 4-1 (10 g, 0.1 mol) in TsOH (80 mL) was heated to 100° C. and stirred for 3 hours. The resulting reaction mixture was cooled, and ice-water (1.5 L) was added to quench the reaction. The resulting mixture was extracted with DCM three times. The combined organic layers were washed with brine, dried over $Na_2SO_4$ and concentrated in vacuo to afford a residue, which was purified by silica gel chromatography (eluting with PE:EA=4:1) to obtain compound 4-2.

Step B: methyl 1,1-dimethyl-3-oxo-2,3-dihydro-1H-indene-5-carboxylate (4-3)

To a mixture of compound 4-2 (2 g, 8.4 mmol) and Pd(dppf)Cl$_2$ (0.31 g, 0.42 mmol) in DMF (15 mL) and MeOH (15 mL) was added Et$_3$N (4.3 g, 42.0 mmol). The mixture was then heated at 80° C. for 24 hr under a CO atmosphere (55 Psi). After cooling to room temperature, the mixture was filtered and the insoluble part was removed. The filtrate was concentrated to afford a residue, which was partitioned with EA and water. The aqueous layer was separated and extracted with EA twice. The combined EA layers were washed with water, dried over $Na_2SO_4$ and concentrated in vacuo to obtain the crude product, which was purified by flash chromatography over silica gel (eluting with PE:EA=5:1) to afford compound 4-3.

Step C: methyl 1,1-dimethyl-3-(((trifluoromethyl)sulfonyl)oxy)-1H-indene-5-carboxylate (4-4)

To a solution of compound 4-3 (110 mg, 0.5 mmol) in dry THF (6 mL) was added KHMDS (1 M in THF, 0.75 mL, 0.75 mmol) dropwise at −78° C. under a nitrogen atmosphere. The mixture was stirred for 2 hours, then Tf$_2$NPh (268 mg, 0.75 mmol) was added. The reaction mixture was then allowed to warm to room temperature and stirred for 16 hr. Then the mixture was quenched with water and neutralized with an aqueous solution of HCl (2N) to pH=7. The organic layer was isolated, and the aqueous layer was separated and extracted with EA two times. The combined organic layers were washed with brine, dried over $Na_2SO_4$ and concentrated in vacuo to afford a residue, which was purified by silica gel preparative TLC (eluting with PE:EA=6:1) to give intermediate 4-4.

Intermediates (5-4) and (5-5)

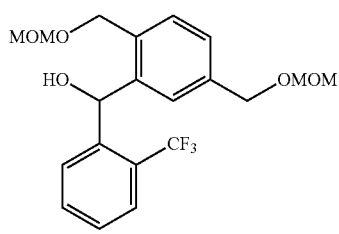

5-4

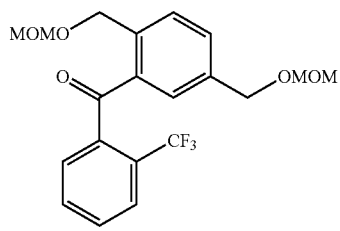

5-5

Step A: 2-bromoterephthalic acid (5-1)

To a mixture of 3-bromo-4-methyl-benzoic acid (10.0 g, 46.5 mmol) in t-BuOH (50 mL) and H$_2$O (50 ml), was added KMnO$_4$ (43 g, 5.7 eq) at room temperature. The mixture was refluxed overnight. After cooling to 50° C., the hot reaction was filtrated and the residue was washed with H$_2$O. The filtrate was acidified to pH=2 with concentrated HCl, and then concentrated to 100 ml and extracted with EtOAc (100 mL) twice. The combined organic layers were washed with water, brine, dried over Na$_2$SO$_4$ and concentrated in vacuo to afford compound 5-1 which was used in the next step without further purification.

Step B: (2-bromo-1,4-phenylene)dimethanol (5-2)

To a suspension of compound 5-1 (7.2 g, 29.3 mmol) in THF (80 mL) was added BH$_3$ (6.0 ml, 2.0 eq) dropwise, then the mixture was refluxed for 6 hr. The reaction was quenched with MeOH (anhydrous) at 0° C. slowly, and then concentrated in vacuo to afford compound 5-2, which was used in the next step without further purification. MS (ESI) m/e (M+H$^+$): 199.2/201.1.

Step C: 2-bromo-1,4-bis((methoxymethoxy)methyl)benzene (5-3)

To a mixture of compound 5-2 (2.5 g, 11.52 mmol) and DIPEA (4.47 g, 3.0 eq) in DMF (15 mL) was added MOMCl (2.32 g, 3.0 eq) dropwise at 0° C. under nitrogen atmosphere. The mixture was stirred at room temperature overnight, then quenched with saturated aqueous NH$_4$Cl. The mixture was extracted with EtOAc (30 ml) twice. The combined organic layers were washed with water, brine, dried over Na$_2$SO$_4$ and concentrated in vacuo to obtain a residue, which was purified by chromatography over silica gel (eluting with PE:EA=3:1) to afford compound 5-3.

Step D: (2,5-bis((methoxymethoxy)methyl)phenyl)(2-(trifluoromethyl)phenyl)methanol (5-4)

To a solution of compound 5-3 (2.5 g, 8.24 mmol) in anhydrous THF (15 mL) was added n-BuLi (2.5 M in hexanes, 4.26 ml, 1.3 eq) at −78° C. under a N$_2$ atmosphere. The mixture was stirred at −20° C. for 2 hours, then 2-(trifluoromethyl)benzaldehyde (1.71 g, 1.2 eq) was added dropwise. The mixture was stirred at −20° C. for 2 hr, then quenched with saturated aqueous NH$_4$Cl, diluted with EtOAc, and extracted with EtOAc twice. The combined organic layers were washed with water, brine, dried over Na$_2$SO$_4$ and concentrated in vacuo to obtain a residue, which was purified by chromatography over silica gel (eluting with PE:EA=3:1) to afford intermediate 5-4. MS (ESI) m/e (M+H$^+$): 400.0.

Step E: (2,5-bis((methoxymethoxy)methyl)phenyl) (2-(trifluoromethyl)phenyl)methanone (5-5)

To a solution of intermediate 5-4 (1.0 g, 2.5 mmol) in DCM (10 mL) was added DMP (1.26 g, 1.3 eq) at 0° C. The mixture was stirred at room temperature for 2 hours. The resulting mixture was filtered over Celite™, washed with DCM, then concentrated in vacuo to obtain a residue, which was purified by chromatography over silica gel (eluting with PE:EA=2:1) to afford intermediate 5-5. MS (ESI) m/e (M+Na$^+$): 421.0.

Example 1

(5aR,6S,6aS)-3-((3'-(2-(trifluoromethyl)phenyl)-2', 3'-dihydrospiro[cyclopropane-1,1'-inden]-5'-yl) methoxy)-5,5a,6,6a-tetrahydrocyclopropa[4,5]cyclopenta[1,2-c]pyridine-6-carboxylic acid (compound A1-8)

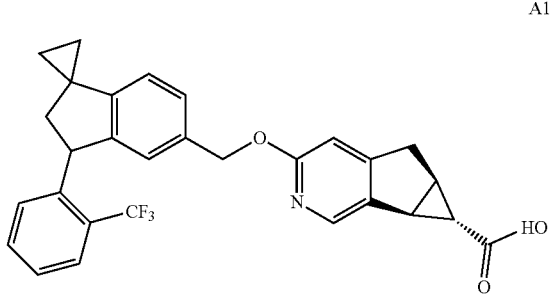

A1-8

Step A: methyl 1-oxo-3-(2-(trifluoromethyl)phenyl)-1H-indene-5-carboxylate (A1-1)

To a mixture of compound 3-5 (1.0 g, 3.14 mmol) in 1,4-dioxane (15 mL) was added SeO$_2$ (1.047 g, 9.4 mmol), and the resulting mixture was heated to reflux for 72 hours. After cooling to room temperature, MeOH was added to quench the reaction. The mixture was stirred for 30 min., and then filtered through Celite®. The filtrate was concentrated in vacuo to afford to a residue, which was purified by chromatography over silica gel to afford compound A1-1. MS (ESI) m/e (M+H$^+$): 333.1

Step B: methyl 1-oxo-3-(2-(trifluoromethyl)phenyl)-2,3-dihydro-1H-indene-5-carboxylate (A1-2)

Rh(PPh$_3$)$_3$Cl (118 mg, 1.27 mmol) was added to a solution of compound A1-1 (848 mg, 2.55 mmol) in a co-solvent of t-BuOH (10 mL) and THF (10 mL), and the resulting mixture was stirred at 30° C. under a H$_2$ balloon atmosphere for 48 hr. The reaction was then concentrated in vacuo to afford a residue, which was purified by chromatography over silica gel to obtain compound A1-2. MS (ESI) m/e (M+H$^+$): 335.1.

Step C: methyl 1-methylene-3-(2-(trifluoromethyl) phenyl)-2,3-dihydro-1H-indene-5-carboxylate (A1-3)

Diiodomethane (400 mg, 1.5 mmol) was added at 25° C. to a stirring suspension of zinc powder (176 mg, 2.7 mmol) in THF (2 mL) under a nitrogen atmosphere. After 30 min, a dichloromethane solution of TiCl$_4$ (57 mg, 0.3 mmol, 0.3 mL) was added at 0° C., and the resulting dark brown mixture was stirred at 25° C. for 30 min. Then a solution of compound A1-2 (100 mg, 0.3 mmol) in THF (1 mL) was then added dropwise to the reaction. After stirring at 25° C. for 30 min, the reaction was diluted with EtOAc (10 mL). The organic layer was separated and washed with 1N HCl (5 mL) and brine, dried over Na$_2$SO$_4$ and concentrated in vacuo. The resulting residue was purified by chromatography over silica gel to afford compound A1-3. MS (ESI) m/e (M+H$^+$): 333.1.

Step D: methyl 3'-(2-(trifluoromethyl)phenyl)-2',3'-dihydrospiro[cyclopropane-1,1'-inden]-5'-carboxylate (A1-4)

A solution of diethylzinc (1.0 M, 1.2 mL, 1.2 mmol) was added to a round bottom flask filled with DCM (2 mL) and the mixture was cooled to 0° C. Then TFA (137 mg, 1.2 mmol) in DCM (0.3 mL) was added to the reaction and the reaction was stirred at 0° C. for 15 min. To the cooled reaction mixture was added CH$_2$I$_2$ (322 mg, 1.2 mmol) in DCM (0.3 mL), and the mixture stirred for an additional 15 min at 0° C. Then a solution of compound A1-3 (50 mg, 0.15 mmol) in DCM (0.3 mL) was added to the reaction. The reaction was stirred at 0° C. for 15 min, and then allowed to warmed to room temperature over 14 hr. The reaction was quenched with saturated aqueous NH$_4$Cl (10 mL) and diluted with DCM (10 mL). The layers were separated and the aqueous layer was extracted with DCM (10 mL) twice. The combined DCM layers were washed with brine, dried over Na$_2$SO$_4$ and concentrated in vacuo to afford a residue, which was purified by preparative TLC over silica gel to obtain compound A1-4. MS (ESI) m/e (M+H$^+$–18): 347.1.

Step E: (3'-(2-(trifluoromethyl)phenyl)-2',3'-dihydrospiro[cyclopropane-1,1'-inden]-5'-yl)methanol (A1-5)

To a suspension of LiAlH$_4$ (46 mg, 1.2 mmol) in dry THF (2 mL) at 0° C. was added a solution of crude A1-4 (68 mg, 0.2 mmol) in THF (1 mL) dropwise. After completion of the addition, the reaction mixture was stirred at this temperature for 1 hour. The reaction was then quenched with saturated aqueous NH$_4$Cl and extracted with EtOAc twice. The combined EtOAc layers were washed with brine, dried over Na$_2$SO$_4$ and concentrated in vacuo to afford crude compound A1-5, which was used in the next step without purification. MS (ESI) m/e (M+H$^+$–18): 301.1 (–17).

Step F: 5'-(bromomethyl)-3'-(2-(trifluoromethyl) phenyl)-2',3'-dihydrospiro[cyclopropane-1,1'-indene] (A1-6)

To a solution of crude compound A1-5 (61 mg, 0.19 mmol) in dry THF (2 mL) at 0° C. was added PBr$_3$ (41 mg, 0.15 mmol) dropwise. The reaction solution was stirred at 0° C. for 1 hour, then warmed to 20° C. and stirred for another 3 hr. The mixture was then quenched with water, and saturated aqueous NaHCO$_3$ was added to neutralize the mixture to pH=7. The reaction was extracted with EtOAc twice. The combined EtOAc layers were washed with brine, dried over anhydrous Na$_2$SO$_4$, filtered and concentrated in vacuo to afford a residue, which was purified by preparative TLC over silica gel to obtain compound A1-6.

Step G: (5aR,6S,6aS)-ethyl 3-((3'-(2-(trifluoromethyl)phenyl)-2',3'-dihydrospiro[cyclopropane-1,1'-inden]-5'-yl)methoxy)-5,5a,6,6a-tetrahydrocyclopropa[4,5]cyclopenta[1,2-c]pyridine-6-carboxylate (A1-7)

A mixture of compound A1-6 (40 mg, 0.10 mmol), intermediate 1-9 (27 mg, 0.12 mmol) and Ag$_2$CO$_3$ (72 mg, 0.26 mmol) in toluene (1.5 mL) was heated to 100° C. for 2 hr. The reaction was then filtered and the filtrate was concentrated to give a residue, which was purified by preparative TLC over silica gel to afford compound A1-7. MS (ESI) m/e (M+H$^+$): 520.2.

Step H: (5aR,6S,6aS)-3-((3'-(2-(trifluoromethyl)phenyl)-2',3'-dihydrospiro[cyclopropane-1,1'-inden]-5'-yl)methoxy)-5,5a,6,6a-tetrahydrocyclopropa[4,5]cyclopenta[1,2-c]pyridine-6-carboxylic acid (A1-8)

To a mixture of compound A1-7 (40 mg, 0.077 mmol) in THF (1 mL), MeOH (1 mL) and H$_2$O (1 mL) was added NaOH (24 mg, 0.8 mmol), and the reaction mixture was stirred at room temperature for 2 hr. The reaction was then acidified with HCl (2 N) to pH=7, and extracted with EtOAc (10 mL) twice. The combined organic layers were washed with water, brine, dried over Na$_2$SO$_4$ and concentrated in vacuo to afford compound A1-8. $^1$H NMR (400 MHz, MeOD-d$_4$) δ: 7.90 (s, 1H), 7.57 (d, J=8.0 Hz, 1H), 7.435 (t, J=7.6 Hz, 1H), 7.25 (t, J=7.6 Hz, 1H), 7.16 (d, J=7.6 Hz, 1H), 7.10 (d, J=8.0 Hz, 1H), 6.79 (s, 1H), 6.68 (d, J=8.0 Hz, 1H), 6.51 (s, 1H), 5.09 (m, 2H), 4.82 (t, J=7.8 Hz, 1H), 3.12 (dd, J=6.3, 18.4 Hz, 1H), 2.91 (d, J=18.4 Hz 1H), 2.81 (d, J=5.2 Hz, 1H), 2.49 (dd, J=9.0, 12.9 Hz, 1H), 2.34 (m, 1H), 2.06 (dd, J=7.0, 12.9 Hz, 1H), 1.07-0.93 (m, 3H), 0.86-0.76 (m, 2H). MS (ESI) m/e (M+H$^+$): 492.1.

Example 3

(5aR,6S,6aS)-3-((1,1-dimethyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (Compound A2-6)

A2-6

Step A: methyl 1,1-dimethyl-3-(2-(trifluoromethyl)phenyl)-1H-indene-5-carboxylate (A2-1)

To a stirred solution of compound 3-5 (0.1 g, 0.31 mmol) in THF (2 ml) and HMPA (0.4 ml) at −78° C. under a nitrogen atmosphere was added KHMDS (1.0 M in THF, 0.93 mL, 0.93 mmol) dropwise. After completion of the addition, the mixture was stirred for 2 hours, then a solution of MeI (107 mg, 0.75 mmol) in THF (0.2 mL) was added dropwise. The resulting mixture was stirred at −78° C. for 1 hr, then warmed to 0° C. slowly and stirred for another 30 min. The reaction was quenched with saturated aqueous NH$_4$Cl. Then the mixture was extracted with EtOAc three times. The combined organic layers were washed with brine, dried over Na$_2$SO$_4$ and concentrated in vacuo to afford a residue, which was purified by preparative TLC over silica gel (eluting with PE:EA=4:1) to obtain compound A2-1. MS (ESI) m/e (M+H$^+$): 347.2

TABLE 1

Example 2 (Compound A1-9) was prepared in a similar manner to Example 1 (compound A1-8) using the appropriate intermediates and commercially available materials, and including procedures described across this application when necessary.

| Example | Structure | M.W. | Compound Name | LC/MS (ESI) observed [M + 1]+ |
| --- | --- | --- | --- | --- |
| 2 | (Compound A1-9) | 479.5 | (5aR,6S,6aS)-3-((1-oxo-3-(2-(trifluoromethyl)-phenyl)-2,3-dihydro-1H-inden-5-yl)methoxy)-5,5a,6,6a-tetrahydro-cyclopropa[4,5]cyclopenta[1,2-c]pyridine-6-carboxylic acid | 480.2 |

Step B: methyl 1,1-dimethyl-3-(2-(trifluoromethyl)phenyl)-2,3-dihydro-1H-indene-5-carboxylate (A2-2)

Palladium (10%) on carbon (20 mg) was added to a solution of compound A2-1 (100 mg) in a mixture of MeOH (4 mL) and THF (2 mL). The resulting mixture was stirred at 25° C. under a $H_2$ balloon atmosphere for 16 hr. The reaction was then filtered over Celite™ and the filtrate was concentrated in vacuo to afford crude compound A2-2, which was used in the next step without purification. MS (ESI) m/e (M+H$^+$): 349.1.

Step C: (1,1-dimethyl-3-(2-(trifluoromethyl)phenyl)-2,3-dihydro-1H-inden-5-yl)methanol (A2-3)

To a suspension of LiAlH$_4$ (58 mg, 1.5 mmol) in dry THF (2 mL) at 0° C. was added a solution of compound A2-2 (105 mg, 0.3 mmol) in THF (2 mL) dropwise. After completion of the addition, the reaction mixture was stirred for 1 hr, then saturated aqueous NH$_4$Cl was added and the mixture was extracted with EtOAc twice. The combined organic layers were washed with brine, dried over Na$_2$SO$_4$ and concentrated in vacuo to afford compound A2-3, which was used in the next step without purification. MS (ESI) m/e (M+H$^+$-18): 303.1 (-17).

Step D: 5-(bromomethyl)-1,1-dimethyl-3-(2-(trifluoromethyl)phenyl)-2,3-dihydro-1H-indene (A2-4)

To a solution of crude compound A2-3 (32 mg, 0.1 mmol) in dry THF (2 mL) at 0° C. was added PBr$_3$ (23 mg, 0.08 mmol) dropwise. The reaction solution was stirred at 0° C. for 1 hr then warm to at 20° C. and stirred for another 3 hrs. The mixture was quenched with water, diluted with saturated aqueous NaHCO$_3$ until pH=7, and extracted with EtOAc twice. The combined organic layers were washed with brine, dried over anhydrous Na$_2$SO$_4$, and concentrated in vacuo to afford a residue, which was purified by preparative TLC over silica gel (eluting with PE:EA=10:1) to obtain compound A2-4.

Step E: (5aR,6S,6aS)-ethyl 3-((1,1-dimethyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylate (A2-5)

A mixture of compound A2-4 (14 mg, 0.037 mmol), intermediate 1-9 (8 mg, 0.037 mmol) and Ag$_2$CO$_3$ (25 mg, 0.091 mmol) in toluene (0.5 mL) was heated at 100° C. for 2 hrs. The reaction was filtered and the filtrate was concentrated in vacuo to give a residue, which was purified by preparative TLC over silica gel (eluting with PE:EA=4:1) to afford compound A2-5. MS (ESI) m/e (M+H$^+$): 522.2.

Step F: (5aR,6S,6aS)-3-((1,1-dimethyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (A2-6)

To a mixture of A2-5 (12 mg, 0.023 mmol) in THF (0.5 mL), MeOH (0.5 mL) and H$_2$O (0.5 mL) was added NaOH (10 mg, 0.25 mmol), and the resulting mixture was stirred at room temperature for 2 hrs. The resulting solution was acidified by HCl (2 N) to pH=7, and extracted with EtOAc (10 mL) twice. The combined organic layers were washed with water, brine, dried over Na$_2$SO$_4$ and concentrated in vacuo to afford compound A2-6. $^1$H NMR (400 MHz, MeOD-d$_4$) δ: 7.89 (s, 1H), 7.60 (d, J=7.8 Hz, 1H), 7.39 (t, J=8.0 Hz, 1H), 7.28 (t, J=8.0 Hz, 1H), 7.20 (d, J=8.0 Hz, 1H), 7.14 (d, J=8.0 Hz, 1H), 7.04 (m, 1H), 6.67 (br. s., 1H), 6.51 (s, 1H), 5.11-5.04 (m, 2H), 4.69 (t, J=8.8 Hz, 1H), 3.11 (dd, J=4.9, 18.6 Hz, 1H), 2.90 (d, J=18.4 Hz, 1H), 2.79 (d, J=5.1 Hz, 1H), 2.42-2.27 (m, 2H), 1.81 (t, J=11.3 Hz, 1H), 1.34 (s, 3H), 1.15 (s, 3H), 1.02 (br. s., 1H). MS (ESI) m/e (M+H$^+$): 494.2.

Example 4

(5aR,6S 6aS)-3-(1,1-dimethyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (Compound A3-5)

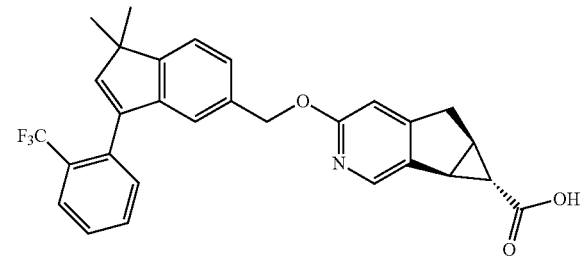

A3-5

Step A: (1,1-dimethyl-3-(2-(trifluoromethyl)phenyl)-1H-inden-5-yl)methanol (A3-2)

To a suspension of LiAlH$_4$ (53 mg, 1.4 mmol) in dry THF (4 mL) at 0° C. was added a solution of compound A2-1 (100 mg, 0.3 mmol) in THF (2 mL) dropwise. After completion of the addition, the reaction mixture was stirred at this temperature for 1 h. Saturated aqueous NH$_4$Cl was then added to quench the reaction and the mixture was extracted with EtOAc twice. The combined organic layers were washed with brine, dried over Na$_2$SO$_4$ and concentrated in vacuo to afford compound A3-2, which was used in the next step without purification.

Step B: 5-(bromomethyl)-1,1-dimethyl-3-(2-(trifluoromethyl)phenyl)-2,3-dihydro-1H-indene (A3-3)

To a solution of crude compound A3-2 (90 mg, 0.3 mmol) in dry THF (5 mL) at 0° C. was added PBr$_3$ (80 mg, 0.3 mmol) dropwise. The reaction was stirred for 1 h then warmed to at 20° C. and stirred for another 3 hrs. The final mixture was quenched with water, neutralized with saturated aqueous NaHCO$_3$ to pH=7, and extracted with EtOAc twice. The combined organic layers were washed with brine, dried over Na$_2$SO$_4$, and concentrated in vacuo to afford a residue, which was purified by preparative TLC over silica gel to obtain compound A3-3.

Step C: (5aR,6S,6aS)-ethyl 3-((1,1-dimethyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylate (A3-4)

A mixture of compound A3-3 (80 mg, 0.21 mmol), intermediate 1-9 (46 mg, 0.21 mmol) and Ag$_2$CO$_3$ (173 mg, 0.63 mmol) in toluene (0.3 mL) was heated to 100° C. for 2 hrs. The reaction was filtered and the filtrate was concentrated to give a residue, which was purified by preparative TLC over silica gel to afford compound A3-4. MS (ESI) m/e (M+H$^+$): 520.22.

Step D: (5aR,6S,6aS)-3-((1,1-dimethyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (A3-5)

To a mixture of compound A3-4 (60 mg, 0.12 mmol) in THF (2 mL), MeOH (2 mL) and H$_2$O (2 mL) was added NaOH (23 mg, 0.58 mmol), and the resulting mixture was stirred at room temperature for 2 hrs. The final mixture was acidified by HCl (2 N) to pH=7, and extracted with EtOAc (10 mL) twice. The combined organic layers were washed with water, brine, dried over Na$_2$SO$_4$ and concentrated in vacuo. The residue was purified by preparative HPLC (on a GILSON 281 instrument fitted with a YMC-Actus Triart C18 (150*20 mm*5 um) using water and acetonitrile as the eluents. Mobile phase A: water, mobile phase B: acetonitrile. Gradient: 25-54% B, 0-10 min; 100% B, 10.5-12.5 min; 5% B, 13-15 min) to afford compound A3-5. $^1$H NMR (400 MHz, MeOD-d$_4$) δ: 8.14 (s, 1H), 7.80 (d, J=8.0 Hz, 1H), 7.66 (t, J=7.6 Hz, 1H), 7.55 (t, J=7.6 Hz, 1H), 7.42 (t, J=9.2 Hz, 2H), 7.34 (d, J=8.0 Hz, 1H), 7.18 (s, 1H), 6.95 (s., 1H), 6.34 (s, 1H), 5.32 (s, 2H), 3.39 (dd, J=4.9, 18.6 Hz, 1H), 3.18 (d, J=18.4 Hz, 1H), 3.01 (d, J=4.8 Hz, 1H), 2.54-2.50 (m, 1H), 1.38 (s, 6H), 1.27 (s., 1H). MS (ESI) m/e (M+H$^+$): 492.17.

Example 5

(5aR,6S,6aS)-3-((1-methyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (Compound A4-5)

A4-5

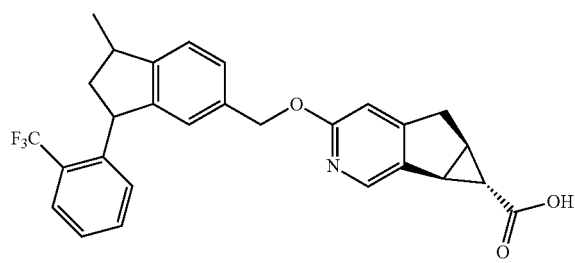

Step A: methyl 1-methyl-3-(2-(trifluoromethyl)phenyl)-2,3-dihydro-1H-indene-5-carboxylate (A4-1)

To a solution of compound A1-3 (44 mg, 0.13 mmol) in MeOH (5 mL) and THF (5 mL) was added 10% Pd/C (40 mg) at room temperature, and the mixture was stirred under H$_2$ (1 atm) for 2 h. The reaction was filtered and concentrated in vacuo to give compound A4-1.

Step B: (1-methyl-3-(2-(trifluoromethyl)phenyl)-2,3-dihydro-1H-inden-5-yl)methanol (A4-2)

To a suspension of LiAlH$_4$ (30 mg, 0.789 mmol) in dry THF (2 mL) at 0° C. was added a solution of crude compound A4-1 (35 mg, 0.104 mmol) in THF (1 mL) dropwise. After completion of the addition, the reaction mixture was stirred at this temperature for 1 hour. Saturated aqueous NH$_4$Cl was added to quench the reaction and the mixture were extracted with EtOAc twice. The EtOAc layers were washed with brine, dried over Na$_2$SO$_4$ and concentrated in vacuo to afford crude compound A4-2, which was used in the next step without purification.

Step C: 5-(bromomethyl)-1-methyl-3-(2-(trifluoromethyl)phenyl)-2,3-dihydro-1H-indene (A4-3)

To a solution of crude A4-2 (32 mg, 0.104 mmol) in dry THF (2 mL) at 0° C. was added PBr$_3$ (24 mg, 0.09 mmol) dropwise. The reaction solution was stirred at 0° C. for 1 hour, then warmed to at 20° C. and stirred for another 3 hr. The reaction was then quenched with water, neutralized with saturated aqueous NaHCO$_3$ to pH=7, and extracted with EtOAc twice. The combined organic layers were washed with brine, dried over anhydrous Na$_2$SO$_4$, and concentrated in vacuo to afford a residue, which was purified by preparative TLC over silica gel to obtain compound A4-3. MS (ESI) m/e (M-Br): 289.1.

Step D: (5aR,6S,6aS)-ethyl 3-((1-methyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylate (A4-4)

A mixture of compound A4-3 (36 mg, 0.10 mmol), intermediate 1-9 (21.9 mg, 0.1 mmol) and Ag$_2$CO$_3$ (55 mg, 0.2 mmol) in toluene (1.5 mL) was heated at 100° C. for 2 hr. The reaction was then filtered and the filtrate was concentrated in vacuo to give a residue, which was purified by HPLC to afford compound A4-4. MS (ESI) m/e (M+H$^+$): 508.2.

Step E: (5aR,6S,6aS)-3-((1-methyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (A4-5)

To a mixture of A4-4 (30 mg, 0.059 mmol) in THF (1 mL), MeOH (1 mL) and H$_2$O (1 mL) was added NaOH (24 mg, 0.8 mmol). The resulting mixture was stirred at room temperature for 2 hr, then acidified with HCl (2 N) to pH=7, and extracted with EtOAc (10 mL) twice. The combined organic layers were washed with water, brine, dried over Na$_2$SO$_4$ and concentrated in vacuo. The resulting residue was purified by preparative HPLC (on a GILSON 281 instrument fitted with a YMC-Actus Triart C18 (150*30 mm*5 um) using water and acetonitrile as the eluents. Mobile phase A: water, mobile phase B: acetonitrile. Gradient: 45-65% B, 0-10 min; 100% B, 10.5-12.5 min; 5% B, 13-15 min) to afford compound A4-5. $^1$H NMR (400 MHz, MeOD-d$_4$) δ: 8.06 (s, 1H), 7.71 (d, 1H), 7.51 (m, 1H), 7.39 (m, 1H), 7.31 (m, 2H), 7.18 (m, 1H), 6.90 (m, 1H), 6.80 (s, 1H), 5.24 (m, 2H), 4.61-4.66 (m, 1H), 3.25 (m, 2H), 3.08 (m, 1H), 2.95 (m, 1H), 2.75-2.85 (m, 1H), 2.5 (m, 1H), 1.6 (m, 1H), 1.4 (d, J=6.8 Hz, 2H),1.30 (d, J=7.2 Hz, 2H), 1.2 (s, 1H). MS (ESI) m/e (M+H$^+$): 480.2.

Example 6

(5aR,6S,6aS)-3-((3'-(2-(trifluoromethyl)phenyl)-2',3'-dihydrospiro[cyclobutane-1,1'-inden]-5'-yl)methoxy)-5,5a,6,6a-tetrahydrocyclopropa[4,5]cyclopenta[1,2-c]pyridine-6-carboxylic acid (Compound A5-6)

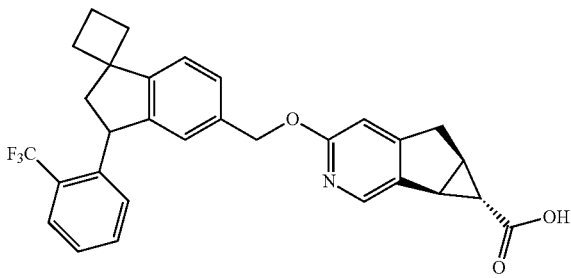

A5-6

Step A: methyl 3'-(2-(trifluoromethyl)phenyl)spiro[cyclobutane-1,1'-indene]-5'-carboxylate (A5-1)

To a solution of compound 3-5 (320 mg, 1 mmol) in THF/HMPA (4:1) (10 mL) at −78° C. was added KHMDS (1 M/L, 2.5 ml, 2.5 mmol) dropwise and the mixture was stirred for 2 hours. Then 1,3-dibromopropane (240 mg, 1.2 mmol) was then added into the reaction and the mixture was allowed to warm to room temperature overnight. The reaction was quenched with saturated aqueous NH$_4$Cl and stirred for 20 minutes. The mixture was then extracted with EtOAc, and the organic layers were concentrated to afford a residue, which was purified by HPLC to afford compound A5-1. MS (ESI) m/e (M+H$^+$): 359.1.

Step B: methyl 3'-(2-(trifluoromethyl)phenyl)-2',3'-dihydrospiro[cyclobutane-1,1'-indene]-5'-carboxylate (A5-2)

10% Pd/C (5 mg) was added to a solution of compound A5-1 (36 mg, 1 mmol) in dry MeOH (5 ml), and the resulting mixture was stirred at 30° C. under a H$_2$ (1 atm) for 24 hr. The reaction was then filtered and the filtrate was concentrated in vacuo to afford a residue, which was purified by preparative TLC over silica gel to afford compound A5-2.

Step C: (3'-(2-(trifluoromethyl)phenyl)-2',3'-dihydrospiro[cyclobutane-1,1'-inden]-5'-yl)methanol (A5-3)

To a suspension of LiAlH$_4$ (19 mg, 0.5 mmol) in dry THF (5 mL) at 0° C. was added a solution of compound A5-2 (36 mg, 0.1 mmol) in THF (5 mL) dropwise. After completion of the addition, the reaction mixture was stirred at 0° C. for 1 h. Then saturated aqueous NH$_4$Cl was added to quench the reaction and the mixture was extracted with EtOAc twice. The combined organic layers were washed with brine, dried over Na$_2$SO$_4$ and concentrated in vacuo to afford compound A5-3, which was used in the next step without purification. MS (ESI) m/e (M+H$^+$): 333.1.

Step D: 5'-(bromomethyl)-3'-(2-(trifluoromethyl)phenyl)-2',3'-dihydrospiro[cyclobutane-1,1'-indene] (A5-4)

To a solution of crude compound A5-3 (30 mg, 0.1 mmol) in dry THF (5 mL) at 0° C. was added PBr$_3$ (25 mg, 0.09 mmol) dropwise. The reaction solution was stirred at 0° C. for 1 hr, then warmed to 20° C. and stirred for another 3 hr. The reaction was quenched with water, neutralized with saturated aqueous NaHCO$_3$ to pH=7, and extracted with EtOAc twice. The combined organic layers were washed with brine, dried over anhydrous Na$_2$SO$_4$, and concentrated in vacuo to afford a residue, which was purified by preparative silica TLC to obtain compound A5-4. MS (ESI) m/e (M+H$^+$): 395.26.

Step E: (5aR,6S,6aS)-ethyl 3-((3'-(2-(trifluoromethyl)phenyl)-2',3'-dihydrospiro[cyclobutane-1,1'-inden]-5'-yl)methoxy)-5,5a,6,6a-tetrahydrocyclopropa[4,5]cyclopenta[1,2-c]pyridine-6-carboxylate (A5-5)

A mixture of compound A5-4 (32 mg, 0.08 mmol), intermediate 1-9 (21 mg, 0.09 mmol) and Ag$_2$CO$_3$ (56 mg, 0.20 mmol) in toluene (3 mL) was heated at 100° C. for 3 hr. The mixture was filtered and the filtrate was concentrated in vacuo to give crude compound A5-5, which was used in the next step without further purification. MS (ESI) m/e (M+H$^+$): 535.2.

Step F: (5aR,5S,6aS)-3-((3'-(2-(trifluoromethyl)phenyl)-2',3'-dihydrospiro[cyclobutane-1,1'-inden]-5'-yl)methoxy)-5,5a,6,6a-tetrahydrocyclopropa[4,5]cyclopenta[1,2-c]pyridine-6-carboxylic acid (A5-6)

To a mixture of compound A5-5 (4 mg, 0.08 mmol) in THF (1 mL), MeOH (1 mL) and H$_2$O (1 mL) was added NaOH (15 mg, 0.38 mmol). The reaction mixture was stirred at room temperature for 2 hr, then acidified with HCl (2 N) to pH=7, and extracted with EtOAc (10 mL) twice. The combined organic layers were washed with water, brine, dried over Na$_2$SO$_4$ and concentrated in vacuo to afford a crude product, which was purified by preparative HPLC (on a GILSON 281 instrument fitted with a Waters XSELECT C18 (150*30 mm*5 um) using water and acetonitrile as the eluents. Mobile phase A: water, mobile phase B: acetonitrile. Gradient: 41-61% B, 0-10 min; 100% B, 10.5-12.5 min; 5% B, 13-15 min) to obtain compound A5-6. $^1$H NMR (400 MHz, MeOD-d$_4$) δ: 8.11 (s, 1H), 7.69 (d, J=8.0 Hz, 1H), 7.55 (d, J=8.0 Hz, 3H), 7.45 (t, J=6.0 Hz, 1H); 7.40~7.32 (m, 2H), 7.10 (s, 1H), 7.02 (d, J=8 Hz, 1H), 6.84 (s, 1H), 5.28 (s, 2H); 4.67 (t, J=6 Hz, 1H), 3.39~3.32 (m, 1H), 3.19~3.14 (m, 1H), 3.00 (d, J=8.0 Hz, 1H), 2.86~2.81 (m, 1H); 2.64~2.60 (m, 1H); 2.53~2.49 (m, 1H), 2.32~2.26 (m, 1H), 2.15-2.05 (m, 5H), 1.25 (s, 1H). MS (ESI) m/e (M+H$^+$): 506.2.

Examples 7 and 8

Compounds A6-15 and A6-18

A6-15

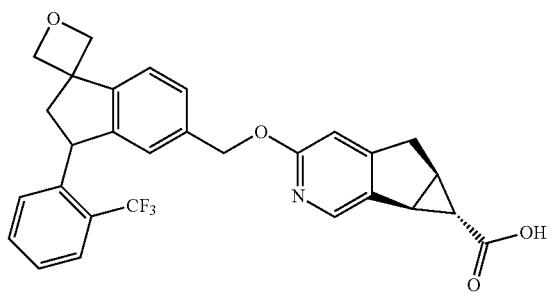

A6-18

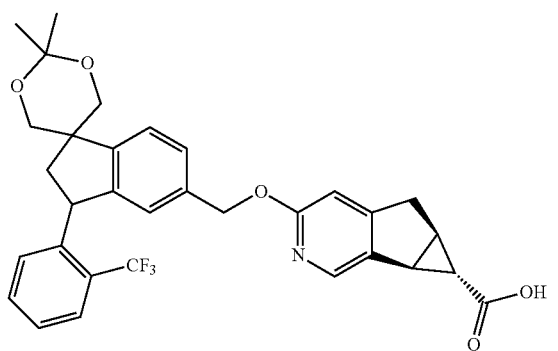

Step A: 6-bromo-1-(2-(trifluoromethyl)phenyl)-2,3-dihydro-1H-inden-1-ol (A6-1)

To a solution of 1-bromo-2-(trifluoromethyl)benzene (10 g, 47.4 mmol) in dry THF (100 mL) at −78° C. under a nitrogen atmosphere was added n-BuLi (2.5 M in hexane, 28.4 mL, 71 mmol) dropwise. The mixture was stirred at −78° C. for 1 hr, then a solution of 6-bromo-2,3-dihydro-1H-inden-1-one (16 g, 71 mmol) in dry THF (25 mL) was added dropwise. The reaction mixture was stirred an additional 3 hr at −78° C., then quenched with saturated aqueous NH$_4$Cl. The mixture was extracted with EtOAc three times. The combined organic layers were washed with brine, dried over Na$_2$SO$_4$ and concentrated in vacuo to afford a residue, which was purified by silica gel chromatography (eluting with PE:EA=20:1) to obtain compound A6-1. MS (ESI) m/e (M+H$^+$): 339.0 (−17).

Step B: 5-bromo-3-(2-(trifluoromethyl)phenyl)-1H-indene (A6-2)

To a solution of compound A6-1 (9.2 g, 25.8 mmol) in toluene (100 mL) was added 4-methylbenzenesulfonic acid (500 mg, 2.6 mmol) in one portion. The reaction was stirred at 100° C. for 10 h and then quenched with aqueous saturated NaHCO$_3$ (50 mL), and extracted with EtOAc (2×100 mL). The combined organic layers were washed with brine, dried over Na$_2$SO$_4$ and concentrated in vacuo. The resulting residue was purified by chromatography over silica gel (eluting with PE:EA=10:1) to give compound A6-2.

Step C: dimethyl 5-bromo-3-(2-(trifluoromethyl)phenyl)-1H-indene-1,1-dicarboxylate (A6-3)

To a solution of compound A6-2 (2 g, 6 mmol) in dry THF (60 mL) at −78° C. under a nitrogen atmosphere was added n-BuLi (2.5 M in hexanes, 7.4 mL, 18 mmol) dropwise. After completion of the addition, the mixture was stirred at −78° C. for 2 hours. Then a solution of methyl 2-chloroacetate (3.8 g, 18 mmol) in dry THF (5 mL) was added dropwise. The resulting reaction was stirred at −78° C. for an additional 3 hr, then quenched with saturated aqueous NH$_4$Cl, and extracted with EtOAc (50 mL) three times. The combined organic layers were washed with brine, dried over Na$_2$SO$_4$ and concentrated to afford a residue, which was purified by chromatography over silica gel (eluting with PE:EA=20:1) to obtain compound A6-3. MS (ESI) m/e (M+H$^+$): 455.0, 457.0.

Step D: 5-ethyl 1,1-dimethyl 3-(2-(trifluoromethyl)phenyl)-1H-indene-1,1,5-tricarboxylate (A6-4)

To a mixture of A6-3 (4.5 g, 9.9 mmol) in EtOH (10 mL) were added NaOAc (1.62 g, 19.8 mmol) and Pd(dppf)Cl$_2$ (731 mg, 0.1 mmol) and the reaction was stirred at 80° C. under CO pressure (50 psi) for 12 hours. The reaction mixture was filtrated and the filtrate was partitioned between EtOAc and water. The aqueous layer was separated, and washed by EtOAc twice. Then the combined organic layers were washed with brine, dried over anhydrous Na$_2$SO$_4$ and concentrated in vacuo. The resulting residue was purified by silica gel column chromatography (eluting with PE:EA=100:0 to 60:40) to give compound A6-4. MS (ESI) m/e (M+H$^+$): 449.1.

Step E: 5-ethyl 1,1-dimethyl 3-(2-(trifluoromethyl)phenyl)-2,3-dihydro-1H-indene-1,1,5-tricarboxylate (A6-5)

Palladium (10%) on carbon (500 mg) was added to a solution of compound A6-4 (3.7 g, 8.2 mmol) in MeOH (150 mL) and the resulting mixture was stirred at 40° C. under H$_2$ (1 atm) for 12 hr. The reaction mixture was filtered through Celite™ and the filtrate was concentrated to give crude compound A6-5. MS (ESI) m/e (M+H$^+$): 451.1.

Step F: (3-(2-(trifluoromethyl)phenyl)-2,3-dihydro-1H-indene-1,1,5-triyl)trimethanol (A6-6)

To a suspension of LiAlH$_4$ (2.5 g, 66.6 mmol) in dry THF (50 mL) at 0° C. was added a solution of A6-5 (2 g, 4.44 mmol) in THF (10 mL) dropwise. After completion of the addition, the reaction mixture was stirred at 0° C. for 12 h. The reaction was carefully quenched with water and 10% aq.NaOH, and then diluted with another 10 mL of THF. The resulting precipitate was removed by filtration and the filtrate was concentrated to give a residue. The residue was purified by column chromatography over silica gel (eluting with DCM:MeOH=50:1 to 20:1) to give compound A6-6. MS (ESI) m/e (M+H$^+$): 335.1(−17).

Step G: (2,2-dimethyl-3'-(2-(trifluoromethyl)phenyl)-2',3'-dihydrospiro[[1,3]dioxane-5,1'-inden]-5'-yl)methanol (A6-7)

To a solution of compound A6-6 (300 mg, 0.85 mmol) in 1,2-dichloroethane (20 mL) at 0° C., was added a catalytic amount of PPTS (21 mg), followed by the slow addition of 2-methoxypropene (92 mg, 1.26 mmol). The reaction was stirred for 15 min at 0° C., and then warmed to room temperature. After 3 h at room temperature, triethylamine (0.6 mL) was added in one portion. The mixture was diluted with DCM (30 mL) and saturated aqueous NaHCO$_3$ (30 mL). The layers were separated and the aqueous layer was extracted with DCM (50 mL). The combined organic layers were washed with water (30 mL) and brine (30 mL), dried over Na$_2$SO$_4$, filtered and concentrated in vacuo to afford crude product A6-7, which was used in the next step without further purification.

Step H: 5'-((benzyloxy)methyl)-2,2-dimethyl-3'-(2-(trifluoromethyl)phenyl)-2',3'-dihydrospiro[[1,3]dioxane-5,1'-indene] (A6-8)

To a solution of compound A6-7 in dry THF (20 mL) at 0° C. under N$_2$, was added 60% NaH (51 mg, 1.28 mmol) in three portions. The mixture was stirred for 30 min, then benzyl bromide (218 mg, 1.28 mmol) was added dropwise. The mixture was stirred for 20 min at 0° C. and then warmed to room temperature for 2 h. The mixture was heated to reflux for 12 h, then cooled and concentrated. The resulting residue was diluted with EtOAc (50 mL) and washed with saturated aqueous NaHCO$_3$ (30 mL), and brine (30 mL), then dried over anhydrous Na$_2$SO$_4$ and concentrated in vacuo. The resulting residue was purified by column chromatography over silica gel (eluting with PE:EA=10:1) to give compound A6-8.

Step I: (5-((benzyloxy)methyl)-3-(2-(trifluoromethyl)phenyl)-2,3-dihydro-1H-indene-1,1-diyl)dimethanol (A6-9)

To a solution of compound A6-8 (310 mg, 0.64 mmol) in THF (5 mL) at room temperature was added 1N HCl (2 mL). The reaction mixture was stirred for 4 h, then 1N NaOH was added to quench the reaction by adjusting the pH to pH 7.0. The reaction mixture was then concentrated under reduced pressure and the resulting residue was purified by preparative TLC over silica gel (eluting with PE:EA=1:1) to give compound A6-9.

Step J: (5-((benzyloxy)methyl)-1-(hydroxymethyl)-3-(2-(trifluoromethyl)phenyl)-2,3-dihydro-1H-inden-1-yl)methyl 4-methylbenzenesulfonate (A6-10)

To a solution of compound A6-9 (100 mg, 0.2 mmol) in THF (5 mL) at −30° C. under nitrogen, was added n-butyllithium (2.5 M in hexane, 0.1 mL, 0.25 mmol), followed, 20 min later, by a solution of tosyl chloride (47 mg, 0.25 mmol) in THF (1.0 mL). The reaction mixture was stirred at −30° C. for another 20 min, then allowed to warm to room temperature over 12 h. The final mixture was quenched with saturated aqueous NH$_4$Cl and extracted with EtOAc twice. The combined organic layers were washed with brine, dried over anhydrous Na$_2$SO$_4$ and concentrated in vacuo to give the crude compound A6-10, which was used in the next step directly. MS (ESI) m/e (M+H$^+$): 619.2.

Step K: 5-((benzyloxy)methyl)-3-(2-(trifluoromethyl)phenyl)-2,3-dihydrospiro[indene-1,3'-oxetane] (A6-11)

The crude compound A6-10 was dissolved in tert-butyl alcohol (15 mL), then t-BuOK (62 mg, 0.56 mmol) was added, and the mixture was heated under reflux for 12 h. After cooling, the solvent was removed by evaporation and the resulting residue was purified by preparative TLC over silica gel (eluting with PE:EA=15:1) to afford compound A6-11.

Step L: (3-(2-(trifluoromethyl)phenyl)-2,3-dihydrospiro[indene-1,3'-oxetan]-5-yl)methanol (A6-12)

Palladium (10%) on carbon (10 mg) was added to a solution of compound A6-11 (35 mg, 0.08 mmol) in MeOH (10 mL) and the resulting mixture was stirred at room temperature under H$_2$ (1 atm) for 1 hr. The mixture was then filtered over Celite™ and the filtrate was concentrated. The resulting residue was purified by preparative TLC over silica gel (eluting with PE:EA=2:1) to give compound A6-12. MS (ESI) m/e (M+H$^+$): 317.1.

Step M: (3-(2-(trifluoromethyl)phenyl)-2,3-dihydrospiro[indene-1,3'-oxetan]-5-yl)methyl methanesulfonate (A6-13)

To a stirred solution of compound A6-12 (33 mg, 0.1 mmol) in DCM (5 mL) at 0° C. was added MsCl (23 mg, 0.2 mmol) and Et$_3$N (20 mg, 0.2 mmol). The mixture was stirred for 2 hr at room temperature, then diluted with saturated aqueous NaHCO$_3$. The mixture was extracted with DCM (50 mL), and the organic layer was washed with brine, dried over anhydrous Na$_2$SO$_4$ and concentrated in vacuo to obtain crude compound A6-13, which was used in the next step without purification.

Step N: (5aR,6S,6aS)-ethyl 3-((3-(2-(trifluoromethyl)phenyl)-2,3-dihydrospiro[indene-1,3'-oxetan]-5-yl)methoxy)-5,5a,6,6a-tetrahydrocyclopropa[4,5]cyclopenta[1,2-c]pyridine-6-carboxylate (A6-14A)

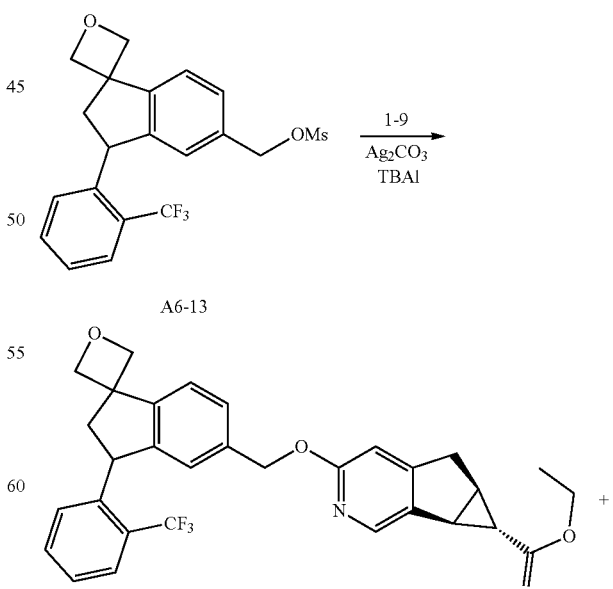

-continued

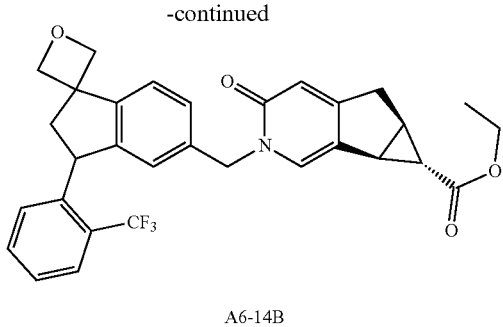

A6-14B

To a mixture of crude compound A6-13 in toluene (10 mL), was added tetrabutylammonium iodide (15 mg, 0.04 mmol). The mixture was heated to 120° C. for 30 min. Then intermediate 1-9 (20 mg, 0.08 mmol) and Ag$_2$CO$_3$ (74 mg, 0.27 mmol) were added. The mixture was stirred at 120° C. for 12 hours under N$_2$, then filtered and concentrated. The resulting residue was purified by preparative TLC over silica gel (eluting with PE:EA=5:1) to afford compound A6-14A and compound A6-14B. MS (ESI) m/e (M+H$^+$): 536.2

Step O: (5aR,6S,6aS)-3-((3-(2-(trifluoromethyl)phenyl)-2,3-dihydrospiro[indene-1,3'-oxetan]-5-yl)methoxy)-5,5a,6,6a-tetrahydrocyclopropa[4,5]cyclopenta[1,2-c]pyridine-6-carboxylic acid (A6-15)

To a mixture of compound A6-14A (28 mg, 0.05 mmol) in THF (2 mL), MeOH (2 mL) and H$_2$O (2 mL) was added NaOH (41 mg, 1 mmol) and the reaction was stirred at room temperature for 12 hr. The reaction mixture was acidified with HCl (1 N) to pH=6, and extracted with EtOAc (50 mL) twice. The combined organic layers were washed with water, brine, dried over Na$_2$SO$_4$ and concentrated in vacuo. The resulting residue was purified by preparative HPLC (on a GILSON 281 instrument fitted with a Waters XSELECT C18 (150*30 mm*5 um) using water and acetonitrile as the eluents. Mobile phase A: water (containing 0.1% TFA, v/v), mobile phase B: acetonitrile. Gradient: 55-75% B, 0-10 min; 100% B, 10.5-12.5 min; 5% B, 13-15 min) to give compound A6-15. $^1$H NMR (400 MHz, MeOD-d$_4$) δ: 1.11 (br. s., 1H) 2.28-2.37 (m, 1H) 2.38-2.45 (m, 1H) 2.89 (d, J=5.09 Hz, 1H) 2.98-3.10 (m, 2H) 3.21 (dd, J=18.59, 4.11 Hz, 1H) 4.72-4.79 (m, 3H) 4.91 (d, J=5.87 Hz, 1H) 5.03 (d, J=6.26 Hz, 1H) 5.20 (s, 2H) 6.62 (s, 1H) 6.83-6.93 (m, 2H) 7.35-7.49 (m, 3H) 7.71 (d, J=7.83 Hz, 1H) 7.77 (d, J=7.83 Hz, 1H) 7.99 (s, 1H). MS (ESI) m/e (M+H$^+$): 508.2

Step P: (2,2-dimethyl-3'-(2-(trifluoromethyl)phenyl)-2',3'-dihydrospiro[[1,3]dioxane-5,1'-inden]-5'-yl)methyl methanesulfonate (A6-16)

To a solution of compound A6-7 (330 mg, 0.84 mmol) and TEA (170 mg, 1.68 mmol) in DCM (30 mL) was added MsCl (193 mg, 1.68 mmol) at 0° C. The mixture was stirred for 30 min at 0° C., and then at room temperature for 2 hr. Then saturated aqueous NaHCO$_3$ was added to quench the reaction and the mixture was extracted with DCM. The DCM layer was washed with brine, dried over Na$_2$SO$_4$ and concentrated in vacuo to give crude compound A6-16, which was used in the next step without further purification.

Step Q: (5aR,6S,6aS)-ethyl 3-((2,2-dimethyl-3'(2-(trifluoromethyl)phenyl)-2',3'-dihydrospiro[[1,3]dioxane-5,1'-inden]-5'-yl)methoxy)-5,5a,6,6a-tetrahydrocyclopropa[4,5]cyclopenta[1,2-c]pyridine-6-carboxylate (A6-17)

To a mixture of crude compound A6-16 in toluene (10 mL) was added tetrabutylammonium iodide (15 mg, 0.04 mmol) and the reaction was heated at 100° C. for 30 min. Then intermediate 1-9 (205 mg, 0.94 mmol) and Ag$_2$CO$_3$ (774 mg, 2.8 mmol) were added. The reaction was stirred at 120° C. for 12 hours under N$_2$ and then filtrated. The filtrate was concentrated and the resulting residue was purified by preparative TLC over silica gel (eluting with PE:EA=5:1) to afford compound A6-17. MS (ESI) m/e (M+H$^+$): 594.2.

Step R: (5aR,6S,6aS)-3-((2,2-dimethyl-3'-(2-(trifluoromethyl)phenyl)-2',3'-dihydrospiro[[1,3]dioxane-5,1'-inden]-5'-yl)methoxy)-5,5a,6,6a-tetrahydrocyclopropa[4,5]cyclopenta[1,2-c]pyridine-6-carboxylic acid (A6-18)

To a solution of compound A6-17 (50 mg, 0.08 mmol) in THF (3 mL), MeOH (3 mL) and H$_2$O (3 mL), was added NaOH (67 mg, 1.7 mmol). The reaction was stirred at room temperature for 12 h, hen neutralized with 1 M HCl to pH=6.0 and extracted with EtOAc (30 mL) twice. The combined organic layers were washed with brine, dried over Na$_2$SO$_4$ and concentrated in vacuo. The resulting residue was purified by preparative TLC over silica gel (eluting with DCM:MeOH=20:1) to give compound A6-18. $^1$H NMR (400 MHz, MeOD-d$_4$) δ: 1.11 (d, J=2.35 Hz, 1H) 1.43 (s, 3H) 1.56 (s, 3H) 1.82-1.93 (m, 1H) 2.36-2.47 (m, 1H) 2.81-2.92 (m, 2H) 2.95-3.03 (m, 1H) 3.20 (dd, J=18.39, 4.70 Hz, 1H) 3.70-3.81 (m, 2H) 3.88 (d, J=11.35 Hz, 1H) 4.25 (d, J=11.35 Hz, 1H) 4.79 (t, J=8.80 Hz, 1H) 5.15-5.21 (m, 2H) 6.59 (s, 1H) 6.83 (br. s., 1H) 7.04-7.12 (m, 1H) 7.28-7.34 (m, 1H) 7.35-7.42 (m, 1H) 7.44-7.51 (m, 1H) 7.54 (d, J=7.83 Hz, 1H) 7.70 (d, J=7.83 Hz, 1H) 7.97 (s, 1H). MS (ESI) m/e (M+H$^+$): 566.2.

Example 9

(5aR,6S,6aS)-3-((1,1-dimethyl-3-phenyl-2,3-dihydro-1H-inden-5-yl)methoxy)-5,5a,6,6a-tetrahydrocyclopropa[4,5]cyclopenta[1,2-c]pyridine-6-carboxylic acid (Compound A7-7)

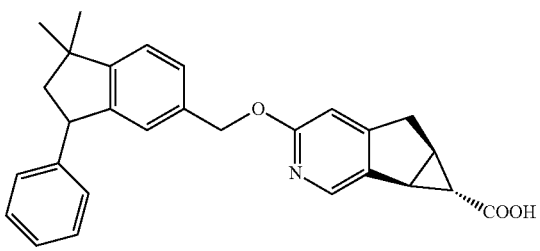

A7-7

Step A: methyl 1,1-dimethyl-3-phenyl-1H-indene-5-carboxylate (A7-2)

A mixture of intermediate 4-4 (120 mg, 0.34 mmol), phenylboronic acid (50 mg, 0.41 mmol), K$_3$CO$_3$ (117 mg, 0.85 mmol) and PdCl$_2$(dffp) (15 mg) in dioxane (3 mL) and water (1 mL) was heated in a microwave at 100° C. for 10 min under nitrogen atmosphere. After cooling to room temperature, the reaction was filtered over Celite™ and the filtrate was extracted with EtOAc twice. The combined organic layers were washed with water, dried over Na$_2$SO$_4$ and concentrated in vacuo to obtain crude compound A7-2, which was used in the next step without purification. MS (ESI) m/e (M+H$^+$): 278.1.

Step B: methyl 1,1-dimethyl-3-phenyl-2,3-dihydro-1H-indene-5-carboxylate (A7-3)

Palladium (10%) on carbon (20 mg) was added to a solution of crude compound A7-2 (150 mg, crude) in MeOH (10 mL), and the resulting mixture was stirred at 25° C. under H$_2$ (1 atm) for 16 h. Then the reaction mixture was filtered over Celite™ and the filtrate was concentrated in vacuo to afford crude compound A7-3, which was used in the next step without purification. MS (ESI) m/e (M+H$^+$): 280.1.

Step C: (1,1-dimethyl-3-phenyl-2,3-dihydro-1H-inden-5-yl)methanol (A7-4)

To a suspension of LiAlH$_4$ (65 mg, 1.7 mmol) in dry THF (5 mL) at 0° C. was added a solution of compound A7-3 (120 mg, crude) in THF (10 mL) dropwise. After completion of the addition, the reaction mixture was stirred at 0° C. for 4 h. Then the reaction was quenched with saturated aqueous NH$_4$Cl and the mixture was extracted with EtOAc twice. The combined organic layers were washed with brine, dried over Na$_2$SO$_4$ and concentrated in vacuo to afford a residue, which was purified by column chromatography over silica gel (eluting with PE:EA=5:1) to give compound A7-4. MS (ESI) m/e (M+H$^+$−18): 252.1 (−17).

Step D: 5-(bromomethyl)-1,1-dimethyl-3-phenyl-2,3-dihydro-1H-indene (A7-5)

To a solution of compound A7-4 (60 mg, 0.17 mmol) in dry DCM (5 mL) at 0° C. was added PBr$_3$ (46 mg, 0.17 mmol) dropwise. The resulting solution was stirred at 0° C. for an hour, then warmed to 20° C. and stirred for 2 hr. The reaction was then quenched with water, neutralized with saturated aqueous NaHCO$_3$ to pH=7, and extracted with EtOAc twice. The combined organic layers were washed with brine, dried over anhydrous Na$_2$SO$_4$, and concentrated in vacuo to afford crude compound A7-5, which was used in the next step without purification.

Step E: (5aR,6S,6aS)-ethyl 3-((1,1-dimethyl-3-phenyl-2,3-dihydro-1H-inden-5-yl)methoxy)-5,5a,6,6a-tetrahydrocyclopropa[4,5]cyclopenta[1,2-c]byridine-6-carboxylate (A7-6)

A mixture of compound A7-5 (80 mg, crude), intermediate 1-9 (31 mg, 0.14 mmol) and Ag$_2$CO$_3$ (94 mg, 0.34 mmol) in toluene (8 mL) was heated at 110° C. for 2 h. The reaction was filtered and the filtrate was concentrated to give crude compound A7-6, which was purified via column chromatography over silica gel to give compound A7-6. MS (ESI) m/e (M+H$^+$): 454.6.

Step F: (5aR,6S,6aS)-3-((1,1-dimethyl-3-phenyl-2,3-dihydro-1H-inden-5-yl)methoxy)-5,5a,6,6a-tetrahydrocyclopropa[4,5]cyclopenta[1,2-c]pyridine-6-carboxylic acid (A7-7)

To a mixture of compound A7-6 (30 mg, 0.066 mmol) in THF (1 mL), MeOH (1 mL) and H$_2$O (1 mL) was added NaOH (26 mg, 0.66 mmol), and the resulting mixture was stirred at room temperature for 2 h. The reaction mixture was then acidified with HCl (2 N) to pH=7, and extracted with EtOAc (10 mL) twice. The combined organic layers were washed with water, brine, dried over Na$_2$SO$_4$ and concentrated in vacuo to afford a residue, which was purified by preparative TLC over silica gel to give compound A7-7. $^1$H NMR (400 MHz, MeOD-d$_4$) δ: 7.97-8.09 (m, 1H) 7.27 (q, J=6.91 Hz, 3H) 7.11-7.21 (m, 4H) 6.73-6.84 (m, 1H) 6.57-6.71 (m, 1H) 5.13-5.27 (m, 2H) 4.37 (t, J=8.61 Hz, 1H) 3.15-3.28 (m, 1H) 2.87-3.07 (m, 2H) 2.34-2.46 (m, 2H) 1.93 (t, J=11.15 Hz, 1H) 1.40 (s, 3H) 1.23 (br. s., 3H) 1.10-1.17 (m, 1H). MS (ESI) m/e (M+H$^+$): 426.2.

TABLE 2

Examples 10-17 (compounds A7-8 to A7-16) were prepared in a similar manner to Example 9 (Compound A7-7) using the appropriate intermediates and commercially available materials, and including procedures described across this application when necessary.

| Example | Structure | M.W. | Compound Name | LC/MS (ESI) observed [M + 1]+ |
|---|---|---|---|---|
| 10 | (Compound A7-8) | 461.5 | (5aR,6S,6aS)-3-((3-(2,6-difluorophenyl)-1,1-dimethyl-2,3-dihydro-1H-inden-5-yl)methoxy)-5,5a,6,6a-tetrahydrocyclopropa[4,5]cyclopenta[1,2-c]pyridine-6-carboxylic acid | 462.2 |

TABLE 2-continued

Examples 10-17 (compounds A7-8 to A7-16) were prepared in a similar manner to Example 9 (Compound A7-7) using the appropriate intermediates and commercially available materials, and including procedures described across this application when necessary.

| Example | Structure | M.W. | Compound Name | LC/MS (ESI) observed [M + 1]+ |
|---|---|---|---|---|
| 11 | 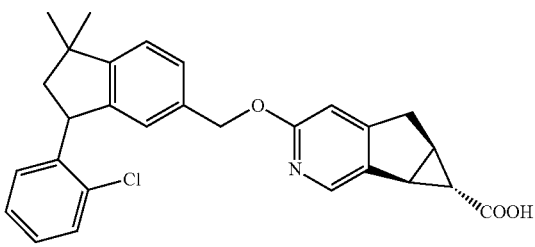 [SMILES: CC1(C)CC(c2ccccc2Cl)c2cc(COc3cc4c(cn3)[C@H]3[C@@H](C4)[C@@H]3C(=O)O)ccc21] (Compound A7-9) | 459.2 | (5aR,6S,6aS)-3-((3-(2-chlorophenyl)-1,1-dimethyl-2,3-dihydro-1H-inden-5-yl)methoxy)-5,5a,6,6a-tetrahydrocyclopropa[4,5]cyclopenta[1,2-c]pyridine-6-carboxylic acid | 460.5 |
| 12 | 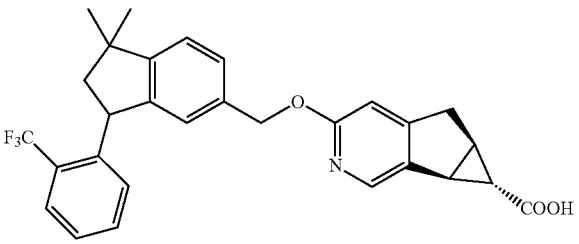 [SMILES: CC1(C)CC(c2ccccc2C(F)(F)F)c2cc(COc3cc4c(cn3)[C@H]3[C@@H](C4)[C@@H]3C(=O)O)ccc21] (Compound A7-10) | 492.6 | (1S,1aS,6aR)-4-((1,1-dimethyl-3-(2-(trifluoromethyl)phenyl)-2,3-dihydro-1H-inden-5-yl)methoxy)-1,1a,6,6a-tetrahydrocyclopropa[a]indene-1-carboxylic acid | 493.2 |
| 13 | 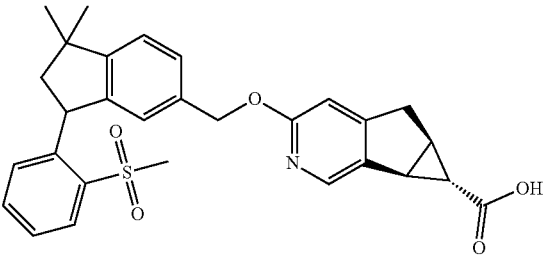 [SMILES: CC1(C)CC(c2ccccc2S(C)(=O)=O)c2cc(COc3cc4c(cn3)[C@H]3[C@@H](C4)[C@@H]3C(=O)O)ccc21] (Compound A7-11) | 503.4 | (5aR,6S,6aS)-3-((1,1-dimethyl-3-(2-(methylsulfonyl)phenyl)-2,3-dihydro-1H-inden-5-yl)methoxy)-5,5a,6,6a-tetrahydrocyclopropa[4,5]cyclopenta[1,2-c]pyridine-6-carboxylic acid | 504.2 |
| 14 | 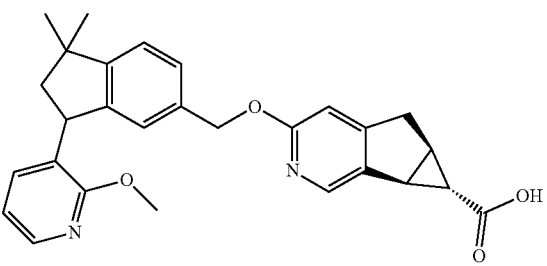 [SMILES: COc1ncccc1C1CC(C)(C)c2ccc(COc3cc4c(cn3)[C@H]3[C@@H](C4)[C@@H]3C(=O)O)cc21] (Compound A7-12) | 456.6 | (5aR,6S,6aS)-3-((3-(2-methoxypyridin-3-yl)-1,1-dimethyl-2,3-dihydro-1H-inden-5-yl)methoxy)-5,5a,6,6a-tetrahydrocyclopropa[4,5]cyclopenta[1,2-c]pyridine-6-carboxylic acid | 457.3 |
| 15 | 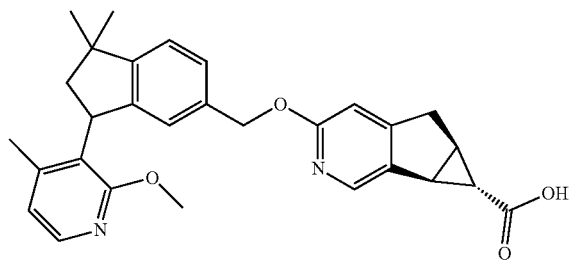 [SMILES: COc1nccc(C)c1C1CC(C)(C)c2ccc(COc3cc4c(cn3)[C@H]3[C@@H](C4)[C@@H]3C(=O)O)cc21] (Compound A7-13) | 470.2 | (5aR,6S,6aS)-3-((3-(2-methoxy-4-methylpyridin-3-yl)-1,1-dimethyl-2,3-dihydro-1H-inden-5-yl)methoxy)-5,5a,6,6a-tetrahydrocyclopropa[4,5]cyclopenta[1,2-c]pyridine-6-carboxylic acid | 471.0 |

TABLE 2-continued

Examples 10-17 (compounds A7-8 to A7-16) were prepared in a similar manner to Example 9 (Compound A7-7) using the appropriate intermediates and commercially available materials, and including procedures described across this application when necessary.

| Example | Structure | M.W. | Compound Name | LC/MS (ESI) observed [M + 1]+ |
|---|---|---|---|---|
| 16 | (Compound A7-14) | 479.4 | (5aR,6S,6aS)-3-((1,1-dimethyl-3-(1-methyl-1H-benzo[d]imidazol-7-yl)-2,3-dihydro-1H-inden-5-yl)methoxy)-5,5a,6,6a-tetrahydrocyclopropa[4,5]cyclopenta[1,2-c]pyridine-6-carboxylic acid | 480.2 |
| 17 | (Compound A7-16) | 443.5 | (5aR,6S,6aS)-3-((1,1-dimethyl-3-(2-fluorophenyl)-2,3-dihydro-1H-inden-5-yl)methoxy)-5,5a,6,6a-tetrahydrocyclopropa[4,5]cyclopenta[1,2-c]pyridine-6-carboxylic acid | 444.2 |

Examples 18 and 19

(5aR,6S,6aS)-3-((1-phenyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (Compounds A8-7A and A8-7B)

A8-7A A8-7B

Step A: ethyl 1-(2-(trifluoromethyl)phenyl)-3-(((trifluoromethyl)sulfonyl)oxy)-1H-indene-6-carboxylate (A8-1)

To a solution of compound A1-2 (1.0 g, 2.87 mmol) in DCM (20 mL) at room temperature was added 2,6-di-tert-butyl-4-methylpyridine (1.179 g, 5.74 mmol) and trifluoromethanesulfonic anhydride (1.782 g, 6.32 mmol) under a nitrogen atmosphere. After completion of the addition, the mixture was stirred for 3 hours. Then the reaction mixture was quenched with water and extracted with EtOAc three times. The combined organic layers were washed with brine, dried over $Na_2SO_4$ and concentrated in vacuo to afford compound A8-1. MS (ESI) m/e (M+H$^+$): 481.0.

Step B: ethyl 3-phenyl-1-(2-(trifluoromethyl)phenyl)-1H-indene-6-carboxylate (A8-2)

A mixture of compound A8-1 (1.2 g, 2.123 mmol), phenylboronic acid (0.311 g, 2.55 mmol), $K_2CO_3$ (0.734 g, 5.31 mmol) and $PdCl_2$ (dppf) (0.078 g, 0.106 mmol) in 1,4-dioxane (4 ml) and water (1.5 ml) was microwaved at 100° C. for 30 min under a nitrogen atmosphere. After cooling to room temperature, the reaction was filtered and the filtrate was extracted with EtOAc. The organic layer was separated, washed with water, dried over $Na_2SO_4$ and concentrated in vacuo to obtain a residue, which was purified by column chromatography over silica gel to give compound A8-2. MS (ESI) m/e (M+H$^+$): 409.1.

Step C: ethyl 1-phenyl-3-(2-(trifluoromethyl)phenyl)-2,3-dihydro-1H-indene-5-carboxylate (A8-3)

10% Pd/C (15.63 mg, 0.147 mmol) was added to a solution of compound A8-2 (600 mg, 1.469 mmol) in MeOH (30 ml), and the resulting mixture was stirred at 50° C. under $H_2$ (50 psi) for 16 h. The reaction was then filtered through Celite™ and the filtrate was concentrated in vacuo to afford crude compound A8-3, which was used in the next step without purification. MS (ESI) m/e (M+H$^+$): 411.1.

Step D: (1-phenyl-3-(2-(trifluoromethyl)phenyl)-2,3-dihydro-1H-inden-5-yl)methanol (A8-4)

To a suspension of LiAlH$_4$ (277 mg, 7.31 mmol) in dry THF (20 mL) at 0° C. was added a solution of compound A8-3 (600 mg, 1.462 mmol) in THF (30 mL) dropwise. After completion of the addition, the reaction mixture was stirred at 0° C. for 3 h. Then the reaction was quenched with saturated aqueous NaOH and the mixture was extracted with EtOAc twice. The combined organic layers were washed and concentrated to afford a residue, which was purified by column chromatography over silica gel to obtain compound A8-4. MS (ESI) m/e (M+H$^+$): 368.1 (−17).

Step E: 5-(bromomethyl)-1-phenyl-3-(2-(trifluoromethyl)phenyl)-2,3-dihydro-1H-indene (A8-5)

To a solution of compound A8-4 (450 mg, 1.222 mmol) in dry DCM (20 mL) at 0° C. was added PBr$_3$ (0.115 ml, 1.222 mmol) dropwise. The resulting solution was stirred for an hour, then warmed to 20° C. and stirred for 2 h. The mixture was then quenched with water, neutralized with saturated aqueous NaHCO$_3$ to pH=7, and extracted with EtOAc twice. The combined organic layers were washed with brine, dried over anhydrous Na$_2$SO$_4$, and concentrated in vacuo to afford crude compound A8-5, which was used in the next step directly. MS (ESI) m/e (M+H$^+$): 430.1, 432.1.

Step F: (5aR,6S,6aS)-ethyl 3-((1-phenyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylate (A8-6)

A mixture of Ag$_2$CO$_3$ (252 mg, 0.912 mmol), compound A8-5 (315 mg, 0.547 mmol) and intermediate 1-9 (80 mg, 0.365 mmol) in toluene (5 mL) was heated to 110° C. for 2 hrs. The reaction was filtered and the filtrate was concentrated to give crude compound A8-6, which was used in the next step directly. MS (ESI) m/e (M+H$^+$): 570.2.

Step G: (5aR,6S,6aS)-3-((1-phenyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (A8-7A and A8-7B)

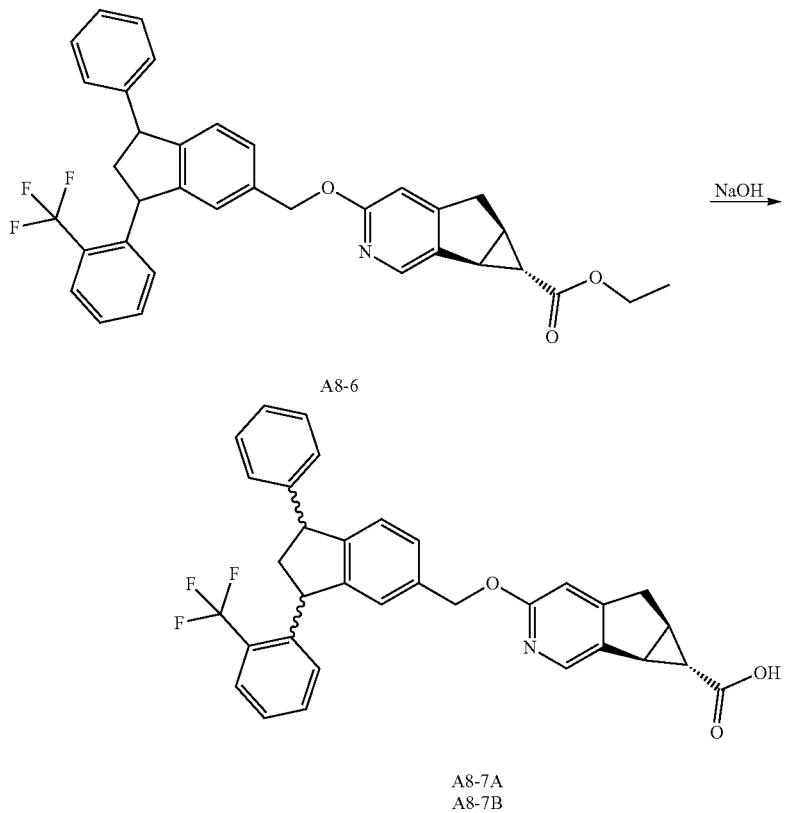

A8-6

A8-7A
A8-7B

To a mixture of compound A8-6 (40 mg, 0.070 mmol) in THF (2 ml), MeOH (2 mL) and H$_2$O (2 mL) was added NaOH (28.1 mg, 0.702 mmol), and the resulting mixture was stirred at room temperature for 2 hrs. The resulting mixture was acidified with HCl (2 N) to pH=7, and extracted with EtOAc (10 mL) twice. The combined organic layers were washed with water, brine, dried over Na$_2$SO$_4$ and concentrated in vacuo to obtain a residue, which was purified by preparative HPLC (on a GILSON 281 instrument fitted with a Waters XSELECT C18 150*30 mm*5 um using water and acetonitrile as the eluents. Mobile phase A: water (containing 0.1% TFA, v/v), mobile phase B: acetonitrile. Gradient: 64-84% B, 0-10 min; 100% B, 10.5-12.5 min; 5% B, 13-15 min) to give compound A8-7A and compound A8-7B. Compound A8-7A: $^1$H NMR (400 MHz, MeOD-d$_4$) δ: 8.13 (s, 1H), 7.73 (d, J=7.53 Hz, 1H), 7.50 (m, 1H), 7.41 (m, 1H), 7.36 (m, 1H), 7.31 (s, 2H), 7.23 (d, J=7.53 Hz, 1H), 7.15 (d, J=7.53 Hz, 3H), 7.07 (m, 3H), 5.33 (m, 2H), 5.02 (t, J=7.03 Hz, 1H), 4.66 (m, 1H), 3.38 (m, 1H), 3.17 (m, 1H), 3.01 (d, J=5.02 Hz, 1H), 2.66 (m, 1H), 2.54 (m, 2H), 1.26 (t, J=2.51 Hz, 1H). MS (ESI) m/e (M+H$^+$): 542.2; Compound A8-7B: $^1$H NMR (400 MHz, MeOD-d$_4$) δ: 8.17 (s, 1H), 7.71-7.78 (m, 1H), 7.56-7.64 (m, 1H), 7.45 (t, J=7.53 Hz, 1H), 7.34 (s, 7H), 7.20 (s, 1H), 6.93-7.00 (m, 2H), 5.34 (s, 2H), 4.77-4.85 (m, 1H), 4.39-4.47 (m, 1H), 3.38-3.47 (m, 1H), 3.19-3.28 (m, 1H), 3.01-3.10 (m, 2H), 2.52-2.60 (m, 1H), 2.05 (s, 1H), 1.29-1.31 (m, 1H). MS (ESI) m/e (M+H$^+$): 542.2.

Example 20

(5aR,6S,6aS)-3-((6-fluoro-3-(2-(trifluoromethyl) phenyl)-2,3-dihydro-1H-inden-5-yl)methoxy)-5,5a,6, 6a-tetrahydrocyclopropa[4,5]cyclopenta[1,2-c]pyridine-6-carboxylic acid (Compound A9-9)

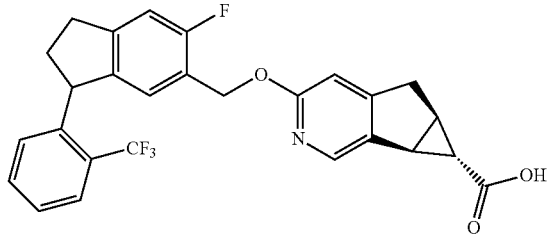

A9-9

Step A: 6-bromo-5-fluoro-1-(2-(trifluoromethyl) phenyl)-2,3-dihydro-1H-inden-1-ol (A9-1)

To a solution of 1-bromo-2-(trifluoromethyl)benzene (2.90 g, 13.1 mmol) in dry THF (50 mL) was added n-BuLi (2.5 M in hexanes, 5.24 mL, 13.1 mmol) dropwise at −78° C. under nitrogen atmosphere. After completion of the addition, the mixture was stirred at −78° C. for an hour. Then a solution of compound 2-3 (2 g, 8.73 mmol) in dry THF (20 mL) was added dropwise and the resulting reaction mixture was stirred at −78° C. for 3 h. Then the reaction was quenched with saturated aqueous NH$_4$Cl and extracted with EtOAc three times. The combined organic layers were washed with brine, dried over Na$_2$SO$_4$ and concentrated in vacuo to afford a residue, which was purified by chromatography over silica gel (eluting with PE:EA=50:1 to 4:1) to obtain compound A9-1. MS (ESI) m/e (M+H$^+$): 375.0.

Step B: 6-fluoro-3-hydroxy-3-(2-(trifluoromethyl) phenyl)-2,3-dihydro-1H-indene-5-carboxylic acid (A9-2)

To a solution of compound A9-1 (2.3 g, 6.1 mmol) in dry THF (50 mL) was added n-BuLi (2.5 M in hexanes, 7.32 mL, 18.3 mmol) dropwise at −78° C. under nitrogen atmosphere. After completion of the addition, the mixture was stirred at −78° C. for 2 hours. Carbon dioxide was then bubbled into the mixture for 30 min. The mixture was stirred at −78° C. for another hour, and then warmed to −20° C. slowly. The reaction mixture was quenched with water, then acidified with diluted HCl (1N) to pH=2, and extracted with EtOAc three times. The combined organic layers were washed with brine, dried over Na$_2$SO$_4$ and concentrated in vacuo to afford a residue, which was washed with petroleum ether to give compound A9-2 which was used in the next step directly.

Step C: methyl 6-fluoro-3-hydroxy-3-(2-(trifluoromethyl)phenyl)-2,3-dihydro-1H-indene-5-carboxylate (A9-3)

To a solution of compound A9-2 (1.1 g, 3.23 mmol) in DMF (15 mL) at 0° C. was added K$_2$CO$_3$ (891 mg, 6.46 mmol) in one portion, followed by MeI (891 mg, 6.46 mmol). The mixture was stirred at 0° C. for 1 h, then warmed to room temperature over 2 hrs. The mixture was then poured into water, and extracted with EtOAc (30 mL) three times. The combined organic layers were washed with water, brine, dried over Na$_2$SO$_4$ and concentrated in vacuo to afford compound A9-3, which was used in the next step without purification. MS (ESI) m/e (M+H$^+$): 338.1 (−17).

Step D: methyl 6-fluoro-3-(2-(trifluoromethyl)phenyl)-1H-indene-5-carboxylate (A9-4)

A solution of compound A9-3 (1 g, 2.82 mmol) and TsOH (107 mg, 0.565 mmol) in dry toluene (20 mL) was stirred at reflux for 3 h, and then cooled to room temperature. The mixture was neutralized with saturated aqueous NaHCO$_3$ and extracted with EtOAc three times. The combined organic layers were washed with brine, dried over Na$_2$SO$_4$ and concentrated in vacuo to obtain compound A9-4, which was used in the next step without purification. MS (ESI) m/e (M+H$^+$): 337.1.

Step E: ethyl 6-fluoro-3-(2-(trifluoromethyl)phenyl)-2,3-dihydro-1H-indene-5-carboxylate (A9-5)

To a solution of compound A9-4 (500 mg, 1.427 mmol) in MeOH (30 ml)) was added 10% Pd/C (15.19 mg, 0.143 mmol) and the reaction was stirred at 25° C. under H$_2$ (1 atm) for 16 h. The mixture was then filtered and the filtrate was concentrated in vacuo to afford crude compound A9-5, which was used in the next step without purification.

Step F: (6-fluoro-3-(2-(trifluoromethyl)phenyl)-2,3-dihydro-1H-inden-5-yl)methanol (A9-6)

To a suspension of crude compound A9-5 (440 mg, 1.249 mmol) in dry THF (15 ml) at 0° C. was added lithium aluminum (III) hydride (95 mg, 2.498 mmol) portionwise. After completion of the addition, the reaction mixture was stirred at 0° C. for 3 h. The reaction was then quenched with saturated aqueous NaOH and extracted with EtOAc twice. The combined organic layers were washed with brine, dried over Na$_2$SO$_4$ and concentrated in vacuo to give crude compound A9-6, which was used in the next step without purification.

Step G: (6-fluoro-3-(2-(trifluoromethyl)phenyl)-2,3-dihydro-1H-inden-5-yl)methyl methanesulfonate (A9-7)

To a solution of compound A9-6 (100 mg, 0.322 mmol) and triethylamine (98 mg, 0.967 mmol) in dry DCM (5 ml)

at 0° C. was added methanesulfonyl chloride (73.8 mg, 0.645 mmol) dropwise. After completion of the addition, the mixture was stirred at this temperature for 16 h, then concentrated in vacuo to give crude compound A9-7, which was used in the next step without purification.

Step H: (5aR,6S,6aS)-ethyl 3-((6-fluoro-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylate (A9-8)

A mixture of crude compound A9-7 (50 mg, 0.129 mmol), intermediate 1-9 (28.2 mg, 0.129 mmol) and Ag$_2$CO$_3$ (35.5 mg, 0.129 mmol) in toluene (10 mL) was heated at 110° C. for 10 h. The reaction was filtered and the filtrate was concentrated in vacuo to give a residue, which was purified by preparative TLC over silica gel (eluting with PE:EA=5:1) to afford compound A9-8. MS (ESI) m/e (M+H$^+$): 512.2.

Step I: (5aR,6S,6aS)-3-((6-fluoro-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (A9-9)

To a mixture of compound A9-8 (52 mg, 0.102 mmol) in THF (2 mL), MeOH (2 mL) and water (2 mL) was added lithium hydroxide (24.35 mg, 1.017 mmol). The resulting mixture was stirred at room temperature for 2 h. Then the reaction mixture was acidified by HCl (2 N) to pH=4, and extracted with EtOAc (30 mL) twice. The combined organic layers were washed with water, brine, dried over Na$_2$SO$_4$ and concentrated in vacuo to afford a residue, which was purified by preparative HPLC (on a GILSON 281 instrument fitted with a Waters XSELECT C18 150*30 mm*5 um using water and acetonitrile as the eluents. Mobile phase A: water (containing 0.1% TFA, v/v), mobile phase B: acetonitrile. Gradient: 53-68% B, 0-9 min; 100% B, 9-11 min) to obtain compound A9-9. $^1$H NMR (400 MHz, MeOD-d$_4$) δ: 8.07-8.14 (m, 1H), 7.68-7.75 (m, 1H), 7.46-7.53 (m, 1H), 7.36-7.45 (m, 1H), 7.07-7.18 (m, 2H), 7.01-7.06 (m, 1H), 6.90-6.96 (m, 1H), 5.33 (s, 2H), 4.71-4.78 (m, 1H), 3.34-3.42 (m, 1H), 3.08-3.21 (m, 2H), 2.97-3.08 (m, 2H), 2.63-2.75 (m, 1H), 2.48-2.56 (m, 1H), 2.00-2.13 (m, 1H), 1.20-1.28 (m, 1H). MS (ESI) m/e (M+H$^+$): 484.1.

Examples 22 and 23

(5aR,6S,6aS)-3-((6-fluoro-1,1-dimethyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (Compounds A10-6A and A10-6B)

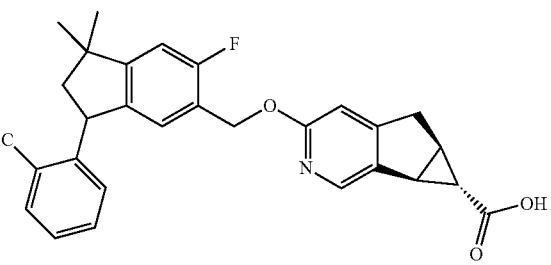

A10-6A A10-6B

Step A: methyl 6-fluoro-1,1-dimethyl-3-(2-(trifluoromethyl)phenyl)-1H-indene-5-carboxylate (A10-1)

To a stirring solution of compound A9-4 (757 mg, 2.25 mmol) in THF (20 mL) and RMPA (3 mL) was added KHMDS (1.0 M in THF, 6.75 mL, 6.75 mmol) dropwise at −78° C. under nitrogen atmosphere. After completion of the addition, the mixture was stirred at this temperature for 2 h, then a solution of MeI (0.43 mL, 6.75 mmol) was added dropwise. The resulting mixture was stirred at −78° C. for 1 h, then warmed to 0° C. slowly and stirred for another 30 min. The final mixture was quenched with saturated aqueous NH$_4$Cl and extracted with EtOAc three times. The combined organic layers were washed with brine, dried over Na$_2$SO$_4$ and concentrated in vacuo to afford a residue, which was purified by chromatography over silica gel (eluting with PE:EA=20:1) to obtain compound A10-1.

TABLE 3

Example 21 (compound A9-10) was prepared in a similar manner to Example 20 (Compound A9-9) using the appropriate intermediates and commercially available materials, but without Steps D and E, and including procedures described across this application when necessary.

| Example | Structure | M.W. | Compound Name | LC/MS (ESI) observed [M + 1]+ |
|---|---|---|---|---|
| 21 | (Compound A9-10) | 480.5 | (1S,1aS,6aR)-4-((3-hydroxy-3-(2-(trifluoromethyl)phenyl)-2,3-dihydro-1H-inden-5-yl)methoxy)-1,1a,6,6a-tetrahydrocyclopropa[a]indene-1-carboxylic acid | 463.1(−17), 503.1(+23) |

Step B: methyl 6-fluoro-1,1-dimethyl-3-(2-(trifluoromethyl)phenyl)-2,3-dihydro-1H-indene-5-Carboxylate (A10-2)

Palladium (10%) on carbon (120 mg) was added to a solution of compound A10-1 (657 mg) in MeOH (20 mL) and THF (10 mL), and the resulting mixture was stirred at 25° C. under $H_2$ (1 atm) for 24 hrs. The reaction was filtered over Celite™, and the filtrate was concentrated in vacuo to afford crude compound A10-2, which was used in the next step without purification. MS (ESI) m/e (M+H$^+$): 367.1.

Step C: (6-fluoro-1,1-dimethyl-3-(2-(trifluoromethyl)phenyl)-2,3-dihydro-1H-inden-5-yl)methanol (A10-3)

To a suspension of LiAlH$_4$ (87 mg, 2.30 mmol) in dry THF (20 mL) at 0° C. was added a solution of compound A10-2 (560 mg, 1.53 mmol) in THF (2 mL) dropwise. After completion of the addition, the reaction mixture was stirred at 0° C. for 1 h. The reaction was then quenched with saturated aqueous NH$_4$Cl and extracted with EtOAc twice. The combined organic layers were washed with brine, dried over Na$_2$SO$_4$ and concentrated in vacuo to afford compound A10-3, which was used in the next step without purification. MS (ESI) m/e (M+H$^+$): 322.1 (−17).

Step D: 5-(chloromethyl)-6-fluoro-1,1-dimethyl-3-(2-(trifluoromethyl)phenyl)-2,3-dihydro-1H-indene (A10-4)

To a solution of crude compound A10-3 (200 mg, 0.59 mmol) in dry DCM (5 mL) at 0° C. was added Et$_3$N (171 mg, 1.77 mmol) and SOCl$_2$ (105 mg, 0.885 mmol) dropwise. The reaction was stirred at 0° C. for 2 h, then quenched with water and extracted with EtOAc twice. The combined organic layers were washed with brine, dried over anhydrous Na$_2$SO$_4$, and concentrated in vacuo to afford a residue, which was purified by preparative TLC over silica gel (eluting with PE:EA=10:1) to obtain compound A10-4.

Step E: (5aR,6S,6aS)-ethyl 3-((6-fluoro-1,1-dimethyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylate (A10-5)

A mixture of compound A10-4 (150 mg, 0.42 mmol), intermediate 1-9 (92 mg, 0.42 mmol) and Ag$_2$CO$_3$ (347 mg, 1.26 mmol) in toluene (4 mL) was heated at 100° C. for 17 hrs. The reaction was filtered and the filtrate was concentrated in vacuo to give a residue, which was purified by preparative TLC over silica gel (eluting with PE:EA=6:1) to afford compound A10-5. MS (ESI) m/e (M+H$^+$): 540.2.

Chiral SFC Resolution of Compound A10-5 (Compounds A10-5A and A10-5B)

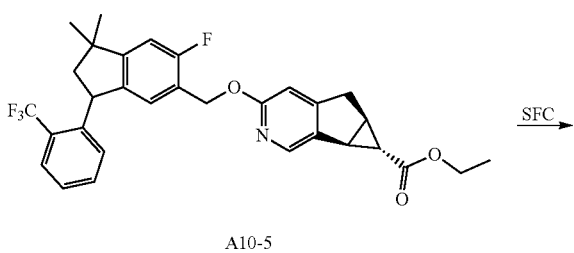

A10-5

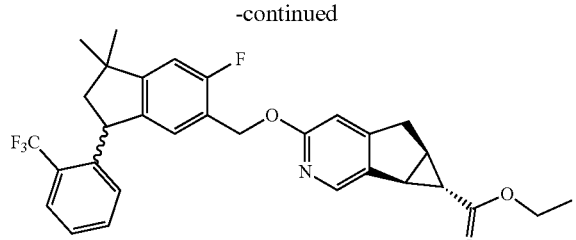

A10-5A
A10-5B

Compound A10-5 was purified by chiral preparative SFC (column: Chiralcel OD-3 150×4.6 mm I.D., 3 um; Mobile phase: iso-propanol (0.05% DEA) in CO$_2$ from 5% to 40%; Flow rate: 2.5 mL/min; Wavelength: 220 nm) to provide compounds A10-5A and A10-5B.

Step F: (5aR,6S,6aS)-3-((6-fluoro-1,1-dimethyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (A10-6A and A10-6B)

To a mixture of compound A10-5A (50 mg, 0.093 mmol) in THF (1 mL), MeOH (1 mL) and water (1 mL) was added LiOH.H$_2$O (38 mg, 0.93 mmol), and the resulting mixture was stirred at room temperature for 2 hrs. The final mixture was acidified with HCl (2 N) to pH=7 and extracted with EtOAc (20 mL) twice. The combined organic layers were washed with water, brine, dried over Na$_2$SO$_4$ and concentrated to give a residue, which was purified by reverse preparative HPLC (preparative HPLC on a GILSON 281 instrument fitted with a Waters XSELECT C18 150*30 mm*5 um using water and acetonitrile as the eluents. Mobile phase A: water (containing 0.1% TFA, v/v), mobile phase B: acetonitrile. Gradient: 68-88% B, 0-10 min; 100% B, 10.5-12.5 min; 5% B, 13-15 min) to give compound A10-6A. $^1$H NMR (400 MHz, MeOD-d$_4$) δ: 8.07 (s, 1H), 7.68 (d, J=7.83 Hz, 1H), 7.44-7.52 (m, 1H), 7.34-7.42 (m, 1H), 7.12 (d, J=7.83 Hz, 1H), 7.04 (d, J=10.17 Hz, 1H), 6.99 (s, 1H), 6.83 (d, J=6.65 Hz, 1H), 5.30 (s, 2H), 4.76 (t, J=8.61 Hz, 1H), 3.31-3.39 (m, 1H), 3.07-3.20 (m, 1H), 2.97 (d, J=7.04 Hz, 1H), 2.42-2.55 (m, 2H), 1.95 (t, J=11.35 Hz, 1H), 1.42 (s, 3H), 1.25 (s, 3H), 1.22 (d, J=2.35 Hz, 1H). MS (ESI) m/e (M+H$^+$): 512.2.

In a similar manner, compound A10-5B was treated with LiOH to afford, after purification by reverse preparative HPLC (preparative HPLC on a GILSON 281 instrument fitted with a Phenomenex Synergi C18 150*30 mm*4 um using water and acetonitrile as the eluents. Mobile phase A: water (containing 0.1% TFA, v/v), mobile phase B: acetonitrile. Gradient: 62-92% B, 0-10 min; 100% B, 10.5-12.5 min; 5% B, 13-15 min), compound A10-6B. $^1$H NMR (400 MHz, MeOD-d$_4$) δ: 8.10 (s, 1H), 7.70 (d, J=7.83 Hz, 1H), 7.46-7.57 (m, 1H), 7.35-7.43 (m, 1H), 7.14 (d, J=7.83 Hz, 1H), 7.04-7.09 (m, 2H), 6.87 (d, J=6.65 Hz, 1H), 5.32 (s, 2H), 4.78 (t, J=8.61 Hz, 1H), 3.32-3.40 (m, 1H), 3.11-3.24 (m, 1H), 3.00 (d, J=7.04 Hz, 1H), 2.43-2.57 (m, 2H), 1.97 (t, J=11.35 Hz, 1H), 1.44 (s, 3H), 1.27 (s, 4H). MS (ESI) m/e (M+H$^+$): 512.2.

Example 24

(5aR,6R,6aR)-5,5-difluoro-3-((6-fluoro-1,1-dimethyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (Compound A11-3)

A11-3

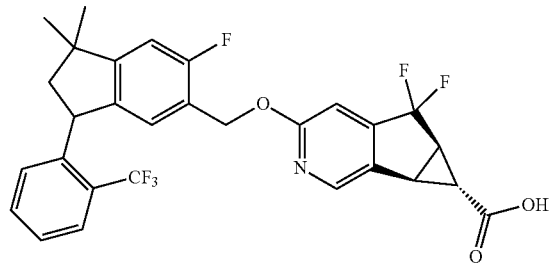

Step A: (5aR,6R,6aR)-tert-butyl 5,5-difluoro-3-((6-fluoro-1,1-dimethyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylate (A11-2)

To a solution of compound A10-3 (50 mg, 0.166 mmol) in toluene (10 ml) was added intermediate 1-12 (67. 3 mg, 0.199 mmol), $Cs_2CO_3$ (162 mg, 0.497 mmol) and Bret-Phos Palladacycle (13.24 mg, 0.017 mmol). The mixture was stirred at 120° C. under $N_2$ overnight. After cooling to room temperature, the mixture was filtered and extracted with DCM. The combined organic layers were washed with brine, dried over anhydrous $Na_2SO_4$, and concentrated in vacuo to give crude compound A11-2, which was used in the step without purification. MS (ESI) m/e (M+H$^+$): 604.2.

Step B: (5aR,6R,6aR)-5,5-difluoro-3-((6-fluoro-1,1-dimethyl-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (A11-3)

To a mixture of compound A11-2 (crude, 65 mg) in MeOH (1.00 mL), THF (1.00 mL) and water (1.00 mL) was added LiOH (120 mg, 5.01 mmol) and the resulting mixture was stirred at room temperature for 2 h. The reaction mixture was acidified with HCl (2 N) to pH=7, and extracted with EtOAc (10 mL) twice. The combined organic layers were washed with water, brine, dried over $Na_2SO_4$ and concentrated in vacuo to obtain a residue, which was purified by preparative HPLC (on a GILSON 281 instrument fitted with a YMC-Actus Triart C18 150*30 mm*5 um using water and acetonitrile as the eluents. Mobile phase A: water (containing 0.05% Ammonia, v/v), mobile phase B: acetonitrile. Gradient: 51-81% B, 0-10 min; 100% B, 10.5-12.5 min; 5% B, 13-15 min) to give compound A11-3. $^1$H NMR (400 MHz, MeOD-d$_4$) δ: 8.17 (br. s., 1H), 7.71 (d, J=7.83 Hz, 1H), 7.48 (d, J=7.43 Hz, 1H), 7.40 (d, J=6.65 Hz, 1H), 7.12 (d, J=7.43 Hz, 1H), 7.02 (d, J=10.17 Hz, 1H), 6.77-6.84 (m, 2H), 5.32 (s, 2H), 4.73-4.81 (m, 1H), 3.17 (br. s., 1H), 2.83 (br. s., 1H), 2.49 (dd, J=7.43, 12.52 Hz, 1H), 1.95 (t, J=11.35 Hz, 1H), 1.88 (br. s., 1H), 1.44 (s, 3H), 1.27 (s, 3H). MS (ESI) m/e (M+H$^+$): 548.1.

Example 25

((5aR,6S,6aS)-3-((6-fluoro-1,1-dimethyl-3-(3-(trifluoromethyl)pyridin-4-yl)-2,3-dihydro-1H-inden-5-yl)methoxy)-5,5a,6,6a-tetrahydrocyclopropa[4,5]cyclopenta[1,2-c]pyridine-6-carboxylic acid (Compound A12-8)

A12-8

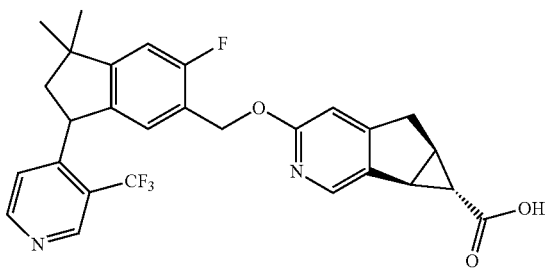

Step A: ethyl 6-fluoro-1,1-dimethyl-3-((((trifluoromethyl)sulfonyl)oxy)-1H-indene-5-carboxylate (A12-1)

To a solution of intermediate 2-7 (3.50 g, 13.99 mmol) in dry DCM (40 mL) at 0° C. was added trifluoromethanesulfonic anhydride (7.89 g, 28.0 mmol) dropwise. The mixture was stirred for 2 h at room temperature, and then quenched with saturated aqueous $NaHCO_3$ (30 mL) and extracted with DCM (50 mL) three times. The combined organic layers were washed with brine, dried over $Na_2SO_4$ and concentrated in vacuo to give a residue which was purified by column chromatography over silica gel (eluting with PE:EA=100:0 to 90:10) to give compound A12-8. MS (ESI) m/e (M+H$^+$): 254.2.

Step B: ethyl 6-fluoro-1,1-dimethyl-3-(4,4,5,5-tetramethyl-1,3,2-dioxaborolan-2-yl)-1H-indene-5-carboxylate (A12-2)

To a solution of compound A12-1 (1.50 g, 1.962 mmol) in 1,4-dioxane (15 mL) was added 4,4,4',4',5,5,5',5'-octamethyl-2,2'-bi(1,3,2-dioxaborolane) (598 mg, 2.354 mmol), potassium acetate (0.578 g, 5.89 mmol) and $PdCl_2(dppf)$ (144 mg, 0.196 mmol). The reaction mixture was heated at 90° C. under an atmosphere of $N_2$ for 12 hours. After cooling, the mixture was filtered over Celite then concentrated in vacuo to provide a residue, which was purified by column chromatography over silica gel (eluting with PE:EA=100:0 to 90:10) to give compound A12-2.

Step C: ethyl 6-fluoro-1, 1-dimethyl-3-(3-(trifluoromethyl)pyridin-4-yl)-1H-indene-5-carboxylate (A12-3)

A mixture of compound A12-2 (200 mg, 0.555 mmol), 4-bromo-3-(trifluoromethyl) pyridine (125 mg, 0.555 mmol), $K_3PO_4$ (354 mg, 1.666 mmol) and $Pd(dtbpf)Cl_2$ (36 mg, 0.056 mmol) in THF (6 mL) and water (2 mL) was microwaved to 100° C. for 30 mins under nitrogen atmosphere. After cooling to room temperature, the reaction was filtered and the filtrate was extracted with EtOAc. The combined organic layers were washed with water, dried over $Na_2SO_4$ and concentrated in vacuo to obtain a residue, which was purified by flash chromatography over silica gel (eluting with PE:EA=5:1) to give compound A12-3.

Step D: ethyl 6-fluoro-1,1-dimethyl-3-(3-(trifluoromethyl)pyridin-4-yl)-2,3-dihydro-1H-indene-5-carboxylate (A12-4)

To a stirred solution of compound A12-3 (165 mg, 0.435 mmol) in MeOH (15 mL) and THF (5 mL) was added 10% Pd/C (9 mg, 0.087 mmol) and the reaction was stirred at 25° C. under $H_2$ (1 atm) for 16 hrs. The mixture was filtered and the filtrate was concentrated in vacuo to afford crude compound A12-4, which was used in the next step without purification. MS (ESI) m/e (M+H$^+$): 382.2.

Step E: (6-fluoro-1,1-dimethyl-3-(3-(trifluoromethyl)pyridin-4-yl)-2,3-dihydro-1H-inden-5-yl)methanol (A12-5)

To a stirred solution of A12-4 (156 mg, 0.409 mmol) in THF (5 mL) was added lithium aluminum(III) hydride (39 mg, 1.023 mmol) at 0° C. and the mixture was stirred for 1 h. The mixture was quenched with water (0.03 mL) and NaOH (0.03 mL, 15%) carefully and stirred for 15 mins. The reaction was then filtered, and the filtrate was concentrated in vacuo to give crude compound A12-5, which was used in the next step directly.

Step F: (6-(bromomethyl)-5-fluoro-3, 3-dimethyl-2, 3-dihydro-1H-inden-1-yl)-3-(trifluoromethyl)pyridine (A12-6)

To a solution of crude compound A12-5 (110 mg, 0.324 mmol) in dry DCM (5.00 mL) at 0° C. was added PBr$_3$ (43.9 mg, 0.162 mmol) dropwise. The reaction was stirred for 3 h at 0° C. then warmed to 20° C. and stirred for 2 h. The reaction mixture was quenched with water, neutralized with saturated aqueous NaHCO$_3$ to pH=7, and extracted with EtOAc three times. The combined organic layers were dried over $Na_2SO_4$ and concentrated in vacuo to afford crude compound A12-6, which was used in the next step without purification.

Step G: (5aR,6S,6aS)-ethyl 3-((6-fluoro-1,1-dimethyl-3-(3-(trifluoromethyl)pyridin-4-yl)-2,3-dihydro-1H-inden-5-yl)methoxy)-5,5a,6,6a-tetrahydrocyclopropa[4,5]cyclopenta[1,2-c]pyridine-6-carboxylate (A12-7)

A mixture of crude compound A12-6 (90 mg, 0.224 mmol), intermediate 1-9 (49.1 mg, 0.224 mmol) and Ag$_2$CO$_3$ (154 mg, 0.559 mmol) in toluene (5.00 mL) was heated at 120° C. for 2 hrs. The reaction was filtered and the filtrate was concentrated in vacuo to give a residue, which was purified by column chromatography over silica gel (eluting with PE:EA=100:0 to 70:30) to provide compound A12-7. MS (ESI) m/e (M+H$^+$): 541.3.

Step H: (5aR,6S,6aS)-3-((6-fluoro-1,1-dimethyl-3-(3-(trifluoromethyl)pyridin-4-yl)-2,3-dihydro-1H-inden-5-yl)methoxy)-5,5a,6,6a-tetrahydrocyclopropa[4,5]cyclopenta[1,2-c]pyridine-6-carboxylic acid (A12-8)

To a mixture of compound A12-7 (80 mg, 0.148 mmol) in THF (2 mL), MeOH (2 mL) and water (2 mL) was added lithium hydroxide (35 mg, 1.480 mmol) and the resulting mixture was stirred at room temperature for 2 hrs. The final mixture was acidified with HCl (2 N) to pH=4, and extracted with EtOAc (30 mL) twice. The combined organic layers were washed with water, brine, dried over Na$_2$SO$_4$ and concentrated in vacuo to afford a residue, which was purified by preparative HPLC (on a GILSON 281 instrument fitted with a Waters XSELECT C18 150*30 mm*5 um using water and acetonitrile as the eluents. Mobile phase A: water (containing 0.1% TFA, v/v), mobile phase B: acetonitrile. Gradient: 51-70% B, 0-9 min; 100% B, 9-11 min) to give compound A12-8. $^1$H NMR (400 MHz, MeOD-d$_4$) δ: 8.89 (br. s., 1H), 8.66 (br. s., 1H), 8.10 (s, 1H), 7.24 (d, J=6.26 Hz, 1H), 7.10 (d, J=10.17 Hz, 1H), 7.00 (br. s., 1H), 6.92 (d, J=3.91 Hz, 1H), 5.32 (s, 2H), 3.32-3.41 (m, 1H), 3.15 (d, J=19.17 Hz, 1H), 2.99 (d, J=5.48 Hz, 1H), 2.48-2.59 (m, 2H), 1.99 (br. s., 1H), 1.45 (s, 3H), 1.28 (s, 3H), 1.21 (s, 1H). MS (ESI) m/e (M+H$^+$): 513.2.

TABLE 4

Example 26 and 27 (Compounds A12-9 and A12-10) was prepared in a similar manner to Example 25 (Compound A12-8) using the appropriate intermediates and commercially available materials, and including procedures described across this application when necessary.

| Example | Structure | M.W. | Compound Name | LC/MS (ESI) observed [M + 1]+ |
|---|---|---|---|---|
| 26 | (Compound A12-9) | 512.2 | (5aR,6S,6aS)-3-((6-fluoro-1,1-dimethyl-3-(2-(trifluoromethyl)pyridin-3-yl)-2,3-dihydro-1H-inden-5-yl)methoxy)-5,5a,6,6a-tetrahydrocyclopropa[4,5]cyclopenta[1,2-c]pyridine-6-carboxylic acid | 513.2 |

TABLE 4-continued

Example 26 and 27 (Compounds A12-9 and A12-10) was prepared in a similar manner to
Example 25 (Compound A12-8) using the appropriate intermediates and commercially available
materials, and including procedures described across this application when necessary.

| Example | Structure | M.W. | Compound Name | LC/MS (ESI) observed [M + 1]+ |
|---|---|---|---|---|
| 27 | (Compound A12-10) | 488.2 | (5aR,6S,6aS)-3-((3-fluoro-8-(2-methoxypyridin-3-yl)-5,5-dimethyl-5,6,7,8-tetrahydronaphthalen-2-yl)methoxy)-5,5a,6,6a-tetrahydrocyclopropa[4,5]cyclopenta[1,2-c]pyridine-6-carboxylic acid | 489.2 |

Example 28

(6S)-3-((6-fluoro-1,1-dimethyl-3-(4-(3-(methylsulfonyl)propoxy)-2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (Compound A13-6)

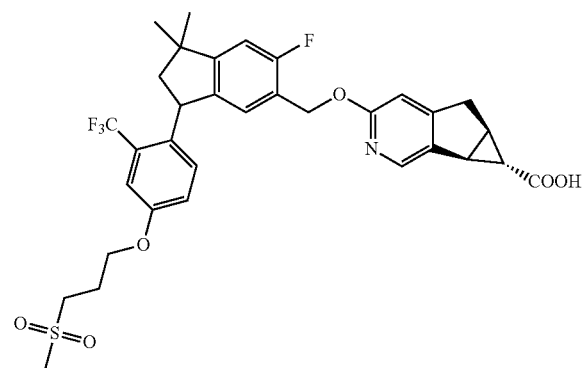

A13-6

Step A: ethyl 6-fluoro-1,1-dimethyl-3-(4-(3-(methylsulfonyl)propoxy)-2-(trifluoromethyl)phenyl)-1H-indene-5-carboxylate (A13-1)

A mixture of compound A12-2 (130 mg, 0.36 mmol), 1-bromo-4-(3-(methylsulfonyl)propoxy)-2-(trifluoromethyl)benzene (143 mg, 0.39 mmol; prepared according to WO2014/022528), K₂CO₃ (99 mg, 0.72 mmol) and Pd(dppf)Cl₂ (15 mg) in THF/H₂O (2 mL/0.5 mL) was microwaved at 100° C. for 30 min. The reaction mixture was cooled, diluted with H₂O (10 mL) then extracted with EtOAc (20 mL) twice. The combined organic layers were washed with brine, dried over anhydrous Na₂SO₄, and concentrated in vacuo. The resulting residue was purified by column chromatography over silica gel (eluting with PE:EA=1:1) to afford compound A13-1.

Step B: ethyl 6-fluoro-1,1-dimethyl-3-(4-(3-(methylsulfonyl)propoxy)-2-(trifluoromethyl)phenyl)-2,3-dihydro-1H-indene-5-carboxylate (A13-2)

A mixture of compound A13-1 (130 mg, 0.25 mmol) and 10% Pd/C (20 mg) in MeOH (5 mL) was hydrogenated (1 atm) at room temperature overnight. The reaction was then filtered; and the filtrate was concentrated to give crude compound A13-2.

Step C: (6-fluoro-1,1-dimethyl-3-(4-(3-(methylsulfonyl)propoxy)-2-(trifluoromethyl)phenyl)-2,3-dihydro-1H-inden-5-yl)methanol (A13-3)

To a stirred solution of LiAlH₄ (14 mg, 0.37 mmol) in dry THF (5 mL) was added compound A13-2 (132 mg, 0.25 mmol) at room temperature and the reaction was stirred for 2 hours. The reaction mixture was quenched with water and NaOH carefully, and stirred for 15 min. The reaction was then filtered, and the filtrate was concentrated in vacuo to give crude compound A13-3, which was used in the next step directly.

Step D: 5-(bromomethyl)-6-fluoro-1,1-dimethyl-3-(4-(3-(methylsulfonyl)propoxy)-2-(trifluoromethyl)phenyl)-2,3-dihydro-1H-indene (A13-4)

To a stirred solution of crude compound A13-3 (45 mg, 0.095 mmol) in dry DCM (5 mL) at room temperature was added PBr₃ (27 mg, 0.1 mmol). The reaction mixture was stirred for 2 hours, and then concentrated to give crude compound A13-4, which was used in the next step directly.

Step E: (6S)-ethyl 3-((6-fluoro-1,1-dimethyl-3-(4-(3-(methylsulfonyl)propoxy)-2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylate (A13-5)

A mixture of crude compound A13-4 (22 mg, 0.041 mmol), intermediate 1-9 (8 mg, 0.037 mmol) and Ag₂CO₃ (20 mg, 0.074 mmol) in toluene (2 mL) was heated at reflux overnight. The cooled mixture was dissolved in H₂O (10 mL) and extracted with EtOAc (20 mL) twice. The combined organic layers were washed with brine, dried over anhydrous Na₂SO₄ and concentrated in vacuo. The resulting residue was purified by column chromatography over silica gel (eluting with PE:EA=1:1) to afford compound A13-5.

Step F: (6S)-3-((6-fluoro-1,1-dimethyl-3-(4-(3-(methylsulfonyl)propoxy)-2-(trifluoro-methyl)phenyl)-2,3-dihydro-1H-inden-5-yl)methoxy)-5,5a,6,6a-tetrahydrocyclopropa[4,5]-cyclopenta[1,2-c]pyridine-6-carboxylic acid (A13-6)

A solution of compound A13-5 (10 mg, 0.014 mmol) and LiOH (4 mg, 0.14 mmol) in THF/MeOH/H₂O (3 mL/0.5 mL/0.5 mL) was stirred at room temperature overnight. The final mixture was acidified with HCl (2 N) to pH=7 and extracted with EtOAc (20 mL) twice. The combined organic layers were washed with brine, dried over Na₂SO₄, concentrated in vacuo and the residue was purified by preparative HPLC (on a GILSON 281 instrument fitted with a Phenomenex Gemini C18 150*30 mm*5 um using water and acetonitrile as the eluents. Mobile phase A: water (containing 0.1% TFA, v/v), mobile phase B: acetonitrile. Gradient: 70-9% B, 0-10 min; 100% B, 10.5-12.5 min; 5% B, 13-15 min) to give compound A13-6. $^1$H NMR (400 MHz, MeOD-d₄) δ: 7.96 (d, J=9.59 Hz, 1H), 7.23 (br. s., 1H), 7.00-7.10 (m, 2H), 6.98 (d, J=9.59 Hz, 1H), 6.80 (d, J=3.72 Hz, 1H), 6.58 (br. s., 1H), 5.23 (d, J=5.09 Hz, 2H), 4.67 (br. s., 1H), 4.17 (t, J=5.77 Hz, 2H), 3.35 (br. s., 2H), 3.19 (br. s., 1H), 2.94-3.10 (m, 4H), 2.89 (br. s., 1H), 2.38-2.47 (m, 2H), 2.26-2.34 (m, 2H), 1.89 (d, J=6.65 Hz, 1H), 1.42 (br. s., 3H), 1.28 (br. s., 3H), 1.12 (br. s., 1H). MS (ESI) m/e (M+H⁺): 648.6.

TABLE 5

Examples 29 to 31 (compounds A13-7 to A13-9) were prepared in a similar manner to Example 28 (Compound A13-6) using the appropriate intermediates and commercially available materials, and including procedures described across this application when necessary.

| Example | Structure | M.W. | Compound Name | LC/MS (ESI) observed [M + 1]+ |
|---|---|---|---|---|
| 29 | (Compound A13-7) | 616.6 | (5aR,6S,6aS)-3-((6-fluoro-3-(4-(3-hydroxy-3-methylbutoxy)-2-(trifluoromethyl)phenyl)-1,1-dimethyl-1H-inden-5-yl)methoxy)-5,5a,6,6a-tetrahydrocyclopropa[4,5]cyclopenta[1,2-c]pyridine-6-carboxylic acid | 617.4 |
| 30 | (Compound A13-8) | 528.6 | (5aR,6S,6aS)-3-((8-(6-(3-hydroxy-3-methylbutoxy)-2-methylpyridin-3-yl)-5,6,7,8-tetrahydronaphthalen-2-yl)methoxy)-5,5a,6,6a-tetrahydrocyclopropa[4,5]cyclopenta[1,2-c]pyridine-6-carboxylic acid | 529.2 |

TABLE 5-continued

Examples 29 to 31 (compounds A13-7 to A13-9) were prepared in a similar manner to Example 28 (Compound A13-6) using the appropriate intermediates and commercially available materials, and including procedures described across this application when necessary.

| Example | Structure | M.W. | Compound Name | LC/MS (ESI) observed [M + 1]+ |
|---|---|---|---|---|
| 31 | (Compound A13-9) | 510.6 | (5aR,6S,6aS)-3-((8-(2-methyl-6-((3-methylbut-3-en-1-yl)oxy)pyridin-3-yl)-5,6,7,8-tetrahydronaphthalen-2-yl)methoxy)-5,5a,6,6a-tetrahydrocyclopropa[4,5]cyclopenta[1,2-c]pyridine-6-carboxylic acid | 511.5 |

Example 32

(5aR,6S,6aS)-3-((5-fluoro-3,3-dimethyl-1-(2-(trifluoromethyl)phenyl)indolin-6-yl)methoxy)-5,5a,6,6a-tetrahydrocyclopropa[4,5]cyclopenta[1,2-c]pyridine-6-carboxylic acid (Compound A14-7)

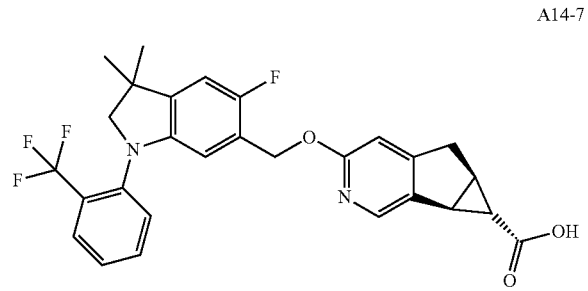

A14-7

Step A: 5-fluoro-3,3-dimethylindoline (A14-1)

4-fluorophenylhydrazine hydrochloride (10.00 g, 61.50 mmol) was added to a stirred solution of isobutyraldehyde (4.43 g, 61.50 mmol) in AcOH (180 mL) and the mixture was stirred at 60° C. for 3 h. The mixture was then cooled to room temperature and 1,2-dichloroethane (180 mL) was added, followed by sodium triacetoxyhydro-borate (13.04 g, 61.50 mmol) in several portions over 30 min at 0° C. After completion of the addition, the mixture was allowed to warm to room temperature and stirred for one hour. The reaction mixture was concentrated, washed with saturated aqueous $Na_2CO_3$, and extracted with EtOAc (300 mL) three times. The combined organic layers were washed with saturated aqueous sodium hydroxide (150 mL), dried over $Na_2SO_4$ and the solvent was evaporated under reduced pressure. The resulting residue was purified by column chromatography over silica gel (eluting with PE:EA=50:1 to 10:1) to give compound A14-1. MS (ESI) m/e (M+H+): 166.1.

Step B: 6-bromo-5-fluoro-3,3-dimethylindoline (A14-2)

To a solution of compound A14-1 (400 mg, 2.42 mmol) in 98% $H_2SO_4$ (5 mL) was added $Ag_2SO_4$ (400 mg, 1.28 mmol) and the suspension was stirred under $N_2$ atmosphere for 30 min. The mixture was then cooled to −5° C., and $Br_2$ (0.125 mL, 2.42 mmol) was slowly added over 5 min while maintaining the temperature for one hour. The reaction mixture was then slowly poured into 50 mL water/ice and filtered over Celite®. The filtrate was treated with 50% aqueous NaOH until pH=9-10 and extracted with EtOAc (30 mL) three times. The combined organic layers were washed with brine, dried over $Na_2SO_4$ and the solvent was evaporated under reduced pressure. The residue was purified by column chromatography over silica gel (eluting with PE:EA=50:1 to 10:1) to give compound A14-2.

Step C: 6-bromo-5-fluoro-3,3-dimethyl-1-(2-(trifluoromethyl)phenyl)indoline (A14-3)

To a suspension of compound A14-2 (600 mg, 2.46 mmol) and 1-fluoro-2-(trifluoromethyl)benzene (1210 mg, 7.37 mmol) in dry NMP (10 mL) at 0° C. under a $N_2$ atmosphere was added sodium hydride (177 mg, 7.37 mmol). The reaction mixture was warmed gradually to 80° C. over 3 hours. Then the reaction mixture was cooled to room temperature, poured into water (20 mL) and extracted with EtOAc (20 mL) twice. The combined organic layers were washed with brine, dried over $Na_2SO_4$ and concentrated in vacuo to give a residue, which was purified by column chromatography over silica gel (eluting with PE 100%) to give compound A14-3. MS (ESI) m/e (M+H+): 388.0, 390.0.

Step D: 6-bromo-5-fluoro-3,3-dimethyl-1-(2-(trifluoromethyl)phenyl)indoline (A14-4)

A mixture of compound A14-3 (650 mg, 1.67 mmol), and Pd(dppf)Cl$_2$ (61 mg, 0.084 mmol) in MeOH (60 mL), DMF (20 mL) and Et$_3$N (20 mL) was heated at 80° C. for 24 hours under CO atmosphere (50 psi). The reaction mixture was then washed with saturated aqueous NH₄Cl, extracted with EtOAc (50 mL) twice and concentrated. The resulting residue was purified by column chromatography over silica gel (eluting with PE:EA=10:1) to give compound A14-4. MS (ESI) m/e (M+H⁺): 368.1.

Step E: methyl 5-fluoro-3,3-dimethyl-1-(2-(trifluoromethyl)phenyl)indoline-6-carboxylate (A14-5)

To a solution of compound A14-4 (110 mg, 0.29 mmol) in dry THF (3 mL) at 0° C. was added lithium aluminum (III) hydride (13 mg, 0.35 mmol). After completion of the addition, the mixture was stirred at this temperature for 1 h. Then the reaction was quenched with anhydrous Na₂SO₄ (2 g) and water (1 mL) and the resulting mixture was filtered over Celite™, rinsing with EtOAc (20 mL). The filtrate was concentrated in vacuo to give compound A14-5, which was used in the next step directly.

Step F: ((5aR,6S,6aS)-ethyl 3-((5-fluoro-3,3-dimethyl-1-(2-(trifluoromethyl)phenyl)indolin-6-yl)methoxy)-5,5a,6,6a-tetrahydrocyclopropa[4,5]cyclopenta[1,2-c]pyridine-6-carboxylate (A14-6)

A mixture of compound A14-5 (60 mg, 0.25 mmol), intermediate 1-10 (85 mg, 0.25 mmol), Brett-Phos palladacycle (10 mg, 0.013 mmol) and Cs₂CO₃ (204 mg, 0.63 mmol) in toluene (10 mL) was heated at 110° C. for 10 hours. The mixture was filtered and the filtrate was concentrated in vacuo to give a residue, which was purified with preparative TLC over silica gel (eluting with PE:EA=5:1) to give compound A14-6. MS (ESI) m/e (M+H⁺): 541.2.

Step G: ((5aR,6S,6aS)-3-((5-fluoro-3,3-dimethyl-1-(2-(trifluoromethyl)phenyl)indolin-6-yl)methoxy)-5,5a,6,6a-tetrahydrocyclopropa[4,5]cyclopenta[1,2-c]pyridine-6-carboxylic acid (A14-7)

To a mixture of compound A14-6 (80 mg, 0.15 mmol) in THF (1 mL), MeOH (1 mL) and H₂O (1 mL) was added lithium hydroxide monohydrate (62 mg, 1.48 mmol) and the resulting mixture was stirred at room temperature for 5 hours. The reaction mixture was acidified with HCl (2 N) to pH=7 and extracted with EtOAc (20 mL) twice. The combined organic layers were washed with water, brine, dried over Na₂SO₄ and concentrated in vacuo to give a residue, which was purified by preparative HPLC (on a GILSON 281 instrument fitted with a Waters XSELECT C18 150*30 mm*5 um using water and acetonitrile as the eluents. Mobile phase A: water (containing 0.1% TFA, v/v), mobile phase B: acetonitrile. Gradient: 58-88% B, 0-10 min; 100% B, 10.5-12.5 min; 5% B, 13-15 min) to give compound A14-7. ¹H NMR (400 MHz, MeOD-d₄) δ: 1.21 (br. s., 1H) 1.37 (br. s., 6H) 2.42-2.54 (m, 1H) 2.96 (d, J=5.09 Hz, 1H) 3.06-3.16 (m, 1H) 3.39-3.66 (m, 2H) 5.21 (s, 2H) 6.12 (d, J=5.87 Hz, 1H) 6.85-6.99 (m, 2H) 7.39-7.52 (m, 2H) 7.67 (t, J=7.63 Hz, 1H) 7.78 (d, J=7.43 Hz, 1H) 8.06 (s, 1H). MS (ESI) m/e (M+H⁺): 513.2.

Example 33

((5aR,6S,6aS)-3-((1-(2-(trifluoromethyl)phenyl)indolin-6-yl)methoxy)-5,5a,6,6a-tetra hydro cyclopropa[4,5]cyclopenta[1,2-c]pyridine-6-carboxylic acid (Compound A15-6)

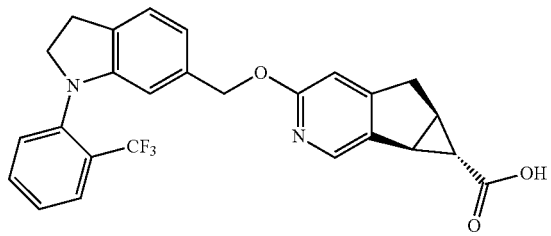

A15-6

Step A: 1-(2-Trifluoromethyl-phenyl)-1H-indole-6-carboxylic acid methyl ester (A15-1)

To a suspension of 1H-Indole-6-carboxylic acid methyl ester (600 mg, 2.46 mmol) and 1-fluoro-2-(trifluoromethyl)benzene (1210 mg, 7.37 mmol) in dry NMP (10 mL) at 0° C. was added sodium hydride (177 mg, 7.37 mmol) under N₂. After completion of the addition, the reaction was warmed gradually to 80° C. for 3 hours. The reaction mixture was then cooled to room temperature, poured into water (20 mL) and extracted with EtOAc (20 mL) twice. The combined organic layers were washed with brine, dried over Na₂SO₄ and concentrated in vacuo to give a residue, which was purified by column chromatography over silica gel (eluting with PE) to give compound A15-1 which was used in the next step without purification.

Step B: methyl 1-(2-(trifluoromethyl)phenyl)indoline-6-carboxylate (A15-1)

To a mixture of compound A15-1 (300 mg, 0.94 mmol) in TFA (10 mL) was added NaCNBH₃ (975 mg, 14.1 mmol) portionwise at 0° C. under N₂ atmosphere. After the addition was complete, the reaction mixture was stirred at room temperature for 24 hours. The whole reaction was poured into aqueous Na₂CO₃ (4M, 150 mL) and the product was extracted with EtOAc. The combined organic layers were washed with water, brine, dried over Na₂SO₄ and concentrated in vacuo to give compound A15-2, which was used in the next step without purification. MS (ESI) m/e (M+H⁺): 322.1.

Step C: (1-(2-(trifluoromethyl)phenyl)indolin-6-yl)methanol (A15-3)

To a suspension of LiAlH₄ (63 mg, 1.66 mmol) in dry THF (15 mL) at 0° C. was added a solution of compound A15-2 (266 mg, 0.83 mmol) in THF (2 mL) dropwise. After completion of the addition, the mixture was stirred at 0° C. for 1 h. The mixture was quenched with saturated aqueous NH₄Cl and extracted with EtOAc twice. The combined organic layers were washed with brine, dried over anhydrous Na₂SO₄, filtered and concentrated in vacuo to afford crude compound A15-3, which was used in the next step without purification. MS (ESI) m/e (M+H⁺): 294.1.

Step D: 6-(bromomethyl)-1-(2-(trifluoromethyl)phenyl)indoline (A15-4)

To a solution of crude compound A15-3 (190 mg, 0.65 mmol) in dry DCM (8 mL) at 0° C. was added PBr₃ (193 mg, 0.71 mmol) dropwise. The reaction solution was stirred at 0° C. for 1 h, then warmed to 20° C. and stirred for another 3 hrs. The reaction mixture was quenched with water, neutralized with saturated aqueous NaHCO₃ to pH=7, and extracted with EtOAc twice. The combined organic layers were washed with brine, dried over anhydrous Na₂SO₄, filtered and concentrated in vacuo to afford a residue, which was purified by preparative TLC over silica gel (PE:EA=10:1) to afford compound A15-4. MS (ESI) m/e (M+H$^+$): 356.0, 358.0.

Step E: (5aR,6S,6aS)-ethyl 3-((1-(2-(trifluoromethyl)phenyl)indolin-6-yl)methoxy)-5,5a,6,6a-tetrahydrocyclopropa[4,5]cyclopenta[1,2-c]pyridine-6-carboxylate (A15-5)

A mixture of compound A15-4 (139 mg, 0.39 mmol), intermediate 1-9 (85 mg, 0.39 mmol) and Ag₂CO₃ (322 mg, 1.17 mmol) in toluene (3 mL) was heated at 100° C. for 2 hrs. The mixture was filtered and the filtrate was concentrated in vacuo to give a residue, which was purified by preparative TLC over silica gel (eluting with PE:EA=3:1) to afford compound A15-5. MS (ESI) m/e (M+H$^+$): 495.2.

Step F: (5aR,6S,6aS)-3-((1-(2-(trifluoromethyl)phenyl)indolin-6-yl)methoxy)-5,5a,6,6a-tetra hydro cyclopropa[4,5]cyclopenta[1,2-c]pyridine-6-carboxylic acid (A15-6)

To a mixture of A15-5 (96 mg, 0.195 mmol) in THF (2 mL), MeOH (2 mL) and H₂O (2 mL) was added LiOH.H₂O (80 mg, 1.95 mmol), and the resulting solution was stirred at room temperature for 5 h. The reaction mixture was acidified with HCl (2 N) to pH=7 in an ice-water bath and then filtered, washed with water (5 mL) and dried in vacuo to give compound A15-6. $^1$H NMR (400 MHz, MeOD-d₄) δ: 7.99 (s, 1H), 7.79 (d, J=7.83 Hz, 1H), 7.64-7.72 (m, 1H), 7.40-7.52 (m, 2H), 7.12 (d, J=7.43 Hz, 1H), 6.76 (d, J=7.04 Hz, 1H), 6.60 (s, 1H), 6.09 (s, 1H), 5.08 (s, 2H), 3.18-3.26 (m, 1H), 3.12 (br. s., 2H), 2.97-3.04 (m, 1H), 2.90 (d, J=5.09 Hz, 1H), 2.37-2.45 (m, 1H), 1.12 (br. s., 1H). MS (ESI) m/e (M+H$^+$): 467.2.

TABLE 6

Examples 34 to 37 (Compounds A15-7 to A15-10) were prepared in a similar manner to Example 33 (Compound A15-6) using the appropriate intermediates and commercially available materials, and including procedures described across this application when necessary.

| Example | Structure | M.W. | Compound Name | LC/MS (ESI) observed [M + 1]+ |
|---|---|---|---|---|
| 34 | (Compound A15-7) | 464.4 | (5aR,6S,6aS)-3-((1-(2-(trifluoromethyl)phenyl)-1H-indol-6-yl)methoxy)-5,5a,6,6a-tetrahydrocyclopropa[4,5]cyclopenta[1,2-c]pyridine-6-carboxylic acid | 465.1 |
| 35 | (Compound A15-8) | 398.5 | (5aR,6S,6aS)-3-((1-(2-phenyl)indolin-6-yl)methoxy)-5,5a,6,6a-tetrahydrocyclopropa[4,5]cyclopenta[1,2-c]pyridine-6-carboxylicacid | 399.2 |
| 36 | (Compound A15-9) | 543.1 | (5aR,6S,6aS)-3-({3-bromo-1-[2-(trifluoromethyl)phenyl]-1H-indol-6-yl}methoxy)-5,5a,6,6a-tetrahydrocyclopropa[4,5]cyclopenta[1,2-c]pyridine-6-carboxylic acid | 544.0 |

TABLE 6-continued

Examples 34 to 37 (Compounds A15-7 to A15-10) were prepared in a similar manner to Example 33 (Compound A15-6) using the appropriate intermediates and commercially available materials, and including procedures described across this application when necessary.

| Example | Structure | M.W. | Compound Name | LC/MS (ESI) observed [M + 1]+ |
|---|---|---|---|---|
| 37 | (Compound A15-10) | 505.2 | (5aR,6S,6aS)-3-({3-cyclopropyl-1-[2-(trifluoromethyl)phenyl]-1H-indol-6-yl}methoxy)-5,5a,6,6a-tetrahydrocyclopropa[4,5]cyclopenta[1,2-c]pyridine-6-carboxylic acid | 506.0 |

Examples 38 and 39

Compounds A16-8 and A16-9

A16-8

A16-9

Step A: 2-(4-(ethoxycarbonyl)-2-(2-(trifluoromethyl)benzoyl)phenyl)-2-methylpropanoic acid (A16-1)

To a biphasic system of compound 3-5 (1.50 g, 4.16 mmol) and sodium periodate (7.12 g, 33.30 mmol) in CCl$_4$ (10 mL), acetonitrile (10 mL) and water (15 mL) was added ruthenium (III) chloride (0.432 g, 2.08 mmol). The reaction mixture was stirred vigorously overnight, then 10 mL of DCM and 5 mL of H$_2$O were added, and the organic layer was separated. The aqueous layer was further extracted with DCM (35 mL), and the combined organic layers were dried over MgSO$_4$ and concentrated in vacuo. The resulting residue was purified by column chromatography over silica gel (eluting with PE:EA=1:1) to give compound A16-1. MS (ESI) m/e (M+H$^+$): 409.1.

Step B: ethyl 1,1-dimethyl-3-(2-(trifluoromethyl)phenyl)-1H-isoindole-5-carboxylate (A16-2)

To a solution of compound A16-1 (900 mg, 2.20 mmol) in 1,4-dioxane (20 mL) was added diphenyl phosphorazidate (607 mg, 2.20 mmol), followed by triethylamine (223 mg, 2.20 mmol). The reaction was stirred at room temperature for 12 h, then 6 mL of 1 M HCl was added and the mixture was refluxed for 1 hr. Then the reaction mixture was cooled, concentrated, treated with saturated aqueous Na$_2$CO$_3$ until pH=10, and then extracted with EtOAc. The combined organic layers were combined and concentrated to give a residue, which was purified by chromatography over silica gel (eluting with PE:EA=2:1) to provide compound A16-2. MS (ESI) m/e (M+H$^+$): 362.2.

Step C: ethyl 1,1-dimethyl-3-(2-(trifluoromethyl)phenyl)isoindoline-5-carboxylate (A16-3)

10% Pd/C (88. mg, 0.83 mmol)) was added to a solution of compound A16-2 (300 mg, 0.83 mmol) in 2-propanol (50 mL) and the resulting mixture was stirred at 50° C. under H$_2$ (50 psi) for 12 h. The mixture was filtered over Celite™ and the filtrate was concentrated in vacuo to give compound A16-3, which was used directly in the next step. MS (ESI) m/e (M+H$^+$): 364.1.

Step D: 1,1-dimethyl-3-(2-(trifluoromethyl)phenyl)isoindolin-5-yl)methanol (A16-4)

To a suspension of LiAlH$_4$ (75 mg, 1.97 mmol) in dry THF (2 mL) at 0° C. was added a solution of compound A16-3 (143 mg, 0.39 mmol) in THF (2 mL) dropwise. After completion of the addition, the reaction mixture was stirred at 0° C. for 12 h. The reaction was then carefully quenched with water and 10% aq.NaOH and diluted with another 10 mL of THF. The resulting precipitate was removed by filtration and the filtrate was concentrated to provide crude compound A16-4, which was used in the next step directly. MS (ESI) m/e (M+H$^+$): 322.1.

Step E: 5-(bromomethyl)-1,1-dimethyl-3-(2-(trifluoromethyl)phenyl)isoindoline (A16-5)

To a solution of crude compound A16-4 (45.0 mg, 0.14 mmol) in dry $CH_2Cl_2$ (15 mL) at 0° C. was added $PBr_3$ (30.3 mg, 0.11 mmol) dropwise. The reaction was stirred at 0° C. for 1 h, then warmed to 20° C. and stirred for another 3 h. The reaction was then quenched with water, neutralized with saturated aqueous $NaHCO_3$ until pH=7, and then extracted with EtOAc twice. The combined organic layers were washed with brine, dried over anhydrous $Na_2SO_4$ and concentrated in vacuo to afford crude compound A16-5, which was used in the next step directly.

Step F: 5-(bromomethyl)-1,1-dimethyl-3-(2-(trifluoromethyl)phenyl)isoindoline (A16-6)

A mixture of crude compound A16-5 (88 mg, 0.23 mmol), intermediate 1-9 (50 mg, 0.23 mmol) and $Ag_2CO_3$ (189 mg, 0.68 mmol) in toluene (20 mL) was heated to 100° C. for 2 h. Then the reaction was filtered and the filtrate was concentrated in vacuo to give a residue, which was purified by preparative TLC over silica gel to afford compound A16-6. MS (ESI) m/e (M+H$^+$): 523.3.

Step G: (5aR,6S,6aS)-ethyl 3-((1,1,2-trimethyl-3-(2-(trifluoromethyl)phenyl)isoindolin-5-yl)methoxy-5,5a,6,6a-tetrahydrocyclopropa[4,5]cyclopenta[1,2-c]pyridine-6-carboxylate (A16-7)

A mixture of compound A16-6 (40 mg, 0.08 mmol), iodomethane (22 mg, 0.15 mmol) and $K_2CO_3$ (32 mg, 0.23 mmol) in DMF (10 mL) was heated at 100° C. for 12 h. The reaction was cooled and concentrated, and the resulting residue was diluted with EtOAc (50 mL) and washed with aqueous saturated $NaHCO_3$ (30 mL), and then brine (30 mL). The organic layer was dried over $Na_2SO_4$, and concentrated under reduced pressure. The resulting residue was purified by preparative TLC over silica gel (eluting with PE:EA=3:1) to give compound A16-7. MS (ESI) m/e (M+H$^+$): 537.3.

Step H: (5aR,6S,6aS)-3-((1,1,2-trimethyl-3-(2-(trifluoromethyl)phenyl)isoindolin-5-yl)methoxy)-5,5a,6,6a-tetrahydrocyclopropa[4,5]cyclopenta[1,2-c]pyridine-6-carboxylic acid (A16-8)

To a mixture of compound A16-7 (40 mg, 0.08 mmol) in THF (1 mL), MeOH (1 mL) and $H_2O$ (1 mL) was added LiOH (37 mg, 1.53 mmol), and the resulting mixture was stirred at room temperature for 12 h. The reaction mixture was acidified with HCl (1 N) to pH=6, and extracted with EtOAc (20 mL) twice. The combined organic layers were washed with water, brine, dried over $Na_2SO_4$ and concentrated in vacuo. The resulting residue was purified by reverse preparative HPLC (on a GILSON 281 instrument fitted with a Phenomenex Gemini C18 150*30 mm*5 um using water and acetonitrile as the eluents. Mobile phase A: water (containing 0.1% TFA, v/v), mobile phase B: acetonitrile. Gradient: 23-43% B, 0-10 min; 100% B, 10.5-12.5 min; 5% B, 13-15 min) to give compound A16-8. $^1$H NMR (400 MHz, MeOD-d$_4$) δ: 8.01 (s, 2H), 7.77-7.82 (m, 2H), 7.61-7.67 (m, 1H), 7.55 (d, J=7.53 Hz, 1H), 7.42 (br. s., 1H), 6.88 (br. s., 1H), 6.71 (s, 1H), 6.08 (br. s., 1H), 5.26-5.36 (m, 2H), 3.24 (br. s., 1H), 3.02-3.12 (m, 1H), 2.89-2.97 (m, 4H), 2.47 (br. s., 1H), 1.96 (s, 3H), 1.70 (s, 3H), 1.12-1.18 (m, 1H). MS (ESI) m/e (M+H$^+$): 509.2.

Step I: (5aR,6S,6aS)-3-((1,1-dimethyl-3-(2-(trifluoromethyl)phenyl)isoindolin-5-yl)methoxy)-5,5a,6,6a-tetrahydrocyclopropa[4,5]cyclopenta[1,2-c]pyridine-6-carboxylic acid (A16-9)

To a mixture of compound A16-6 (40 mg, 0.08 mmol) in THF (2 mL), MeOH (2 mL) and $H_2O$ (2 mL) was added LiOH (37 mg, 1.53 mmol), and the resulting mixture was stirred at room temperature for 12 hrs. Then the reaction mixture was acidified with HCl (1 N) to pH=6, and extracted with EtOAc (30 mL) twice. The combined organic layers were washed with water, brine, dried over $Na_2SO_4$ and concentrated in vacuo. The resulting residue was purified by reverse preparative HPLC (preparative HPLC on a GILSON 281 instrument fitted with a YMC-pack ODS-AQ 150*30 mm*5 um using water and acetonitrile as the eluents. Mobile phase A: water (containing 0.1% TFA, v/v), mobile phase B: acetonitrile. Gradient: 25-55% B, 0-10 min; 100% B, 10.5-12.5 min; 5% B, 13-15 min) to give compound A16-9. $^1$H NMR (400 MHz, MeOD-d$_4$) δ: 8.02 (s, 1H), 7.94 (d, J=7.53 Hz, 1H), 7.61-7.75 (m, 3H), 7.51 (d, J=8.03 Hz, 1H), 7.11-7.18 (m, 2H), 6.71 (s, 1H), 6.42 (s, 1H), 5.30-5.40 (m, 2H), 3.20-3.29 (m, 1H), 2.99-3.10 (m, 1H), 2.93 (d, J=4.77 Hz, 1H), 2.38-2.49 (m, 1H), 1.80 (s, 6H), 1.13 (dt, J=6.09, 2.85 Hz, 1H). MS (ESI) m/e (M+H$^+$): 495.2.

Example 40

(5aR,6 S,6aS)-3-methyl-3-(2-(trifluoromethyl)phenyl)-1,3-dihydroisobenzofuran-5-yl)methoxy)-5,5a,6,6a-tetrahydrocyclopropa[4,5]cyclopenta[1,2-c]pyridine-6-carboxylic acid (Compound A17-4)

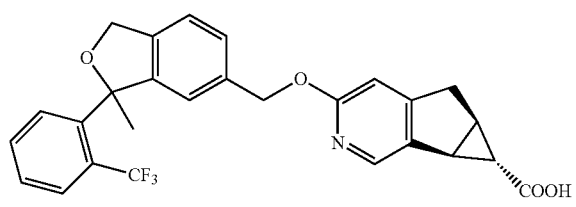

A17-4

Step A: 1-(2,5-bis((methoxymethoxy)methyl)phenyl)-1-(2-(trifluoromethyl)phenyl)ethanol (A17-1)

To a solution of intermediate 5-5 (300 mg, 0.76 mmol) in anhydrous DCM (3 mL), was added MeMgBr (0.75 ml, 3.0 eq) at 0° C. under a nitrogen atmosphere. The reaction mixture was allowed to warm to room temperature overnight, and then quenched with saturated aqueous $NH_4Cl$, diluted with DCM and $H_2O$, then extracted with DCM twice. The combined organic layers were washed with water, brine, dried over $Na_2SO_4$ and concentrated in vacuo to obtain compound A17-1, which was used in the next step without further purification.

Step B: 6-(chloromethyl)-1-methyl-1-(2-(trifluoromethyl)phenyl)-1,3-dihydroisobenzofuran (A17-2)

A solution of compound A17-1 (230 mg, 0.555 mmol) in 1,4-dioxane (5.0 mL) and concentrated HCl (5.0 mL) was heated under refluxed overnight. Then the reaction mixture was concentrated in vacuo to obtain a residue, which was purified by preparative TLC over silica gel (eluting with PE:EA=3:1) to afford compound A17-2. MS (ESI) m/e (M+H⁺): 327.2.

Step C: (5aR,6S,6aS)-ethyl 3-((3-methyl-3-(2-(trifluoromethyl)phenyl)-1,3-dihydroisobenzofuran-5-yl)methoxy)-5,5a,6,6a-tetrahydrocyclopropa[4,5]cyclopenta[1,2-c]pyridine-6-carboxylate (A17-3)

To a solution of compound A17-2 (20 mg, 0.06 mmol) in toluene (2 mL) were added Ag$_2$CO$_3$ (25.3 mg, 1.5 eq) and intermediate 1-9 (13.2 mg, 0.06 mmol). The reaction mixture was stirred at 120° C. for 18 hours, then cooled, filtered through Celite™ and concentrated in vacuo. The resulting residue was purified by preparative TLC over silica gel to afford compound A17-3. MS (ESI) m/e (M+H⁺): 524.4

Step D: (5aR,6S,6aS)-3-((3-methyl-3-(2-(trifluoromethyl)phenyl)-1,3-dihydroisobenzofuran-5-yl)methoxy)-5,5a,6,6a-tetrahydrocyclopropa[4,5]cyclopenta[1,2-c]pyridine-6-carboxylic acid (A17-1)

To a mixture of compound A17-3 (10.0 mg, 0.019 mmol) in THF (0.5 mL), MeOH (0.5 mL) and H$_2$O (0.5 mL) was added LiOH (5.0 mg, 10.0 eq). The reaction mixture was stirred at room temperature for 3 h, then acidified with HCl (2 N) to pH=6 and extracted with EtOAc (5 mL) twice. The combined organic layers were washed with water, brine, dried over Na$_2$SO$_4$ and concentrated in vacuo to afford a residue, which was purified by preparative TLC over silica gel to obtain compound A17-4. $^1$H NMR (400 MHz, MeOD-d$_4$) δ: 8.07 (s, 1H), 7.76 (d, J=8.8 HZ, 1H), 7.60 (d, J=8 HZ, 1H), 7.51-7.43 (m, 2H), 7.42-7.33 (m, 2H), 7.25 (d, J=8 HZ, 1H), 6.67 (s, 1H), 5.34 (s, 2H), 5.00 (d, J=12 HZ, 1H), 4.88-4.84 (m, 1H), 3.29-3.21 (m, 1H), 3.04 (d, J=16 HZ, 1H), 2.93 (d, J=8 HZ, 1H), 2.47-2.40 (m, 1H), 1.87 (s, 3H), 1.14 (s, 1H). MS (ESI) m/e (M+H⁺): 496.2.

Example 41

(5aR,6S,6aS)-3-((6-fluoro-1,1-dimethyl-3-(2-(trifluoromethyl)phenyl)-1,3-dihydroisobenzofuran-5-yl)methoxy)-5,5a,6,6a-tetrahydrocyclopropa[4,5]cyclopenta[1,2-c]pyridine-6-carboxylic acid (Compound A18-9)

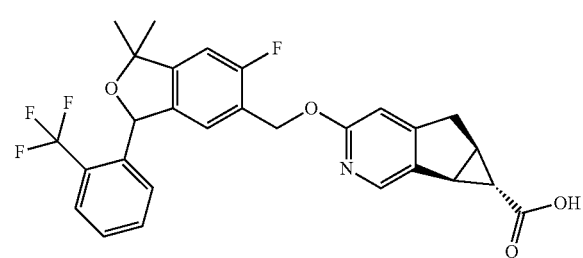

A18-9

Step A:
(2-bromo-5-fluoro-1,4-phenylene)dimethanol (A18-2)

A mixture of methyl 5-bromo-2-fluoro-4-formylbenzoate A18-1 (1.0 g, 3.83 mmol) in THF (10 ml) at 0° C. under nitrogen was treated with LiAlH$_4$ (0.363 g, 9.58 mmol). The reaction mixture was stirred at that temperature for 12 hours, then Na$_2$SO$_4$ (6.0 g) was added. The resulting mixture was quenched with water slowly, then filtered and concentrated in vacuo. The resulting residue was purified by column chromatography over silica gel (eluting with PE:EA=3:1) to give compound A18-2. MS (ESI) m/e (M−OH⁻): 216.3/218.3.

Step B: 1-bromo-4-fluoro-2,5-bis((methoxymethoxy)methyl)benzene (A18-3)

A solution of compound A18-2 (0.5 g, 2.127 mmol) in DMF (5.0 ml) at 0° C. was treated with N-ethyl-N-isopropylpropan-2-amine (0.412 g, 3.19 mmol), followed by the dropwise addition of chloro(methoxy)methane (0.685 g, 8.51 mmol). The reaction was allowed to warm to room temperature and stirred for 18 hrs. The reaction mixture was then filtered and extracted with EtOAc (10 ml) three times. The combined organic layers were washed with water and brine, dried over Na$_2$SO$_4$, filtered and concentrated in vacuo to give a residue, which was purified by flash chromatography over silica gel (eluting with PE:EA=8:1) to give compound A18-3.

Step C: (4-fluoro-2,5-bis((methoxymethoxy)methyl)phenyl)(2-(trifluoromethyl)phenyl)methanol (A18-4)

To a solution of compound A18-3 (0.4 g, 1.238 mmol) in THF (5.0 ml) at −78° C. was added n-BuLi (2.5N in hexanes, 0.743 ml, 1.857 mmol) and the resulting solution was stirred at that temperature for 30 min. Then, 2-(trifluoromethyl)benzaldehyde (0.323 g, 1.857 mmol) in 0.5 ml of THF was added dropwise to the reaction and the reaction mixture was stirred at −78° C. for 30 min. Then the reaction was quenched with 1N HCl, and extracted with EtOAc. The combined EtOAc layers were washed with brine, dried over Na$_2$SO$_4$, and concentrated in vacuo to give a residue, which was purified by flash chromatography over silica gel (eluting with PE:EA=3:1) to afford compound A18-4. MS (ESI) m/e (M+Na⁺): 441.4.

Step D: 6-(chloromethyl)-5-fluoro-1-(2-(trifluoromethyl)phenyl)-1,3-dihydroisobenzofuran (A18-5)

A solution of compound A18-4 (100 mg, 0.239 mmol) in 1,4-dioxane (4 ml) and concentrated HCl (4.00 ml) was stirred at 100° C. overnight. The reaction mixture was extracted with DCM (5 ml), and the DCM layer was washed with water, brine, dried over Na$_2$SO$_4$, and concentrated in vacuo to provide compound A18-5, which was used in the next step without purification. MS (ESI) m/e (M+H⁺+ACN): 394.2.

Step E: 5-(chloromethyl)-6-fluoro-3-(2-(trifluoromethyl)phenyl)isobenzofuran-1(3H)-one (A18-6)

A mixture of compound A18-5 (60.0 mg, 0.181 mmol) and PCC (78 mg, 0.363 mmol) in anhydrous DCM (3 ml) was stirred at 50° C. overnight. The reaction mixture was filtered through a Celite™ pad and the residue was washed with DCM. The filtrate was concentrated and purified by preparative TLC over silica gel to give compound A18-6. MS (ESI) m/e (M+H+): 345.2.

Step F: 2-(4-(chloromethyl)-5-fluoro-2-(hydroxy(2-(trifluoromethyl)phenyl)methyl)-phenyl)propan-2-ol (A18-7)

To a solution of compound A18-6 (35 mg, 0.102 mmol) in THF (2.0 ml) at 0° C. was added methylmagnesium bromide (0.085 ml, 0.254 mmol) dropwise. The resulting solution was allowed to warm to room temperature and stirred for 2 h. Then the reaction was quenched with saturated aqueous NH$_4$Cl, and extracted with EtOAc. The organic layer washed with brine, dried over Na$_2$SO$_4$, and concentrated in vacuo to give crude product A18-7, which was used in the next step without purification.

Step G: (5aR,6S,6aS)-ethyl 3-((6-fluoro-1,1-dimethyl-3-(2-(trifluoromethyl)phenyl)-1,3-dihydroisobenzofuran-5-yl)methoxy)-5,5a,6,6a-tetrahydrocyclopropa[4,5]cyclopenta[1,2-c]pyridine-6-carboxylate (A18-8)

To a solution of compound A18-7 (30 mg, 0.064 mmol) in toluene (3 ml) was added Ag$_2$CO$_3$ (26.3 mg, 0.096 mmol) and intermediate 1-9 (16.76 mg, 0.076 mmol). The mixture was stirred at 120° C. for 4 hours. Then the reaction mixture was filtered through Celite™ and washed with DCM, The filtrate was concentrated in vacuo to obtain a residue, which was purified by preparative TLC over silica gel (eluting with PE:EA=5:1) to give compound A18-8. MS (ESI) m/e (M+H$^+$): 541.2.

Step H: (5aR,6S,6aS)-3-((6-fluoro-1,1-dimethyl-3-(2-(trifluoromethyl)phenyl)-1,3-dihydroisobenzofuran-5-yl)methoxy)-5,5a,6,6a-tetrahydrocyclopropa[4,5]cyclopenta[1,2-c]pyridine-6-carboxylic acid (A18-9)

To a mixture of compound A18-8 (15 mg, 0.028 mmol) in THF (1 mL), MeOH (1 mL) and H$_2$O (1 mL) was added LiOH (3.32 mg, 0.138 mmol). The mixture was stirred at room temperature for 3 h, then acidified with HCl (2 N) to pH=6, and extracted with EtOAc (8 mL) twice. The combined organic layers were washed with water, brine, dried over Na$_2$SO$_4$ and concentrated in vacuo to afford a residue, which was purified by preparative HPLC (on a GILSON 281 instrument fitted with a Phenomenex Synergi C18 100*21.2 mm*4 um) using water and acetonitrile as the eluents. Mobile phase A: water (containing 0.1% TFA, v/v), mobile phase B: acetonitrile. Gradient: 66-86% B, 0-10 min; 100% B, 10.5-12.5 min; 5% B, 13-15 min) to afford compound A18-9. $^1$H NMR (400 MHz, MeOD-d$_4$) δ: 8.02 (d, J=3.6 HZ, 1H), 7.77 (d, J=8.0 HZ, 1H), 7.64 (t, J=8.0 HZ, 1H), 7.50 (t, J=8.0 HZ, 1H), 7.37 (d, J=7.2 HZ, 1H), 7.13 (d, J=9.6 HZ, 1H), 6.92 (t, J=8.0 HZ, 1H), 6.74 (s, 1H), 6.49 (s, 1H), 5.31 (br. s., 2H), 3.30-3.22 (m, 1H), 3.10-3.03 (m, 1H), 2.94 (d, J=5.6 HZ, 1H), 2.50-2.44 (m, 1H), 1.73 (s, 3H), 1.55 (s, 3H), 1.16 (s, 1H). MS (ESI) m/e (M+H$^+$): 513.2.

Example 42

(5aR,6S,6aS)-3-((8-(2-(trifluoromethyl)phenyl)-5,6,7,8-tetrahydronaphthalen-2-yl)methoxy)-5,5a,6,6a-tetrahydrocyclopropa[4,5]cyclopenta[1,2-c]pyridine-6-carboxylic acid (Compound A19-9A)

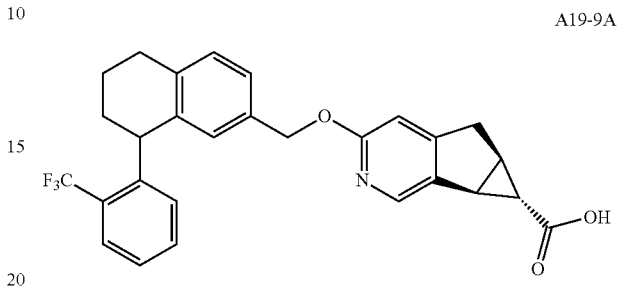

A19-9A

Step A: methyl 8-oxo-5,6,7,8-tetrahydronaphthalene-2-carboxylate (A19-2)

To a mixture of 7-bromo-3,4-dihydronaphthalen-1(2H)-one A19-1 (15 g, 67 mmol) and Pd(OAc)$_2$ (0.75 g, 3.4 mmol) in DMF (20 mL) and MeOH (300 mL) were added Xant-Phos (3.9 mg, 4.7 mmol) and Et$_3$N (34 g, 0.33 mmol). Then the mixture was heated to 70° C. for 48 h under a CO atmosphere (55 psi). After cooling to room temperature, the reaction was filtered and the filtrate was concentrated in vacuo to afford a residue, which was partitioned between EA and water. The organic layer was separated and the aqueous layer was extracted with EA twice. The combined organic layers were washed with water, dried and concentrated in vacuo to obtain a residue, which was purified by column chromatography over silica gel to afford A19-2. MS (ESI) m/e (M+H$^+$): 204.1/205.1.

Step B: methyl 8-(((trifluoromethyl)sulfonyl)oxy)-5,6-dihydronaphthalene-2-carboxylate (A19-3)

To a solution of compound A19-2 (3 g, 15 mmol) in dry THF (60 mL) at −78° C. was added KHMDS (1 M in THF, 20 mL, 20 mmol) dropwise, followed by Tf$_2$NPh (6.43 g, 18 mmol). The reaction mixture was allowed to warm to room temperature and stirred for 16 hrs. Then the reaction was quenched with water, and neutralized with aqueous HCl (2N) to pH=7. The organic layer was separated and the aqueous solution was extracted with EtOAc two times. The combined organic layers were washed with brine, dried over Na$_2$SO$_4$ and concentrated in vacuo to afford a residue, which was purified by column chromatography over silica gel to obtain compound A19-3. MS (ESI) m/e (M+H$^+$): 336.0/337.1.

Step C: methyl 8-(2-(trifluoromethyl)phenyl)-5,6-dihydronaphthalene-2-carboxylate (A19-5)

A mixture of compound A19-3 (300 mg, 0.89 mmol), 2-CF$_3$-phenyl boronic acid (204 mg, 1.07 mmol)), K$_2$CO$_3$ (308 mg, 2.23 mmol), and Pd(dppf)Cl$_2$ (33 mg, 0.04 mmol) in 1,4-dioxane (5 mL) and H$_2$O (1 mL) was microwaved to 100° C. for 30 min under a nitrogen atmosphere. After cooling to room temperature, the reaction was filtered, and the filtrate was extracted with EtOAc. The combined organic layers were washed with water, dried over $Na_2SO_4$, and concentrated in vacuo to obtain a residue, which was purified by preparative TLC over silica gel to give compound A19-4. MS (ESI) m/e (M+H$^+$): 332.1/333.0.

Step D: methyl 8-(2-(trifluoromethyl)phenyl)-5,6,7,8-tetrahydronaphthalene-2-carboxylate (A19-5)

To a solution of compound A19-4 (200 mg, 0.6 mmol) in MeOH (10 mL) and THF (5 mL) was added 10% Pd/C (10 mg). The reaction was stirred at 25° C. under $H_2$ (1 atm) for 16 hrs. Then the mixture was filtered and the filtrate was concentrated in vacuo to give a residue, which was purified by preparative TLC over silica gel to afford compound A19-5. MS (ESI) m/e (M+H$^+$): 334.1/335.2.

Step E: (8-(2-(trifluoromethyl)phenyl)-5,6,7,8-tetrahydronaphthalen-2-yl)methanol (A19-6)

To a mixture of $LiAlH_4$ (137 mg, 3.6 mmol) in dry THF (6 mL) at 0° C. was added a solution of compound A19-5 (120 mg, 0.36 mmol) in THF (4 mL) dropwise. After completion of the addition, the reaction mixture was stirred at 0° C. for 4 hrs. The mixture was then quenched with saturated aqueous $NH_4Cl$, and extracted with EtOAc twice. The organic layers were combined and concentrated in vacuo to afford a residue, which was purified by preparative TLC over silica gel to obtain compound A19-6. MS (ESI) m/e (M+H$^+$): 306.2/307.1.

Step F: 7-(bromomethyl)-1-(2-(trifluoromethyl)phenyl)-1,2,3,4-tetrahydronaphthalene (A19-8)

To a solution of compound A19-6 (80 mg, 0.26 mmol) in dry THF (2 mL) at 0° C. was added $PBr_3$ (57 mg, 021 mmol) dropwise. The reaction was stirred at 0° C. for 1 h, then warmed to 20° C. and stirred for 2 hrs. The reaction was quenched with water, and neutralized with saturated aqueous $NaHCO_3$ to pH=7. The organic layer was separated and concentrated in vacuo to afford a residue, which was purified by preparative TLC over silica gel to obtain compound A19-7.

Step G: (5aR,6S,6aS)-ethyl 3-((8-(2-(trifluoromethyl)phenyl)-5,6,7,8-tetrahydronaphthalen-2-yl)methoxy-5,5a,6,6a-tetrahydrocyclopropa[4,5]cyclopenta[1,2-c]pyridine-6-carboxylate (A19-10)

A mixture of compound A19-7 (100 mg, 0.27 mmol), intermediate 1-9 (54 mg, 0.24 mmol) and $Ag_2CO_3$ (186 mg, 0.68 mmol) in toluene (3 mL) was heated to 120° C. for 3 hrs. The reaction was filtered and the filtrate was concentrated in vacuo to give a residue, which was purified by Preparative TLC over silica gel to give compound A19-8. MS (ESI) m/e (M+H$^+$): 507.2/507.5.

Step H: (5aR,6S,6aS)-3-((8-(2-(trifluoromethyl)phenyl)-5,6,7,8-tetrahydronaphthalen-2-yl)methoxy)-5,5a,6,6a-tetrahydrocyclopropa[4,5]cyclopenta[1,2-c]pyridine-6-carboxylic acid (A19-9)

To a solution of compound A19-8 (80 mg) in THF (2 mL), MeOH (2 mL) and $H_2O$ (2 mL) was added NaOH (32 mg) and the reaction was stirred at room temperature for 5 hrs. The reaction mixture was acidified with HCl (2 N) to pH=5 and extracted with EtOAc (10 mL) twice. The combined organic layers were washed with water, brine, dried over $Na_2SO_4$ and concentrated in vacuo to afford a residue, which was purified by preparative TLC over silica gel (eluting with PE:EA=1:1) to obtain compound A19-9. $^1$H NMR (400 MHz, MeOD-d$_4$) δ: 8.12 (s, 1H), 7.67 (d, J=8 Hz, 1H), 7.41 (t, J=7.6 Hz, 1H), 7.34 (t, J=7.6 Hz, 1H), 7.22-6.99 (m, 3H), 7.00 (d, J=7.6 Hz, 1H), 6.68 (d, J=4.8 Hz, 1H), 5.21 (s, 2H), 4.50-4.47 (m, 1H), 3.43-3.35 (m, 1H), 3.32-3.17 (m, 1H), 3.03-2.97 (m, 1H), 2.94-2.88 (m, 1H), 2.84 (s, 1H), 2.56-2.51 (m, 1H), 2.22-2.16 (m, 1H), 2.03-1.99 (m, 1H), 1.80-1.76 (m, 1H), 1.30 (d, J=2.8 Hz, 1H). MS (ESI) m/e (M+H$^+$): 480.5.

Chiral SFC Resolution of Compound A19-9 (Compound A19-9A)

Compound A19-9 was purified by chiral preparative SFC (Column: Chiralcel OD-3 150×4.6 mm I.D., 3 um; Mobile phase: iso-propanol in $CO_2$ from 10% to 50%; Flow rate: 2.5 mL/min; Wavelength: 220 nm). The first peak with shorter retention time is the isomer A19-9A. $^1$H NMR (400 MHz, MeOD-d$_4$) δ: 8.12 (s, 1H), 7.67 (d, J=8 Hz, 1H), 7.41 (t, J=7.6 Hz, 1H), 7.34 (t, J=7.6 Hz, 1H), 7.22-6.99 (m, 3H), 7.00 (d, J=7.6 Hz, 1H), 6.68 (d, J=4.8 Hz, 1H), 5.21 (s, 2H), 4.50-4.47 (m, 1H), 3.43-3.35 (m, 1H), 3.32-3.17 (m, 1H), 3.03-2.97 (m, 1H), 2.94-2.88 (m, 1H), 2.84 (s, 1H), 2.56-2.51 (m, 1H), 2.22-2.16 (m, 1H), 2.03-1.99 (m, 1H), 1.80-1.76 (m, 1H), 1.30 (d, J=2.8 Hz, 1H). MS (ESI) m/e (M+H$^+$): 480.5.

TABLE 7

Examples 43 to 45 (Compounds A19-10 to A19-12) were prepared in a similar manner to Example 42 (Compound A19-9) using the appropriate intermediates and commercially available materials, and including procedures described across this application when necessary.

| Example | Structure | M.W. | Compound Name | LC/MS (ESI) observed [M + 1]+ |
|---|---|---|---|---|
| 43 | (Compound A19-10) | 492.5 | (5aR,6S,6aS)-3-((1-methyl-8-(2-(trifluoromethyl)phenyl)-5,6,7,8-tetrahydro-naphthalen-2-yl)methoxy)-5,5a,6,6a-tetrahydrocyclopropa[4,5]cyclopenta[1,2-c]pyridine-6-carboxylic acid | 493.2 |

TABLE 7-continued

Examples 43 to 45 (Compounds A19-10 to A19-12) were prepared in a similar manner to Example 42 (Compound A19-9) using the appropriate intermediates and commercially available materials, and including procedures described across this application when necessary.

| Example | Structure | M.W. | Compound Name | LC/MS (ESI) observed [M + 1]+ |
|---|---|---|---|---|
| 44 | (Compound A19-11) | 497.5 | (5aR,6S,6aS)-3-((3-fluoro-8-(2-(trifluoromethyl)phenyl)-5,6,7,8-tetrahydronaphthalen-2-yl)methoxy)-5,5a,6,6a-tetrahydrocyclopropa[4,5]cyclopenta[1,2-c]pyridine-6-carboxylic acid | 498.3 |
| 45 | (Compound A19-12) | 491.5 | (5aR,6S,6aS)-3-((6-fluoro-3-(2-fluoro-5-methoxy henyl)-1,1-dimethyl-2,3-dihydro-1H-inden-5-yl)methoxy)-5,5a,6,6a-tetrahydrocyclopropa[4,5]cyclopenta[1,2-c]pyridine-6-carboxylic acid | 492.1 |

Example 46

(5aR,6S,6aS)-3-((7-methyl-8-(2-(trifluoromethyl)phenyl)-5,6,7,8-tetrahydronaphthalen-2-yl)methoxy)-5,5a,6,6a-tetrahydrocyclopropa[4,5]cyclopenta[1,2-c]pyridine-6-carboxylic acid (Compound A20-9)

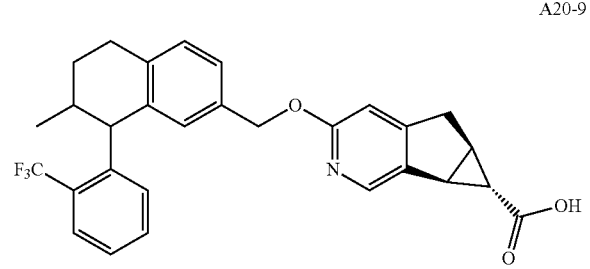 [SMILES: CC1CCc2ccc(COc3cc4c(cn3)[C@H]3[C@@H](C4)[C@@H]3C(=O)O)cc2C1c1ccccc1C(F)(F)F]

A20-9

Step A: methyl 7-methyl-8-oxo-5,6,7,8-tetrahydronaphthalene-2-carboxylate (A20-2)

To a solution of DIPEA (1.11 g, 0.011 mmol) in THF (8 mL) at −78° C. under $N_2$ was added n-BuLi (2.5 N in hexanes, 4.2 mL, 0.011 mmol) dropwise and the mixture was stirred for 30 min. Then the resulting solution was added to a mixture of compound A19-2 (2.04 g, 0.01 mol) and RMPA (18 g, 0.1 mmol) in THF (50 mL) at −78° C. over 2 hrs. To the resulting solution was added a solution of MeI (1.7 g, 0.012 mol) in THF (5 mL) dropwise via syringe at −78° C. The reaction was quenched by addition of saturated aqueous $NH_4Cl$ and water and the resulting mixture was filtered. The filtrate was concentrated in vacuo to give a residue, which was purified by flash chromatography over silica gel (eluting with PE:EA=4:1) to afford compound A20-2. MS (ESI) m/e (M+H+): 218.3.

Step B: methyl 7-methyl-8-(((trifluoromethyl)sulfonyl)oxy)-5,6-dihydronaphthalene-2-carboxylate (A20-3)

A mixture of compound A20-2 (1.0 g, 4.59 mmol) in THF (20 mL) at −78° C. under $N_2$ was treated with KHMDS (1 N in THF, 9.2 mL, 9.17 mmol) slowly, followed by stirring for one hour at −78° C. Then the reaction mixture was treated with PhN(Tf)$_2$ (2.10 g, 5.86 mmol) slowly. The reaction was stirred 6 h, then acidified with diluted hydrochloric acid. The reaction was further quenched by the addition of saturated aqueous $NH_4Cl$ and water. The organic layer was separated and concentrated in vacuo. The resulting residue was purified by flash chromatography over silica gel (eluting with PE:EA=4:1) to afford compound A20-3. MS (ESI) m/e (M+H+): 350.1

Step C: methyl 7-methyl-8-(2-(trifluoromethyl)phenyl)-5,6-dihydronaphthalene-2-carboxylate (A20-4)

To a solution of compound A20-3 (600 mg, 1.7 mmol), $K_3PO_4$ (600 mg, 2.9 mmol) and (2-(trifluoromethyl)phenyl)boronic acid (423 mg, 2.2 mmol) in THF (30 mL) and $H_2O$ (10 mL) was added DTBPF-PdCl$_2$ (80 mg). The reaction was heated at 100° C. for 30 minutes, then cooled. The cooled mixture was filtered and the filtrate was concentrated in vacuo to give a residue, which was purified by flash chromatography over silica gel (eluting with PE:EA=4:1) to give compound A20-4. MS (ESI) m/e (M+H⁺): 346.2.

Step D: methyl 7-methyl-8-(2-(trifluoromethyl)phenyl)-5,6,7,8-tetrahydronaphthalene-2-carboxylate (A20-5)

To a mixture of compound A20-4 (500 mg, 1.445 mmol) in MeOH/THF (25 mL/5 mL) was added 10% Pd/C (50 mg). The reaction was stirred at room temperature under $H_2$ (50 psi) for 6 hrs. The reaction was filtered and concentrated in vacuo, and the resulting residue was purified by preparative HPLC to obtain compound A20-5. MS (ESI) m/e (M+H⁺): 348.4.

Step E: (7-methyl-8-(2-(trifluoromethyl)phenyl)-5,6,7,8-tetrahydronaphthalen-2-yl)methanol (A20-6)

To a solution of compound A20-5 (150 mg, 0.431 mmol) in THF (15 mL) at 0° C. under $N_2$ was added $LiAlH_4$ (150 mg, 3.95 mmol) slowly. The mixture was stirred for 3 h, then quenched with NaOH and water slowly, and filtered. The organic layer was separated, and concentrated in vacuo. The resulting residue was purified by flash chromatography over silica gel (eluting with PE:EA=4:1) to give compound A20-6. MS (ESI) m/e (M+H⁺): 320.1 (−17).

Step F: 7-(bromomethyl)-2-methyl-1-(2-(trifluoromethyl)phenyl)-1,2,3,4-tetrahydronaphthalene (A20-7)

To a stirred solution of compound A20-6 (50 mg, 0.156 mmol) in THF (5 mL) at 0° C. was added $PBr_3$ (42 mg, 0.156 mmol) dropwise and the resulting mixture was stirred at 0° C. for 3 h. Then water (5 mL) was added to the mixture, and the mixture was extracted with EtOAc (5 mL) three times. The combined organic layers were washed with brine, dried over $Na_2SO_4$ and concentrated in vacuo to afford a residue, which was purified by flash chromatography over silica gel (eluting with PE:EA=4:1) to give compound A20-7. MS (ESI) m/e (M+H⁺): 382.3.

Step G: (5aR,6S,6aS)-ethyl 3-((7-methyl-8-(2-(trifluoromethyl)phenyl)-5,6,7,8-tetrahydro-naphthalen-2-yl)methoxy)-5,5a,6,6a-tetrahydrocyclopropa[4,5]cyclopenta[1,2-c]pyridine-6-carboxylate (A20-8)

To a stirred solution of compound A20-7 (50 mg, 0.1309 mmol) and intermediate 1-9 (23.8 mg, 0.109 mmol) in toluene (10 mL), was added $Ag_2CO_3$ (72 mg, 0.26 mmol) in one portion. The resulting mixture was heated to 120° C. under $N_2$ overnight. The mixture was then filtered and the filtrate was concentrated to afford crude compound A20-8, which was used in the next step without further purification. MS (ESI) m/e (M+H⁺): 521.2.

Step H: (5aR,5S,6aS)-3-((7-methyl-8-(2-(trifluoromethyl)phenyl)-5,6,7,8-tetrahydronaphthalen-2-yl)methoxy)-5,5a,6,6a-tetrahydrocyclopropa[4,5]cyclopenta[1,2-c]pyridine-6-carboxylic acid (A20-9)

To a mixture of compound A20-8 (60 mg, crude) in THF (2 mL), MeOH (2 mL) and $H_2O$ (2 mL) was added NaOH (46 mg, 1.15 mmol). The reaction was stirred at room temperature for 2 h, then acidified with HCl (2 N) to pH=2, and extracted with EtOAc (10 mL) twice. The combined organic layers were washed with water, brine, dried over $Na_2SO_4$ and concentrated in vacuo to afford a residue, which was purified by preparative HPLC (on a GILSON 281 instrument fitted with a YMC-Actus Triart C18 150*30 mm*5 um using water and acetonitrile as the eluents. Mobile phase A: water (containing 0.1% TFA, v/v), mobile phase B: acetonitrile. Gradient: 49-79% B, 0-11 min; 100% B, 10.5-12.5 min; 5% B, 13-15 min).to obtain compound A20-9. ¹H NMR (400 MHz, MeOD-$d_4$) δ: 8.05 (s, 1H), 7.65 (dd, J=8.0 Hz, 1H), 7.33-7.30 (m, 1H), 7.27-7.24 (m, 1H), 7.14 (s, 2H), 7.00 (dd, J=8.0 Hz, 1H), 6.82 (s, 1H), 6.60 (s, 1H), 5.09 (s, 2H), 4.64 (dd, J=8.0 Hz, 1H), 3.23-3.17 (m, 1H), 3.03-2.96 (m, 1H), 2.92-2.91 (m, 1H), 2.87-2.85 (m, 1H), 2.84-2.80 (m, 1H), 2.47-2.43 (m, 1H), 2.26-2.25 (m, 1H), 1.88-1.75 (m, 2H), 1.15 (s, 1H). MS (ESI) m/e (M+H⁺): 493.2.

TABLE 8

Example 47 (compound A20-10) was prepared in a similar manner to Example 46 (Compound A20-9) using the appropriate intermediates and commercially available materials, but without Step D, and including procedures described across this application when necessary.

| Example | Structure | M.W. | Compound Name | LC/MS (ESI) observed [M + 1]+ |
|---|---|---|---|---|
| 47 | 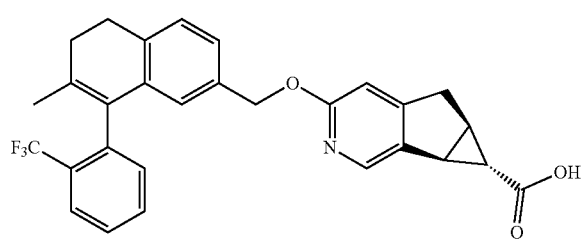 [SMILES: CC1=C(c2ccccc2C(F)(F)F)c2cc(COc3cc4c(cn3)[C@H]3[C@@H](C4)[C@@H]3C(=O)O)ccc2CC1] (Compound A20-10) | 491.5 | (5aR,6S,6aS)-3-((7-methyl-8-(2-(trifluoromethyl)-phenyl)-5,6-dihydro-naphthalen-2-yl)methoxy)-5,5a,6,6a-tetrahydrocyclopropa[4,5]cyclopenta[1,2-c]pyridine-6-carboxylic acid | 492.2 |

Example 48

(5aR,6S,6aS)-3-((4-(2-(trifluoromethyl)phenyl)chroman-6-yl)methoxy)-5,5a,6,6a-tetrahydrocyclopropa[4,5]cyclopenta[1,2-c]pyridine-6-carboxylic acid (Compound A21-10)

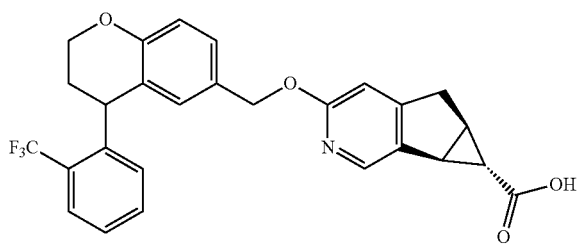

A21-10

Step A: 6-bromo-4-(2-(trifluoromethyl)phenyl)chroman-4-ol (A21-2)

To a solution of 1-bromo-2-(trifluoromethyl)benzene (4.5 g, 0.02 mol) in dry THF (50 mL) at −78° C. under $N_2$ was added n-BuLi (2.5 M in hexanes, 8 mL, 0.02 mol) dropwise. After completion of the addition, the mixture was stirred at −78° C. for an hour. Then a solution of 6-bromochroman-4-one A21-1 (2.27 g, 0.01 mol) in dry THF (20 mL) was added dropwise. The reaction mixture was stirred 3 h at −78° C., then quenched with saturated aqueous $NH_4Cl$, and extracted with EtOAc three times. The combined organic layers were washed with brine, dried over $Na_2SO_4$ and concentrated in vacuo to afford a residue, which was purified by chromatography over silica gel to give compound A21-2. MS (ESI) m/e (M+H$^+$−18): 372.0 (−17).

Step B: 4-hydroxy-4-(2-(trifluoromethyl)phenyl)chroman-6-carboxylic acid (A21-3)

To a stirred solution of compound A21-2 (1.2 g, 3.22 mmol) in dry THF (20 mL) at −78° C. under $N_2$ was added n-BuLi (2.5 M in hexanes, 3.86 mL, 9.66 mmol) dropwise. After completion of the addition, the mixture was stirred for 2 hours, then carbon dioxide was bubbled into the mixture for 30 min. The reaction was stirred at −78° C. for 1 h, and then warmed to −20° C. slowly. The reaction was quenched with water, then acidified with dilute HCl (1N) to pH=2 and extracted with EtOAc three times. The combined organic layers were washed with brine, dried over $Na_2SO_4$ and concentrated in vacuo to afford crude compound A21-3 which was used in the next step directly.

Step C: methyl 4-hydroxy-4-(2-(trifluoromethyl)phenyl)chroman-6-carboxylate (A21-4)

To a mixture of crude compound A21-3 (1.247 mg, 3.69 mmol) in DMF (20 mL) at 0° C. was added $K_2CO_3$ (764 mg, 5.54 mmol) in one portion, followed by MeI (1.048 g, 7.38 mmol). The resulting mixture was stirred at 0° C. for 1 h, then warmed to room temperature for 2 hrs. The mixture was then poured into water, and extracted with EtOAc (15 mL) three times. The combined organic layers were washed with brine, dried over $Na_2SO_4$ and concentrated to afford a residue, which was purified by chromatography over silica gel to obtain compound A21-4. MS (ESI) m/e (M+H$^+$−18): 352.1 (−17).

Step D: methyl 4-(2-(trifluoromethyl)phenyl)-2H-chromene-6-carboxylate (A21-5)

A solution of compound A21-4 (400 mg, 1.136 mmol) and $Et_3SiH$ (264 mg, 2.276 mmol) in dry DCM (20 mL) was stirred at room temperature for 30 min, and then cooled to 0° C. Then TFA (1.2 mL) was added in one portion and the resulting mixture was stirred for one hour. The reaction was neutralized with $NaHCO_3$, and extracted with EtOAc three times. The combined organic layers were washed with brine, dried over $Na_2SO_4$ and concentrated in vacuo to afford crude compound A21-5, which was used in the next step without purification. MS (ESI) m/e (M+H$^+$): 334.1.

Step E: methyl 4-(2-(trifluoromethyl)phenyl)chroman-6-carboxylate (A21-6)

Palladium (10%) on carbon (60 mg) was added to a solution of compound A21-5 (500 mg, crude) in MeOH (30 mL) and THF (30 mL). The resulting mixture was stirred at 25° C. under $H_2$ (1 atm) for 16 hrs. The mixture was then filtered over Celite™ and the filtrate was concentrated in vacuo to afford crude compound A21-6, which was used in the next step without purification. MS (ESI) m/e (M+H$^+$): 336.1.

Step F: (4-(2-(trifluoromethyl)phenyl)chroman-6-yl)methanol (A21-7)

To a suspension of $LiAlH_4$ (400 mg, 10.53 mmol) in dry THF (10 mL) at 0° C. was added a solution of crude compound A21-6 (600 mg, crude) in THF (20 mL) dropwise. After completion of the addition, the reaction mixture was stirred at 0° C. for 1 h. The reaction was then quenched with saturated aqueous $NH_4Cl$ and extracted with EtOAc twice. The combined organic layers were washed with brine, dried over $Na_2SO_4$ and concentrated in vacuo to afford a residue, which was purified by preparative TLC over silica gel to obtain compound A21-7. MS (ESI) m/e (M+H$^+$−18): 308.1 (−17).

Step G: 6-(chloromethyl)-4-(2-(trifluoromethyl)phenyl)chroman (A21-8)

To a solution of compound A21-7 (60 mg, 0.19 mmol) in dry DCM (5 mL) at 0° C. was added $SOCl_2$ (23 mg, 0.19 mmol) dropwise. The reaction solution was stirred at 0° C. for 1 h, then warmed to 20° C. and stirred for 2 h. The reaction was quenched with water, neutralized with aqueous saturated $NaHCO_3$ to pH=7, and the mixture was extracted with DCM twice. The combined organic layers were washed with brine, dried over $Na_2SO_4$, filtered and concentrated in vacuo to afford a residue, which was purified by preparative TLC over silica gel to obtain compound A21-8. MS (ESI) m/e (M+H$^+$): 327.1.

Step H: (5aR,6S,6aS)-ethyl 3-((4-(2-(trifluoromethyl)phenyl)chroman-6-yl)methoxy)-5,5a,6,6a-tetrahydrocyclopropa[4,5]cyclopenta[1,2-c]pyridine-6-carboxylate (A21-9)

A mixture of compound A21-8 (30 mg, 0.092 mmol), intermediate 1-9 (16.8 mg, 0.077 mmol) and $Ag_2CO_3$ (275 mg, 0.184 mmol) in toluene (1 mL) was heated at 100° C. for 2 h. Then the reaction was filtered and the filtrate was concentrated in vacuo to give a residue, which was purified by preparative TLC over silica gel to obtain compound A21-9. MS (ESI) m/e (M+H$^+$): 510.2.

Step I: (5aR,6S,6aS)-3-((4-(2-(trifluoromethyl)phenyl)chroman-6-yl)methoxy)-5,5a,6,6a-tetrahydrocyclopropa[4,5]cyclopenta[1,2-c]pyridine-6-carboxylic acid (A21-10)

To a mixture of compound A21-9 (25 mg, 0.049 mmol) in THF (1 mL), MeOH (1 mL) and H$_2$O (1 mL) was added NaOH (20 mg, 0.49 mmol), and the resulting mixture was stirred at room temperature for 2 h. The mixture was acidified with HCl (2 N) to pH=7, and extracted with EtOAc (10 mL) twice. The combined organic layers were washed with water, brine, dried over Na$_2$SO$_4$ and concentrated in vacuo to afford a residue, which was purified by preparative TLC over silica gel to obtain compound A21-10. $^1$H NMR (400 MHz, MeOD-d$_4$) δ: 7.76 (d, J=7.83 Hz, 1H) 7.63 (d, J=7.83 Hz, 1H) 7.35-7.41 (m, 1H) 7.28-7.34 (m, 1H) 7.07 (d, J=8.22 Hz, 1H) 6.99 (dd, J=7.24, 3.72 Hz, 1H) 6.73 (d, J=8.22 Hz, 1H) 6.57 (s, 1H) 6.40 (s, 1H) 4.88-4.97 (m, 2H) 4.49 (t, J=7.24 Hz, 1H) 4.18-4.26 (m, 1H) 4.04-4.10 (m, 1H) 3.05 (dd, J=18.39, 4.30 Hz, 1H) 2.80-2.88 (m, 1H) 2.64 (d, J=5.09 Hz, 1H) 2.15-2.24 (m, 2H) 1.95-2.03 (m, 1H) 0.92 (br. s., 1H). MS (ESI) m/e (M+H$^+$): 482.2.

20 min, then the solution was quenched with Me$_2$S (0.93 g, 15 mmol) dropwise. The resulting mixture was stirred at −78° C. for 1 h, then warmed to 0° C. slowly and stirred overnight. The reaction was filtered through Celite™ and the filtrate was concentrated in vacuo to afford crude compound A22-2, which was used in the next step without purification. MS (ESI) m/e (M+H$^+$): 351.3.

Step B: methyl 3-(hydroxy(2-(trifluoromethyl)phenyl)methyl)-4-(2-hydroxyethyl)benzoate (A22-3)

To a solution of compound A22-2 (1.5 g, crude) in MeOH (50 mL) at 0° C. was added NaBH$_4$ (750 mg, 23 mmol) in one portion. After stirring at 0° C. for 4 hours, the reaction was quenched with saturated aqueous NH$_4$Cl, and extracted with EtOAc twice. The combined organic layers were concentrated in vacuo to afford crude compound A22-3, which was used in the next step without purification. MS (ESI) m/e (M+H$^+$−18): 354.1 (−17).

TABLE 9

Example 49 (compound A21-11) was prepared in a similar manner to Example 48 (Compound A21-10) using the appropriate intermediates and commercially available materials, but without Steps D and E, and including procedures described across this application when necessary.

| Example | Structure | M.W. | Compound Name | LC/MS (ESI) observed [M + 1]+ |
|---|---|---|---|---|
| 49 | (Compound A21-11) | 497.5 | (5aR,6S,6aS)-3-((7-methyl-8-(2-(trifluoromethyl)phenyl)-5,6-dihydronaphthalen-2-yl)methoxy)-5,5a,6,6a-tetrahydrocyclopropa[4,5]cyclopenta[1,2-c]pyridine-6-carboxylic acid | 498.1 |

Example 50

(5aR,6S,6aS)-3-((1-(2-(trifluoromethyl)phenyl)isochroman-7-yl)methoxy)-5,5a,6,6a-tetrahydrocyclopropa[4,5]cyclopenta[1,2-c]pyridine-6-carboxylic acid (Compound A22-8)

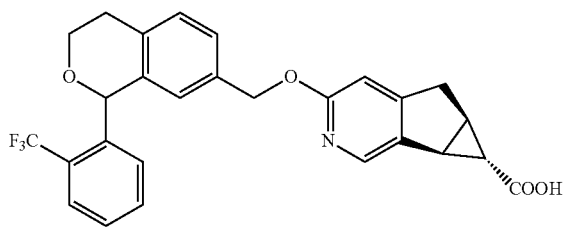

A22-8

Step A: methyl 4-(2-oxoethyl)-3-(2-(trifluoromethyl)benzoyl)benzoate (A22-2)

To a stirring mixture of intermediate 3-5 (1.2 g, 3.77 mmol) in DCM (50 mL) at −78° C. was bubbled ozone for Step C: methyl 1-(2-(trifluoromethyl)phenyl)isochroman-7-carboxylate (A22-4)

A mixture of compound A22-3 (1.5 g, crude) and H$_3$PO$_4$ (4 mL) in toluene (40 mL) was heated at reflux overnight. After cooling to room temperature, the reaction mixture was acidified with HCl (1 N) to pH=7, and extracted with EtOAc (40 mL) twice. The combined organic layers were concentrated in vacuo to give a residue, which was purified by flash chromatography over silica gel to afford compound A22-4. MS (ESI) m/e (M+H$^+$): 337.1.

Step D: (1-(2-(trifluoromethyl)phenyl)isochroman-7-yl)methanol (A22-5)

To a suspension of LiAlH$_4$ (115 mg, 2.97 mmol) in dry THF (10 mL) at 0° C. was added a solution of compound A22-4 (200 mg, 0.59 mmol) in THF (20 mL) dropwise. After completion of the addition, the reaction mixture was stirred at 0° C. for 4 h. Then the reaction was quenched with saturated aqueous NH$_4$Cl and extracted with EtOAc twice. The combined organic layers were washed with brine and concentrated to afford a residue, which was purified by flash chromatography over silica gel to obtain compound A22-5. MS (ESI) m/e (M+H$^+$): 308.1 (−17).

Step E: 7-(bromomethyl)-1-(2-(trifluoromethyl)phenyl)isochroman (A22-6)

To a solution of compound A22-5 (100 mg, 0.32 mmol) in dry DCM (10 mL) at 0° C. was added PBr₃ (87 mg, 0.32 mmol) dropwise. The resulting reaction solution was stirred at 0° C. for an hour, then warmed to 20° C. and stirred for 2 h. The reaction was quenched with water, and neutralized with saturated aqueous NaHCO₃ to pH=7. The organic layer was separated, dried and concentrated in vacuo to afford a residue, which was purified by flash chromatography over silica gel to obtain compound A22-6. MS (ESI) m/e (M+H$^+$): 372.0/374.0.

Step F: (5aR,6S,6aS)-ethyl 3-((1-2-(trifluoromethyl)phenyl)isochroman-7-yl)methoxy)-5,5a,6,6a-tetrahydrocyclopropa[4,5]cyclopenta[1,2-c]pyridine-6-carboxylate (A22-7)

A mixture of compound A22-6 (60 mg, 0.16 mmol), intermediate 1-9 (29 mg, 0.13 mmol) and Ag₂CO₃ (90 mg, 0.32 mmol) in toluene (5 mL) was heated at 110° C. for 2 h. The reaction was filtered and the filtrate was concentrated in vacuo to afford a residue, which was purified by flash chromatography over silica gel to give compound A22-7. MS (ESI) m/e (M+H$^+$): 510.2.

Step G: (5aR,6S,6aS)-3-((1-(2-(trifluoromethyl)phenyl)isochroman-7-yl)methoxy)-5,5a,6,6a-tetrahydrocyclopropa[4,5]cyclopenta[1,2-c]pyridine-6-carboxylic acid (A22-8)

To a mixture of compound A22-7 (40 mg, 0.079 mmol) in THF (2 mL), MeOH (2 mL) and H₂O (2 mL) was added NaOH (32 mg, 0.8 mmol). The resulting mixture was stirred at room temperature for 2 h. Then the mixture was acidified with HCl (2 N) to pH=7, and extracted with EtOAc (10 mL) twice. The combined organic layers were washed with water, brine, dried over Na₂SO₄ and concentrated in vacuo to afford a residue, which was purified by preparative TLC over silica gel to obtain compound A22-8. $^1$H NMR (400 MHz, MeOD-d₄) δ: 7.90 (d, J=9.00 Hz, 1H) 7.74 (d, J=6.26 Hz, 1H) 7.45-7.52 (m, 2H) 7.20 (q, J=7.83 Hz, 3H) 6.56 (s, 1H) 6.51 (s, 1H) 6.06 (s, 1H) 5.07-5.14 (m, 2H) 4.18-4.26 (m, 1H) 3.92 (td, J=11.05, 3.33 Hz, 1H) 3.14-3.24 (m, 2H) 2.94-3.02 (m, 1H) 2.88 (d, J=5.48 Hz, 1H) 2.78 (d, J=16.43 Hz, 1H) 2.41 (br. s., 1H) 1.10 (br. s., 1H). MS (ESI) m/e (M+H$^+$): 482.2.

Example 51

(5aR,6S,6aS)-3-((8-fluoro-4,4-dimethyl-1-(2-(trifluoromethyl)phenyl)-1,2,3,4-tetrahydroisoquinolin-7-yl)methoxy)-5,5a,6,6a-tetrahydrocyclopropa[4,5]cyclopenta[1,2-c]pyridine-6-carboxylic acid (Compound C6-6)

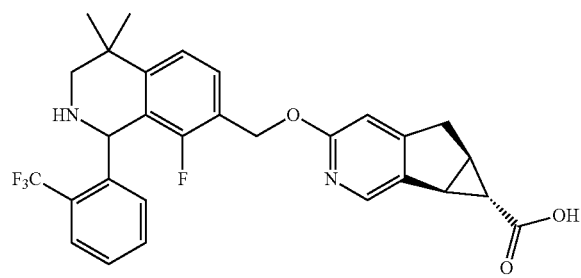

C6-6

Step A: ethyl 8-fluoro-4,4-dimethyl-1-(2-(trifluoromethyl)phenyl)-1,2,3,4-tetrahydroisoquinoline-7-carboxylate (C6-2)

To a stirred solution of compound C4-9B (350 mg, 0.890 mmol, 1.0 eq) in MeOH (7.0 mL) was added 10% Pd/C (35 mg), and the mixture was stirred at room temperature under a H₂ (1 atm) for 3 h. Then the reaction mixture was filtered and the filtrate was concentrated in vacuo to afford crude compound C6-2, which was used in the next step without purification. MS (ESI) m/e (M+H$^+$): 396.2.

Step B: (8-fluoro-4,4-dimethyl-1-(2-(trifluoromethyl)phenyl)-1,2,3,4-tetrahydroisoquinolin-7-yl)methanol (C6-3)

To a mixture of LAH (144 mg, 3.79 mmol, 5.0 eq) in dry THF (10.0 mL) at 0° C. under N₂ was added dropwise a solution of crude compound C6-2 (300 mg, 0.759 mmol, 1.0 eq) in THF (5.0 mL). After addition, the reaction mixture was stirred at room temperature for 2 h. Then the reaction was quenched with 0.2 mL H₂O, 0.2 mL NaOH (15%) and 0.2 mL H₂O. Then the reaction mixture was filtered, and the filtrate was concentrated in vacuo to afford crude compound C6-3, which was used in the next step without purification. MS (ESI) m/e (M+H$^+$): 354.2.

Step C: 7-(bromomethyl)-8-fluoro-4,4-dimethyl-1-(2-(trifluoromethyl)phenyl)-1,2,3,4-tetrahydroisoquinoline (C6-4)

To a solution of crude compound C6-3 (100 mg, 283 mmol, 1.0 eq) in DCM (5.0 mL) at 0° C. under N₂ was added PBr₃ (76.6 mg, 0.283 mmol, 1.0 eq) dropwise and the reaction mixture was stirred for 1 h. A solution of saturated aqueous NaHCO₃ was added to adjust the reaction mixture to pH=7, then the reaction mixture was extracted with EtOAc (5.0 mL) three times. The combined organic layers were washed with brine, dried over MgSO₄, and concentrated in vacuo to give compound C6-4.

Step D: (5aR,6S,6aS)-ethyl 3-((8-fluoro-4,4-dimethyl-1-(2-(trifluoromethyl)phenyl)-1,2,3,4-tetrahydroisoquinolin-7-yl)methoxy)-5,5a,6,6a-tetrahydrocyclopropa[4,5]cyclopenta[1,2-c]pyridine-6-carboxylate (C6-5)

To a solution of compound C6-4 (22.8 mg, 0.0548 mmol, 1.2 eq) and intermediate 1-9 (10 mg, 0.0457 mmol, 1.0 eq) in toluene (2.0 mL) was added Ag₂CO₃ (37.8 mg, 0.137 mmol, 3.0 eq) in one portion. The reaction mixture was heated at 110° C. for 5 h. Then the reaction was cooled to room temperature and filtered. The filtrate was concentrated in vacuo to afford a residue, which was purified by preparative TLC over silica gel (eluting with PE:EA=5:1) to give compound C6-5. MS (ESI) m/e (M+H$^+$): 555.2.

Step E: (5aR,6S,6aS)-3-((8-fluoro-4,4-dimethyl-1-(2-(trifluoromethyl)phenyl)-1,2,3,4-tetrahydroisoquinolin-7-yl)methoxy)-5,5a,6,6a-tetrahydrocyclopropa[4,5]cyclopenta[1,2-c]pyridine-6-carboxylic acid (C6-6)

To a solution of compound C6-5 (12.0 mg, 0.0222 mmol, 1.0 eq) in THF (0.5 mL), MeOH (0.5 mL) and H₂O (0.5 mL) was added LiOH.H₂O (9.31 mg, 0.222 mmol, 10.0 eq) and the reaction was stirred at room temperature for 1 h. Then the reaction mixture was acidified with HCl (1 N) to pH=2, and extracted with EtOAc (5.00 mL) three times. The combined organic layers were washed with brine, dried over MgSO$_4$, and concentrated in vacuo to afford a residue, which was purified by preparative HPLC (on a GILSON 281 instrument fitted with a Diamonsil (150*20 mm*5 um) using water and acetonitrile as the eluents. Mobile phase A: water (containing 0.1% TFA, v/v), mobile phase B: acetonitrile. Gradient: 10-40% B, 0-10 min; 100% B, 10.5-12.5 min; 5% B, 13-15 min) to give compound C6-6. $^1$H NMR (400 MHz, MeOD-d$_4$) δ: 8.00 (s, 1H), 7.98 (d, J=7.2 Hz, 1H), 7.73~7.61 (m, 3H), 7.52 (d, J=8.4 Hz, 1H), 7.16 (d, J=7.6 Hz, 1H), 6.64 (s, 1H), 6.22 (s, 1H), 5.26 (s, 2H), 3.28~3.21 (m, 3H), 3.05 (d, J=18.8 Hz, 1H), 2.92 (d, J=4.8 Hz, 1H), 2.45~2.42 (m, 1H), 1.60 (s, 3H), 1.49 (s, 3H), 1.13 (t, J=2.8 Hz, 1H). MS (ESI) m/e (M+H$^+$): 527.3.

Example 52

(5aR,6S,6aS)-3-((8-fluoro-4,4-dimethyl-1-(2-(trifluoromethyl)phenyl)-1,2,3,4-tetrahydroquinolin-7-yl)methoxy)-5,5a,6,6a-tetrahydrocyclopropa[4,5]cyclopenta[1,2-c]pyridine-6-carboxylic acid (Compound A24-8)

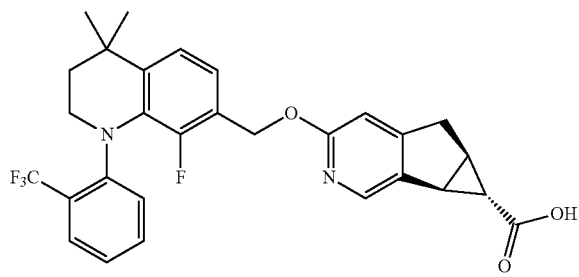

A24-8

Step A: 2-fluoro-3-methyl-N-(2-(trifluoromethyl)phenyl)aniline (A24-2)

A mixture of 2-(dicyclohexylphosphino)-2',4',6'-triisopropylbiphenyl (133 mg, 0.28 mmol), Cs$_2$CO$_3$ (19.53 g, 59.91 mmol), Pd$_2$(dba)$_3$ (183 mg, 0.21 mmol). 1-bromo-2-(trifluoromethyl)benzene (13.48 g, 59.91 mmol) and 2-fluoro-3-methyl-aniline A24-1 (6.00 g, 22.29 mmol) in 1,4-dioxane (100 mL) was heated to 100° C. for 16 h. Then the reaction was filtered and the filtrate was concentrated in vacuo to give the crude product, which was purified by column chromatography on silica gel (eluting with PE:EA=100:0 to 95:5) to afford compound A24-2. MS (ESI) m/e (M+H$^+$): 270.1.

Step B: N-(2-fluoro-3-methylphenyl)-3-methyl-N-(2-(trifluoromethyl)phenyl)but-2-enamide (A24-3)

To a stirring solution of compound A24-2 (5.00 g, 18.57 mmol) in DMF (50 mL) was added 60% NaH (1.49 g, 37.11 mmol) dropwise at 0° C. under nitrogen atmosphere. After completion of the addition, the mixture was stirred at room temperature for 30 min. Then 3-methyl-but-2-enoyl chloride (2.64 g, 22.29 mmol) was added dropwise at 0° C. The resulting mixture was warmed to 30° C. and stirred 3 h. Then the reaction was washed with water and extracted with EtOAc twice. The combined organic layers were washed with water, brine, dried over Na$_2$SO$_4$ and concentrated in vacuo to afford a residue, which was purified by flash chromatography over silica gel (eluting with PE:EA=10:1) to give compound A24-3. MS (ESI) m/e (M+H$^+$): 352.1.

Step C: 8-fluoro-4,4,7-trimethyl-1-(2-(trifluoromethyl)phenyl)-3,4-dihydroquinolin-2(1H)-one (A24-4)

A mixture of compound A24-3 (500 mg, 1.42 mmol) in trifluoromethanesulfonic acid (5.00 mL, 1.42 mmol) was heated at 30° C. for 16 h. Then the reaction mixture was quenched with saturated aqueous NaHCO$_3$ and was extracted with EtOAc three times. The combined organic layers were washed with brine, dried over Na$_2$SO$_4$ and concentrated in vacuo to afford a residue, which was purified by flash chromatography over silica gel to provide compound A24-4. MS (ESI) m/e (M+H$^+$): 352.1.

Step D: 8-fluoro-4,4-dimethyl-2-oxo-1-(2-(trifluoromethyl)phenyl)-1,2,3,4-tetrahydroquinoline-7-carboxylic acid (A24-5)

A mixture of compound A24-4 (600 mg, 1.71 mmol) and KMnO4 (1.35 g, 8.54 mmol) in water (15.00 mL) and t-BuOH (15.00 mL, 157.00 mmol) was heated to 80° C. for 20 h. The resulting mixture was basified with NaOH to pH=10, and washed with EtOAc twice. The water layer was acidified with HCl (2 N) to pH=5, then extracted with EtOAc twice. The combined organic layers were dried over Na$_2$SO$_4$ and concentrated in vacuo to give crude compound A24-5, which was used directly in the next step. MS (ESI) m/e (M+H$^+$): 382.1.

Step E: (8-fluoro-4,4-dimethyl-1-(2-(trifluoromethyl)phenyl)-1,2,3,4-tetrahydroquinolin-7-yl)methanol (A24-6)

To a solution of crude compound A24-5 (200 mg, 0.52 mmol) in THF (10 mL) at 0° C. was added BH$_3$DMS (0.52 mL, 5.24 mmol) dropwise. The reaction mixture was stirred at 0° C. for one hour, then warmed to 20° C. and stirred for 16 h. Then the reaction was quenched with MeOH and concentrated in vacuo to afford a residue, which was purified by preparative TLC over silica gel to obtain compound A24-6. MS (ESI) m/e (M+H$^+$): 354.1.

Step F: ((5aR,6S,6aS)-tert-butyl 3-((8-fluoro-4,4-dimethyl-1-(2-(trifluoromethyl)phenyl)-1,2,3,4-tetrahydroquinolin-7-yl)methoxy)-5,5a,6,6a-tetrahydrocyclopropa[4,5]cyclopenta[1,2-c]pyridine-6-carboxylate (A24-7)

A mixture of Brett-Phos Palladacycle (27 mg, 0.034 mmol), compound A24-6 (120 mg, 0.34 mmol), intermediate 1-11 (108 mg, 0.41 mmol) and Cs$_2$CO$_3$ (277 mg, 0.85 mmol) in toluene (15 mL) was heated at 110° C. for 16 h. Then the reaction was filtered and the filtrate was concentrated in vacuo to give a residue, which was purified by preparative TLC over silica gel (PE:EA=4:1) to afford compound A24-7. MS (ESI) m/e (M+H$^+$): 583.3.

Step G: ((5aR,6S,6aS)-3-((8-fluoro-4,4-dimethyl-1-(2-(trifluoromethyl)phenyl)-1,2,3,4-tetrahydroquinolin-7-yl)methoxy)-5,5a,6,6a-tetrahydrocyclopropa[4,5]cyclopenta[1,2-c]pyridine-6-carboxylic acid (A24-8)

To a mixture of compound A24-7 (90 mg, 0.15 mmol) in THF (5 mL), MeOH (5 mL) and H$_2$O (5 mL) was added NaOH (30 mg, 0.77 mmol). The resulting mixture was stirred at room temperature for 2 h. Then the reaction was acidified with HCl (2 N) to pH=7, and extracted with EtOAc (10 mL) twice. The combined organic layers were washed with water, brine, dried over Na₂SO₄ and concentrated in vacuo to obtain a residue, which was purified by preparative HPLC (on a GILSON 281 instrument fitted with a Waters XSELECT C18 150*30 mm*5 um using water and acetonitrile as the eluents. Mobile phase A: water (containing 0.1% TFA, v/v), mobile phase B: acetonitrile. Gradient: 71-93% B, 0-10 min; 100% B, 10.5-12.5 min; 5% B, 13-15 min) to give compound A24-8. ¹H NMR (400 MHz, MeOD-d₄) δ: 8.11 (s, 1H), 7.74 (d, J=7.83 Hz, 1H), 7.48-7.55 (m, 1H), 7.35 (t, J=7.63 Hz, 1H), 7.23 (d, J=7.83 Hz, 1H), 7.14 (d, J=8.22 Hz, 1H), 6.95-7.02 (m, 2H), 5.20 (s, 2H), 3.54-3.65 (m, 1H), 3.33-3.42 (m, 2H), 3.10-3.24 (m, 1H), 2.99 (d, J=5.48 Hz, 1H), 2.47-2.55 (m, 1H), 1.83-1.94 (m, 1H), 1.68-1.79 (m, 1H), 1.44 (s, 3H), 1.37 (s, 3H), 1.25 (br. s., 1H). MS (ESI) m/e (M+H⁺): 527.2.

Example 53

(5aR,6S,6aS)-3-((6-fluoro-4,4-dimethyl-1-(2-(trifluoromethyl)phenyl)-1,2,3,4-tetrahydroquinolin-7-yl)methoxy)-5,5a,6,6a-tetrahydrocyclopropa[4,5]cyclopenta[1,2-c]pyridine-6-carboxylic acid (Compound A25-10)

A25-10

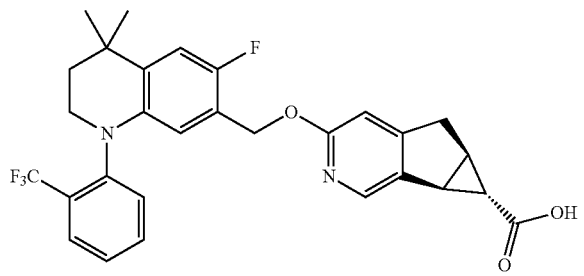

Step A: N-(3-bromo-4-fluorophenyl)-3-methylbut-2-enamide (A25-1)

To a solution of 3-bromo-4-fluoroaniline (2.00 g, 10.53 mmol) and DMAP (0.129 g, 1.05 mmol) in pyridine (10 mL) at 0° C. under N₂, was added 3-methylbut-2-enoyl chloride (2.50 g, 21.05 mmol) dropwise. The resulting solution was warmed to room temperature and stirred 2 h. The reaction was quenched with 1N HCl, extracted with EtOAc, washed with brine, dried over Na₂SO₄, and concentrated in vacuo to give a residue, which was purified by flash chromatography over silica gel (eluting with PE:EA=5:1) to provide compound A25-1. MS (ESI) m/e (M+H⁺): 272.0, 274.0.

Step B: 7-bromo-6-fluoro-4,4-dimethyl-3,4-dihydroquinolin-2(1H)-one (A25-2)

To a solution of compound A25-1 (2.60 g, 9.55 mmol) in DCM (10 mL) under N₂ was added aluminum trichloride (1.91 g, 14.33 mmol) dropwise. The reaction was stirred at room temperature for 16 h, and then quenched with 1N NaHCO₃, and extracted with EtOAc. The combined organic layers were washed with brine, dried over Na₂SO₄, and concentrated in vacuo to give a residue, which was purified by flash chromatography over silica gel (eluting with PE:EA=5:1) to provide 7-bromo-6-fluoro-4,4-dimethyl-3,4-dihydroquinolin-2(1H)-one and compound A25-2. MS (ESI) m/e (M+H⁺): 271.9, 273.9.

Step C: ethyl 6-fluoro-4,4-dimethyl-2-oxo-1,2,3,4-tetrahydroquinoline-7-carboxylate (A25-3)

A mixture of 7-bromo-6-fluoro-4,4-dimethyl-3,4-dihydroquinolin-2(1H)-one A25-2 (200 mg, 0.74 mmol), PdCl₂(dppf) (54 mg, 0.073 mmol) and sodium acetate (121 mg, 1.47 mmol) in EtOH (100 mL) was heated to 80° C. for 16 h under a CO atmosphere (50 psi). After cooling to room temperature, the reaction was filtered and the filtrate was concentrated in vacuo to afford a residue, which was diluted with EtOAc and water. The organic layer was separated and the aqueous layer was extracted with EtOAc twice. The combined organic layers were washed with water, dried over Na₂SO₄ and concentrated in vacuo to obtain a residue, which was purified by preparative TLC over silica gel (eluting with PE:EA=2:1) to give compound A25-3. MS (ESI) m/e (M+H⁺): 266.2.

Step D: ethyl 6-fluoro-4,4-dimethyl-1-(4-nitro-2-(trifluoromethyl)phenyl)-2-oxo-1,2,3,4-tetrahydroquinoline-7-carboxylate (A25-4)

To a solution of 1-fluoro-4-nitro-2-(trifluoromethyl)benzene (1.30 g, 6.22 mmol) and compound A25-3 (1.10 g, 4.15 mmol) in DMSO (5 ml) under N₂ was added t-BuOK (0.93 g, 8.29 mmol). The mixture was stirred at room temperature until completion, and then quenched with H₂O and extracted with EtOAc. The combined organic extracts were washed brine, dried over Na₂SO₄ and concentrated in vacuo to obtain a residue, which was purified by column chromatography over silica gel (eluting with PE:EA=4:1) to give compound A25-4. MS (ESI) m/e (M+H⁺): 477.4.

Step E: ethyl 1-(4-amino-2-(trifluoromethyl)phenyl)-6-fluoro-4,4-dimethyl-2-oxo-1,2,3,4-tetrahydroquinoline-7-carboxylate (A25-5)

10% Pd/C (995 mg, 9.35 mmol) was added to a solution of compound A25-4 (850 mg, 1.87 mmol) in MeOH (50 mL). The resulting mixture was stirred at room temperature under H₂ (50 atm) for 6 h. The reaction mixture was filtered through Celite™ and the filtrate was concentrated in vacuo to give crude compound A25-5, which was used in the next step directly. MS (ESI) m/e (M+H⁺): 411.1.

Step F: methyl6-fluoro-4,4-dimethyl-2-oxo-1-(2-(trifluoromethyl)phenyl)-1,2,3,4-tetrahydroquinoline-7-carboxylate (A25-6)

Tert-Butyl nitrite (109 mg, 1.06 mmol) was added to a mixture of crude compound A25-5 (300 mg, 0.71 mmol) in DMF (10 ml) at room temperature. The reaction mixture was heated at 80° C. for 1 h. Then the reaction was cooled, water (50 mL) was added, and the mixture was extracted with ethyl acetate (60 mL) twice. The combined ethyl acetate layers were washed with brine, dried over Na₂SO₄ and concentrated in vacuo to obtain crude compound A25-6, which was used in the next step directly. MS (ESI) m/e (M+H⁺): 396.1.

Step G: 6-fluoro-7-(hydroxymethyl)-4,4-dimethyl-1-(2-(trifluoromethyl)phenyl)-3,4-dihydroquinolin-2(1H)-one (A25-7)

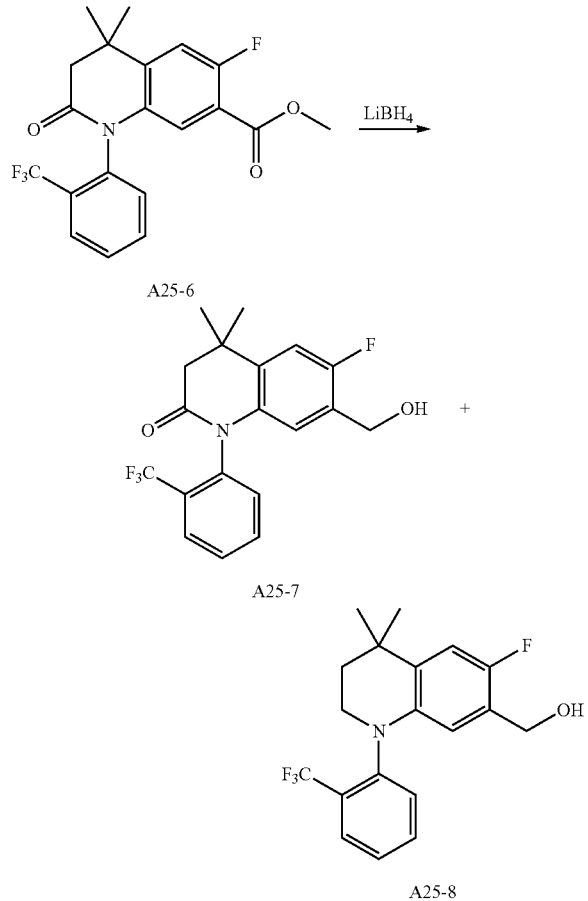

A25-6

A25-7

A25-8

To a solution of crude compound A25-6 (200 mg, 0.49 mmol) in dry THF (10 mL), was added LiBH$_4$ (32 mg, 1.47 mmol). The mixture was stirred for 12 h, then ice water was added to quench the reaction. The reaction mixture was extracted with DCM (50 mL), then the combined organic layers were washed with H$_2$O (30 mL), brine (30 mL), dried with Na$_2$SO$_4$, and concentrated in vacuo to give a residue, which was purified by preparative TLC over silica gel (eluting with PE:EA=2:1) to give compound A25-7 and compound A25-8. MS (ESI) m/e (M+H$^+$): 368.1.

Step H: (5aR,6S,6aS)-tert-butyl 3-((6-fluoro-4,4-dimethyl-1-(2-(trifluoromethyl)phenyl)-1,2,3,4-tetrahydroquinolin-7-yl)methoxy)-5,5a,6,6a-tetrahydrocyclopropa[4,5]cyclopenta[1,2-c]pyridine-6-carboxylate (A25-9)

A mixture of compound A25-8 (60 mg, 0.17 mmol), intermediate 1-11 (45 mg, 0.17 mmol), Brett-Phos Palladacycle (13.6 mg, 0.017 mmol), and cesium carbonate (138 mg, 0.43 mmol) in toluene (20 ml) was heated at 100° C. for 16 h. The reaction was then filtered and the filtrate was concentrated in vacuo to give a residue, which was purified by preparative TLC over silica gel (eluting with PE:EA=3:1) to give compound A25-9. MS (ESI) m/e (M+H$^+$): 583.2.

Step I: (5aR,6S,6aS)-3-((6-fluoro-4,4-dimethyl-1-(2-(trifluoromethyl)phenyl)-1,2,3,4-tetrahydroquinolin-7-yl)methoxy)-5,5a,6,6a-tetrahydrocyclopropa[4,5]cyclopenta[1,2-c]pyridine-6-carboxylic acid (A25-10)

To a mixture of compound A25-9 (40 mg, 0.069 mmol) in THF (1 mL), MeOH (1 mL) and H$_2$O (1 mL) was added LiOH (49 mg, 2.06 mmol). The reaction mixture was stirred at room temperature for 12 h, then acidified with HCl (1 N) to pH=6, and extracted with EtOAc (20 mL) twice. The combined organic layers were washed with water, brine, dried over Na$_2$SO$_4$ and concentrated in vacuo. The resulting residue was purified by preparative. HPLC (on a GILSON 281 instrument fitted with a Phenomenex Synergi C18 100*21.2 mm*4 um using water and acetonitrile as the eluents. Mobile phase A: water (containing 0.1% TFA, v/v), mobile phase B: acetonitrile. Gradient: 55-74% B, 0-10 min; 100% B, 10.5-12.5 min; 5% B, 13-15 min) to give compound A25-10. $^1$H NMR (400 MHz, MeOD-d$_4$) δ: 8.03-8.09 (m, 1H), 7.82 (d, J=7.43 Hz, 1H), 7.72 (br. s., 1H), 7.54 (t, J=7.24 Hz, 1H), 7.35 (t, J=6.85 Hz, 1H), 7.08 (d, J=11.35 Hz, 1H), 6.91 (d, J=3.91 Hz, 1H), 5.92 (d, J=5.87 Hz, 1H), 5.21 (br.s., 2H), 3.49-3.58 (m, 1H), 3.40 (d, J=15.65 Hz, 2H), 3.12-3.20 (m, 1H), 3.01 (d, J=5.09 Hz, 1H), 2.54 (br. s., 1H), 1.94-2.05 (m, 1H), 1.78-1.87 (m, 1H), 1.40 (d, J=9.78 Hz, 6H), 1.28 (br s., 1H). MS (ESI) m/e (M+H$^+$): 527.2.

TABLE 10

Example 54 (compound A25-11) was prepared in a similar manner to Example 53 (Compound A25-10) using compound A25-7 and commercially available materials, and including procedures described across this application when necessary.

| Example | Structure | M.W. | Compound Name | LC/MS (ESI) observed [M + 1]+ |
|---|---|---|---|---|
| 54 | 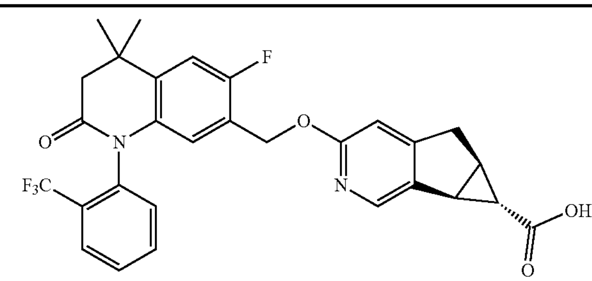 | 540.5 | (5aR,6S,6aS)-3-((6-fluoro-4,4-dimethyl-2-oxo-1-(2-(trifluoromethyl)phenyl)-1,2,3,4-tetrahydroquinolin-7-yl)methoxy)-5,5a,6,6a-tetrahydrocyclopropa[4,5]cyclopenta[1,2-c]pyridine-6-carboxylic acid | 541.2 |

(Compound A25-11)

Example 55

(5aR,6S,6aS)-3-((3-fluoro-5,5-dimethyl-8-(2-(trifluoromethyl)phenyl)-5,6,7,8-tetrahydronaphthalen-2-yl)methoxy)-5,5a,6,6a-tetrahydrocyclopropa[4,5]cyclopenta[1,2-c]pyridine-6-carboxylic acid
(Compound A26-16)

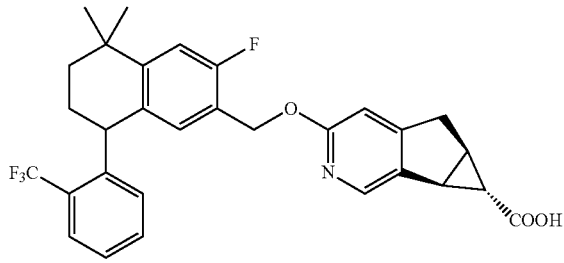

A26-16

Step A: (4-bromo-3-fluorophenyl)methanol (A26-1)

To a solution of 4-bromo-3-fluoro-benzaldehyde (20 g, 99.5 mmol) in MeOH (200 mL) at 0° C. was added NaBH$_4$ (5.7 g, 150 mmol) portion wise, and the reaction was stirred for 3 h. Then the mixture was quenched with water, and extracted with EtOAc three times. The combined organic layers were concentrated to afford crude compound A26-1, which was used in the next step without purification.

Step B: 1-bromo-4-(bromomethyl)-2-fluorobenzene (A26-2)

To a solution of compound A26-1 (19 g, crude) in dry DCM (200 mL) at 0° C. was added PBr$_3$ (13.7 g, 50 mmol) dropwise. The reaction was stirred for 3 h, then warmed to 20° C. and stirred for 2 h. Then the reaction was quenched with water, neutralized with saturated aqueous NaHCO$_3$ to pH=7, and extracted with DCM twice. The combined organic layers were washed with brine, dried over anhydrous Na$_2$SO$_4$, filtered and concentrated in vacuo to afford crude compound A26-2, which was used in the next step without purification.

Step C: 2-(4-bromo-3-fluorophenyl)acetonitrile (A26-3)

A mixture of compound A26-2 (20 g, 75 mmol) and KCN (8.6 g, 138 mmol) in ethanol (150 mL) and water (50 ml) was heated to 80° C. for 4 h. The cooled reaction mixture was concentrated in vacuo. The resulting residue was taken up in H$_2$O (50 mL) and extracted with EtOAc (80 mL) three times. The combined organic layers were washed with brine (50 mL), dried over Na$_2$SO$_4$, and concentrated in vacuo to afford a residue, which was purified by chromatography over silica gel (eluting with PE:EA=5:1) to give compound A26-3.

Step D: 2-(4-bromo-3-fluorophenyl)-2-methylpropanenitrile (A26-4)

To a solution of compound A26-3 (9.6 g, 45 mmol) in THF (100 ml) under N$_2$ at room temperature was added LDA (2M in THF, 56 ml) over 1 h. Then the mixture was treated with iodomethane (22.3 g, 157.5 mmol). The mixture was then quenched by adding H$_2$O (50 mL) and extracted with EtOAc (100 mL) three times. The combined organic layers were washed with brine, dried over Na$_2$SO$_4$, and concentrated in vacuo to provide a residue, which was purified by chromatography over silica gel (eluting with PE:EA=10:1) to give compound A26-4.

Step E: 2-(4-bromo-3-fluorophenyl)-2-methylpropanal (A26-5)

To a stirring solution of compound A26-4 (4 g, 16.5 mmol) in DCM (40 mL) at −78° C. under nitrogen was added a solution of DIBAl-H (1.0 M in toluene, 33 mL) dropwise. After completion of the addition, the mixture was stirred at this temperature for 1 hour. The reaction was then cooled to 0° C. and quenched by addition of 1.3 mL of H$_2$O, followed by 1.3 mL of 15% aqueous NaOH. After stirring at room temperature for 1 hour, the reaction was filtered and the filtrate was concentrated in vacuo to give a residue, which was purified by chromatography over silica gel (eluting with PE:EA=5:1) to give compound A26-5.

Step F: (E)-ethyl 4-(4-bromo-3-fluorophenyl)-4-methylpent-2-enoate (A26-6)

To a stirring solution of ethyl 2-(diethoxyphosphoryl)acetate (3.8 g, 17.1 mmol) in dry THF at 0° C. was added 60% NaH (912 mg, 22.8 mmol) portionwise. After stirring for 1 h at 0° C., a solution of compound A26-5 (2.8 g, 17.1 mmol) in 10 ml of THF was added portion wise. The resulting mixture was stirred at 0° C. for 1 h, then quenched with water, and acidified with HCl (1 N) to pH=7. The aqueous layer was separated and extracted with EtOAc twice. The combined organic layers were concentrated in vacuo to afford crude compound A26-6, which was used in the next step without purification. MS (ESI) m/e (M+H$^+$): 315.

Step G: ethyl 4-(4-bromo-3-fluorophenyl)-4-methylpentanoate (A26-7)

A mixture of crude compound A26-6 (2.6 g, 8 mmol) and bismuth(III) chloride (5.1 g, 16.4 mmol)) in 80 ml of EtOH at 0° C. was treated with NaBH$_4$ portion wise. Then the reaction was filtered through Celite™, and washed with EtOH. The filtrate was concentrated in vacuo and the resulting residue was taken up in water and EtOAc. The aqueous layer was separated and extracted with EtOAc three times. The combined organic layers were washed with brine, dried over Na$_2$SO$_4$, and concentrated in vacuo to afford a residue, which was purified by chromatography over silica gel (eluting with PE:EA=10:1) to give compound A26-7. MS (ESI) m/e (M+H$^+$): 317.

Step H: 7-bromo-6-fluoro-4,4-dimethyl-3,4-dihydronaphthalen-1(2H)-one (A26-8)

A mixture of compound A26-7 (2.0 g, 6.3 mmol) and triflic acid (10 ml) in 10 ml of TFA was heated to 80° C. for 2 h. Then the reaction was concentrated in vacuo to give a residue, which was purified by chromatography over silica gel (eluting with PE:EA=5:1) to give product A26-8. MS (ESI) m/e (M+H$^+$): 271/273.

Step I: methyl 3-fluoro-5,5-dimethyl-8-oxo-5,6,7,8-tetrahydronaphthalene-2-carboxylate (A26-9)

A mixture of compound A26-8 (1.5 g, 5.5 mmol), Et$_3$N (10 ml) and Pd(dppf)Cl$_2$ (150 mg, 10%) in DMF (10 mL) and MeOH (50 mL) was heated to 80° C. for 16 h under a CO atmosphere (55 psi). After cooling to room temperature, the reaction was filtered and the filtrate was concentrated in vacuo to afford a residue, which was partitioned with EtOAc and water. The aqueous layer was separated and extracted with EtOAc twice. The combined organic layers were washed with water, dried over Na$_2$SO$_4$, and concentrated in vacuo to afford a residue, which was purified by chromatography over silica gel (eluting with PE:EA=8:1 to give compound A26-9. MS (ESI) m/e (M+H$^+$–18): 251.

Step J: methyl 3-fluoro-5,5-dimethyl-8-(((trifluoromethyl)sulfonyl)oxy)-5,6-dihydronaphthalene-2-carboxylate (A26-10)

To a suspension of compound A26-9 (500 mg, 2 mmol) in dry THF (10 mL) at –78° C. under nitrogen was added LiHMDS (1 M in THF, 3 mL) dropwise. Then the reaction mixture was stirred for 30 min at –78° C., followed by treatment with a solution of PhNTf$_2$ in 2 ml of THF. The reaction mixture was stirred for 3 hours, then quenched with water and neutralized with aqueous HCl (2N) to pH=7. The mixture was extracted with EtOAc and the combined organic layers were washed with brine, dried over Na$_2$SO$_4$ and concentrated in vacuo to afford a residue, which was purified by chromatography over silica gel to obtain A26-10. MS (ESI) m/e (M+H$^+$): 383.

Step K: methyl 3-fluoro-5,5-dimethyl-8-(2-(trifluoromethyl)phenyl)-5,8-dihydronaphthalene-2-carboxylate (A26-11)

A mixture of compound A26-10 (550 mg, 1.4 mmol), 2-CF$_3$-phenylboronic acid (408 mg, 2.1 mmol)), K$_3$PO$_4$ (890 mg, 4.25 mmol) and Pd(dtbpf)Cl$_2$ (50 mg) in THF (10 mL) and H$_2$O (3 mL) was microwaved at 100° C. for 30 min under a nitrogen atmosphere. After cooling to room temperature, the reaction was filtered and the filtrate was extracted with EtOAc. The combined organic layers were washed with water, dried over Na$_2$SO$_4$ and concentrated in vacuo to obtain a residue, which was purified flash chromatography over silica gel to afford compound A26-11. MS (ESI) m/e (M+H$^+$): 380.

Step L: methyl 3-fluoro-5,5-dimethyl-8-(2-(trifluoromethyl)phenyl)-5,6,7,8-tetrahydronaphthalene-2-carboxylate (A26-12)

To a stirred solution of compound A26-11 (487 mg, 1.28 mmol) in MeOH was added 10% Pd/C (48 mg) and the reaction was stirred at 25° C. under H$_2$ (55 psi) for 16 h. The reaction mixture was then filtered and the filtrate was concentrated in vacuo to afford crude compound A26-12, which was used in the next step without purification. MS (ESI) m/e (M+H$^+$): 381.

Step M: (3-fluoro-5,5-dimethyl-8-(2-(trifluoromethyl)phenyl)-5,6,7,8-tetrahydronaphthalen-2-yl)methanol (A26-13)

To a solution of crude compound A26-12 (450 mg, crude) in dry THF (10 mL) at 0° C. was added LiAlH$_4$ (90 mg, 2.36 mmol) portion wise. After completion of the addition, the reaction mixture was stirred at 0° C. for 1 h, then quenched with saturated aqueous NH$_4$Cl, and extracted with EtOAc twice. The combined organic layers were dried over Na$_2$SO$_4$ and concentrated in vacuo to obtain crude compound A26-13, which was used in the next step without purification. MS (ESI) m/e (M+H$^+$–18): 336.

Step N: 6-(bromomethyl)-7-fluoro-1,1-dimethyl-4-(2-(trifluoromethyl)phenyl)-1,2,3,4-tetrahydronaphthalene (A26-14)

To a solution of crude compound A26-13 (340 mg, crude) in dry DCM (5 mL) at 0° C. was added SOCl$_2$ (350 mg, 3 mmol) dropwise. The reaction was stirred at 0° C. for 1 h, then warmed to 20° C. and stirred for 2 h. Then the reaction was quenched with water, neutralized with saturated aqueous NaHCO$_3$ to pH=7 and extracted with EtOAc. The combined organic layers were dried over Na$_2$SO$_4$ and concentrated in vacuo to obtain compound A26-14, which was used in the next step without purification. MS (ESI) m/e (M+H$^+$): 370,372.

Step O: (5aR,6S,6aS)-3-((3-fluoro-5,5-dimethyl-8-(2-(trifluoromethyl)phenyl)-5,6,7,8-tetrahydronaphthalen-2-yl)methoxy)-5,5a,6,6a-tetrahydrocyclopropa[4,5]cyclopenta[1,2-c]pyridine-6-carboxylic acid (A26-15)

A mixture of compound A26-14 (170 mg, 0.46 mmol), intermediate 1-9 (110 mg, 0.5 mmol) and Ag$_2$CO$_3$ (248 mg, 0.92 mmol) in toluene (5 mL) was heated at 100° C. for 2 h. The reaction mixture was filtered and the filtrate was concentrated in vacuo to give a residue, which was purified by flash chromatography over silica gel to obtain compound A26-15. MS (ESI) m/e (M+H$^+$): 554

Step P: (5aR,6S,6aS)-3-((3-fluoro-5,5-dimethyl-8-(2-(trifluoromethyl)phenyl)-5,6,7,8-tetrahydronaphthalen-2-yl)methoxy)-5,5a,6,6a-tetrahydrocyclopropa[4,5]cyclopenta[1,2-c]pyridine-6-carboxylic acid (A26-16)

To a mixture of compound A26-15 (80 mg) in THF (3 mL), MeOH (3 mL) and H$_2$O (3 mL) was added LiOH (56 mg). The resulting mixture was stirred at room temperature for 2 h. Then the reaction mixture was acidified with HCl (1 N) to pH=2, and extracted with EtOAc (10 mL) twice. The combined organic layers were washed with water, brine, dried over Na$_2$SO$_4$ and concentrated in vacuo to afford a residue, which was purified by preparative HPLC (on a GILSON 281 instrument fitted with a YMC-pack ODS-AQ YMC-Actus Triart C18 150*30 mm*5 um using water and acetonitrile as the eluents. Mobile phase A: water, mobile phase B: acetonitrile. Gradient: 56-76% B, 0-10 min; 100% B, 10.5-12.5 min; 5% B, 13-15 min) to obtain compound A26-16. $^1$H NMR (400 MHz, MeOD-d$_4$) δ: 1.17 (br. s., 1H) 1.34 (s, 3H) 1.39 (s, 3H) 1.67-1.81 (m, 2H) 1.88 (d, J=11.35 Hz, 1H) 2.06 (br. s., 1H) 2.45 (br. s., 1H) 2.92 (d, J=5.09 Hz, 1H) 3.04 (d, J=18.78 Hz, 1H) 3.23 (d, J=7.43 Hz, 1H) 4.38 (br. s., 1H) 5.20 (s, 2H) 6.62 (d, J=7.04 Hz, 1H) 6.71 (d, J=10.17 Hz, 1H) 6.92 (t, J=8.80 Hz, 1H) 7.16 (dd, J=11.74, 2.74 Hz, 1H) 7.31-7.42 (m, 2H) 7.67 (d, J=7.43 Hz, 1H) 7.93 (d, J=11.35 Hz, 1H). MS (ESI) m/e (M+H$^+$): 526.2.

Example 56

(5aR,6S,6aS)-3-((5-fluoro-1-(2-fluoro-5-methoxyphenyl)-3,3-dimethylindolin-6-yl)methoxy)-5,5a,6,6a-tetrahydrocyclopropa[4,5]cyclopenta[1,2-c]pyridine-6-carboxylic acid (Compound A28-5)

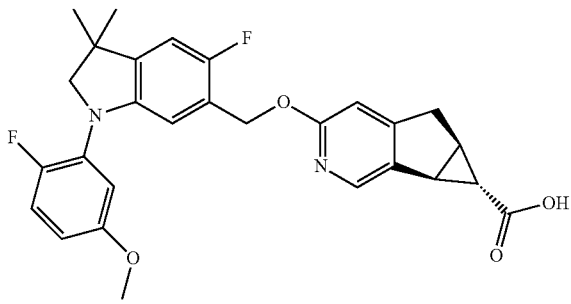

A28-5

Step A: 6-bromo-5-fluoro-1-(2-fluoro-5-methoxyphenyl)-3,3-dimethylindoline (A28-1)

A mixture of BINAP (255 mg, 0.41 mmol), t-BuONa (787 mg, 8.2 mmol), Pd$_2$(dba)$_3$ (188 mg, 0.21 mmol), 2-bromo-1-fluoro-4-methoxybenzene (1.26 g, 6.14 mmol) and 6-bromo-5-fluoro-3,3-dimethylindoline A14-2 (1.0 g, 4.10 mmol) in toluene (30 mL) was heated under N$_2$ at 100° C. for 16 h. After cooling to room temperature, the mixture was diluted with EtOAc and filtered. The filtrate was concentrated in vacuo and the resulting residue was purified by flash chromatography over silica gel (eluting with PE:EA=10:1) to give compound A28-1. MS (ESI) m/e (M+H$^+$): 368.0, 370.0.

Step B: 5-fluoro-1-(2-fluoro-5-methoxyphenyl)-3,3-dimethylindoline-6-carbaldehyde (A28-2)

To a stirring solution of compound A28-1 (900 mg, 2.44 mmol) in THF (15 mL) was added n-BuLi (2.5 M in hexane, 1.17 ml, 2.93 mmol) dropwise at −78° C. under a nitrogen atmosphere. After completion of the addition, the mixture was stirred at −78° C. for 15 min, then DMF (0.28 mL, 3.67 mmol) was added dropwise. The resulting mixture was stirred at −78° C. for 1 h, then quenched with saturated aqueous NH$_4$Cl and extracted with ethyl acetate three times. The combined organic layers were washed with brine, dried over Na$_2$SO$_4$ and concentrated in vacuo to afford compound A28-2. MS (ESI) m/e (M+H$^+$): 318.1.

Step C: (5-fluoro-1-(2-fluoro-5-methoxyphenyl)-3,3-dimethylindolin-6-yl)methanol (A28-3)

NaBH$_4$ (274 mg, 7.25 mmol) was added to a mixture of compound A28-2 (460 mg, 1.45 mmol) in MeOH (20 mL) at 0° C., and the mixture was stirred at 0° C. for 1 h. Then the reaction was quenched with water (20 mL) and extracted with ethyl acetate (20 mL) two times. The combined organic layers were washed with brine, dried over anhydrous Na$_2$SO$_4$, and concentrated in vacuo. The resulting residue was purified by flash chromatography over silica gel (eluting with PE:EA=5:1) to give compound A28-3. MS (ESI) m/e (M+H$^+$): 319.1 (−17).

Step D: (5aR,6S,6aS)-tert-butyl 3-((5-fluoro-1-(2-fluoro-5-methoxyphenyl)-3,3-dimethylindolin-6-yl)methoxy)-5,5a,6,6a-tetrahydrocyclopropa[4,5]cyclopenta[1,2-c]pyridine-6-carboxylate (A28-4)

A mixture of Brett-Phos Palladacycle (8.75 mg, 11 μmol), compound A28-3 (70 mg, 0.22 mmol), intermediate 1-11 (64 mg, 0.24 mmol) and Cs$_2$CO$_3$ (179 mg, 0.548 mmol) in toluene (15 mL) was heated at 100° C. under an atmosphere of N$_2$ for 16 h. After cooling to room temperature, the mixture was diluted with EtOAc and filtered. The filtrate was concentrated in vacuo and the resulting residue was purified by preparative TLC over silica gel (eluting with PE:EA=4:1) to give compound A28-4. MS (ESI) m/e (M+H$^+$): 549.2.

Step E: (5aR,6S,6aS)-3-((5-fluoro-1-(2-fluoro-5-methoxyphenyl)-3,3-dimethylindolin-6-yl)methoxy)-5,5a,6,6a-tetrahydrocyclopropa[4,5]cyclopenta[1,2-c]pyridine-6-carboxylic acid (A28-5)

To a mixture of compound A28-4 (58 mg, 0.11 mmol) in THF (1 mL), MeOH (1 mL) and H$_2$O (1 mL) was added NaOH (42.3 mg, 1.1 mmol), and the resulting mixture was stirred at 50° C. for 10 h. The reaction mixture was acidified with HCl (2 N) to pH=7, and extracted with ethyl acetate (10 mL) twice. The combined organic layers were washed with water, brine, dried over Na$_2$SO$_4$ and concentrated in vacuo, to provide a residue, which was purified by preparative HPLC (preparative HPLC on a GILSON 281 instrument fitted with a Waters XSELECT C18 150*30 mm*5 um using water and acetonitrile as the eluents. Mobile phase A: water (containing 0.1% TFA, v/v), mobile phase B: acetonitrile. Gradient: 60-80% B, 0-10 min; 100% B, 10.5-12.5 min; 5% B, 13-15 min) to give compound A28-5. $^1$H NMR (400 MHz, MeOD-d$_4$) δ: 8.36 (s, 1H), 7.02 (s, 1H), 6.75-6.87 (m, 3H), 6.59-6.67 (m, 1H), 6.51-6.59 (m, 1H), 5.30 (br. s., 2H), 3.73 (s, 3H), 3.66 (s, 2H), 3.27-3.40 (m, 1H), 3.02-3.19 (m, 2H), 2.51-2.62 (m, 1H), 1.34 (s, 6H), 1.28 (br. s., 1H). MS (ESI) m/e (M+H$^+$): 493.2.

Example 57

(5aR,6S,6aS)-3-((6-fluoro-1-(1H-pyrazol-1-yl)-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (Compound A29-8A)

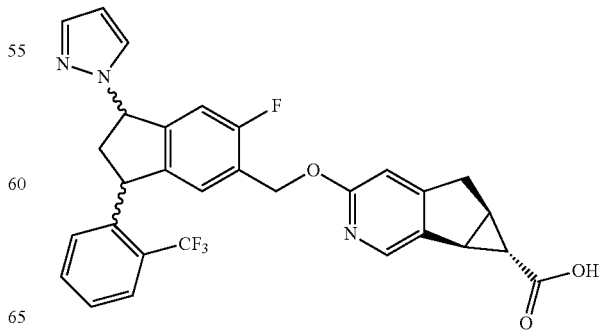

A29-8A

Step A: 5-bromo-6-fluoro-3-(2-(trifluoromethyl) phenyl)-1H-inden-1-one (A29-1)

A mixture of compound A9-4 (0.5 g, 1.400 mmol) and selenium dioxide (0.777 g, 7.00 mmol) in 1,4-dioxane (30 mL) was heated at 100° C. for 16 h. After cooling to room temperature, the mixture was diluted with EtOAc and filtered. The filtrate was concentrated in vacuo and the resulting residue was purified by flash chromatography over silica gel (eluting with PE:EA=20:1) to give compound A29-1. MS (ESI) m/e (M+H$^+$): 371.2, 373.1.

Step B: ethyl 6-fluoro-1-oxo-3-(2-(trifluoromethyl) phenyl)-1H-indene-5-carboxylate (A29-2)

A mixture of compound A29-1 (400 mg, 1.08 mmol), PdCl$_2$(dppf) (79 mg, 0.108 mmol), and sodium acetate (177 mg, 2.156 mmol) in EtOH (10 mL) was heated at 80° C. for 16 h under a CO atmosphere (50 psi). After cooling to room temperature, the mixture was diluted with EtOAc and filtered. The EtOAc layer was separated, washed with water and brine, dried over anhydrous Na$_2$SO$_4$ and concentrated in vacuo. The resulting residue was purified by flash chromatography over silica gel (eluting with PE:EA=2:1) to give compound A29-2. MS (ESI) m/e (M+H$^+$): 365.2.

Step C: ethyl 6-fluoro-1-hydroxy-3-(2-(trifluoromethyl)phenyl)-2,3-dihydro-1H-indene-5-carboxylate (A29-3)

10% Pd—C (35 mg) was added to a solution of compound A29-2 (350 mg, 0.96 mmol) in MeOH (30 ml), and the resulting mixture was stirred at 50° C. under H$_2$ atmospheres (50 psi) for 12 h. The mixture was filtered over Celite™ and the filtrate was concentrated in vacuo. The resulting residue was purified by flash chromatography over silica gel (eluting with P:E=10:1) to give compound A29-3. MS (ESI) m/e (M+H$^+$): 369.1.

Step D: ethyl 1-chloro-6-fluoro-3-(2-(trifluoromethyl)phenyl)-2,3-dihydro-1H-indene-5-carboxylate (A29-4)

To a solution of compound A29-3 (180 mg, 0.489 mmol) and triethylamine (99 mg, 0.977 mmol) in dry DCM (3 mL) at 0° C. under N$_2$, was added MsCl (0.076 mL, 0.977 mmol) dropwise. The mixture was stirred for 12 h while warming to room temperature. Then saturated aqueous NaHCO$_3$ was added to quench the reaction. The reaction mixture was extracted with DCM (10 mL) three times. The combined organic layers were washed with brine, dried over anhydrous Na$_2$SO$_4$ and concentrated in vacuo to give crude compound A29-4, which was used for the next step without purification. MS (ESI) m/e (M+H$^+$): 387.2.

Step E: ethyl 1-chloro-6-fluoro-3-(2-(trifluoromethyl)phenyl)-2,3-dihydro-1H-indene-5-carboxylate (A29-5A and A29-5B)

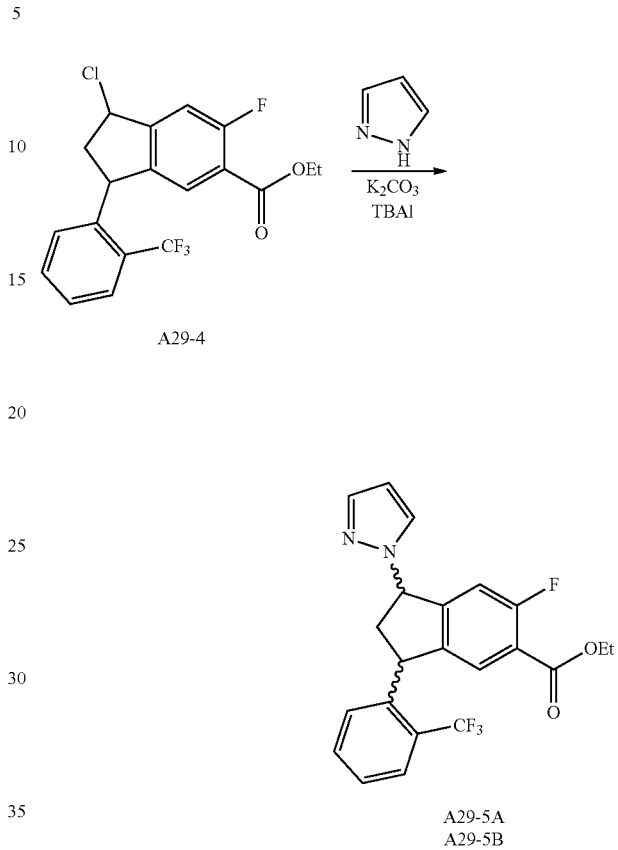

A29-4

A29-5A
A29-5B

A mixture of compound A29-4 (250 mg, 0.65 mmol), 1H-pyrazole (440 mg, 6.46 mmol) and K$_2$CO$_3$ (268 mg, 1.94 mmol) in DMF (4 mL) was heated at 65° C. for 12 h. After cooling to room temperature, the mixture was diluted with EtOAc, filtered and concentrated in vacuo to give a residue. The residue was purified by reverse Preparative HPLC (on a GILSON 281 instrument fitted with a Phenomenex Synergi C18 100*21.2 mm*4 um using water and acetonitrile as the eluents. Mobile phase A: water (containing 0.1% TFA, v/v), mobile phase B: acetonitrile. Gradient: 56-71% B, 0-10 min; 100% B, 10.5-12.5 min; 5% B, 13-15 min) to give compound A29-5A, followed by compound A29-5B. MS (ESI) m/e (M+H$^+$): 419.2 for both.

Step F: ethyl 6-fluoro-1-(1H-pyrazol-1-yl)-3-(2-(trifluoromethyl)phenyl)-2,3-dihydro-1H-indene-5-carboxylate (A29-6A)

To a solution of compound A29-5A (35 mg, 0.082 mmol) in dry THF (10 mL) at 0° C. under N$_2$ was added LiBH$_4$ (8 mg, 0.25 mmol), and the mixture was stirred for 3 h. Then ice water was added to quench the reaction, and the reaction mixture was extracted with DCM (10 mL) three times. The combined organic layers were washed with water, brine, dried over anhydrous Na$_2$SO$_4$ and concentrated in vacuo to give crude compound A29-6A. MS (ESI) m/e (M+H$^+$): 377.2.

Step G: ethyl 6-fluoro-1-(1H-pyrazol-1-yl)-3-(2-(trifluoromethyl)phenyl)-2,3-dihydro-1H-indene-5-carboxylate (A29-7A)

A mixture of compound A29-6A (14 mg, 0.037 mmol), intermediate 1-11 (9.89 mg, 0.037 mmol), Brett-Phos Palladacycle (3 mg, 4 μmol), and cesium carbonate (36.4 mg, 0.112 mmol) in toluene (10 mL) was heated at 100° C. for 16 h. After cooling to room temperature, the mixture was diluted with EtOAc, and filtered. The filtrate was concentrated and the resulting residue was purified by preparative TLC over silica gel (eluting with P:E=7:1) to give compound A29-7A. MS (ESI) m/e (M+H$^+$): 606.2.

Step H: (5aR,6S,6aS)-3-((6-fluoro-1-(1H-pyrazol-1-yl)-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (A29-8A)

To a mixture of compound A29-7A (10 mg, 0.017 mmol) in MeOH (1 mL), THF (1 mL) and water (1 mL) was added LiOH (6 mg, 0.165 mmol), and the resulting mixture was stirred at room temperature for 24 h. Then the reaction mixture was acidified with HCl (1 N) to pH=6, and extracted with ethyl acetate (20 mL) twice. The combined organic layers were washed with water, brine, dried over Na$_2$SO$_4$ and concentrated in vacuo to afford a residue, which was purified by preparative HPLC (on a GILSON 281 instrument fitted with a YMC-Actus Triart C18 150*30 mm*5 um) using water and acetonitrile as the eluents. Mobile phase A: water (containing 0.1% TFA, v/v), mobile phase B: acetonitrile. Gradient: 40-70% B, 0-10 min; 100% B, 10.5-12.5 min; 5% B, 13-15 min) to give product A29-8A. $^1$H NMR (400 MHz, MeOD-d$_4$) δ: 8.07 (s, 1H), 7.73 (d, J=7.83 Hz, 1H), 7.63 (s, 1H), 7.46-7.57 (m, 2H), 7.43 (d, J=7.43 Hz, 1H), 7.13 (t, J=6.06 Hz, 1H), 7.04 (d, J=9.39 Hz, 2H), 6.95 (s, 1H), 6.33 (s, 1H), 6.14 (dd, J=7.83, 3.52 Hz, 1H), 5.37 (s, 2H), 5.16 (t, J=7.24 Hz, 1H), 3.32-3.37 (m, 1H), 3.05-3.19 (m, 1H), 2.86-3.02 (m, 2H), 2.63 (dt, J=13.99, 7.29 Hz, 1H), 2.49 (br. s., 1H), 1.11-1.26 (m, 1H). MS (ESI) m/e (M+H$^+$): 550.2.

Example 59

((5aR,6S,6aS)-3-((6-fluoro-1-(2-(trifluoromethyl)phenyl)isochroman-7-yl)methoxy)-5,5a,6,6a-tetrahydrocyclopropa[4,5]cyclopenta[1,2-c]pyridine-6-carboxylic acid (Compound A30-6A)

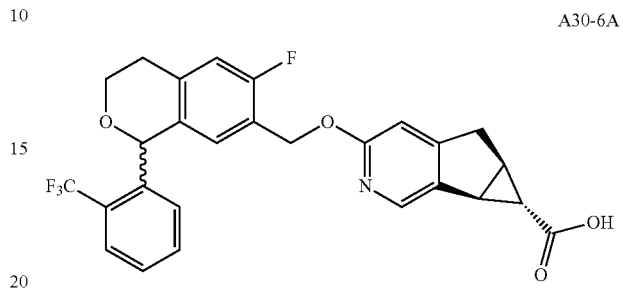

A30-6A

Step A: ethyl 2-fluoro-4-(2-oxoethyl)-5-(2-(trifluoromethyl)benzoyl)benzoate (A30-1)

Ozone was bubbled through a mixture of compound A9-4 (1.5 g, 4.28 mmol) in DCM (80 mL) at −78° C. under N$_2$ for 10 min until the solution turned blue. Then reaction was quenched by adding dimethylsulfane (1.33 g, 21.4 mmol) dropwise. The resulting mixture was stirred at −78° C. for 1 h, and then warmed to 0° C. and stirred overnight. The reaction mixture was concentrated in vacuo to afford crude compound A30-1, which was used in the next step without purification. MS (ESI) m/e (M+H$^+$): 383.1.

Step B: ethyl 2-fluoro-5-(hydroxy(2-(trifluoromethyl)phenyl)methyl)-4-(2-hydroxyethyl)benzoate (A30-2)

To a stirred mixture of crude compound A30-1 (1.2 g, 2.040 mmol) in MeOH (15 mL) at 0° C. was added NaBH$_4$ (0.386 g, 10.20 mmol) and the mixture was stirred for 2 h.

TABLE 11

Example 58 (compound A29-8B) was prepared in a similar manner to Example 57 (Compound A29-8A) using compound A29-5B and commercially available materials, and including procedures described across this application when necessary.

| Example | Structure | M.W. | Compound Name | LC/MS (ESI) observed [M + 1]+ |
|---|---|---|---|---|
| 58 | (Compound A29-8B) | 549.5 | (5aR,6S,6aS)-3-((6-fluoro-1-(1H-pyrazol-1-yl)-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid | 550.2 |

The mixture was then quenched with water (40 mL) and extracted with ethyl acetate (20 mL) twice. The combined organic layers were washed with brine, dried over anhydrous $Na_2SO_4$, and concentrated in vacuo to give a residue, which was purified by flash chromatography over silica gel (eluting with PE:EA=1:1) to give compound A30-2. MS (ESI) m/e ($M+H^+$): 386.1 (−17).

Step C: ethyl 6-fluoro-1-(2-(trifluoromethyl)phenyl) isochroman-7-carboxylate (A30-3)

A mixture of compound A30-2 (450 mg, 1.17 mmol) and $Ph_3P$ (397 mg, 1.514 mmol) in DCM (20 ml) at 0° C. was treated with DIAD (0.27 mL, 1.40 mmol) dropwise. The resulting solution was stirred for 1 h and then warmed to room temperature and stirred 6 h. The reaction mixture was quenched with water (40 mL) and extracted with DCM (20 mL) twice. The combined organic layers were washed with brine, dried over anhydrous $Na_2SO_4$, and concentrated in vacuo to give a residue, which was purified by preparative TLC over silica gel (eluting with PE:EA=4:1) to give compound A30-3. MS (ESI) m/e ($M+H^+$): 369.1.

Step D: (6-fluoro-1-(2-(trifluoromethyl)phenyl)isochroman-7-yl)methanol (A30-4)

To a suspension of $LiAlH_4$ (54 mg, 1.43 mmol) in dry THF (5 mL) at 0° C. was added a solution of compound A30-3 (350 mg, 0.95 mmol) in THF (5 mL) dropwise and the mixture was stirred at this temperature for 3 hrs. Then the reaction mixture was warmed to room temperature and 1N NaOH aqueous solution was added slowly. The reaction mixture was diluted with THF and filtered through Celite®. The filtrate was concentrated in vacuo to provide a residue, which was purified by preparative TLC over silica gel (eluting with PE:EA=4:1) to afford compound A30-4. MS (ESI) m/e ($M+H^+$): 326.1 (−17).

Step E: (5aR,6S,6aS)-tert-butyl 3-((6-fluoro-1-(2-(trifluoromethyl)phenyl)isochroman-7-yl)methoxy)-5,5a,6,6a-tetrahydrocyclopropa[4,5]cyclopenta[1,2-c]pyridine-6-carboxylate (A30-5)

A mixture of Brett-Phos Palladacycle (9.55 mg, 0.012 mmol), compound A30-4 (78 mg, 0.24 mmol), intermediate 1-11 (69.9 mg, 0.263 mmol) and $Cs_2CO_3$ (195 mg, 0.598 mmol) in toluene (15 mL) was heated at 110° C. under $N_2$ for 16 h. After cooling to room temperature, the mixture was diluted with EtOAc, and filtered. The filtrate was concentrated in vacuo to give a residue, which was purified by preparative TLC over silica gel (eluting with PE:EA=10:1) to give compound A30-5. MS (ESI) m/e ($M+H^+$): 556.2.

Chiral SFC Resolution of Compound A30-5 (Compounds A30-5A and A30-5B)

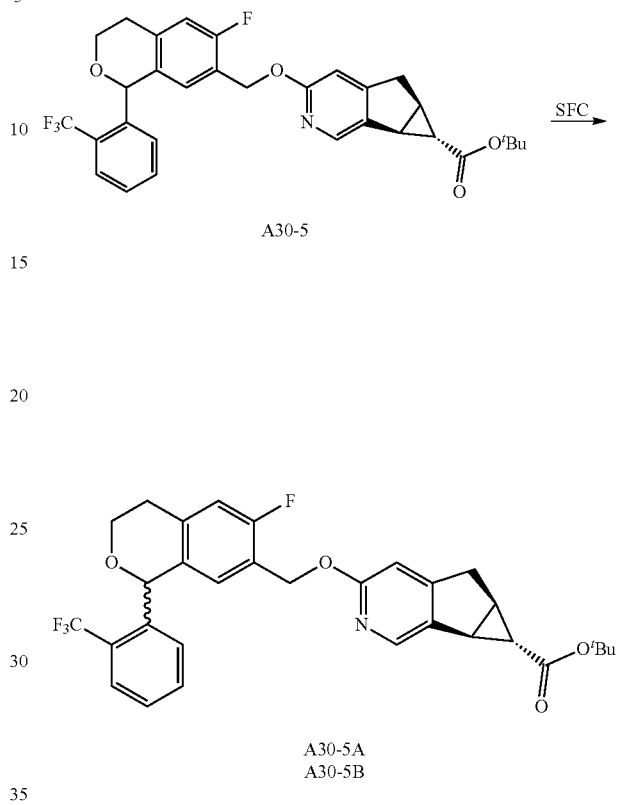

A30-5

A30-5A
A30-5B

Compound A30-5 was purified by chiral preparative SFC (Column: AD 250×30 mm, 5 um; Conditions: 25% $NH_4OH$ in EtOH; Wavelength: 220 nm) to provide compounds A30-5A and A30-5B. MS (ESI) m/e ($M+H^+$): 556.2 for both.

Step F: (5aR,6S,6aS)-3-((6-fluoro-1-(2-(trifluoromethyl)phenyl)isochroman-7-yl)methoxy)-5,5a,6,6a-tetrahydrocyclopropa[4,5]cyclopenta[1,2-c]pyridine-6-carboxylic acid (A30-6A)

To a mixture of compound A30-5A (43 mg, 0.077 mmol) in THF (1 mL), MeOH (1 mL) and $H_2O$ (1 mL) was added NaOH (31 mg, 0.77 mmol), and the mixture was stirred at room temperature for 2 h. The resulting mixture was acidified with HCl (2 N) to pH=7, and extracted with ethyl acetate (10 mL) twice. The combined organic layer was washed with water, brine, dried over $Na_2SO_4$ and concentrated in vacuo to provide a residue, which was purified by reverse preparative HPLC (on a GILSON 281 instrument fitted with a Waters XSELECT C18 150*30 mm*5 um using water and acetonitrile as the eluents. Mobile phase A: water (containing 0.1% TFA, v/v), mobile phase B: acetonitrile. Gradient: 53-73% B, 0-11 min; 100% B, 10.5-12.5 min; 5% B, 13-15 min) to give compound A30-6A. $^1H$ NMR (400 MHz, $CDCl_3$) δ: 8.11 (s, 1H), 7.71 (d, J=7.53 Hz, 1H), 7.36-7.53 (m, 2H), 7.25-7.30 (m, 1H), 6.92 (d, J=10.04 Hz, 1H), 6.67 (d, J=7.03 Hz, 1H), 6.59 (s, 1H), 6.06 (s, 1H), 5.14-5.30 (m, 2H), 4.27 (dd, J=11.54, 4.52 Hz, 1H), 3.89-4.04 (m, 1H), 3.16-3.32 (m, 2H), 3.04 (d, J=18.57 Hz, 2H), 2.78 (d, J=16.56 Hz, 1H), 2.54 (br. s., 1H), 1.22 (br. s., 1H). MS (ESI) m/e ($M+H^+$): 500.1.

TABLE 12

Example 60 (Compound A30-6B) was prepared in a similar manner to Example 59 (Compound A30-6A) using compound A30-5B and commercially available materials, and including procedures described across this application when necessary.

| Example | Structure | M.W. | Compound Name | LC/MS (ESI) observed [M + 1]+ |
|---|---|---|---|---|
| 60 | (compound A30-5B) | 501.5 | (5aR,6S,6aS)-3-((6-fluoro-1-(2-(trifluoromethyl)-phenyl)isochroman-7-yl)methoxy)-5,5a,6,6a-tetrahydrocyclopropa[4,5]-cyclopenta[1,2-c]pyridine-6-carboxylic acid | 500.1 |

Example 61

(5aR,6S,6aS)-3-((4-phenyl-3,4-dihydro-2H-benzo[b][1,4]oxazin-6-yl)methoxy)-5,5a,6,6a-tetrahydrocyclopropa[4,5]cyclopenta[1,2-c]pyridine-6-carboxylic acid (Compound B15-7)

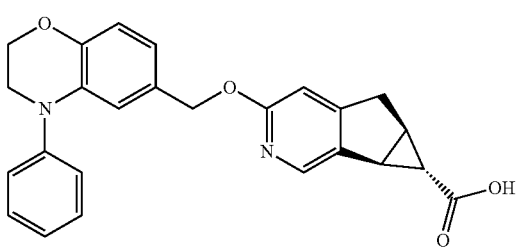

B15-7

Step A: methyl 4-hydroxy-3-(phenylamino)benzoate (B15-2)

Copper (I) iodide (190 mg, 0.1 mmol) and N,N-dimethylenediamine (180 mg, 0.2 mmol) were added to a suspension of methyl 3-amino-4-hydroxybenzoate B15-1 (1.67 g, 10 mmol), iodobenzene (2.45 g, 12 mmol) and $K_3PO_4$ (6.36 g, 3.0 mmol) in DMF (20 ml) under a $N_2$ atmosphere. The reaction was heated to 110° C. for 5 h, then cooled to room temperature. Water was added, and the organic layer was separated and concentrated in vacuo. The resulting crude product was then purified by flash chromatography over silica gel to afford compound B15-2. MS (ESI) m/e (M+H+): 244.1.

Step B: methyl 4-phenyl-3,4-dihydro-2H-benzo[b][1,4]oxazine-6-carboxylate (B15-3)

To a suspension of compound B15-2 (1.5 g, 6.18 mmol), and $K_2CO_3$ (4.26 g, 30.88 mmol) in dry DMF (20 ml) was added 1,2-dibromoethane (2.3 g, 12.35 mmol). The mixture was heated at 120° C. for 12 h. After cooling, the mixture was treated with water, and then extracted with EtOAc. The combined organic layers were washed with water, dried over $Na_2SO_4$ and concentrated in vacuo to obtain a residue, which was purified by flash chromatography over silica gel to give compound B15-3.

Step C: (4-phenyl-3,4-dihydro-2H-benzo[b][1,4]oxazin-6-yl)methanol (B15-4)

To a solution of compound B15-3 (870 mg, 3.23 mmol) in THF (10 mL) was added LAH (184 mg, 4.85 mmol) at 0° C. and the resulting mixture was stirred for 2 h. The reaction was quenched with $H_2O$ (0.5 mL), followed by 15% NaOH (0.2 mL). After stirring at room temperature for 5 min, the resulting solid was removed by filtration. The filtrate was concentrated in vacuo to give crude compound B15-4, which was used in the next step without purification.

Step D: (4-phenyl-3,4-dihydro-2H-benzo[b][1,4]oxazin-6-yl)methyl 4-methylbenzenesulfonate (B15-5)

To a solution of compound B15-4 (130 mg, 0.54 mmol) in DCM (15 mL) at 0° C. was added $Et_3N$ (109 mg, 1.08 mol), TosCl (113 mg, 0.60 mol) and DMAP (cat amount) slowly. The resulting mixture was warmed to room temperature and stirred for 2 h. The reaction was quenched with $H_2O$, and extracted with DCM (15 mL) three times. The combined organic layers were dried over $Na_2SO_4$ and concentrated in vacuo to provide crude compound B15-5, which was used in the next step without further purification. MS (ESI) m/e (M+H+): 396.3.

Step E: (5aR,6S,6aS)-ethyl 3-((4-phenyl-3,4-dihydro-2H-benzo[b][1,4]oxazin-6-yl)methoxy)-5,5a,6,6a-tetrahydrocyclopropa[4,5]cyclopenta[1,2-c]pyridine-6-carboxylate (B15-6)

To a solution of compound B15-5 (190 mg, 0.49 mmol) in toluene (10 mL) was added intermediate 1-9 (118 mg, 0.54 mmol) and $Ag_2CO_3$ (406 mg, 1.47 mmol). The reaction mixture was heated to 80° C. and stirred for 12 hours. Then the reaction mixture was filtered and the filtrate was concentrated in vacuo to give a residue, which was purified by preparative TLC on silica gel to give compound B15-6.

Step F: (5aR,6S,6aS)-3-((4-phenyl-3,4-dihydro-2H-benzo[b][1,4]oxazin-6-yl)methoxy)-5,5a,6,6a-tetrahydrocyclopropa[4,5]cyclopenta[1,2-c]pyridine-6-carboxylic acid (B15-7)

To a solution of compound B15-6 (27 mg, 0.06 mmol) in EtOH (2.5 mL) and $H_2O$ (0.5 mL) was added $LiOH·H_2O$ (26 mg, 0.61 mmol). The resulting mixture was stirred at room temperature for 16 hours, and then diluted with water, acidified with HCl (1M) to pH=2.5, and extracted with EtOAc (5 mL) three times. The combined organic layers were washed with brine, dried over $Na_2SO_4$ and concentrated in vacuo to give a residue, which was purified by preparative TLC over silica gel to give compound B15-7. $^1$H NMR (400 MHz, MeOD-$d_4$) δ: 8.00 (s, 1H), 7.36-7.28 (m, 2H), 7.18 (d, J=7.8 Hz, 2H), 7.11-7.05 (m, 1H), 6.87 (s, 1H), 6.81-6.72 (m, 2H), 6.58 (s, 1H), 5.06 (s, 2H), 4.28-4.22 (m, 2H), 3.71-3.64 (m, 2H), 3.22 (dd, J=6.3, 18.4 Hz, 1H), 3.01 (d, J=18.4 Hz, 1H), 2.91 (d, J=5.1 Hz, 1H), 2.46-2.39 (m, 1H), 1.14 (br. s., 1H). MS (ESI) m/e (M+H$^+$): 415.2.

Example 62

(5aR,6S,6aS)-3-((1-phenyl-2,3,4,5-tetrahydro-1H-benzo[b]azepin-8-yl)methoxy)-5,5a,6,6a-tetrahydro-cyclopropa[4,5]cyclopenta[1,2-c]pyridine-6-carboxylic acid (Compound B16-8)

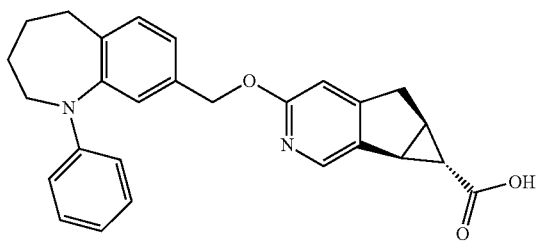

B16-8

Step A: (Z)-methyl 8-(hydroxyimino)-5,6,7,8-tetrahydronaphthalene-2-carboxylate (B16-2)

To a solution of compound B16-1 (1.0 g, 5.68 mmol) in MeOH (10 mL) was added $NH_2OH \cdot HCl$ (431 mg, 6.25 mmol) and NaOAc (513 mg, 6.25 mmol) at room temperature, then the resulting mixture was heated to reflux and stirred for 4 hours. Then the reaction was concentrated in vacuo, $H_2O$ was added, and the mixture was extracted with EtOAc (15 mL) three times. The combined organic layers were washed with brine, dried over $Na_2SO_4$ and concentrated in vacuo to obtain a residue, which was purified by flash chromatography over silica gel (PE:EA=8:1) to give compound B16-2.

Step B: methyl 2-oxo-2,3,4,5-tetrahydro-1H-benzo[b]azepine-8-carboxylate (B16-3)

A solution of compound B16-2 (300 mg, 1.4 mmol) in PPA (3 mL) was heated to 120° C. and stirred for 1 hour. Then $H_2O$ was added and the solution was extracted with EtOAc (10 mL) three times. The combined organic layers were washed with brine, dried over $Na_2SO_4$ and concentrated in vacuo to give crude compound B16-3, which was used in the next step directly. MS (ESI) m/e (M+H$^+$): 220.1

Step C: methyl 2-oxo-1-phenyl-2,3,4,5-tetrahydro-1H-benzo[b]azepine-8-carboxylate (B16-4)

To a solution of crude compound B16-3 (120 mg, 0.55 mmol) in 1,4-dioxane (5 mL) was added iodobenzene (167 mg, 0.82 mmol), N,N-dimethylethane-1,2-diamine (4.8 mg, 0.06 mmol), CuI (5.2 mg, 0.03 mmol) and $K_3PO_4$ (348 mg, 1.64 mmol). The resulting mixture was heated to reflux and stirred for 5 hours. Then water was added and the mixture was extracted with EtOAc (10 mL) three times. The combined organic layers were washed with brine, dried over $Na_2SO_4$ and concentrated in vacuo to give a residue, which was purified by preparative TLC over silica gel (eluting with PE:EA=1:1) to give compound B16-4. MS (ESI) m/e (M+H$^+$): 295.9.

Step D: (1-phenyl-2,3,4,5-tetrahydro-1H-benzo[b]azepin-8-yl)methanol (B16-5)

To a solution of compound B16-4 (20 mg, 0.07 mmol) in THF (10.0 mL) was added $LiAlH_4$ (21 mg, 0.54 mmol), and the solution was stirred for 30 min under reflux. The cooled reaction mixture was then quenched with $H_2O$ and concentrated NaOH. The resulting mixture was stirred for 10 min, then filtered, and the filtrate was concentrated in vacuo to give crude compound B16-5. MS (ESI) m/e (M+H$^+$): 254.2.

Step E: 8-(bromomethyl)-1-phenyl-2,3,4,5-tetrahydro-1H-benzo[b]azepine (B16-6)

To a solution of compound B16-5 (15 mg, 0.06 mmol) in DCM (2 mL) at 0° C. was added $PBr_3$ (19 mg, 0.07 mmol), and the solution was stirred for 30 min. The reaction mixture was quenched with ice-water, and extracted with EtOAc. The combined organic layers were dried over $Na_2SO_4$ and concentrated in vacuo to give a residue, which was purified by preparative TLC over silica gel (eluting with PE:EA=2:1) to give compound B16-6. MS (ESI) m/e (M+H$^+$): 316.3.

Step F: (5aR,6S,6aS)-ethyl 3-((1-phenyl-2,3,4,5-tetrahydro-1H-benzo[b]azepin-8-yl)methoxy)-5,5a,6,6a-tetrahydrocyclopropa[4,5]cyclopenta[1,2-c]pyridine-6-carboxylate (B16-7)

To a solution of compound B16-6 (15 mg, 0.05 mmol) in toluene (2.0 mL) was added intermediate 1-9 (13 mg, 0.06 mmol) and $Ag_2CO_3$ (42 mg, 0.15 mmol). The resulting mixture was heated to 110° C. and stirred for 18 hours. Then the reaction mixture was filtered, and the filtrate was concentrated in vacuo to give a residue, which was purified by preparative TLC over silica gel (eluting with PE:EA=5:1) to give compound B16-7. MS (ESI) m/e (M+H$^+$): 455.4.

Step G: (5aR,6S,6aS)-3-((1-phenyl-2,3,4,5-tetrahydro-1H-benzo[b]azepin-8-yl)methoxy)-5,5a,6,6a-tetrahydrocyclopropa[4,5]cyclopenta[1,2-c]pyridine-6-carboxylic acid (B16-8)

To a solution of compound B16-7 (13 mg, 0.03 mmol) in THF (3.0 mL), MeOH (1.0 mL) and $H_2O$ (1.0 mL) was added $LiOH \cdot H_2O$ (5 mg, 0.12 mmol). The resulting mixture was stirred at room temperature for 4 hours. Then water was added and the reaction mixture was acidified with HCl (1 M) to pH=5, and extracted with EtOAc (10 mL) three times. The combined organic layers were washed with brine, dried over $Na_2SO_4$ and concentrated in vacuo to give compound B16-8. $^1$H NMR (400 MHz, MeOD-$d_4$) δ: 8.04 (s, 1H), 7.30-7.25 (m, 1H), 7.24-7.19 (m, 1H), 7.17 (s, 1H), 7.06 (t, J=7.6 Hz, 2H), 6.67 (s, 1H), 6.60 (t, J=7.0 Hz, 1H), 6.54 (d, J=8.2 Hz, 2H), 5.25 (s, 2H), 3.65 (br. s., 2H), 3.23 (dd, J=6.1, 18.6 Hz, 1H), 3.02 (d, J=18.4 Hz, 1H), 2.92 (d, J=5.5 Hz, 1H), 2.68-2.58 (m, 2H), 2.43 (d, J=2.7 Hz, 1H), 1.82 (br. s., 2H), 1.67 (br. s., 2H), 1.14 (br. s., 1H). MS (ESI) m/e (M+H+): 427.5.

Example 63

(5aR,6S,6aS)-3-((6-fluoro-1-phenyl-3-(2-(trifluoromethyl)phenyl)-1H-indol-5-yl)methoxy)-5,5a,6,6a-tetrahydrocyclopropa[4,5]cyclopenta[1,2-c]pyridine-6-carboxylic acid (Compound B18-9)

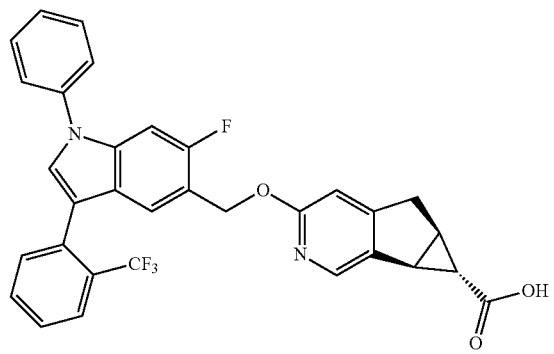

B18-9

Step A: 6-fluoro-1-(triisopropylsilyl)-1H-indole (B18-1)

To a stirred solution of 6-fluoro-1H-indole (10 g, 74.0 mmol) in THF (100 mL) at −78° C. was added n-BuLi (2.5 M in hexanes, 29.6 mL, 74.0 mmol) dropwise, followed by chlorotriisopropylsilane (17.12 g, 89 mmol). The reaction was stirred at −78° C. for 30 min, then quenched with water (50 mL) and tert-butylmethylether (100 mL). The organic layer was separated, washed with brine, dried over Na$_2$SO$_4$ and concentrated in vacuo to provide a residue, which was purified by chromatography over silica gel (eluting with PE:EA=10:1) to give compound B18-1. MS (ESI) m/e (M+H+): 292.3.

Step B: 6-fluoro-1-(triisopropylsilyl)-1H-indole-5-carboxylic acid (B18-2)

To a stirred solution of compound B18-1 (2980 mg, 10.22 mmol) in THF (30 mL)) at −78° C. was added s-BuLi (12.27 mmol) dropwise. The reaction mixture was stirred at −78° C. for 2 hour, then CO$_2$ was vented into the mixture. The reaction was stirred at −78° C. for 1 hour, then warmed to 0° C. and quenched with water. The reaction mixture was washed with brine (100 mL) and extracted with EtOAc (40 mL). The combined organic layers were dried over Na$_2$SO$_4$ and concentrated in vacuo to provide a residue, which was purified by flash chromatography over silica gel (eluting with PE:EA=3:1) to give compound B18-2.

Step C: methyl 6-fluoro-1-(triisopropylsilyl)-1H-indole-5-carboxylate (B18-3)

To a solution of compound B18-2 (90 mg, 0.268 mmol) in dry DCM (2 mL) was added oxalyl chloride (102 mg, 0.805 mmol), followed by DMF (1.961 mg, 0.027 mmol). The reaction was stirred 30 min, then concentrated. The resulting residue was dissolved in DCM (2 mL) and cooled to 0° C. Then TEA (136 mg, 1.341 mmol) was added, followed by the slow addition of MeOH (1 mL). The reaction mixture was stirred for 30 min, then concentrated. The resulting residue was diluted with water and EtOAc, and extracted with EtOAc. The combined organic layers were concentrated to provide a residue, which was purified by preparative TLC over silica gel (eluting with PE:EA=15:1) to afford compound B18-3. MS (ESI) m/e (M+H+): 350.3.

Step D: methyl 3-bromo-6-fluoro-1H-indole-5-carboxylate (B18-4)

To a solution of compound B18-3 (6.00 g, 17.17 mmol) in DMF (30 mL) was added dropwise Br$_2$ (3.4 g, 20.60 mmol). The reaction was stirred for 15 min at room temperature, then washed with 5% Na$_2$SO$_3$ (200 mL) and brine (350 mL), and extracted with EtOAc (150 mL) three times. The combined organic layers were concentrated in vacuo to afford crude compound B18-4, which was used in the next step directly.

Step E: methyl 6-fluoro-3-(2-(trifluoromethyl)phenyl)-1H-indole-5-carboxylate (B18-5)

A mixture of K$_3$PO$_4$ (3228 mg, 34.0 mmol), PdCl$_2$(dppf) (1244 mg, 1.700 mmol), crude compound B18-4 (4624 mg, 17.00 mmol) and (2-(trifluoromethyl)phenyl)boronic acid (6456 mg, 34.0 mmol) in THF (60 mL) and water (10 mL) was stirred at 105° C. under N$_2$ for 18 h. The solvent was removed in vacuo, and the resulting residue was treated with brine (150 mL) and extracted with EtOAc (80 mL) three times. The combined organic layers were concentrated in vacuo to provide a residue, which was purified by chromatography over silica gel (eluting with PE:EA=5:1) to give compound B18-5.

Step F: methyl 6-fluoro-1-phenyl-3-(2-(trifluoromethyl)phenyl)-1H-indole-5-carboxylate (B18-6)

A mixture of K$_3$PO$_4$ (47.2 mg, 0.222 mmol), compound B18-5 (30 mg, 0.089 mmol), N,N-dimethylcyclohexane-1,2-diamine (3.80 mg, 0.027 mmol), copper(I) iodide (1.694 mg, 8.89 µmol) and iodobenzene (21.78 mg, 0.107 mmol) in toluene (1.5 mL) was stirred at 120° C. for 6 h. The reaction was filtered and the filtrate concentrated in vacuo to provide a residue, which was purified by preparative TLC over silica gel (eluting with PE:EA=10:1) to afford compound B18-6.

Step G: (6-fluoro-1-phenyl-3-(2-(trifluoromethyl) phenyl)-1H-indol-5-yl)methanol (B18-7)

To a solution of compound B18-6 (25 mg, 0.060 mmol) in THF (1.5 mL) at 0° C. was added LAH (2.099 mg, 0.302 mmol) and the mixture was stirred for 30 min. The reaction was quenched with 1 drop of water and 1 drop of 15% NaOH, then stirred for 10 min and filtered. The filtrate was concentrated in vacuo to provide crude compound B18-7, which was used directly in the next step. MS (ESI) m/e (M+H+): 368.1.

Step H: (5aR,6S,6aS)-tert-butyl 3-((6-fluoro-1-phenyl-3-(2-(trifluoromethyl)phenyl)-1H-indol-5-yl) methoxy)-5,5a,6,6a-tetrahydrocyclopropa[4,5]cyclopenta[1,2-c]pyridine-6-carboxylate (B18-8)

A mixture of Brett-Phos Palladacycle (2.089 mg, 3.89 µmol), Cs$_2$CO$_3$ (7.01 mg, 0.117 mmol), compound B18-7

(15 mg, 0.039 mmol) and intermediate 1-11 (10.34 mg, 0.039 mmol) in toluene (1 mL) was stirred at 100-110° C. for 18 h under $N_2$. The reaction mixture was filtered and concentrated in vacuo to provide a residue, which was purified by preparative TLC over silica gel (eluting with PE:EtOAc=5:1) to give compound B18-8. MS (ESI) m/e ($M+H^+$): 352.1.

Step I: ((5aR,6S,6aS)-3-((6-fluoro-1-phenyl-3-(2-(trifluoromethyl)phenyl)-1H-indol-5-yl)methoxy)-5,5a,6,6a-tetrahydrocyclopropa[4,5]cyclopenta[1,2-c]pyridine-6-carboxylic acid (B18-9)

To a solution of compound B18-8 (10 mg, 0.016 mmol) in THF (1 mL), water (0.4 mL) and MeOH (1 mL) was added LiOH (2.258 mg, 0.325 mmol) and the solution was stirred for 36 h at room temperature. The reaction mixture was then acidified by adding HCl (1 N) and extracted with EtOAc (3 mL) three times. The combined organic layers were concentrated in vacuo and the resulting residue was purified by preparative HPLC (on a GILSON 281 instrument fitted with a YMC-Actus Triart C18 150*30 mm*5 um using water and acetonitrile as the eluents. Mobile phase A: water (containing 0.05% Ammonia, v/v), mobile phase B: acetonitrile. Gradient: 49-79% B, 0-10 min; 100% B, 10.5-12.5 min; 5% B, 13-15 min) to give compound B18-9. $^1$H NMR (400 MHz, MeOD-$d_4$) δ: 8.00 (s, 1H), 6.62 (s, 1H), 7.84 (d, J=7.83 Hz, 1H), 7.65-7.72 (m, 1H), 7.58 (br. s., 6H), 7.38-7.51 (m, 3H), 7.30 (d, J=10.96 Hz, 1H), 4.87 (s, 2H), 3.19 (dd, J=18.78, 6.26 Hz, 1H), 2.98 (d, J=18.39 Hz, 1H), 2.81 (d, J=5.48 Hz, 1H), 2.33 (d, J=3.13 Hz, 1H), 1.06 (br. s., 1H). MS (ESI) m/e ($M+H^+$): 559.1.

Example 64

((5aR,6S,6aS)-3-((1-(2-(trifluoromethyl)phenyl)-2,3-dihydro-1H-inden-4-yl)methoxy)-5,5a,6,6a-tetrahydrocyclopropa[4,5]cyclopenta[1,2-c]pyridine-6-carboxylic acid Compound (B19-9B)

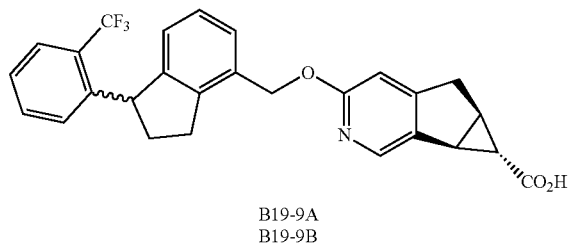 [SMILES: O=C(O)[C@H]1[C@@H]2Cc3cc(OCc4cccc5c4CCC5c4ccccc4C(F)(F)F)ncc3[C@@H]21]

B19-9A
B19-9B

Step A: 4-bromo-1-(2-(trifluoromethyl)phenyl)-2,3-dihydro-1H-inden-1-ol (B19-2)

To a stirred solution of 1-bromo-2-(trifluoromethyl)benzene (13.86 g, 61.6 mmol) in THF (150 mL) at −78° C. under nitrogen was added n-BuLi (56.9 mmol), and the mixture was stirred for 1 h. Then a mixture of 4-bromo-1-indanone B19-1 (13.00 g, 61.6 mmol) in THF (50 mL) was added slowly to the reaction and the reaction was stirred at −78° C. for 2 h. Then the reaction was warmed to room temperature over 10 h. The reaction was quenched with saturated aqueous $NH_4Cl$ (50 mL), and extracted with ethyl acetate (100 mL) twice. The combined organic fractions were washed with brine, dried ($Na_2SO_4$), and concentrated in vacuo to provide a residue, which was purified by column chromatography over silica gel (eluting with PE:EA=10:1) to give compound B19-2.

Step B: 7-bromo-3-(2-(trifluoromethyl)phenyl)-1H-indene (B19-3)

To a mixture of compound B19-2 (6.5 g, 18.2 mmol) in toluene (80 mL) was added p-TsOH (0.35 g, 1.8 mmol) and the mixture was stirred at reflux for 12 h. The mixture was filtered, and washed with ethyl acetate (20 mL). The filtrate was concentrated in vacuo to provide a residue, which was purified by column chromatography over silica gel (eluting with PE:EA=10:1) to give compound B19-3.

Step C: ethyl 3-(2-(trifluoromethyl)phenyl)-1H-indene-7-carboxylate (B19-4)

A mixture of sodium acetate (1.45 g, 17.7 mmol), $PdCl_2$(dppf) (0.54 g, 0.74 mmol) and compound B19-3 (2.5 g, 7.4 mmol) in EtOH (50 mL) was heated at 80° C. for 16 h under a CO atmosphere (50 psi). After cooling to room temperature, the mixture was filtered and the filtrate was concentrated in vacuo to afford a residue. The residue was taken up in EtOAc and water, and extracted with EtOAc. The combined organic layers were washed with water, dried over $Na_2SO_4$ and concentrated in vacuo to give a residue, which was purified by chromatography over silica gel (eluting with PE:EA=10:1) to give compound B19-4.

Step D: ethyl 1-(2-(trifluoromethyl)phenyl)-2,3-dihydro-1H-indene-4-carboxylate (B19-5)

10% Pd—C (0.3 g, 2.82 mmol) was added to a stirred solution of compound B19-4 in EtOH (40 ml) and the solution was stirred for 10 h at room temperature. The reaction mixture was filtered, and concentrated in vacuo to give crude compound B19-5. MS (ESI) m/e ($M+H^+$): 335.1.

Chiral SFC Resolution of Compound B19-5 (Compounds B19-5A and B19-5B)

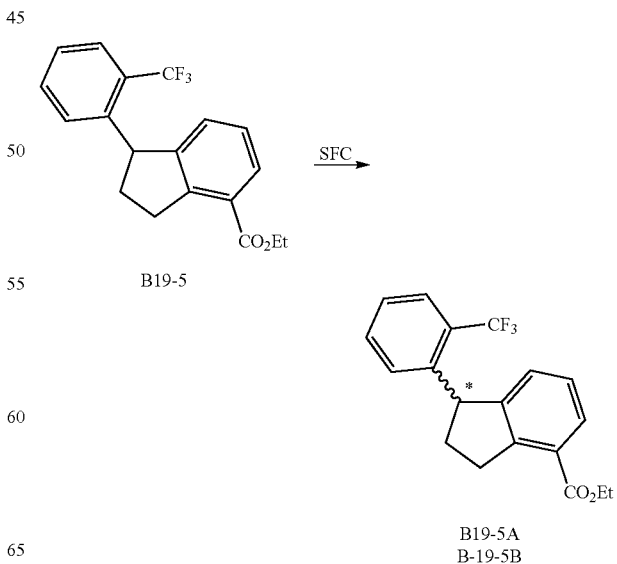

B19-5

B19-5A
B-19-5B

Compound B19-5 was purified by chiral preparative SFC (Column: Chiralpak AD-H 250×4.6 mm I.D., 5 um; Mobile phase: methanol (0.05% DEA) in $CO_2$ from 5% to 40%; Flow rate: 2.35 mL/min; Wavelength: 220 nm) to provide compound B19-5A, followed by compound B19-5B.

Step E: (1-(2-(trifluoromethyl)phenyl)-2,3-dihydro-1H-inden-4-yl)methanol (B19-6B)

$LiAlH_4$ (136 mg, 3.59 mmol) was added to a mixture of compound B19-5B (600 mg, 1.80 mmol) in THF (10 mL) at 0° C., and the mixture was stirred for 1 h. Then the reaction was carefully quenched by the addition of $H_2O$ (0.1 mL), NaOH (0.1 mL, 15%), and $H_2O$ (0.3 mL), and stirred for 15 min. The reaction mixture was filtered, and the filtrate was dried over $Na_2SO_4$ and concentrated in vacuo to give crude compound B19-6B, which was used in the next step directly. MS (ESI) m/e (M−18$^+$): 275.1

Step F: 4-(bromomethyl)-1-(2-(trifluoromethyl)phenyl)-2,3-dihydro-1H-indene (B19-7B)

To stirred mixture of crude compound B19-6B (200 mg, 0.684 mmol) in THF (5 mL) at 0° C. was added $PBr_3$ (0.129 ml, 1.368 mmol), and the mixture was stirred for 1 h. Then the reaction was quenched with $H_2O$ (10 mL), and extracted with ethyl acetate (15 mL) twice. The combined organic layers were washed with brine, dried over $Na_2SO_4$, and concentrated in vacuo to give crude compound B19-7B, which was used in the next step directly.

Step G: (5aR,6S,6aS)-ethyl 3-((1-(2-(trifluoromethyl)phenyl)-2,3-dihydro-1H-inden-4-yl)methoxy)-5,5a,6,6a-tetrahydrocyclopropa[4,5]cyclopenta[1,2-c]pyridine-6-carboxylate (B19-8B)

To a stirred mixture of crude compound B19-7B (80 mg, 0.23 mmol) and intermediate 1-9 (49.4 mg, 0.225 mmol) in toluene (5 mL) was added $Ag_2CO_3$ (155 mg, 0.563 mmol), and the mixture was stirred at 100° C. for 12 h. Then the reaction mixture was filtered, and the filtrate was concentrated in vacuo to provide a residue, which was purified by preparative TLC over silica gel (eluting with PE:EA=5:1) to give compound B19-8B. MS (ESI) m/e (M+H$^+$): 494.2.

Step H: (5aR,6S,6aS)-3-((1-(2-(trifluoromethyl)phenyl)-2,3-dihydro-1H-inden-4-yl)methoxy)-5,5a,6,6a-tetrahydrocyclopropa[4,5]cyclopenta[1,2-c]pyridine-6-carboxylic acid (B19-9B)

To a stirred mixture of compound B19-8B (45 mg, 0.091 mmol) in MeOH (2 mL) and water (1 mL) was added LiOH (38.3 mg, 0.912 mmol), and the mixture was stirred at room temperature for 5 h. The reaction mixture was acidified with 2N HCl to pH=3, and extracted with ethyl acetate (15 mL) twice. The combined organic layers were washed with brine, dried over $Na_2SO_2$, and concentrated in vacuo to give compound B19-9B. $^1$H NMR (400 MHz, $CDCl_3$) δ: 8.16 (s, 1H), 7.67 (d, J=7.83 Hz, 1H), 7.37-7.48 (m, 1H), 7.27-7.35 (m, 2H), 7.09-7.21 (m, 2H), 6.86 (d, J=7.43 Hz, 1H), 6.67 (s, 1H), 5.38 (s, 2H), 4.76-4.90 (m, 1H), 3.27 (dd, J=5.87, 18.39 Hz, 1H), 3.10-3.21 (m, 1H), 2.94-3.10 (m, 3H), 2.64-2.76 (m, 1H), 2.55 (br. s., 1H), 1.97-2.07 (m, 1H), 1.26-1.20 (m, 1H). MS (ESI) m/e (M+H$^+$): 466.1.

TABLE 13

Example 65 (compound B19-9A) was prepared in a similar manner to Example 64 (Compound B19-9B) using compound B19-5A and commercially available materials, and including procedures described across this application when necessary.

| Example | Structure | M.W. | Compound Name | LC/MS (ESI) observed [M + 1]+ |
|---|---|---|---|---|
| 65 | (Compound B19-9A) | 465.1 | (5aR,6S,6aS)-ethyl 3-((1-(2-(trifluoromethyl)phenyl)-2,3-dihydro-1H-inden-4-yl)methoxy)-5,5a,6,6a-tetrahydrocyclopropa[4,5]cyclopenta[1,2-c]pyridine-6-carboxylate | 466.1 |

Example 66

(1S,1aS,6aR)-ethyl 4-((1-phenyl-1,2,3,4-tetrahydroquinolin-7-yl)methoxy)-1,1a,6,6a-tetrahydrocyclopropa[a]indene-1-carboxylate (Compound B20-5)

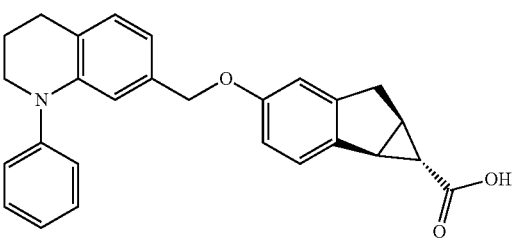

B20-5

Step A: methyl 1-phenyl-1,2,3,4-tetrahydroquinoline-7-carboxylate (B20-2)

To a solution of palladium (II) acetate (53.3 mg, 0.237 mmol), (R)-(+)-2,2'-bis(diphenyl-phosphino)-1,1'-binaphthyl B20-1 (163 mg, 0.261 mmol) in toluene (6.33 ml) were added bromobenzene (0.5 ml, 4.75 mmol), methyl 1,2,3,4- tetrahydroquinoline-7-carboxylate (1090 mg, 5.70 mmol) and t-BuOK (746 mg, 6.65 mmol). The reaction was degassed, and then heated at 100° C. for 3 h. Then the reaction mixture was filtered and the filtrate concentrated in vacuo to provide a residue, which was purified by flash chromatography over silica gel (eluting with hexanes: EA=100:0 to 70:30) to provide compound B20-2. MS (ESI) m/e (M+H$^+$): 267.9.

Step B:
(1-phenyl-1,2,3,4-tetrahydroquinolin-7-yl)methanol (B20-3)

To a solution of compound B20-2 (641.3 mg, 2.399 mmol) in THF (15.99 mL) at −78° C. was added LAH (1 M in THF, 2.999 mL, 3.00 mmol) dropwise, and the reaction mixture was allowed to warm to room temperature over 15 h. The reaction was then cooled to 0° C. and slowly quenched with water, and extracted with EtOAc. The combined organic layers were dried over Na$_2$SO$_4$ and concentrated in vacuo to give a residue, which was purified by flash chromatography over silica gel (eluting with hexanes: EA=100:0 to 0:100) to provide compound B20-3. MS (ESI) m/e (M+H$^+$): 240.0.

Step C: (1S,1aS,6aR)-ethyl 4-((1-phenyl-1,2,3,4-tetrahydroquinolin-7-yl)methoxy)-1,1a,6,6a-tetrahydrocyclopropa[a]indene-1-carboxylate (B20-4)

To a solution of compound B20-3 (110.7 mg, 0.463 mmol), (1S,1aS,6aR)-ethyl 4-hydroxy-1,1a,6,6a-tetrahydrocyclopropa[a]indene-1-carboxylate (101 mg, 0.463 mmol) and triphenylphosphine (121 mg, 0.463 mmol, prepared according to the procedure disclosed in WO2009/058237) in toluene (925 µL) at 0° C. was added DIAD (90 µL, 0.463 mmol). The reaction was allowed to warm to room temperature over 18 h. Then the reaction mixture was diluted with EtOAc and water. The organic layer was separated, dried over Na$_2$SO$_4$ and concentrated in vacuo to give a residue, which was purified by flash chromatography over silica gel (eluting with hexanes:EA=100:0 to 70:30) to give compound B20-4. MS (ESI) m/e (M+H$^+$): 439.9.

Step D: (1S,1aS,6aR)-4-((1-phenyl-1,2,3,4-tetrahydroquinolin-7-yl)methoxy)-1,1a,6,6a-tetrahydrocyclopropa[a]indene-1-carboxylic acid (B20-5)

To a solution of compound B20-4 (144.5 mg, 0.329 mmol) in THF (5.0 mL) and MeOH (3.3 mL) was added 1 M NaOH (1644 µL, 1.644 mmol), and the reaction was stirred at room temperature over 15 h. Then the reaction mixture was concentrated in vacuo and the resulting residue was purified by preparative HPLC (on a GILSON instrument using a Phenomenex Gemini column 5 µm C18 110A 21.20×150 mm; gradient elution 10-100% (10 min; 20 mL/min) CH$_3$CN/H$_2$O+0.1% TFA) to provide compound B20-5. MS (ESI) m/e (M+H$^+$): 412.2.

TABLE 14

Examples 67 to 68 (compound B20-6 and B20-7) were prepared in a similar manner to Example 66 (Compound B20-5) using commercially available materials, and including procedures described across this application when necessary.

| Example | Structure | M.W. | Compound Name | LC/MS (ESI) observed [M + 1]+ |
|---|---|---|---|---|
| 67 | (Compound B20-6) | 412.2 | (1S,1aS,6aR)-4-((1-(pyridin-2-yl)-1,2,3,4-tetrahydroquinolin-7-yl)methoxy)-1,1a,6,6a-tetrahydrocyclopropa[a]indene-1-carboxylic acid | 413.0 |
| 68 | (Compound B20-7) | 425.2 | (1S,1aS,6aR)-4-((1-(o-tolyl)-1,2,3,4-tetrahydroquinolin-7-yl)methoxy)-1,1a,6,6a-tetrahydrocyclopropa[a]indene-1-carboxylic acid | 426.0 |

Examples 69 and 70

(5aR,6S,6aS)-3-((1,1,6-trifluoro-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (Compounds C1-11A and C1-11B)

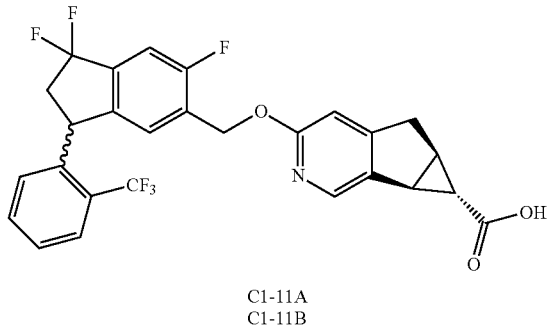 [SMILES: O=C(O)[C@H]1[C@@H]2Cc3cc(OCc4cc5c(cc4F)C(F)(F)CC5c4ccccc4C(F)(F)F)ncc3[C@@H]21]

C1-11A
C1-11B

Step A: 6-bromo-5-fluoro-1-(2-(trifluoromethyl)phenyl)-2,3-dihydro-1H-inden-1-ol (C1-2)

To a solution of 2-bromobenzotrifluoride (495 mg, 2.17 mmol, 1.5 eq) in dry THF (10.0 mL) at −78° C. under nitrogen was added n-BuLi (2.5 M in hexanes, 0.868 mL, 2.17 mmol, 1.5 eq) dropwise. After completion of the addition, the mixture was stirred at −78° C. for an hour, then a solution of compound 2-3 (337 mg, 1.48 mmol, 1.0 eq) in dry THF (5.0 mL) was added dropwise. The resulting mixture was stirred at −78° C. for 3 h. Then saturated aqueous NH$_4$Cl was added to quench the reaction, and the reaction mixture was extracted with EtOAc (5.0 mL) three times. The combined organic layers were washed with brine, dried over Na$_2$SO$_4$ and concentrated in vacuo to afford a residue, which was purified by chromatography over silica gel (eluting with PE:EA=4:1) to give compound C1-2.

Step B: 6-fluoro-3-hydroxy-3-(2-(trifluoromethyl)phenyl)-2,3-dihydro-1H-indene-5-carboxylic acid (C1-3)

To a stirring solution of compound C1-2 (1.00 g, 2.67 mmol, 1.0 eq) in dry THF (20.0 mL) at −78° C. under a nitrogen atmosphere was added n-BuLi (2.5 M in hexanes, 3.4 mL, 8.02 mmol, 3.0 eq) dropwise. After completion of the addition, the mixture was stirred at this temperature for 2 h. Then carbon dioxide was bubbled into the mixture for 30 min. The reaction was stirred at −78° C. for 1 hour, then warmed to −20° C. slowly. Then the reaction mixture was quenched with water, acidified with diluted HCl (1.0 N) to pH=2 and extracted with EtOAc (5.0 mL) three times. The combined organic layers were washed with brine, dried over Na$_2$SO$_4$ and filtered. The filtrate was concentrated to afford a residue, which was washed with petroleum ether (5.0 mL) to afford compound C1-3.

Step C: methyl 6-fluoro-3-hydroxy-3-(2-(trifluoromethyl)phenyl)-2,3-dihydro-1H-indene-5-carboxylate (C1-4)

To a mixture of compound C1-3 (318 mg, 0.935 mmol, 1.0 eq) in DMF (6.0 mL) at 0° C. was added K$_2$CO$_3$ (258 mg, 1.87 mmol, 2.0 eq) in one portion, followed by MeI (266 mg, 1.87 mmol, 2.0 eq). The resulting mixture was stirred at 0° C. for 1 hour, then warmed to room temperature over 2 hours. Then the reaction was poured into water, and the mixture was extracted with EtOAc (15.0 mL) three times. The combined organic layers were washed with brine, dried over Na$_2$SO$_4$ and concentrated in vacuo to afford crude compound C1-4, which was used in the next step without purification.

Step D: methyl 6-fluoro-3-(2-(trifluoromethyl)phenyl)-1H-indene-5-carboxylate (C1-5)

A solution of crude compound C1-4 (317 mg, 0.895 mmol, 1.0 eq) and Et$_3$SiH (274 mg, 2.39 mmol, 2.5 eq) in dry DCM (5 mL) was stirred at room temperature for 30 min, then cooled to 0° C. Then TFA (2.0 mL) was added in one portion and the resulting mixture was stirred for 1 hour. Then saturated aqueous NaHCO$_3$ was added to neutralize the reaction, and the reaction mixture was extracted with EtOAc (5.0 mL) three times. The combined organic layers were washed with brine, dried over Na$_2$SO$_4$ and concentrated in vacuo to afford a residue, which was purified by chromatography over silica gel (eluting with PE:EA=10:1) to give compound C1-5.

Step E: methyl 1,1,6-trifluoro-3-(2-(trifluoromethyl)phenyl)-1H-indene-5-carboxylate (C$_{1-6}$)

To a stirring solution of compound C1-5 (0.100 g, 0.298 mmol, 1.0 eq) in THF/RMPA (2.0 mL/0.4 ml) at −78° C. under nitrogen atmosphere was added KHMDS (1.0 M in THF, 0.930 mL, 0.893 mmol, 3.0 eq) dropwise. After completion of the addition, the mixture was stirred at this temperature for 2 h. Then a solution of NFSI (225 mg, 0.714 mmol, 2.4 eq) in THF (0.20 mL) was added dropwise. The reaction was then stirred at −78° C. for 1 hour, and then warmed to 0° C. slowly and stirred for half an hour. The reaction was quenched with saturated aqueous NH$_4$Cl, and extracted with EtOAc (5.0 mL) three times. The combined organic layers were washed with brine, dried over Na$_2$SO$_4$ and concentrated in vacuo to afford a residue, which was purified by preparative TLC over silica gel (eluting with PE:EA=4:1) to obtain compound C1-6.

Step F: methyl 1,1,6-trifluoro-3-(2-(trifluoromethyl)phenyl)-2,3-dihydro-1H-indene-5-carboxylate (C1-7)

To a solution of compound C1-6 (100 mg, 0.376 mmol, 1.0 eq) in MeOH (4.0 mL) and THF (2.0 mL) was added 10% Pd/C (20.0 mg). The reaction mixture was stirred under H$_2$ (1 atm) for 16 h. Then the reaction was filtered through Celite™, and the filtrate was concentrated in vacuo to afford crude compound C1-7.

Step G: (1,1,6-trifluoro-3-(2-(trifluoromethyl)phenyl)-2,3-dihydro-1H-inden-5-yl)methanol (C1-8)

To a suspension of LiAlH$_4$ (58.0 mg, 1.53 mmol, 1.0 eq) in dry THF (2.0 mL) at 0° C. was added a solution of compound C1-7 (105 mg, 0.306 mmol, 0.2 eq) in THF (2.0 mL) dropwise. After completion of the addition, the reaction mixture was stirred at 0° C. for 1 h. Then 0.06 mL H$_2$O, 0.06 mL NaOH (15%) and 0.18 mL H$_2$O were added to quench the reaction. Then the reaction was filtered and the filtrate was concentrated in vacuo to provide a residue, which was purified by chromatography over silica gel (eluting with PE:EA 100:1) to afford compound C1-8.

Step H: 5-(bromomethyl)-1,1,6-trifluoro-3-(2-(trifluoromethyl)phenyl)-2,3-dihydro-1H-indene (C1-9)

To a solution of compound C1-8 (32.0 mg, 0.0925 mmol, 1.0 eq) in dry THF (2.0 mL) at 0° C. was added PBr$_3$ (25.1 mg, 0.0925 mmol, 1.0 eq) dropwise. The reaction solution was stirred at 0° C. for 1 hour, then warmed to 20° C. and stirred for 3 h. Then the reaction was quenched with water (1.0 mL). Then saturated aqueous NaHCO$_3$ was added to neutralize the mixture to pH=7, and the mixture was extracted with EtOAc (5 mL) twice. The combined organic layers were washed with brine, dried over anhydrous Na$_2$SO$_4$ and concentrated in vacuo to afford a residue, which was purified by preparative TLC over silica gel (eluting with PE:EA=5:1) to obtain compound C1-9.

Step I: (5aR,6S,6aS)-ethyl 3-((1,1,6-trifluoro-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylate (C1-10)

A mixture of compound C1-9 (14.0 mg, 0.0370 mmol, 1.0 eq), intermediate 1-9 (8 mg, 0.0370 mmol, 1.0 eq) and Ag$_2$CO$_3$ (25.0 mg, 0.0910 mmol, 2.5 eq) in toluene (0.5 mL) was heated to 100° C. for 2 h. Then the reaction mixture was filtered and the filtrate was concentrated in vacuo to give a residue, which was purified by preparative TLC over silica gel (eluting with PE:EA=5:1) to afford compound C1-10. MS (ESI) m/e (M+H$^+$): 548.2.

Step J: (5aR,6S,6aS)-3-((1,1,6-trifluoro-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (C1-11)

To a solution of compound C1-10 (12.0 mg, 0.0230 mmol, 1.0 eq) in THF (0.5 mL), MeOH (0.5 mL) and H$_2$O (0.5 mL) was added LiOH (10.0 mg, 0.230 mmol, 5.0 eq), and the resulting mixture was stirred at room temperature for 2 h. The reaction mixture was acidified with HCl (2 N) to pH=7 and the mixture was extracted with EtOAc (10 mL) twice. The combined organic layers were washed with brine, dried over Na$_2$SO$_4$ and concentrated in vacuo to afford a residue, which was purified by preparative HPLC (GILSON 281 instrument fitted with a YMC-Actus Triart (150*30 mm*5 um) using water and acetonitrile as the eluents. Mobile phase A: water (containing 0.1% TFA, v/v), mobile phase B: acetonitrile. Gradient: 40-70% B, 0-10 min; 100% B, 10.5-12.5 min; 5% B, 13-15 min) to give C1-11. $^1$H NMR (400 MHz, MeOD-d$_4$) δ: 8.05 (s, 1H), 7.75 (d, J=7.6 Hz, 1H), 7.74-7.75 (m, 3H), 7.12 (t, J=8.0 Hz, 1H), 7.00 (d, J=8.0 Hz, 1H), 6.87 (s, 1H), 5.41 (s, 2H), 3.11-3.12 (m, 3H), 2.97 (d, J=5.6 Hz, 1H), 2.48-2.57 (m, 2H), 1.15 (q, J=3.2 Hz, 1H). MS (ESI) m/e (M+H$^+$): 520.1.

Chiral SFC Resolution of Compound C1-11 (Compounds C1-11A and C1-11B)

Compound C1-11 (150 mg, 0.290 mmol) was purified by chiral preparative SFC (column: Chiralcel OD-3 150×4.6 mm I.D., 3 um; Mobile phase: methanol (0.05% DEA) in CO$_2$ from 5% to 40%; Flow rate: 2.5 mL/min; Wavelength: 220 nm) to provide compound C1-11A, followed by compound C1-11B. Compound C1-11A: MS (ESI) m/e (M+H$^+$): 520.1. Compound C1-11B: MS (ESI) m/e (M+H$^+$): 520.1.

Example 71

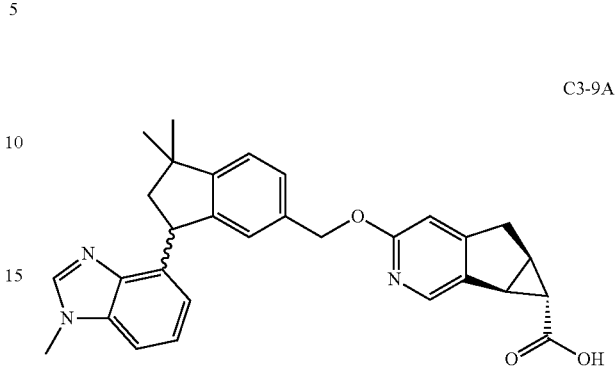

C3-9A

Step A: ethyl 1,1-dimethyl-3-(((trifluoromethyl)sulfonyl)oxy)-1H-indene-5-carboxylate (C3-2)

To a solution of compound C3-1 (prepared similarly to intermediate 2-4; 20.0 g, 86.2 mmol, 1.0 eq) in dry THF (400 mL) at −78° C. under nitrogen was added KHMDS (1 M in THF, 259 mL, 259 mmol, 3.0 eq) dropwise. The reaction mixture was stirred for 30 min at −78° C., then a solution of PhNTf$_2$ (92.2 g, 259 mmol, 3.0 eq) in 100 mL of THF was added. The mixture was warmed to room temperature and stirred for 16 h. Then the reaction was quenched with water (100 ml), neutralized with aqueous HCl (2N) to pH=7, and extracted with EtOAc (300 ml) three times. The organic layers were combined, washed with brine, dried over anhydrous Na$_2$SO$_4$, and concentrated in vacuo to afford a residue, which was purified by chromatography over silica gel (eluting with PE:EA=100:1) to give compound C3-2. MS (ESI) m/e (M+H$^+$): 365.

Step B: ethyl 1,1-dimethyl-3-(4,4,5,5-tetramethyl-1,3,2-dioxaborolan-2-yl)-1H-indene-5-carboxylate (C3-3)

A mixture of compound C3-2 (25.0 g, 68.6 mmol, 1.0 eq), 4,4,4',4',5,5,5',5'-octamethyl-2,2'-bi(1,3,2-dioxaborolane) (26.1 g, 103 mmol, 1.5 eq), AcOK (20.2 g, 206 mmol, 3.0 eq) and Pd(dppf)Cl$_2$ (0.502 g, 0.686 mmol, 0.1 eq) in 1,4-dioxane (500 mL) was stirred at 100° C. for 3 h under nitrogen. After cooling to room temperature, the reaction was filtered, and the filtrate was diluted with water and extracted with EtOAc (300 ml) three times. The combined organic layers were washed with brine, dried over $MgSO_4$, and concentrated in vacuo to obtain a residue, which was purified by chromatography over silica gel (eluting with PE:EA=100:1) to afford compound C3-3. MS (ESI) m/e $(M+H^+)$: 343.

Step C: ethyl 1,1-dimethyl-3-(1-methyl-1H-benzo[d]imidazol-4-yl)-1H-indene-5-carboxylate (C3-4)

A mixture of compound C3-3 (3.91 g, 11.4 mmol, 1.2 eq), 4-bromo-1-methyl-1H-benzo[d]imidazole (2.00 g, 9.52 mmol, 1 eq), $K_2CO_3$ (3.94 g, 28.6 mmol, 3.0 eq) and $Pd(dppf)Cl_2$ (0.348 g, 0.476 mmol, 0.05 eq) in 1,4-dioxane (40.0 mL) and $H_2O$ (10.0 ml) was stirred at 100° C. for 3 h under nitrogen atmosphere. After cooling to room temperature, the reaction mixture was filtered, and the filtrate was diluted with water and extracted with EtOAc (300 ml) three times. The combined organic layers were washed with brine, dried over $MgSO_4$, and concentrated in vacuo to obtain a residue, which was purified by chromatography over silica gel (eluting with PE:EA=10:1) to afford compound C3-4. MS (ESI) m/e $(M+H^+)$: 347.

Step D: ethyl 1,1-dimethyl-3-(1-methyl-1H-benzo[d]imidazol-4-yl)-2,3-dihydro-1H-indene-5-carboxylate (C3-5)

To a solution of compound C3-4 (2.00 g, 5.78 mmol, 1.0 eq) in THF (40.0 mL) was added 10% Pd/C (0.200 g) and the mixture was stirred at room temperature under $H_2$ (1 atm) for 18 h. The reaction mixture was filtered and the filtrate was concentrated in vacuo to provide crude compound C3-5, which was used in the next step without purification. MS (ESI) m/e $(M+H^+)$: 349.

Step E: (1,1-dimethyl-3-(1-methyl-1H-benzo[d]imidazol-4-yl)-2,3-dihydro-1H-inden-5-yl)methanol ($C_{3-6}$)

To a suspension of $LiAlH_4$ (983 mg, 25.9 mmol, 5.0 eq) in dry THF (20.0 mL) at 0° C. under $N_2$ atmosphere was added dropwise a solution of crude compound C3-5 (1.80 g, 5.17 mmol, 1.0 eq) in THF (10.0 mL). After completing the addition, the reaction mixture was warmed to room temperature and stirred for 2 h. Then the reaction was quenched with 1.0 mL of $H_2O$, 1.0 mL of NaOH (10%) and 3.0 mL of $H_2O$. The resulting mixture was filtered and the filtrate was concentrated in vacuo to afford crude compound C3-6, which was used in the next step without purification. MS (ESI) m/e $(M+H^+)$: 307.

Step F: 4-(6-(bromomethyl)-3,3-dimethyl-2,3-dihydro-1H-inden-1-yl)-1-methyl-1H-benzo[d]imidazole (C3-7)

To a solution of compound $C_{3-6}$ (1.40 g, 4.57 mmol, 1.0 eq) in DCM (40.0 mL) at 0° C. under $N_2$ was added $PBr_3$ (1.24 g, 4.57 mmol, 1.0 eq) dropwise. The reaction mixture was stirred for 1 h, then a solution of saturated aqueous $NaHCO_3$ was added until the pH=7, and the mixture was extracted with EtOAc (20.0 ml) three times. The combined organic layers were washed with brine (15.0 ml), dried over $MgSO_4$, filtered, and the filtrate was concentrated in vacuo to give crude compound C3-7. MS (ESI) m/e $(M+H^+)$: 369, 371.

Step G: ((5aR,6S,6aS)-methyl 3-((1,1-dimethyl-3-(1-methyl-1H-benzo[d]imidazol-4-yl)-2,3-dihydro-1H-inden-5-yl)methoxy)-5,5a,6,6a-tetrahydrocyclopropa[4,5]cyclopenta[1,2-c]pyridine-6-carboxylate (C3-8)

To a solution of crude compound C3-7 (300 mg, 0.812 mmol, 1.0 eq) and intermediate 1-9 (180 mg, 0.812 mmol, 1.1 eq) in toluene (10.0 mL) under $N_2$ atmosphere, was added $Ag_2CO_3$ (672 mg, 2.44 mmol, 3.0 eq) in one portion. The reaction mixture was heated to 110° C. and stirred at 110° C. for 5 h. The reaction mixture was then cooled to room temperature and filtered. The filtrate was concentrated to afford a residue, which was purified by preparative TLC over silica gel (eluting with PE:EA=2:1) to give compound C3-8.

Chiral SFC Resolution of Compound C3-8
(Compounds C3-8A and C3-8B)

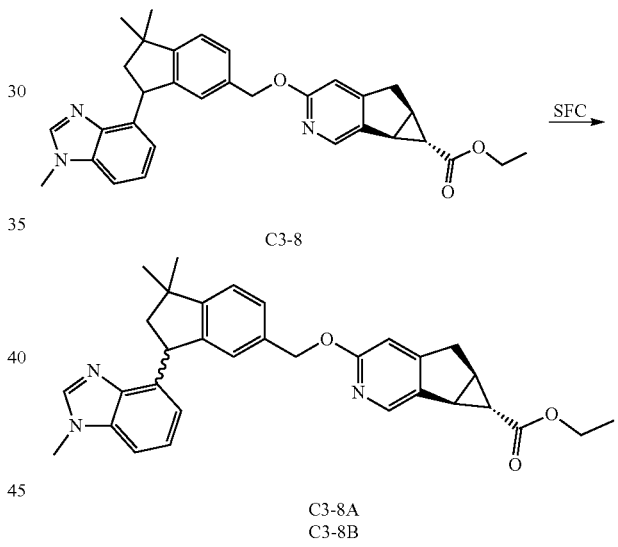

C3-8

C3-8A
C3-8B

Compound C3-8 was purified by chiral preparative SFC (Column: Chiralpak AD-3 50*4.6 mm I.D., 3 um; Mobile phase:ethanol (0.05% DEA) in $CO_2$ from 5% to 40%; Flow rate: 4 mL/min; Wavelength: 220 nm) to provide compound C3-8A, followed by compound C3-8B: MS (ESI) m/e $(M+H^+)$: 508 for both.

Step H: ((5aR,6S,6aS)-3-(((S)-1,1-dimethyl-3-(1-methyl-1H-benzo[d]imidazol-4-yl)-2,3-dihydro-1H-inden-5-yl)methoxy)-5,5a,6,6a-tetrahydrocyclopropa[4,5]cyclopenta[1,2-c]pyridine-6-carboxylic acid (C3-9A)

To a solution of compound C3-8A (70.0 mg, 0.138 mmol, 1.0 eq) in THF (1.0 mL), MeOH (1.0 mL) and $H_2O$ (1.0 mL) was added $LiOH·H_2O$ (58.0 mg, 1.38 mmol, 10.0 eq) and the mixture was stirred at room temperature for 1 h. The reaction mixture was acidified with HCl (1 N) to pH=2, and extracted with ethylyl acetate (5.00 mL) three times. The combined organic layers were washed with brine (5.00 ml), dried over MgSO₄, and concentrated in vacuo to afford a residue, which was purified by preparative (on a GILSON 281 instrument fitted with a Diamonsil 150*20 mm*5 um using water and acetonitrile as the eluents. Mobile phase A: water containing 0.1% TFA, v/v), mobile phase B: acetonitrile. Gradient: 24.5-44.5% B, 0-10 min; 100% B, 10.5-12.5 min; 5% B, 13-15 min) to give compound C3-9A. $^1$H NMR (400 MHz, CDCl₃) δ: 9.41 (s, 1H), 8.03 (s, 1H), 7.81-7.79 (d, J=8.4 Hz, 1H), 7.60 (t, J=7.6 Hz, 1H), 7.39-7.29 (m, 3H), 6.93 (s, 1H), 6.74 (s, 1H), 5.23 (s, 2H), 5.03 (t, J=8.4 Hz, 1H), 4.17 (s, 3H), 3.28-3.23 (m, 1H), 3.09-3.04 (d, J=19.2 Hz, 1H), 2.95-2.93 (d, J=5.2 Hz, 1H), 2.61-2.56 (m, 1H), 2.49-2.44 (m, 1H), 2.04 (t, J=10.0 Hz, 1H), 1.43 (s, 3H), 1.35 (s, 3H), 1.15 (s, 1H). MS (ESI) m/e (M+H⁺): 480.2.

Example 72

(5aR,6S,6aS)-3-(((S)-6-fluoro-4,4-dimethyl-1-(2-(trifluoromethyl)phenyl)-1,2,3,4-tetrahydroisoquinolin-7-yl)methoxy)-5,5a,6,6a-tetrahydrocyclopropa[4,5]cyclopenta[1,2-c]pyridine-6-carboxylic acid (Compound C4-16A1)

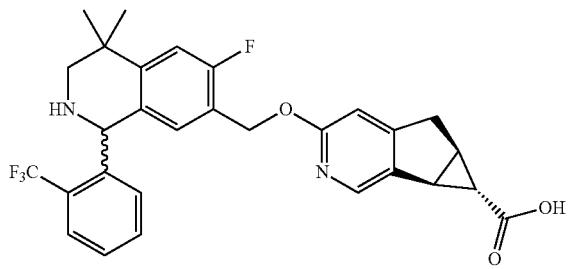

C4-16A1

Step A: (4-bromo-3-fluorophenyl)methanol (C4-2)

To a solution of 4-bromo-3-fluorobenzaldehyde C4-1 (100 g, 0.493 mol, 1.0 eq) in MeOH (1.00 L) at 0° C. under nitrogen was slowly added NaBH₄ (28.0 g, 0.739 mol, 1.5 eq) in portions. The resulting mixture was warmed to room temperature and stirred for 16 h. Then the reaction mixture was poured into ice water, and extracted with EtOAc three times. The combined organic layers were dried over anhydrous MgSO₄ and concentrated in vacuo to give a residue, which was purified by chromatography over silica gel (eluting with PE:EA=10:1 to 5:1) to give compound C4-2. MS (ESI) m/e (M+H⁺): 228, 230.

Step B: 1-bromo-4-(bromomethyl)-2-fluorobenzene (C4-3)

To a stirred solution of compound C4-2 (95.5 g, 0.466 mol, 1.0 eq) in DCM (1.00 L) at 0° C. under nitrogen was added PBr₃ (63.0 g, 0.233 mol, 0.5 eq) dropwise. The resulting mixture was warmed to room temperature and stirred for 16 h. The reaction mixture was then cooled, poured into ice water, and the pH was adjusted to pH=7 with saturated aqueous NaHCO₃. Then the reaction mixture was extracted with DCM (500 mL) three times. The combined organic layers were dried over anhydrous MgSO₄ and concentrated in vacuo to give a residue, which was purified by chromatography over silica gel (eluting with PE:EtOAc=20:1 to 10:1) to give compound C4-3.

Step C: 2-(4-bromo-3-fluorophenyl)acetonitrile (C4-4)

To a stirred solution of compound C4-3 (116 g, 0.431 mol, 1.0 eq) in CH₃CN (1.50 L) were added TMSCN (64.2 g, 0.647 mol, 1.5 eq) and K₃PO₄ (275 g, 1.29 mol, 3.0 eq). Then the mixture was stirred for 16 h at 80° C. under a nitrogen atmosphere. The reaction mixture was then cooled to room temperature and the solvent was partly removed under reduced pressure. The reaction mixture was then poured into ice water (1.00 L), and extracted with EtOAc (500 mL) three times. The combined organic layers were dried over anhydrous MgSO₄ and concentrated in vacuo to give a residue, which was purified by chromatography over silica gel (eluting with PE:EtOAc=10:1 to 5:1) to afford compound C4-4.

Step D: 2-(4-bromo-3-fluorophenyl)-2-methylpropanenitrile (C4-5)

To a stirred solution of compound C4-4 (76.5 g, 0.357 mol, 1.0 eq) in DMF (800 mL) at 0° C. under N₂ was added iodomethane (152 g, 1.07 mol, 3.0 eq), followed 5 min later by 60% NaH (21.5 g, 0.894 mol, 2.5 eq) added in portions. The reaction mixture was warmed to room temperature and stirred for 16 h. Then the reaction was quenched with H₂O (300 mL) and extracted with EtOAc (400 mL) three times. The combined organic layers were washed with brine, dried over anhydrous MgSO₄ and concentrated in vacuo to afford a residue, which was purified by chromatography over silica gel (eluting with PE:EtOAc=10:1 to 5:1) to provide compound C4-5.

Step E: ethyl 4-(2-cyanopropan-2-yl)-2-fluorobenzoate (C4-6)

To a mixture of compound C4-5 (10.0 g, 41.3 mmol, 1.0 eq) and AcONa (6.77 g, 82.6 mmol, 2.0 eq) in EtOH (200 mL) was added Pd(dppf)Cl₂ (3.02 g, 4.13 mmol, 0.01 eq). The mixture was heated at 80° C. for 16 h under a CO atmosphere (50 psi). After cooling to room temperature, the reaction was filtered, and the filtrate was concentrated in vacuo to afford a residue. The residue was partitioned between EtOAc (100 mL) and water. The aqueous layer was separated and further extracted with EtOAc. The combined organic layers were washed with brine, dried over anhydrous MgSO₄ and concentrated in vacuo to afford a crude product, which was purified by chromatography over silica gel (eluting with PE:EtOAc=10:1 to 5:1) to give compound C4-6. MS (ESI) m/e (M+H⁺): 236.3.

Step F: ethyl 4-(1-amino-2-methylpropan-2-yl)-2-fluorobenzoate (C4-7)

To a stirred solution of compound C4-6 (8.00 g, 34.0 mmol, 1.0 eq) in MeOH (400 mL) were added Pd/C (800 mg, 10%) and concentrated HCl (8.0 mL). The mixture was stirred at room temperature under a H₂ atmosphere (50 psi) for 3 h, then filtered. The filtrate was concentrated in vacuo to afford crude compound C4-7, which was used in the next step without purification. MS (ESI) m/e (M+H⁺): 240.0.

Step G: ethyl 2-fluoro-4-(2-methyl-1-(2-(trifluoromethyl)benzamido)propan-2-yl)benzoate (C4-8)

To a suspension of crude compound C4-7 (5.00 g, 20.9 mmol, 1.0 eq) and 2-(trifluoromethyl)-benzoic acid (3.97 g, 20.9 mmol, 1.0 eq) in DCM (50.0 mL) and DMF (50.0 mL) at 0° C. was added DIPEA (16.2 g, 125 mmol, 6.0 eq). The mixture was stirred for 5 min, then propylphosphonic anhydride (19.9 g, 62.7 mmol, 3.0 eq) was added, and the reaction was warmed to room temperature and stirred for 16 h. The reaction was then concentrated in vacuo, and treated with water (200 mL) and extracted with EtOAc. The combined organic layers were washed with water and brine, dried over anhydrous MgSO$_4$ and concentrated in vacuo to provide a residue, which was purified by chromatography over silica gel (eluting with PE:EtOAc=10:1 to 5:1) to provide compound C4-8. MS (ESI) m/e (M+H$^+$): 412.1.

Step H: ethyl 6-fluoro-4,4-dimethyl-1-(2-(trifluoromethyl)phenyl)-3,4-dihydroisoquinoline-7-carboxylate (C4-9A) and ethyl 8-fluoro-4,4-dimethyl-1-(2-(trifluoromethyl)phenyl)-3,4-dihydroisoquinoline-7-carboxylate (C4-9B)

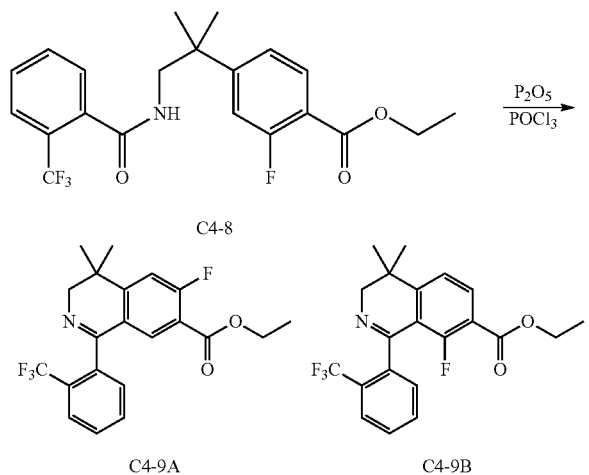

To a solution of compound C4-8 (5.10 g, 12.4 mmol, 1.0 eq) in toluene (100 mL) were added phosphorus pentaoxide (5.28 g, 37.2 mmol, 3.0 eq) and phosphorous oxychloride (15.2 g, 99.2 mmol, 8.0 eq). The reaction mixture was heated at 110° C. for 16 h, then allowed to cool to room temperature. The reaction was then poured into ice-water and neutralized with NaOH (10%). The organic layer was separated and the aqueous layer was extracted with EtOAc (100 mL) three times. The combined organic layers were washed with saturated aqueous NaHCO$_3$, water, brine, dried over MgSO$_4$ and concentrated in vacuo to provide a residue, which was purified by preparative HPLC (on a GILSON 281 instrument fitted with a SYNERGI (250*50*10 um) using water and acetonitrile as the eluents. Mobile phase A: water (containing 0.1% TFA, v/v), mobile phase B: acetonitrile. Gradient: 28-58% B, 0-10 min; 100% B, 10.5-12.5 min; 5% B, 13-15 min) to give compound C4-9A and compound C4-9B. MS (ESI) m/e (M+H$^+$): 394.1 for both.

Step I: ethyl 6-fluoro-4,4-dimethyl-1-(2-(trifluoromethyl)phenyl)-1,2,3,4-tetrahydroisoquinoline-7-carboxylate (C4-10A)

To a stirred solution of compound C4-9A (1.51 g, 3.84 mmol, 1.0 eq) in MeOH (20 mL) was added 10% Pd/C (150 mg). The mixture was stirred at room temperature under a H$_2$ (1 atm) for 3 h. Then the reaction mixture was filtered and the filtrate was concentrated in vacuo to afford crude compound C4-10A, which was used in the next step without purification. MS (ESI) m/e (M+H$^+$): 396.2.

Step J: (6-fluoro-4,4-dimethyl-1-(2-(trifluoromethyl)phenyl)-1,2,3,4-tetrahydroisoquinolin-7-yl)methanol (C4-11A)

To a mixture of LAH (649 mg, 17.1 mmol, 5.0 eq) in dry THF (20.0 mL) at 0° C. under N$_2$ atmosphere was added dropwise a solution of compound C4-10A (1.35 g, 3.41 mmol, 1.0 eq) in THF (10.0 mL). After addition, the reaction mixture was warmed to room temperature and stirred for 2 h. Then the reaction was quenched by the addition of 0.65 mL H$_2$O, 0.65 mL NaOH (15%) and 0.65 mL H$_2$O. The reaction mixture was then filtered and the filtrate was concentrated in vacuo to afford crude compound C4-11A, which was used in the next step without purification. MS (ESI) m/e (M+H$^+$): 354.2.

Step K: tert-butyl 6-fluoro-7-(hydroxymethyl)-4,4-dimethyl-1-(2-(trifluoromethyl)phenyl)-3,4-dihydroisoquinoline-2(1H)-carboxylate (C4-12A)

To a stirred solution of crude compound C4-11A (800 mg, 2.26 mmol, 1.0 eq) in DCM (10.0 mL) were added Boc$_2$O (543 mg, 2.49 mmol, 1.1 eq) and TEA (686 mg, 6.79 mmol, 3.0 eq), and the mixture was stirred for 3 h. Then water (50 mL) was added and the reaction mixture was extracted with EtOAc (30 mL) three times. The combined organic layers were washed with brine, dried over MgSO$_4$, and concentrated in vacuo to afford crude compound C4-12A, which was used in the next step without purification. MS (ESI) m/e (M+H$^+$): 398.2.

Step L: tert-butyl 7-(bromomethyl)-6-fluoro-4,4-dimethyl-1-(2-(trifluoromethyl)phenyl)-3,4-dihydroisoquinoline-2(1H)-carboxylate (C4-13A)

To a solution of crude compound C4-12A (900 mg, 1.99 mmol, 1.0 eq) in DCM (10 mL) at 0° C. were added TEA (602 mg, 5.98 mmol, 4.0 eq) and PBr$_3$ (538 mg, 1.99 mmol, 1.0 eq). The reaction was allowed to warm to room temperature and stirred for 1 h. To the reaction mixture were added saturated aqueous NaHCO$_3$ solution and EtOAc. The aqueous layer was separated and extracted with EtOAc. The combined organic layers were washed with brine, dried over MgSO$_4$ and concentrated in vacuo to afford compound C4-13A, which was used in the next step without purification. MS (ESI) m/e (M+H$^+$): 503.1.

Step M: (5aR,6S,6aS)-ethyl 3-(((S)-2-(tert-butoxycarbonyl)-6-fluoro-4,4-dimethyl-1-(2-(trifluoromethyl-phenyl)-1,2,3,4-tetrahydroisoquinolin-7-yl)methoxy)-5,5a,6,6a-tetrahydro-cyclopropa[4,5]cyclopenta[1,2-c]pyridine-6-carboxylate (C4-14A) and (5aR,6S,6aS)-ethyl 3-(((R)-2-(tert-butoxycarbonyl)-6-fluoro-4,4-dimethyl-1-(2-(trifluoromethyl)phenyl)-1,2,3,4-tetrahydroisoquinolin-7-yl)methoxy)-5,5a,6,6a-tetrahydrocyclopropa-[4,5]cyclopenta[1,2-c]pyridine-6-carboxylate (C4-14A-2)

To a solution of compound C4-13A (389 mg, 0.753 mmol, 1.1 eq) and intermediate 1-9 (150 mg, 0.685 mmol, 1.0 eq) in toluene (5.0 mL) was added Ag$_2$CO$_3$ (567 mg, 2.05 mmol, 3.0 eq) in one portion under a N$_2$ atmosphere. The reaction mixture was heated at 110° C. for 5 h, then cooled to room temperature and filtered. The filtrate was concentrated in vacuo to afford a residue, which was purified by preparative TLC over silica gel (eluting with PE:EA=5:1) to give compound C4-14A.

Chiral SFC Resolution of Compound C4-14A
(Compounds C4-14A1 and C4-14A2)

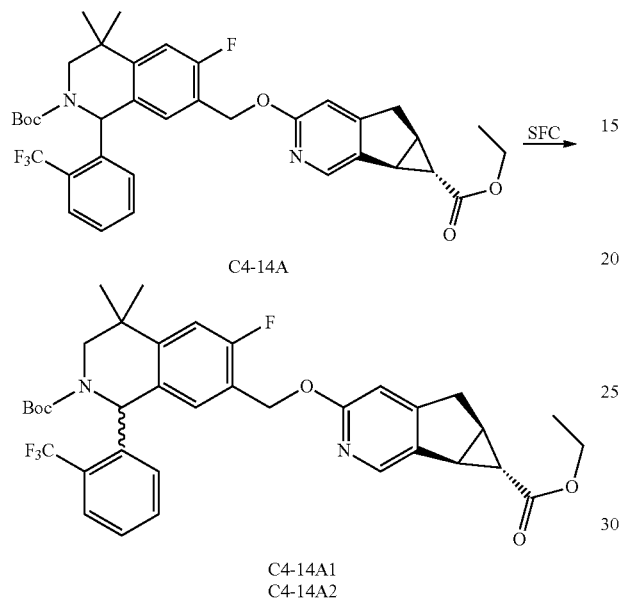

C4-14A

C4-14A1
C4-14A2

Compound C4-14A was purified by chiral preparative SFC (Column: Chiralpak AD-3 150×4.6 mm I.D., 3 um; Mobile phase: ethanol (0.05% DEA) in $CO_2$ from 5% to 40%; Flow rate: 2.5 mL/min; Wavelength: 220 nm) to provide compound C4-14A1, followed by compound C4-14A2: MS (ESI) m/e (M+H$^+$): 655.3 for both.

Step O: (5aR,6S,6aS)-ethyl 3-(4S)-6-fluoro-4,4-dimethyl-1-(2-(trifluoromethyl)phenyl)-1,2,3,4-tetrahydroisoquinolin-7-yl)methoxy)-5,5a,6,6a-tetrahydrocyclopropa[4,5]cyclopenta[1,2-c]pyridine-6-carboxylate (C4-15A1)

To a solution of compound C4-14A1 (50 mg, 0.076 mmol, 1.0 eq) in dry DCM (2.5 mL) at 0° C. was added TFA (0.5 mL) dropwise. The reaction mixture was allowed to warm to room temperature and stirred for 1 h. Then the solvent was removed under reduced pressure to give crude compound C4-15A1, which was used in the next step without purification. MS (ESI) m/e (M+H$^+$): 555.2.

Step P: (5aR,6S,6aS)-3-(((S)-6-fluoro-4,4-dimethyl-1-(2-(trifluoromethyl)phenyl)-1,2,3,4-tetrahydroisoquinolin-7-yl)methoxy)-5,5a,6,6a-tetrahydrocyclopropa[4,5]cyclopenta[1,2-c]pyridine-6-carboxylic acid (C4-16A1)

To a solution of compound C4-15A1 (8.0 mg, 0.0144 mmol, 1.0 eq) in THF (0.5 mL), MeOH (0.5 mL) and $H_2O$ (0.5 mL) was added LiOH.$H_2O$ (6.05 mg, 0.144 mmol, 10.0 eq) and the reaction was stirred at room temperature for 1 h. The reaction was then acidified with HCl (1 N) to pH=2, and extracted with EtOAc (5 mL) three times. The combined organic layers were washed with brine, dried over MgSO$_4$, and concentrated in vacuo to afford a residue, which was purified by preparative HPLC (on a GILSON 281 instrument fitted with a Phenomenex Gemini C18 (150*30 mm*5 um) using water and acetonitrile as the eluents. Mobile phase A: water (containing 0.1% TFA, v/v), mobile phase B: acetonitrile. Gradient: 30-36% B, 0-10 min; 100% B, 10.5-12.5 min; 5% B, 13-15 min) to give compound C4-16A1. $^1$H NMR (400 MHz, CDCl$_3$) δ: 7.89 (d, J=8.0 Hz, 1H), 7.78 (d, J=5.2 Hz, 1H), 7.56-7.50 (m, 2H), 7.19 (d, J=7.2 Hz, 1H), 7.16 (d, J=10.0 Hz, 1H), 6.74 (d, J=6.4 Hz, 1H), 6.46 (d, J=6.0 Hz, 1H), 5.86 (s, 1H), 5.33-5.21 (m, 2H), 3.35 (d, J=12.8 Hz, 1H), 3.23-3.13 (m, 2H), 2.97 (d, J=18.4 Hz, 1H), 2.88 (s, 1H), 2.44 (s, 1H), 1.56 (s, 3H), 1.45 (s, 3H), 1.10 (t, J=2.8 Hz, 1H). MS (ESI) m/e (M+H$^+$): 527.3.

Example 73

(5aR,6S,6aS)-3-(((S)-6-fluoro-2,4,4-trimethyl-1-(2-(trifluoromethyl)phenyl)-1,2,3,4-tetrahydroisoquinolin-7-yl)methoxy)-5,5a,6,6a-tetrahydrocyclopropa[4,5]cyclopenta[1,2-c]pyridine-6-carboxylic acid
(Compound C5-3)

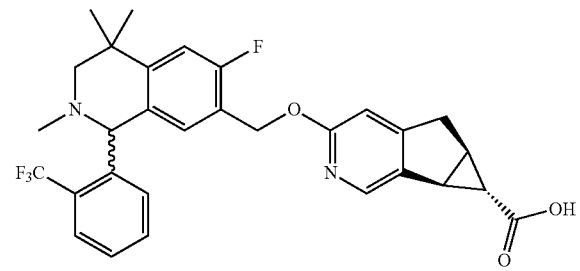

C5-3

Step A: (5aR,6S,6aS)-ethyl 3-(((S)-6-fluoro-2,4,4-trimethyl-1-(2-(trifluoromethyl)phenyl)-1,2,3,4-tetrahydroisoquinolin-7-yl)methoxy)-5,5a,6,6a-tetrahydrocyclopropa[4,5]cyclopenta[1,2-c]pyridine-6-carboxylate (C5-2)

To a solution of compound C4-15A1 (10.0 mg, 0.0180 mmol, 1.0 eq) in THF (1.0 mL) were added formalin (1.08 mg, 0.0360 mmol, 2.0 eq) and acetic acid (2.16 mg, 0.0360 mmol, 2.0 eq) and the mixture was stirred at room temperature for 30 min. The reaction was then cooled to 0° C., and excess sodium triacetoxyborohydride was added in one portion. The resulting suspension was stirred for 16 h at room temperature. Then water (8.0 mL) was added and the reaction mixture was extracted with EtOAc (5 mL) three times. The combined organic layers were washed with water, brine, dried over MgSO$_4$, and concentrated in vacuo to give crude compound C5-2, which was used in the next step without purification. MS (ESI) m/e (M+H$^+$): 569.3.

Step B: (5aR,6S,6aS)-3-(((S)-6-fluoro-2,4,4-trimethyl-1-(2-(trifluoromethyl)phenyl)-1,2,3,4-tetrahydroisoquinolin-7-yl)methoxy)-5,5a,6,6a-tetrahydrocyclopropa[4,5]cyclopenta[1,2-c]pyridine-6-carboxylic acid (C5-3)

To a solution of C5-2 (8.00 mg, 0.0141 mmol, 1.0 eq) in THF (0.5 mL), MeOH (0.5 mL) and H$_2$O (0.5 mL)

was added LiOH.H$_2$O (5.92 mg, 0.141 mmol, 10.0 eq) and the mixture was stirred at room temperature for 1 h. The reaction mixture was acidified with HCl (1 N) to pH=2, and extracted with EtOAc (5.00 mL) three times. The combined organic layers were washed with brine, dried over MgSO$_4$, and concentrated in vacuo to afford a residue, which was purified by preparative HPLC (on a GILSON 281 instrument fitted with a YMC-pack ODS-AQ (150*30 mm*5 um) using water and acetonitrile as the eluents. Mobile phase A: water (containing 0.1% TFA, v/v), mobile phase B: acetonitrile. Gradient: 34-64% B, 0-10 min; 100% B, 10.5-12.5 min; 5% B, 13-15 min) to give compound C5-3. $^1$H NMR (400 MHz, CDCl$_3$) δ: 7.91 (s, 1H), 7.79 (d, J=7.2 Hz, 1H), 7.68~7.55 (m, 3H), 7.10 (d, J=10.8 Hz, 1H), 6.49 (d, J=7.2 Hz, 1H), 6.42 (s, 5.24~5.13 (m, 3H), 3.20 (d, J=6.0 Hz, 1H), 3.02~2.95 (m, 3H), 2.58 (s, 3H), 2.01~2.00 (m, 3H), 1.65 (s, 3H), 1.42 (s, 3H), 1.21 (t, J=2.8 Hz, 1H). MS (ESI) m/e (M+H$^+$): 541.4.

Example 74

(5aR,6S,6aS)-3-((8-fluoro-4,4-dimethyl-1-(2-(trifluoromethyl)phenyl)-1,2,3,4-tetrahydroisoquinolin-7-yl)methoxy)-5,5a,6,6a-tetrahydrocyclopropa[4,5]cyclopenta[1,2-c]pyridine-6-carboxylic acid (Compound C6-6)

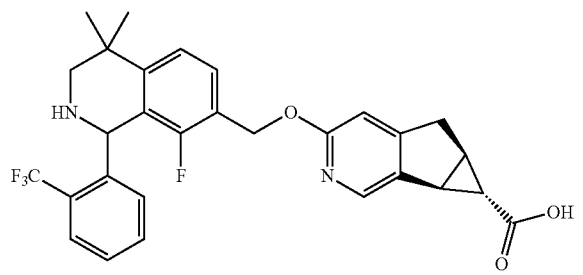

C6-6

Step A: ethyl 8-fluoro-4,4-dimethyl-1-(2-(trifluoromethyl)phenyl)-1,2,3,4-tetrahydroisoquinoline-7-carboxylate (C6-2)

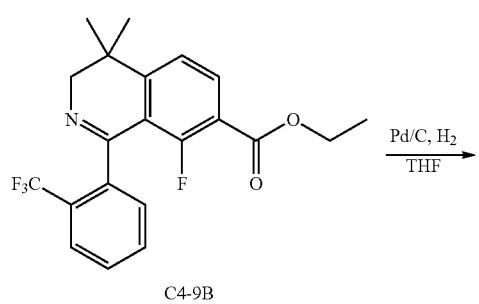

C4-9B

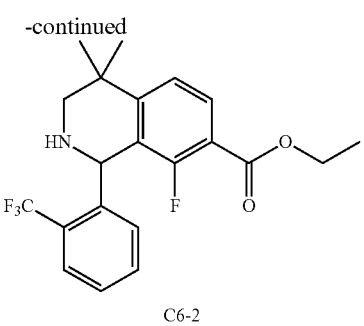

C6-2

To a stirred solution of compound C4-9B (350 mg, 0.890 mmol, 1.0 eq) in MeOH (7.0 mL) was added 10% Pd/C (35 mg), and the mixture was stirred at room temperature under a H$_2$ (1 atm) for 3 h. Then the reaction mixture was filtered and the filtrate was concentrated in vacuo to afford crude compound C6-2, which was used in the next step without purification. MS (ESI) m/e (M+H$^+$): 396.2.

Step B: (8-fluoro-4,4-dimethyl-1-(2-(trifluoromethyl)phenyl)-1,2,3,4-tetrahydroisoquinolin-7-yl)methanol (C6-3)

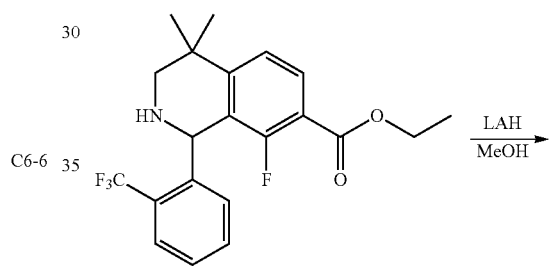

C6-2

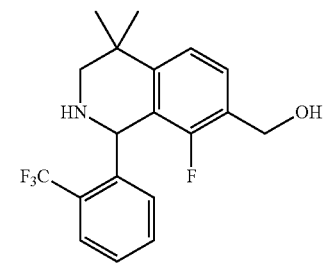

C6-3

To a mixture of LAH (144 mg, 3.79 mmol, 5.0 eq) in dry THF (10.0 mL) at 0° C. under N$_2$ was added dropwise a solution of crude compound C6-2 (300 mg, 0.759 mmol, 1.0 eq) in THF (5.0 mL). Then the reaction mixture was stirred at room temperature for 2 h, quenched with 0.2 mL H$_2$O, 0.2 mL NaOH (15%) and 0.2 mL H$_2$O. Then resulting reaction mixture was filtered, and the filtrate was concentrated in vacuo to afford crude compound C6-3, which was used in the next step without purification. MS (ESI) m/e (M+H$^+$): 354.2.

Step C: 7-(bromomethyl)-8-fluoro-4,4-dimethyl-1-(2-(trifluoromethyl)phenyl)-1,2,3,4-tetrahydroisoquinoline (C6-4)

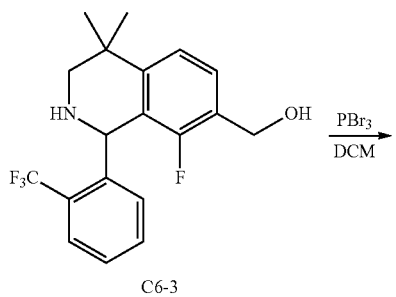

C6-3

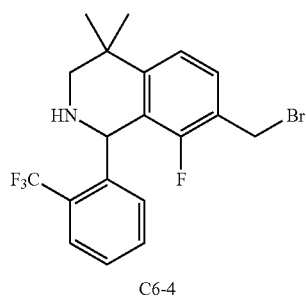

C6-4

To a solution of crude compound C6-3 (100 mg, 283 mmol, 1.0 eq) in DCM (5.0 mL) at 0° C. under N₂ was added PBr₃ (76.6 mg, 0.283 mmol, 1.0 eq) dropwise and the reaction mixture was stirred for 1 h. A solution of saturated aqueous NaHCO₃ was added to adjust the reaction mixture to pH=7, then the reaction mixture was extracted with EtOAc (3×5 mL). The combined organic layers were washed with brine, dried over MgSO₄, and concentrated in vacuo to give compound C6-4.

Step D: (5aR,6S,6aS)-ethyl 3-48-fluoro-4,4-dimethyl-1-(2-(trifluoromethyl)phenyl)-1,2,3,4-tetrahydroisoquinolin-7-yl)methoxy)-5,5a,6,6a-tetrahydrocyclopropa[4,5]cyclopenta[1,2-c]pyridine-6-carboxylate (C6-5)

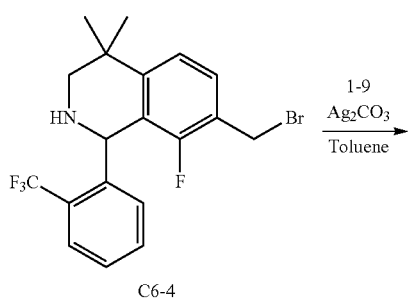

C6-4

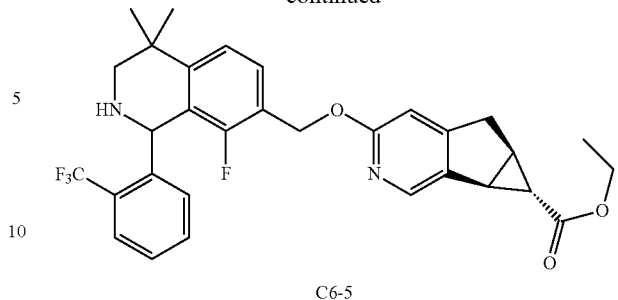

C6-5

To a solution of compound C6-4 (22.8 mg, 0.0548 mmol, 1.2 eq) and intermediate 1-9 (10 mg, 0.0457 mmol, 1.0 eq) in toluene (2.0 mL) was added Ag₂CO₃ (37.8 mg, 0.137 mmol, 3.0 eq) in one portion. The reaction mixture was heated at 110° C. for 5 h. Then the reaction was cooled to room temperature and filtered. The filtrate was concentrated in vacuo to afford a residue, which was purified by preparative TLC over silica gel (eluting with PE:EA=5:1) to give compound C6-5. MS (ESI) m/e (M+H⁺): 555.2.

Step E: (5aR,6S,6aS)-3-((8-fluoro-4,4-dimethyl-1-(2-(trifluoromethyl)phenyl)-1,2,3,4-tetrahydroisoquinolin-7-yl)methoxy)-5,5a,6,6a-tetrahydrocyclopropa[4,5]cyclopenta[1,2-c]pyridine-6-carboxylic acid (C6-6)

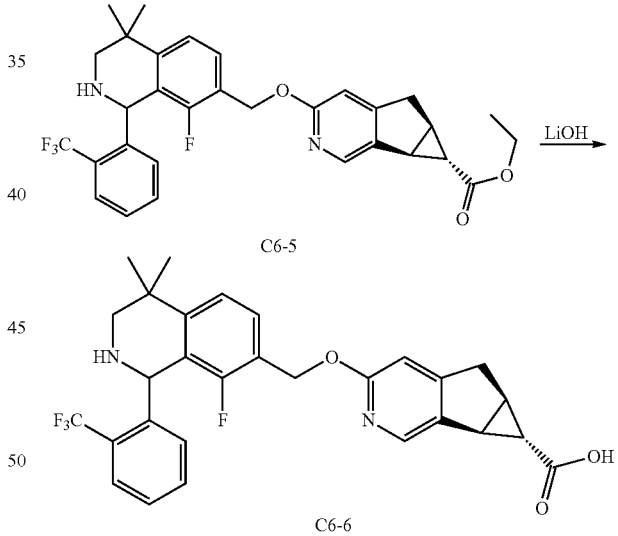

C6-5

C6-6

To a solution of compound C6-5 (12.0 mg, 0.0222 mmol, 1.0 eq) in THF (0.5 mL), MeOH (0.5 mL) and H₂O (0.5 mL) was added LiOH.H₂O (9.31 mg, 0.222 mmol, 10.0 eq) and the reaction was stirred at room temperature for 1 h. Then the reaction mixture was acidified with HCl (1 N) to pH=2, and extracted with EtOAc (5.00 mL) three times. The combined organic layers were washed with brine, dried over MgSO₄, and concentrated in vacuo to afford a residue, which was purified by preparative HPLC (on a GILSON 281 instrument fitted with a Diamonsil (150*20 mm*5 um) using water and acetonitrile as the eluents. Mobile phase A: water (containing 0.1% TFA, v/v), mobile phase B: acetonitrile. Gradient: 10-40% B, 0-10 min; 100% B, 10.5-12.5 min; 5%

B, 13-15 min) to give compound C6-6. ¹H NMR (400 MHz, MeOD-$d_4$) δ: 8.00 (s, 1H), 7.98 (d, J=7.2 Hz, 1H), 7.73~7.61 (m, 3H), 7.52 (d, J=8.4 Hz, 1H), 7.16 (d, J=7.6 Hz, 1H), 6.64 (s, 1H), 6.22 (s, 1H), 5.26 (s, 2H), 3.28-3.21 (m, 3H), 3.05 (d, J=18.8 Hz, 1H), 2.92 (d, J=4.8 Hz, 1H), 2.45-2.42 (m, 1H), 1.60 (s, 3H), 1.49 (s, 3H), 1.13 (t, J=2.8 Hz, 1H). MS (ESI) m/e (M+H⁺): 527.3.

Example 75

(5aS,6S,6aS)-3-((6-fluoro-1,1-dimethyl-3-(2-(trifluoromethyl)phenyl)-2,3-dihydro-1H-inden-5-yl)methoxy)-6a-methyl-5,5a,6,6a-tetrahydrocyclopropa[4,5]cyclopenta[1,2-c]pyridine-6-carboxylic acid (C7-9)

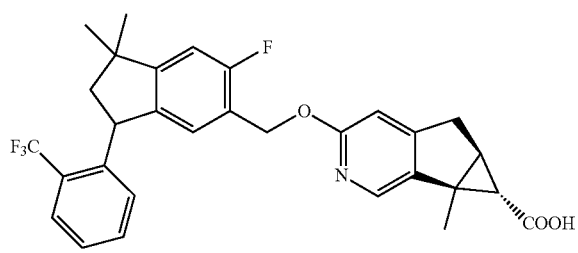 [SMILES: CC1(C)CC(c2ccccc2C(F)(F)F)c2cc(COc3cc4c(cn3)[C@@]3(C)[C@@H](C4)[C@@H]3C(=O)O)c(F)cc21]

Step A: 4-bromo-N,N-bis(4-methoxybenzyl)-5-(prop-1-en-2-yl)pyridin-2-amine (C7-1)

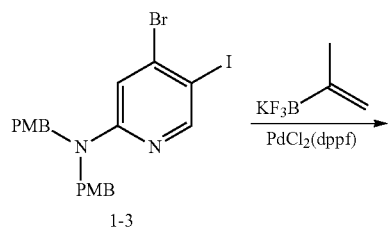

A mixture of potassium trifluoro (prop-1-en-2-yl)borate (3.02 g, 20.40 mmol), PdCl₂(dppf) (0.679 g, 0.927 mmol), intermediate 1-3 (10 g, 18.55 mmol) and sodium carbonate (4.91 g, 46.4 mmol) in THF (120 mL) and water (30 mL) was heated at 80° C. for 18 h. The reaction mixture was extracted with EtOAc. Then the combined organic fractions were washed with brine, dried over anhydrous Na₂SO₄, filtered. The filtrate was concentrated under reduced pressure to give the crude product, which was purified by chromatography over silica gel (eluting with PE:EtOAc=85:15) to provide compound C7-1. MS (ESI) m/e (M+H⁺): 453.1/455.1.

Step B: 4-allyl-N,N-bis(4-methoxybenzyl)-5-(prop-1-en-2-yl)pyridin-2-amine (C7-2)

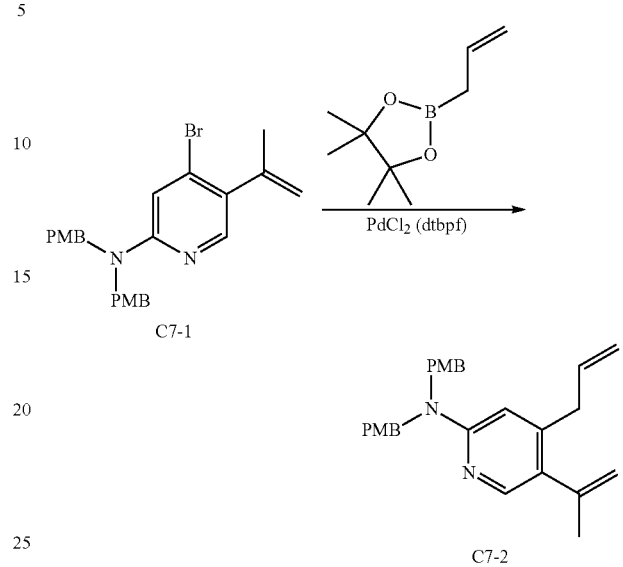

A mixture of PdCl₂(dtbpf) (0.431 g, 0.662 mmol), 2-allyl-4,4,5,5-tetramethyl-1,3,2-dioxaborolane (3.34 g, 19.85 mmol), compound C7-1 (6 g, 13.23 mmol) and K₂CO₃ (4.57 g, 33.1 mmol) in THF (90 mL) and water (30 mL) was heated at 80° C. for 18 h under N₂. The mixture was extracted with EtOAc (2×200 mL). The combined organic layers were washed with brine, dried over anhydrous Na₂SO₄, and filtered. The filtrate was concentrated under reduced pressure to give the crude product. The crude product was purified by preparative HPLC (on a GILSON 281 instrument fitted with a Phenomenex Synergi Max-RP 250*50 mm*10 um using water and acetonitrile as the eluents. Mobile phase A: water (containing 0.1% TFA, v/v), mobile phase B: acetonitrile. Gradient: 30-60% B, 0-10 min; 100% B, 10.5-12.5 min; 5% B, 13-15 min) to give compound C7-2 as a yellow oil.

Step C: N,N-bis(4-methoxybenzyl)-7-methyl-5H-cyclopenta[c]pyridin-3-amine (C7-3)

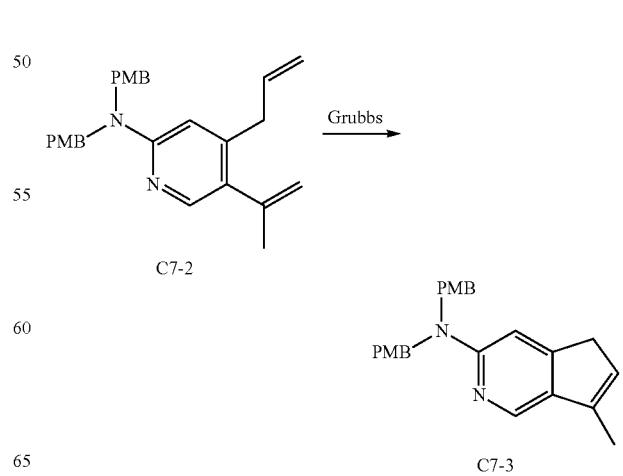

Compound C7-2 (2.5 g, 6.03 mmol) was dissolved in dry toluene (50 mL). Then Grubbs reagent (II) (0.512 g, 0.603 mmol) was added into the mixture and the flask was evacuated and back-filled with nitrogen three times. The reaction mixture was stirred at 75° C. for 16 hours. Then the reaction mixture was filtered and concentrated to give a crude product, which was purified by chromatography over silica gel (eluting with PE:EtOAc=90:10) to provide compound C7-3. MS (ESI) m/e (M+H$^+$): 387.2.

Step D: (5aS,6S,6aS)-ethyl 3-(bis(4-methoxybenzyl)amino)-6a-methyl-5,5a,6,6a-tetrahydrocyclopropa[4,5]cyclopenta[1,2-c]pyridine-6-carboxylate (1-F) & (5aS,6R,6aS)-ethyl 3-(bis(4-methoxybenzyl)amino)-6a-methyl-5,5a,6,6a-tetrahydrocyclopropa[4,5]cyclopenta[1,2-c]pyridine-6-carboxylate (C7-4 and C7-5)

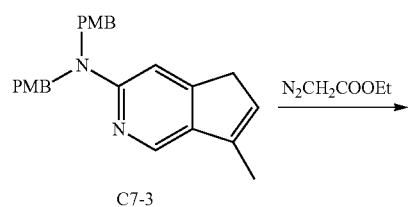

To a suspension of compound C7-3 (2 g, 5.17 mmol) in DCM (80 mL) was added Rhodium (II) acetate dimer (0.229 g, 0.517 mmol). Then ethyl diazoacetate (4.29 ml, 41.4 mmol) in DCM (15 ml) was added slowly for 5 h at 43° C. The mixture was stirred at 43° C. for 16 h, then concentrated in vacuo to give crude product. The crude product was purified by chromatography over silica gel (eluting with PE:EtOAc=20:1) to provide compound C7-4 and crude product C7-5. Crude product C7-5 was further purified by prep-HPLC (preparative HPLC on a GILSON 281 instrument fitted with a Phenomenex Synergi Max-RP 250*80 10u using water and acetonitrile as the eluents. Mobile phase A: water (containing 0.1% TFA, v/v), mobile phase B: acetonitrile. Gradient: 30-60% B, 0-10 min; 100% B, 10.5-12.5 min; 5% B, 13-15 min) to give compound C7-5.

Step E: (5aS,6S,6aS)-ethyl 3-(bis(4-methoxybenzyl)amino)-6a-methyl-5,5a,6,6a-tetrahydro-cyclopropa[4,5]cyclopenta[1,2-c]pyridine-6-carboxylate (C7-4-1 and C7-4-2)

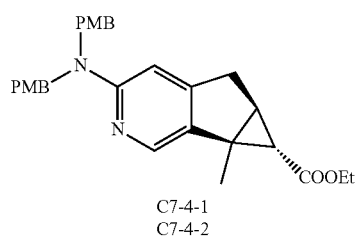

Compound C7-4 (635 mg, 1.344 mmol) was separated by SFC (Column: Chiralpak AD-H 250×4.6 mm I.D., 5 um Mobile phase: 40% of iso-propanol (0.05% DEA) in CO$_2$, Flow rate: 2.5 mL/min Wavelength: 220 nm) to give compound C7-4-1, followed by compound C7-4-2.

Step F: (5aS,6R,6aS)-ethyl 3-(bis(4-methoxybenzyl)amino)-6a-methyl-5,5a,6,6a-tetrahydrocyclopropa[4,5]cyclopenta[4,5]cyclopenta[1,2-c]pyridine-6-carboxylate (C7-5-1 and C7-5-2)

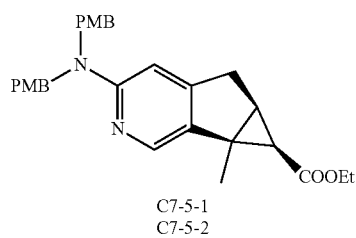

Compound C7-5 (460 mg, 0.973 mmol) was separated by SFC (Column: Chiralpak AD-H 250×4.6 mm I.D., 5 um Mobile phase: 40% of methanol (0.05% DEA) in CO$_2$, Flow rate: 2.5 mL/min Wavelength: 220 nm) to give compound C7-5-1, followed by compound C7-5-2.

Step G: (5aS,6S,6aS)-ethyl 3-amino-6a-methyl-5,5a,6,6a-tetrahydrocyclopropa[4,5]-cyclopenta[1,2-c]pyridine-6-carboxylate (C7-6)

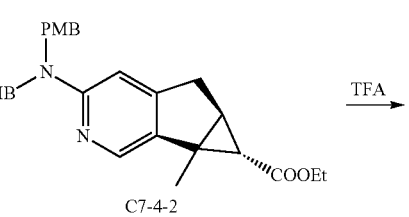

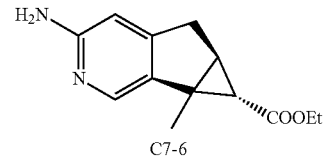

Compound C7-4-2 (200 mg, 0.423 mmol) was added to a stirred solution of TFA (5 mL) in DCM (5 mL), and the resulting mixture was stirred at 15° C. for 18 h. The mixture was evaporated under reduced pressure to give the crude product C7-6, which was used directly for next step. MS (ESI) m/e (M+H⁺): 233.2.

Step H: (5aS,6S,6aS)-ethyl 3-hydroxy-6a-methyl-5,5a,6,6a-tetrahydrocyclopropa[4,5]cyclopenta[1,2-c]pyridine-6-carboxylate (C7-7)

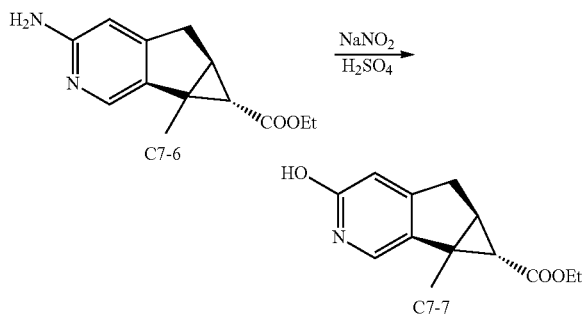

Sodium nitrite (137 mg, 1.989 mmol) was added to a stirred, mixture of (5aS,6S,6aS)-ethyl 3-amino-6a-methyl-5,5a,6,6a-tetrahydrocyclopropa[4,5]cyclopenta[1,2-c]pyridine-6-carboxylate C7-6 (140 mg, 0.398 mmol) and concentrated $H_2SO_4$ (1 mL) in water (6 mL) in portions at 0° C. The resulting mixture was stirred at 15° C. for 18 h. Then the mixture was alkalized with 2N NaOH to pH=8 and extracted with DCM (2×20 mL). The combined organic fractions were washed with brine, dried anhydrous $Na_2SO_4$, and filtered. The filtrate was concentrated under reduced pressure to give the crude product, which was purified by preparative TLC over silica gel (eluting with PE:EtOAc=1:1) to give compound C7-7. MS (ESI) m/e (M+H⁺): 234.1.

Step I: (5aR,6S,6aR)-3-((6-fluoro-1,1-dimethyl-3-(2-(trifluoromethyl)phenyl)-2,3-dihydro-1H-inden-5-yl)methoxy)-6a-methyl-5,5a,6,6a-tetrahydrocyclopropa[4,5]cyclopenta[1,2-c]pyridin-6-yl propionate (C7-8)

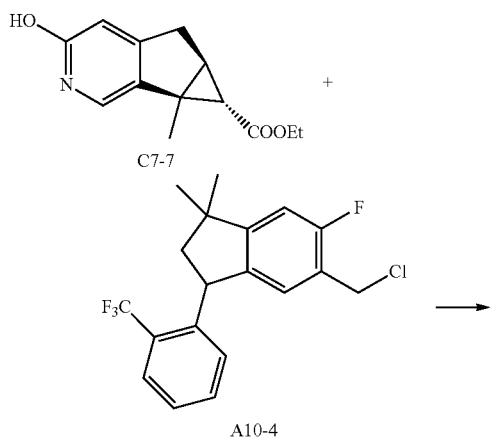

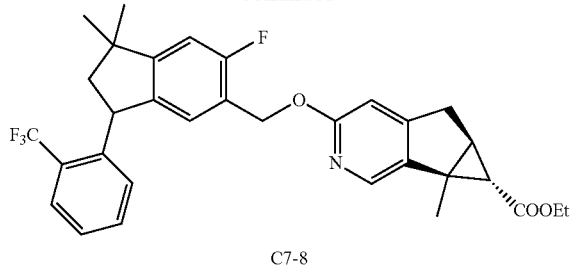

Silver carbonate (284 mg, 1.029 mmol) was added to a mixture of compound C7-7 (80 mg, 0.343 mmol) and compound A10-4 (151 mg, 0.377 mmol) in toluene (5 mL) and the mixture was stirred at 115° C. for 4 h. Then the mixture was filtered and the filtrate was concentrated under reduced pressure to give the crude product, which was purified by preparative TLC over silica gel (eluting with PE:EtOAc=5:1) to afford compound C7-8. MS (ESI) m/e (M+H⁺): 554.3.

Step J: (5aS,6S,6aS)-3-((6-fluoro-1,1-dimethyl-3-(2-(trifluoromethyl)phenyl)-2,3-dihydro-1H-inden-5-yl)methoxy)-6a-methyl-5,5a,6,6a-tetrahydrocyclopropa[4,5]cyclopenta[1,2-c]pyridine-6-carboxylic acid (C7-9)

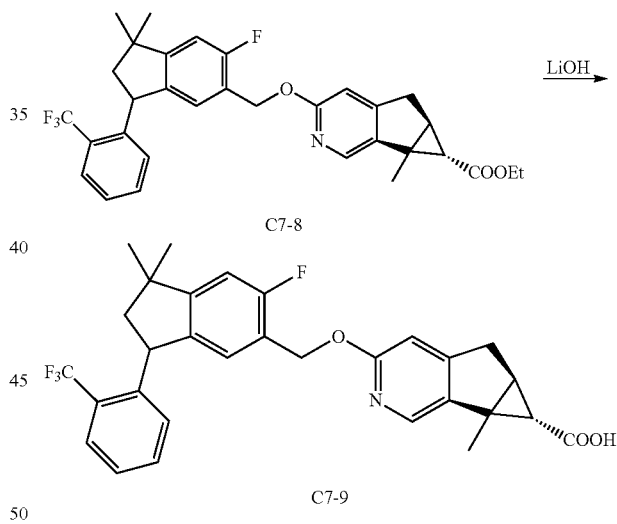

Compound C7-8 (100 mg, 0.181 mmol) was added to a mixture of lithium hydroxide monohydrate (114 mg, 2.71 mmol) in MeOH (3 ml), THF (2 ml) and water (1 ml) and the mixture was stirred at 15° C. for 18 h. Then the mixture was acidified with 2N HCl to pH=7 and evaporated under reduced pressure to give the crude product. The crude product was purified by prep-HPLC (preparative HPLC on a GILSON 281 instrument fitted with a Phenomenex Gemini C18 250*21.2 mm*5 um using water and acetonitrile as the eluents. Mobile phase A: water (containing 0.1% $NH_4HCO_3$, v/v), mobile phase B: acetonitrile. Gradient: 33-63% B, 0-10 min; 100% B, 10.5-12.5 min; 5% B, 13-15 min) to give compound C7-9. ¹H NMR (400 MHz, MeOH-$d_4$) δ 1.19 (d, J=3.75 Hz, 1H) 1.27 (s, 3H) 1.40-1.50 (m, 3H) 1.67 (s, 3H) 1.88-2.01 (m, 1H) 2.24-2.34 (m, 1H) 2.48 (dd, J=12.57, 7.50 Hz, 1H) 2.92 (d, J=18.30 Hz, 1H) 3.17 (dd, J=18.41, 5.84 Hz, 1H) 4.73-4.81 (m, 1H) 5.19-5.30 (m, 2H) 6.57 (s, 1H) 6.83 (d, J=6.62 Hz, 1H) 7.01 (d, J=10.14 Hz, 1H) 7.11 (d, J=7.72 Hz, 1H) 7.34-7.44 (m, 1H) 7.45-7.56 (m, 1H) 7.70 (d, J=7.94 Hz, 1H) 7.90 (s, 1H). MS (ESI) m/e (M+H$^+$): 526.2.

Example 76

(5aR,6S,6aS)-3-((6-fluoro-1,1,3,3-tetramethyl-2,3-dihydro-1H-inden-5-yl)methoxy)-5,5a,6,6a-tetrahydrocyclopropa[4,5]cyclopenta[1,2-c]pyridine-6-carboxylic acid (C8-11)

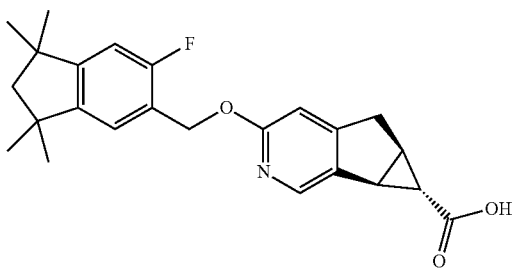 [SMILES: CC1(C)CC(C)(C)c2cc(COc3cc4c(cn3)[C@H]3[C@@H](C4)[C@@H]3C(=O)O)c(F)cc21]

Step A: (Z)-ethyl 3-(3-bromo-4-fluorophenyl)-2-cyanobut-2-enoate and (E)-ethyl 3-(3-bromo-4-fluorophenyl)-2-cyanobut-2-enoate (C8-2)

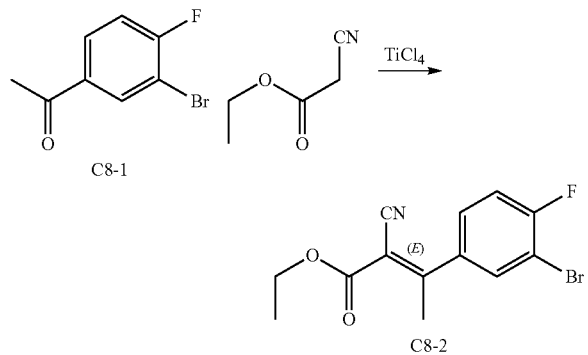

1-(3-bromo-4-fluorophenyl)ethanone C8-1 (6 g, 27.6 mmol) and ethyl 2-cyanoacetate (3.75 g, 33.2 mmol) were dissolved in dry CH$_2$Cl$_2$ (100 mL) and cooled to 0° C. in an ice bath. Neat TiCl$_4$ (6.10 ml, 55.3 mmol) was added dropwise. After completion of the addition, the mixture was stirred for 0.5 h and then dry pyridine (1.8 mL) was added dropwise. The ice bath was subsequently removed, and the mixture was stirred at room temperature for 1 h. A further aliquot of dry pyridine (5.4 mL) was added dropwise and the mixture was allowed to stir for 2 hours. The mixture was poured into 3M HCl (110 mL) and the organic layer was separated. The organic layer was washed with brine, dried over anhydrous Na$_2$SO$_4$ and concentrated to give compound C8-2, which was used in the next step without purification.

Step B: ethyl 3-(3-bromo-4-fluorophenyl)-2-cyano-3-methylbutanoate (C8-3)

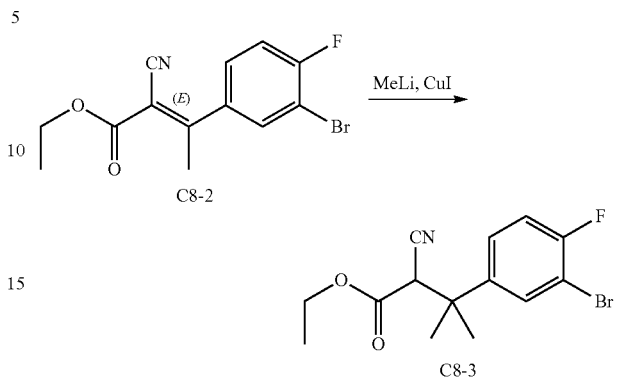

Methyllithium (24.03 mL, 38.4 mmol) was added to a stirred, cooled 0° C. mixture of CuI (3.66 g, 19.22 mmol) in THF (20 mL) under N$_2$. After the addition was complete, the mixture was stirred at for 30 min under N$_2$, then the mixture was cooled to –30° C., and a solution of compound C8-2 (3.0 g, 9.61 mmol) in THF (60 mL) was added. The reaction mixture was allowed to warm to room temperature, stirred for 10 hours, and then quenched with aqueous ammonium chloride (saturated, 20 mL). The mixture was extracted with EtOAc (3×100 mL). The combined organic layers were washed with brine, dried over Na$_2$SO$_4$, and filtered. The filtrate was concentrated under reduced pressure. The resulting residue was purified by chromatography over silica gel (eluting with PE:EtOAc=10:1) to give compound C8-3.

Step C: 3-(3-bromo-4-fluorophenyl)-3-methylbutanoic acid (C8-4)

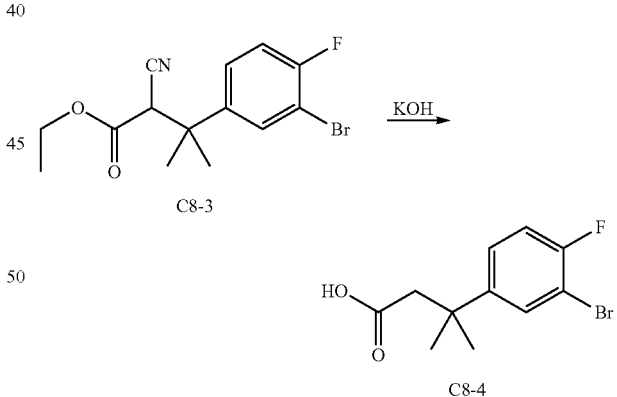

Compound C8-3 (2.2 g, 6.70 mmol) was dissolved in ethylene glycol (60 mL) and treated with KOH (3.76 g, 67.0 mmol) in water (12 mL). The reaction mixture was stirred at 130° C. for 24 hours. The reaction mixture was cooled, and water (80 mL) was added. Then the mixture was acidified with aqueous HCl (3M) to pH=3, and extracted with EtOAc (3×30 mL). The combined organic fractions were washed with water (2×30 mL), brine, dried over Na$_2$SO$_4$, and filtered. The filtrate was concentrated under reduced pressure to give crude compound C8-4, which was used in the next step without purification.

Step D: ethyl 3-(3-bromo-4-fluorophenyl)-3-methylbutanoate (C8-5)

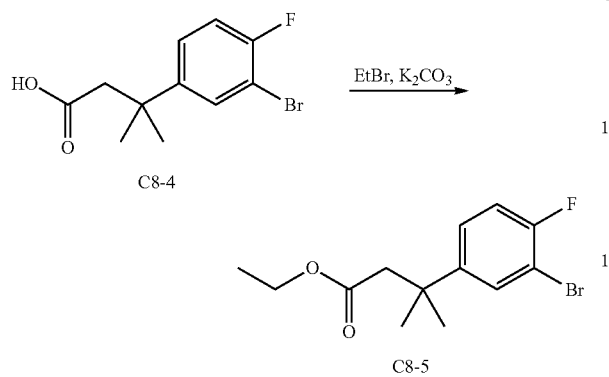

A mixture of 3-(3-bromo-4-fluorophenyl)-3-methylbutanoic acid C8-4 (3.3 g, 12.00 mmol), bromoethane (2.61 g, 23.99 mmol), K$_2$CO$_3$ (3.32 g, 23.99 mmol) and DMF (20 mL) was stirred at 25° C. for 3 hours. The reaction mixture was poured into aqueous ammonium chloride (saturated, 100 mL) and the resulting mixture extracted with EtOAc (3×50 mL). The combined organic fractions were washed with water, brine, dried over Na$_2$SO$_4$, and filtered. The filtrate was concentrated under reduced pressure. The resulting residue was purified by chromatography over silica gel (eluting with PE:EtOAc=10:1) to give compound C8-5.

Step E: 4-(3-bromo-4-fluorophenyl)-2,4-dimethylpentan-2-ol (C8-6)

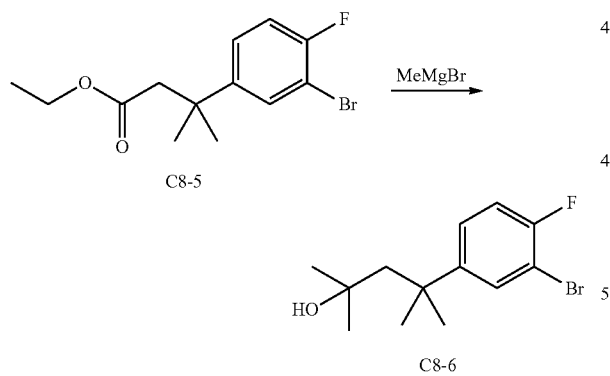

MeMgBr (3.08 ml, 9.24 mmol) ethoxyethane solution was added dropwise to a stirred, cooled 0° C. mixture of compound C8-5 (700 mg, 2.309 mmol) in THF (5 mL). After the addition was complete, the mixture was stirred at 0° C. for one hour. Then the reaction mixture was quenched with aqueous ammonium chloride (saturated, 20 mL) and extracted with EtOAc (3×30 mL). The combined organic layers were washed with brine (saturated, 30 mL), dried (Na$_2$SO$_4$), and filtered. The filtrate was concentrated under reduced pressure. The resulting residue was purified by chromatography over silica gel (eluting with PE:EtOAc=20:1 to 5:1) to give compound C8-6.

Step F: 5-bromo-6-fluoro-1,1,3,3-tetramethyl-2,3-dihydro-1H-indene (C8-7)

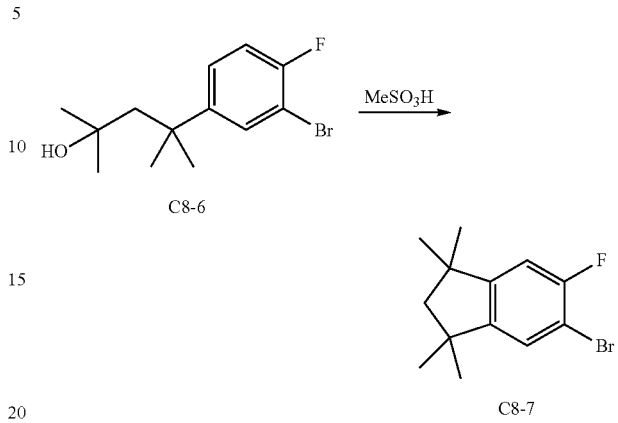

A mixture of compound C8-6 (580 mg, 2.006 mmol) in methanesulfonic acid (30 mL) was stirred at 0° C. for 30 min and then allowed to warm to 20° C. for 10 hours. Then the mixture was poured into ice-water and extracted with EtOAc (3×50 mL). The combined organic fractions were washed with brine, dried over Na$_2$SO$_4$, and filtered. The filtrate was concentrated under reduced pressure. The resulting crude product was purified by chromatography over silica gel (eluting with PE:EtOAc=20:1 to 5:1) to give compound C8-7.

Step G: ethyl 6-fluoro-1,1,3,3-tetramethyl-2,3-dihydro-1H-indene-5-carboxylate (C8-8)

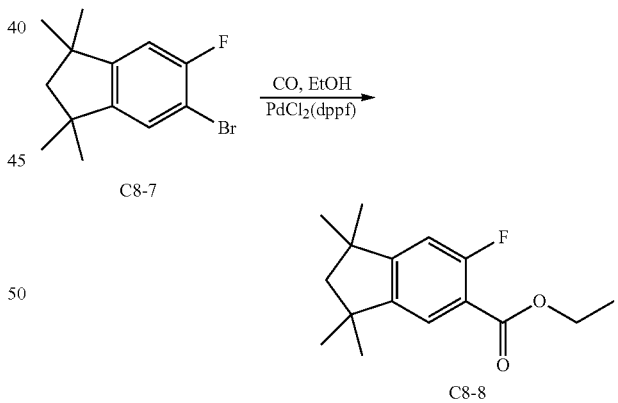

A mixture of compound C8-7 (480 mg, 1.770 mmol), PdCl$_2$(dppf) (130 mg, 0.177 mmol), sodium acetate (363 mg, 4.43 mmol) and EtOH (40 mL) was stirred at 80° C. for 20 h under CO (50 Psi) atmosphere. The mixture was cooled, concentrated, and water (30 mL) was added. The resulting mixture was extracted with EtOAc (3×30 mL). The combined organic fractions were washed with brine, dried over Na$_2$SO$_4$, and filtered. The filtrate was concentrated under reduced pressure. The resulting crude product was purified by chromatography over silica gel (eluting with PE:EtOAc=99:1 to 90:10) to give compound C8-8.

Step H: (6-fluoro-1,1,3,3-tetramethyl-2,3-dihydro-1H-inden-5-yl)methanol (C8-9)

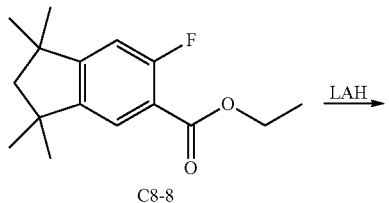

LAH (25.8 mg, 0.681 mmol) was added to a cooled to 0° C. mixture of compound C8-8 (90 mg, 0.340 mmol) in THF (3 mL). After the addition was complete, the mixture was stirred at 0° C. for one hour. Then the mixture was quenched by the addition of Na$_2$SO$_4$ (1 g) and water (2 mL), and the mixture was filtered, and washed with EtOAc (30 mL). The filtrate was evaporated under reduced pressure to give compound C8-9, which was used in the next step without purification.

Step I: (5aR,6S,6aS)-tert-butyl 3-((6-fluoro-1,1,3,3-tetramethyl-2,3-dihydro-1H-inden-5-yl)methoxy)-5,5a,6,6a-tetrahydrocyclopropa[4,5]cyclopenta[1,2-c]pyridine-6-carboxylate (C8-10)

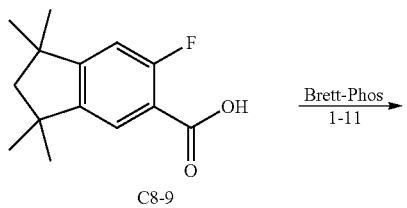

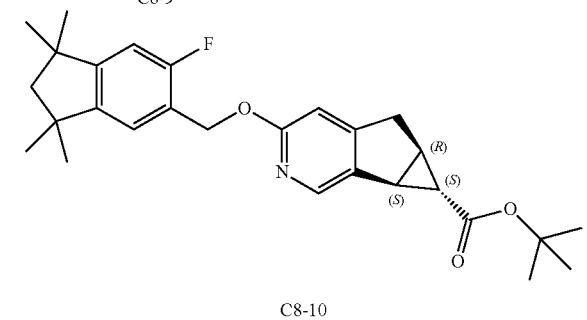

A mixture of C8-9 (60 mg, 0.270 mmol), intermediate 1-11 (86 mg, 0.324 mmol), Cs$_2$CO$_3$ (88 mg, 0.270 mmol), Brett-Phos Palladacycle (21.56 mg, 0.027 mmol) and toluene (3 mL) was stirred at 110° C. for 12 h under N$_2$. Then the mixture was cooled, water (10 mL) was added, and the mixture was extracted with EtOAc (3×20 mL). The combined organic layers were washed with brine, dried over Na$_2$SO$_4$, and filtered. The filtrate was concentrated under reduced pressure to give the crude product. The crude product was purified by chromatography over silica gel (eluting with PE:EtOAc=99:1 to 70:30) to give compound C8-10. MS (ESI) m/e (M+H$^+$): 452.2.

Step J: (5aR,6S,6aS)-3-((6-fluoro-1,1,3,3-tetramethyl-2,3-dihydro-1H-inden-5-yl)methoxy)-5,5a,6,6a-tetrahydrocyclopropa[4,5]cyclopenta[1,2-c]pyridine-6-carboxylic acid (C8-11)

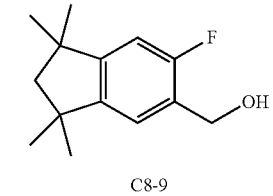

A mixture of compound C8-10 (85 mg, 0.188 mmol) and lithium hydroxide monohydrate (79 mg, 1.882 mmol) in THF (2 mL), MeOH (1.5 mL) and water (1.5 mL) was stirred at 50° C. for 12 hours. The reaction mixture was cooled to 20° C., neutralized with HCl aq. (1 M) to pH=7, and extracted with EtOAc (3×20 mL). The combined organic layers were washed with brine, dried over Na$_2$SO$_4$ and concentrated to give a residue, which was purified by reverse preparative HPLC (preparative HPLC on an instrument fitted with a YMC-Actus Triart C18 150*30 mm*5 um using water and acetonitrile as the eluents. Mobile phase A: water (containing 0.1% TFA, v/v) mobile phase B: acetonitrile. Gradient: 44-74% B, 0-10 min; 100% B, 10.5-12.5 min; 5% B, 13-15 min) to give compound C8-11. $^1$H NMR (400 MHz, MeOH-d$_4$) δ 8.10 (s, 1H), 7.21 (d, J=6.65 Hz, 1H), 6.85 (d, J=10.17 Hz, 1H), 6.81 (s, 1H), 5.28 (s, 2H), 3.26 (m, 1H), 3.02-3.13 (m, 1H), 2.94 (d, J=4.70 Hz, 1H), 2.45 (d, J=2.74 Hz, 1H), 1.93 (s, 2H), 1.27 (d, J=4.70 Hz, 12H), 1.18 (t, J=2.54 Hz, 1H). MS (ESI) m/e (M+H$^+$): 396.2.

Example 77

(5aR,6S,6aS)-3-((5-fluoro-1-(2-(trifluoromethyl)phenyl)-1H-indazol-6-yl)methoxy)-5,5a,6,6a-tetrahydrocyclopropa[4,5]cyclopenta[1,2-c]pyridine-6-carboxylic acid (C9-9)

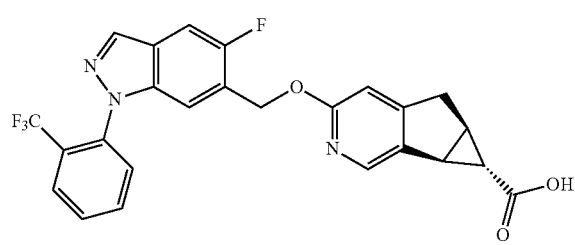 [SMILES: O=C(O)[C@H]1[C@@H]2Cc3cc(OCc4cc5c(cnn5-c5ccccc5C(F)(F)F)cc4F)ncc3[C@@H]21]

Step A: 6-bromo-5-fluoro-1-(4-nitro-2-(trifluoromethyl)phenyl)-1H-indazole (C9-2)

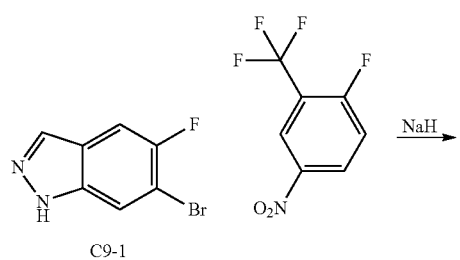

NaH (209 mg, 5.23 mmol) (60% in oil) was added to a stirred, cooled 0° C. mixture of commercially available 6-bromo-5-fluoro-1H-indazole C9-1 (750 mg, 3.49 mmol) in DMF (5 mL). The mixture was stirred at 0° C. for 15 min, then 1-fluoro-4-nitro-2-(trifluoromethyl)-benzene (729 mg, 3.49 mmol) was added and the mixture was further stirred for 2 h at 0° C. The mixture was poured into water (70 mL), filtered, washed with water (30 mL) and the filtrate concentrated to give a crude product, which was purified by chromatography over silica gel (eluting with PE:EtOAc=99:1 to 9:1) to give compound C9-2.

Step B: 4-(6-bromo-5-fluoro-1H-indazol-1-yl)-3-(trifluoromethyl)aniline (C9-3)

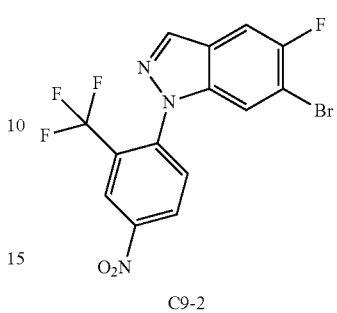

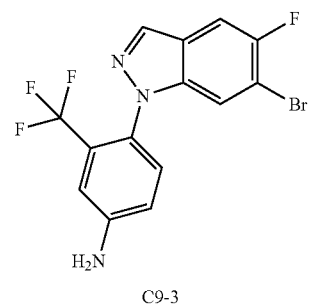

A mixture of 6-bromo-5-fluoro-1-(4-nitro-2-(trifluoromethyl)phenyl)-1H-indazole C9-2 (700 mg, 1.732 mmol), iron (484 mg, 8.66 mmol) and ammonium chloride (927 mg, 17.32 mmol) in EtOH (20 mL) and water (4 mL) was stirred at 80° C. for 2 h. The mixture was cooled, filtered, washed with EtOH (20 mL) and the filtrate was concentrated under reduced pressure. The resulting residue was washed with water (30 mL) and the mixture was extracted with EtOAc (3×50 mL). The combined organic layers were washed with brine, dried over $Na_2SO_4$, filtered and the filtrate was concentrated under reduced pressure to give compound C9-3, which was used in the next step without further purification. MS (ESI) m/e (M+H$^+$+41): 415, 417.

Step C: 6-bromo-5-fluoro-1-(2-(trifluoromethyl)phenyl)-1H-indazole (C9-4)

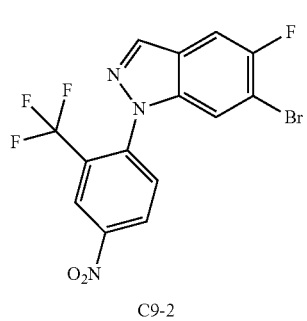

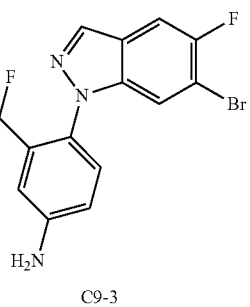

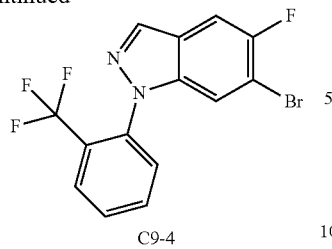

C9-4

A mixture of C9-3 (600 mg, 1.604 mmol) and tert-butyl nitrite (248 mg, 2.406 mmol) in DMF (4 mL) was stirred at 60° C. for 1 h. The mixture was cooled, water (20 mL) was added and the mixture was extracted with EtOAc (3×50 mL). The combined organic layers were washed with water (2×30 mL), dried over Na$_2$SO$_4$, filtered and the filtrate was concentrated under reduced pressure. The resulting crude product was purified by chromatography over silica gel (eluting with PE:EtOAc=99:1 to 9:1) to afford compound C9-4.

Step D: methyl 5-fluoro-1-(2-(trifluoromethyl)phenyl)-1H-indazole-6-carboxylate (C9-5)

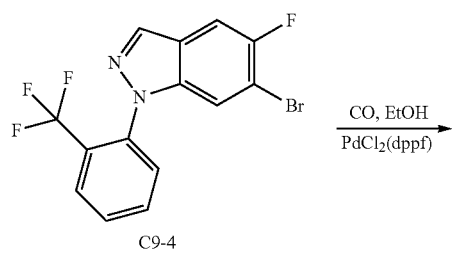

C9-4

C9-5

A mixture of compound C9-4 (550 mg, 1.532 mmol), PdCl$_2$(dppf) (112 mg, 0.153 mmol) and sodium acetate (0.205 ml, 3.83 mmol) in EtOH (50 mL) was stirred at 80° C. for 24 h under a CO (50 psi) atmosphere. The mixture was cooled and the solvent was evaporated under reduced pressure. Water (20 mL) was added and the mixture was extracted with EtOAc (3×30 mL). The combined organic layers were washed with brine, dried over Na$_2$SO$_4$, filtered and the filtrate was evaporated under reduced pressure. The resulting crude product was purified by chromatography over silica gel (eluting with PE:EtOAc=99:1 to 9:1) to provide compound C9-5.

Step E: (5-fluoro-1-(2-(trifluoromethyl)phenyl)-1H-indazol-6-yl)methanol (C9-6)

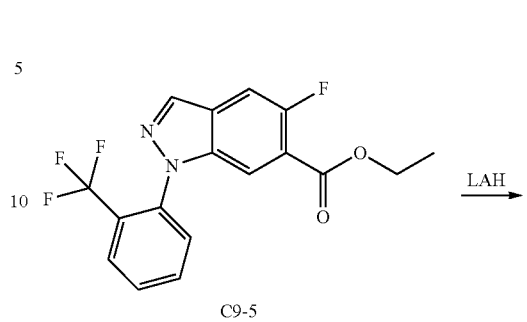

C9-5

C9-6

LAH (43.1 mg, 1.135 mmol) was added to a stirred, cooled 0° C. mixture of compound C9-5 (200 mg, 0.568 mmol) in THF (3 mL) and the mixture was stirred at 0° C. for 2 h. Then the mixture was quenched with Na$_2$SO$_4$ (500 mg) and water (1 mL). The resulting mixture was filtered and the filtrate was evaporated under reduced pressure to give compound C9-6, which was used in the next step without further purification. MS (ESI) m/e (M+H$^+$+41): 311.1.

Step F: 6-(bromomethyl)-5-fluoro-1-(2-(trifluoromethyl)phenyl)-1H-indazole (C9-7)

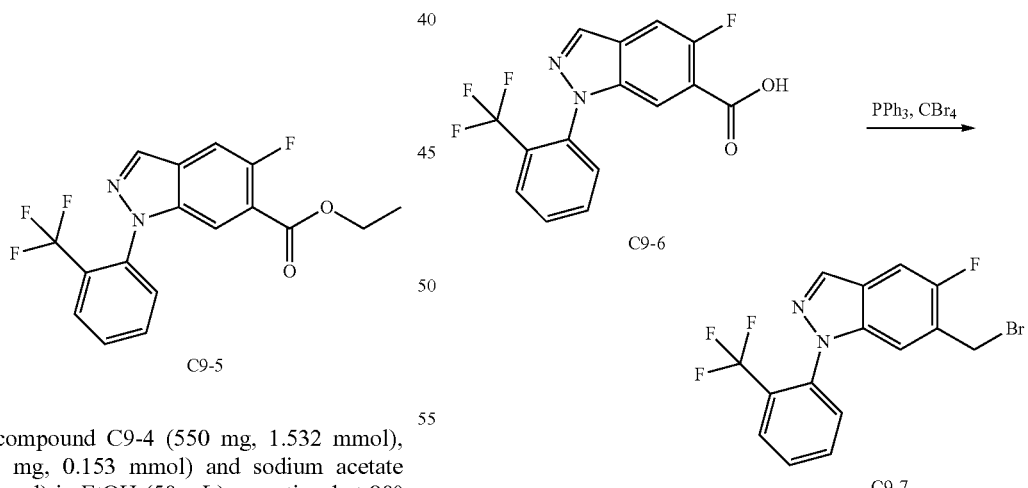

C9-6

C9-7

Triphenylphosphine (298 mg, 1.135 mmol) was added to a stirred, cooled 0° C. mixture of compound C9-6 (176 mg, 0.567 mmol) and tetrabromomethane (377 mg, 1.135 mmol) in DCM (2 mL). The reaction mixture was stirred at 0° C. for 5 h, then concentrated and directly purified by chromatography over silica gel (eluting with PE:EtOAc=99:1 to 9:1) to provide compound C9-7. MS (ESI) m/e (M+H$^+$): 373.1, 375.1.

Step G: (5aR,6S,6aS)-ethyl-3-((5-fluoro-1-(2-(trifluoromethyl)phenyl)-1H-indazol-6-yl)methoxy)-5,5a,6,6a-tetrahydrocyclopropa[4,5]cyclopenta[1,2-c]pyridine-6-carboxylate (C9-8)

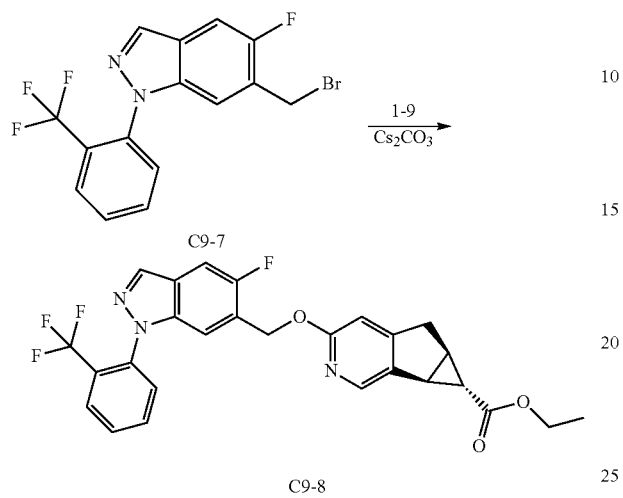

A mixture of compound C9-8 (45 mg, 0.121 mmol), intermediate 1-9 (29.8 mg, 0.121 mmol) and silver carbonate (100 mg, 0.362 mmol) in toluene (2 mL) was stirred at 100° C. for 12 h. Then the mixture was cooled, filtered, washed with EtOAc (20 mL) and the filtrate was evaporated under reduced pressure. The resulting crude product was purified by chromatography over silica gel (eluting with PE:EtOAc=99:1 to 75:25) to provide compound C9-8.

Step H: (5aR,6S,6aS)-3-((5-fluoro-1-(2-(trifluoromethyl)phenyl)-1H-indazol-6-yl)methoxy)-5,5a,6,6a-tetrahydrocyclopropa[4,5]cyclopenta-[1,2-c]pyridine-6-carboxylic acid (C9-9)

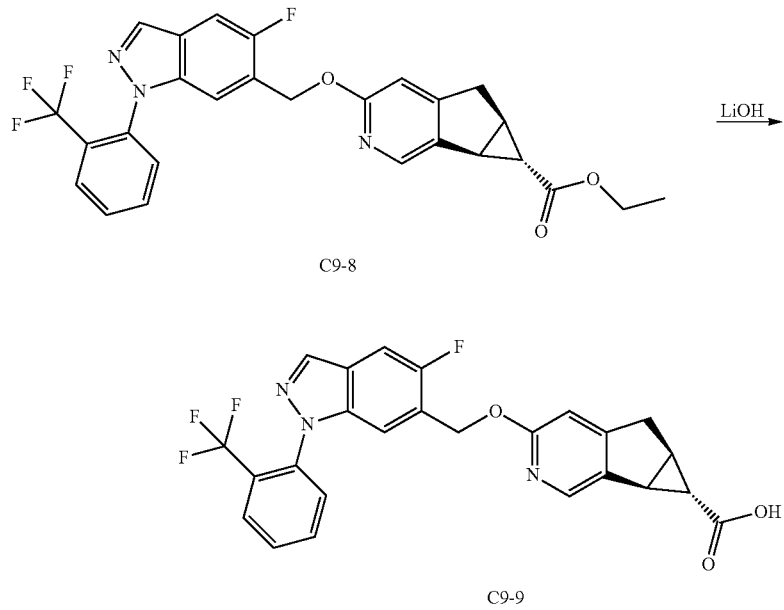

A mixture of compound C9-8 (50 mg, 0.093 mmol) and lithium hydroxide monohydrate (38.9 mg, 0.927 mmol) in THF (1 mL), MeOH (1 mL) and water (1 mL) was stirred at 45° C. for 3 hours. Then the reaction mixture was cooled to 20° C., neutralized with HCl aq. (1 M) to pH=7, and extracted with EtOAc (3×20 mL). The combined organic layers were washed with brine, dried over Na$_2$SO$_4$, filtered and the filtrate was evaporated under reduced pressure. The resulting residue was purified by reverse preparative HPLC (preparative HPLC on an instrument fitted with a Waters Xbridge Prep OBD C18 150*30 5 um using water and acetonitrile as the eluents. Mobile phase A: water (containing 0.1% NH$_3$.H$_2$O, v/v), B: acetonitrile. Gradient: 20-50% B, 0-10 min; 100% B, 10.5-12.5 min; 5% B, 13-15 min) to provide compound C9-9. $^1$H NMR (400 MHz, MeOH-d$_4$) δ 8.24 (s, 1H), 7.93-8.04 (m, 2H), 7.71-7.90 (m, 2H), 7.47-7.62 (m, 2H), 7.28 (d, J=5.09 Hz, 1H), 6.64 (s, 1H), 5.41 (s, 2H), 3.20 (dd, J=6.06, 18.59 Hz, 1H), 2.93-3.06 (m, 1H), 2.84 (d, J=5.48 Hz, 1H), 2.36 (br. s., 1H), 1.07 (br. s., 1H). MS (ESI) m/e (M+H$^+$): 484.2.

Example 78

(5aR,6S,6aS)-3-((5-fluoro-1-(2-(trifluoromethyl)benzyl)-1H-indol-6-yl)methoxy)-5,5a,6,6a-tetrahydrocyclopropa[4,5]cyclopenta[12-c]pyridine-6-carboxylic acid (C10-7)

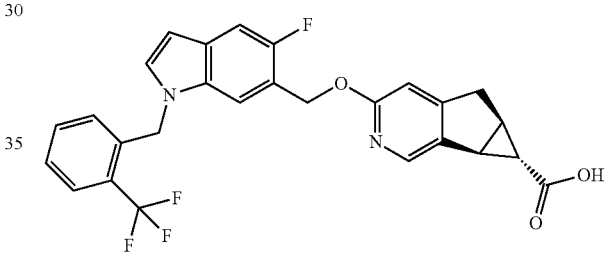

Step A: (2-(trifluoromethyl)phenyl)methanol (C10-1)

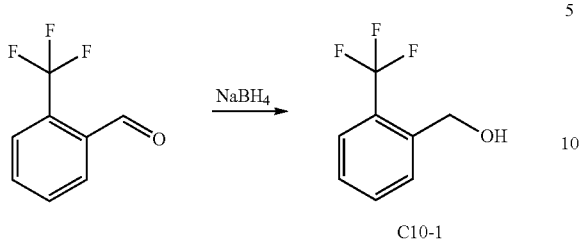

C10-1

NaBH$_4$ (0.435 g, 11.49 mmol) was added to a stirred, cooled 0° C. mixture of 2-(trifluoromethyl) benzaldehyde (1 g, 5.74 mmol) in MeOH (10 ml) and the mixture was stirred at 20° C. for 2 h. The reaction mixture was concentrated in vacuo, washed with water (30 ml), and extracted with EtOAc (3×50 mL). The combined organic layers were washed with brine, dried over Na$_2$SO$_4$, filtered and the filtrate was evaporated under reduced pressure to give a crude product. The crude product was purified by chromatography over silica gel (eluting with PE:EtOAc=99:1 to 70:30) to give compound C10-1.

Step B: 1-(bromomethyl)-2-(trifluoromethyl)benzene (C10-2)

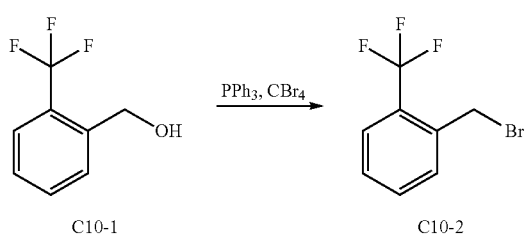

Triphenylphosphine (1899 mg, 7.24 mmol) was added to a cooled to 0° C. mixture of compound C10-1 (850 mg, 4.83 mmol), followed by CBr$_4$ (1920 mg, 5.79 mmol) in DCM (10 ml) under N$_2$. The reaction mixture was stirred at 0° C. for 1 h, then concentrated in vacuo to give the crude product. The crude product was purified by chromatography over silica gel (eluting with PE:EtOAc=99:1 to 85:15) to provide compound C10-2.

Step C: 6-bromo-5-fluoro-1-(2-(trifluoromethyl)benzyl)-1H-indole (C10-3)

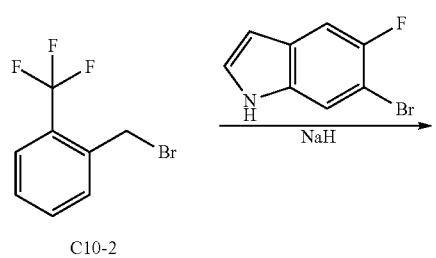

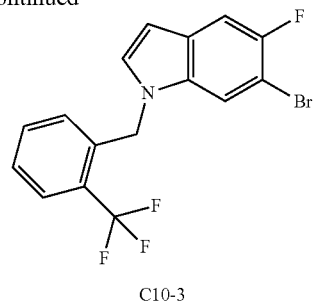

C10-3

To a solution of commercially available 6-bromo-5-fluoro-1H-indole (500 mg, 2.336 mmol) in DMF (10 ml) was added NaH (112 mg, 2.80 mmol) at 0° C. for 1 h. To the reaction mixture was added compound C10-2 (585 mg, 2.453 mmol) at 0° C. and the reaction mixture was stirred for 1 h at 0° C. Then water (10 mL) was added and the mixture was extracted with EtOAc (3×30 mL). The combined organic layers were washed with water, dried over Na$_2$SO$_4$, filtered and the filtrate was evaporated under reduced pressure to give a crude product, that was purified by chromatography over silica gel (eluting with PE:EtOAc=99:1 to 9:1) to give compound C10-3.

Step D: ethyl 5-fluoro-1-(2-(trifluoromethyl)benzyl)-1H-indole-6-carboxylate (C10-4)

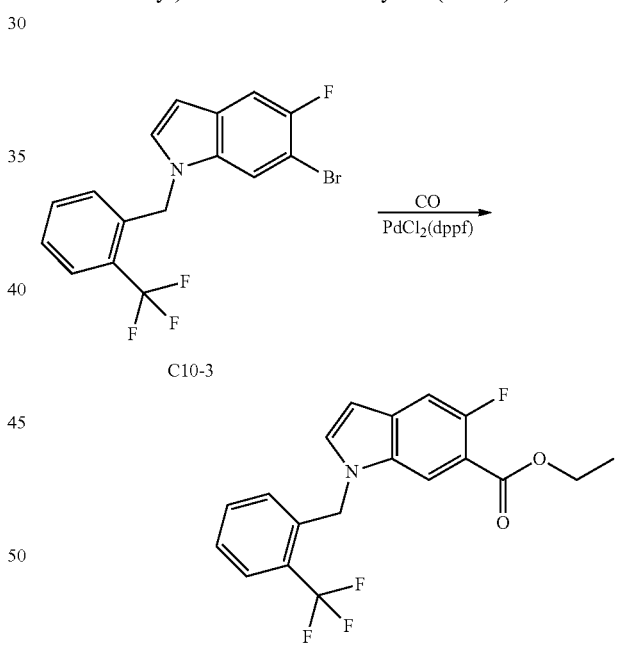

A mixture of compound C10-3 (230 mg, 0.618 mmol), sodium acetate (0.083 ml, 1.545 mmol) and PdCl$_2$(dppf) (90 mg, 0.124 mmol) in EtOH (20 ml) was stirred at 80° C. under CO (50 psi) for 24 h. The reaction mixture was cooled, and evaporated under reduced pressure. Then, water (10 mL) was added and the mixture was extracted with EtOAc (3×20 mL). The combined organic layers were washed with brine, dried over Na$_2$SO$_4$, filtered and the filtrate was evaporated under reduced pressure to give a residue that was purified by chromatography over silica gel (eluting with PE:EtOAc=99:1 to 85:15) to provide compound C10-4.

Step E: (5-fluoro-1-(2-(trifluoromethyl)benzyl)-1H-indol-6-yl)methanol (C10-5)

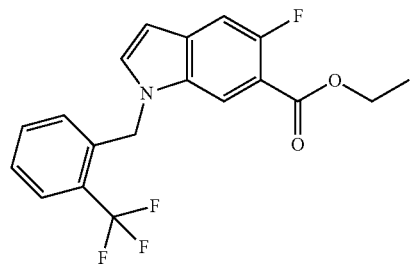

C10-4

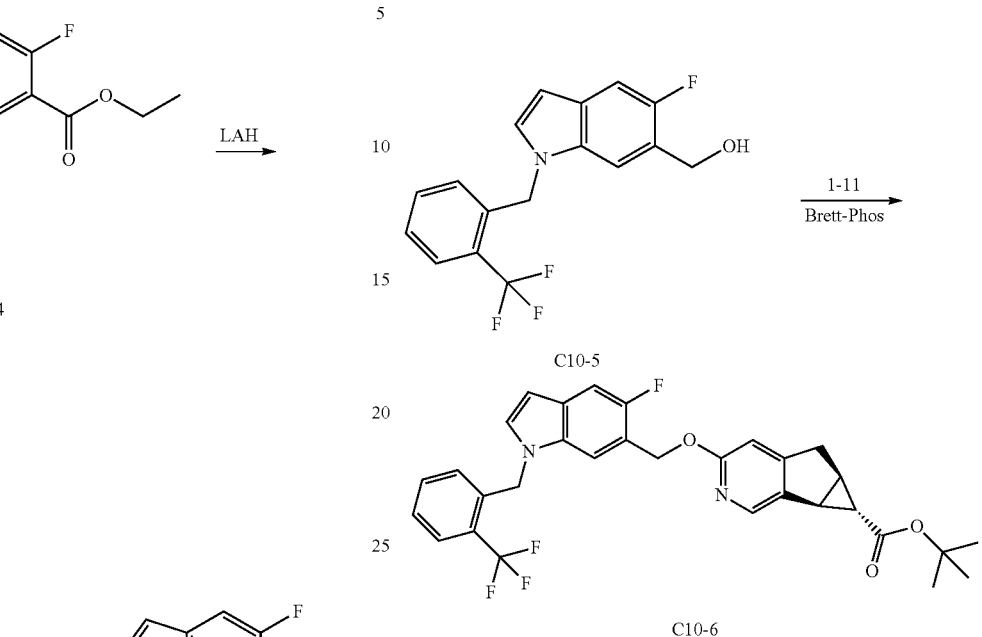

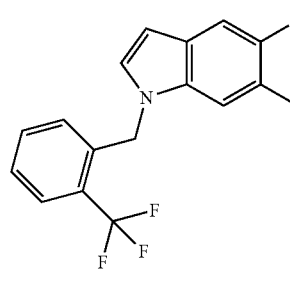

C10-5

To a solution of compound Cl 0-4 (160 mg, 0.438 mmol) in THF (3 ml) at 0° C. was added LAH (33.2 mg, 0.876 mmol) and the mixture was stirred for 1 h. Then the reaction mixture was quenched with Na$_2$SO$_4$ (2.5 g) and water (1 mL), filtered, and extracted with EtOAc (30 mL). The filtrate was concentrated under reduced pressure to give the crude compound C10-5, which was used in the next step without further purification.

Step F: (5aR,6S,6aS)-tert-butyl 3-((5-fluoro-1-(2-(trifluoromethyl)benzyl)-1H-indol-6-yl)methoxy)-5,5a,6,6a-tetrahydrocyclopropa[4,5]cyclopenta[1,2-c]pyridine-6-carboxylate (C10-6)

Brett-Phos Palladacycle (19.38 mg, 0.024 mmol) was added to a mixture of compound C10-5 (58.8 mg, 0.182 mmol), intermediate 1-11 (30 mg, 0.121 mmol) and Cs$_2$CO$_3$ (119 mg, 0.364 mmol) in toluene (5 mL). The mixture was stirred at 110° C. for 12 h, then cooled to room temperature, and filtered over Celite™. The filtrate was diluted with EtOAc (30 mL) and water (10 mL). The aqueous layer was separated and extracted with EtOAc (2×20 mL). The combined organic layers were washed with brine, dried over Na$_2$SO$_4$, filtered and concentrated in vacuo to give the crude product, that was purified by preparative TLC over silica gel (eluting with PE:EtOAc=5:1) to give compound C10-6. MS (ESI) m/e (M+H$^+$): 553.3.

Step G: (5aR,6S,6aS)-3-((5-fluoro-1-(2-(trifluoromethyl)benzyl)-1H-indol-6-yl)methoxy)-5,5a,6,6a-tetrahydrocyclopropa[4,5]cyclopenta[1,2-c]pyridine-6-carboxylic acid (C10-7)

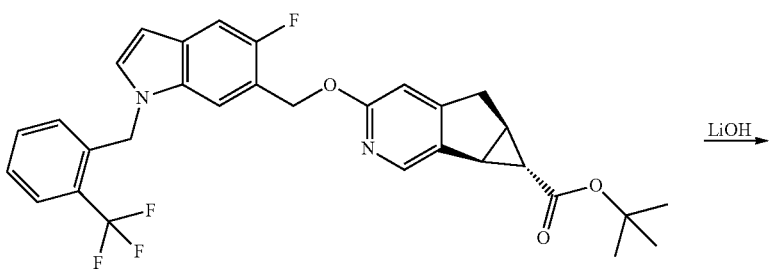

C10-6

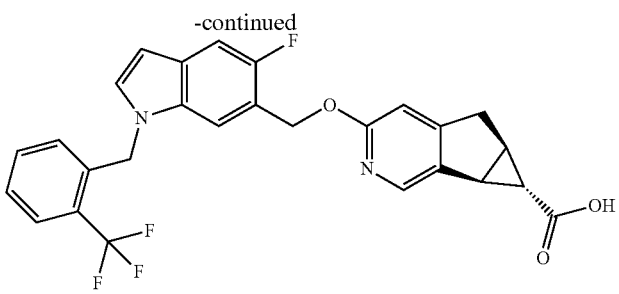

C10-7

A mixture of compound C10-6 (32 mg, 0.058 mmol) and LiOH.H₂O (24.30 mg, 0.579 mmol) in THF (3 ml), MeOH (1 ml) and water (1 ml) was stirred at 50° C. for 16 hours. After cooling to room temperature, the mixture was acidified with 2N HCl to pH=6, and extracted with EtOAc (2×20 mL). The combined organic layers were washed with brine, dried over anhydrous Na₂SO₄, filtered and the filtrate was evaporated under reduced pressure to give the crude product. The crude product was purified by preparative HPLC (on a GILSON 281 instrument fitted with a Waters Xbridge Prep OBD C18 150*30 5 um using water and acetonitrile as the eluents. Mobile phase A: water (containing 0.005 NH₃H₂O v/v), mobile phase B: acetonitrile. Gradient: 30-60% B, 0-10 min; 100% B, 10.5-12.5 min; 5% B, 13-15 min) to give compound C10-7. ¹H NMR (400 MHz, MeOH-d4) δ 7.88 (s, 1H), 7.78-7.71 (m, 1H), 7.45-7.38 (m, 1H), 7.34 (d, J=2.7 Hz, 2H), 7.32-7.26 (m, 1H), 7.23-7.18 (m, 1H), 6.57 (s, 2H), 6.52-6.46 (m, 1H), 5.57 (s, 2H), 5.36 (s, 2H), 3.23-3.14 (m, 1H), 3.03-2.94 (m, 1H), 2.87-2.82 (m, 1H), 2.42-2.35 (m, 1H), 1.12-1.06 (m, 1H). MS (ESI) m/e (M+H⁺): 497.2.

Example 79

(5aR,6S,6aS)-3-(((1S,3S)-1-(dimethylamino)-6-fluoro-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid, or (5aR,6S,6aS)-3-(((1R,3R)-1-(dimethylamino)-6-fluoro-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (C11-8-1)

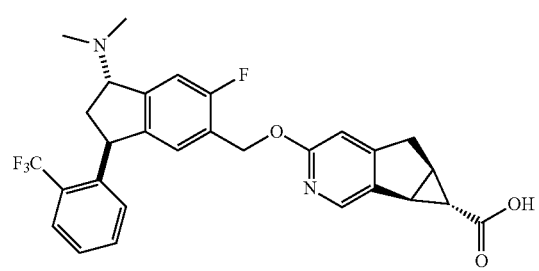

C11-8-1a and

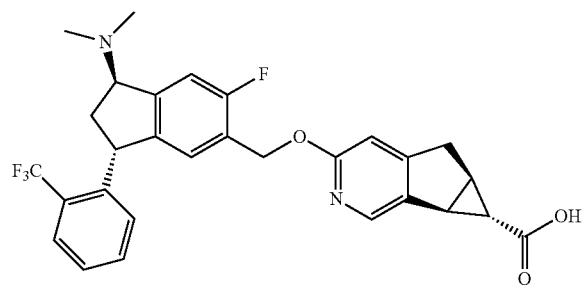

C11-8-1b

Step A: ethyl 6-fluoro-1-hydroxy-3-(2-(trifluoromethyl)phenyl)-2,3-dihydro-1H-indene-5-carboxylate (C11-1)

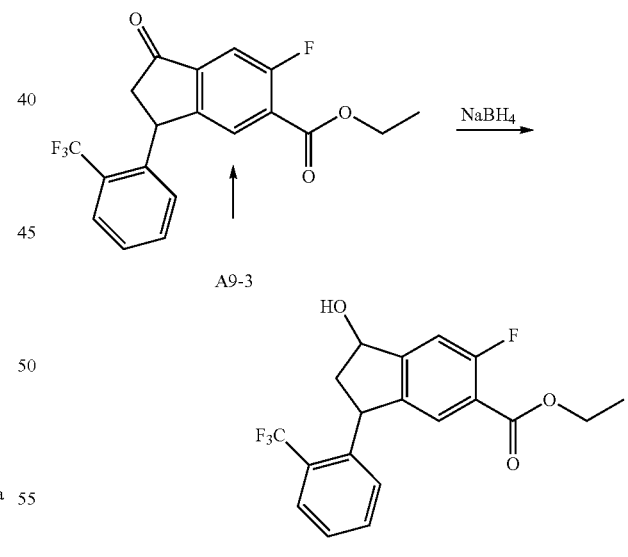

Sodium tetrahydroborate (0.310 g, 8.19 mmol) was added to a cooled 0° C. mixture of ethyl-6-fluoro-1-oxo-3-(2-(trifluoromethyl)phenyl)-2,3-dihydro-1H-indene-5-carboxylate (1.5 g, 4.09 mmol, prepared from A9-3 according to the procedure of Example 1, Step B) in THF (10 mL). The mixture was stirred at 0° C. for 45 min, then diluted with water (20 mL) and extracted with EtOAc (2×50 mL). The combined organic layers were washed with brine, dried over Na₂SO₄, filtered and the filtrate was evaporated under reduced pressure to give the crude product. The crude product was purified by chromatography over silica gel (eluting with PE:EtOAc=10:1) to give compound C11-1. MS(ESI) m/e (M+H⁺): 369.0.

Step B: ethyl 1-bromo-6-fluoro-3-(2-(trifluoromethyl)phenyl)-2,3-dihydro-1H-indene-5-carboxylate (C11-2)

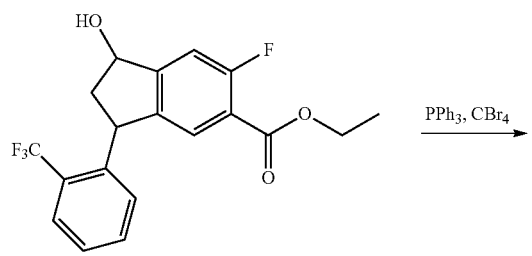

C11-1

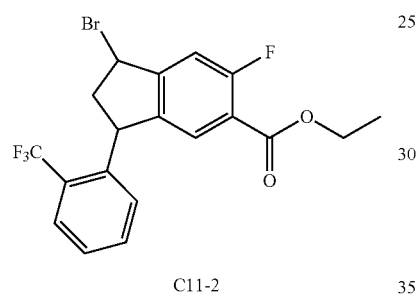

C11-2

Triphenylphosphine (1.685 g, 6.42 mmol) was added to a mixture of compound C11-1 (1.5 g, 4.28 mmol) and tetrabromomethane (1.704 g, 5.14 mmol) in DCM (10 ml) at 0° C. and the mixture was stirred at 0° C. for 2 h. Then the mixture was concentrated and the resulting residue was purified by chromatography over silica gel (eluting with PE:EtOAc=5:1) to give compound C11-2.

Step C: cis-ethyl 1-(dimethylamino)-6-fluoro-3-(2-(trifluoromethyl)phenyl)-2,3-dihydro-1H-indene-5-carboxylate (C11-3) & trans-ethyl 1-(dimethylamino)-6-fluoro-3-(2-(trifluoromethyl)phenyl)-2,3-dihydro-1H-indene-5-carboxylate (C11-4)

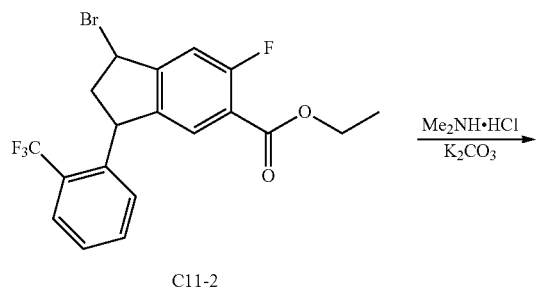

C11-2

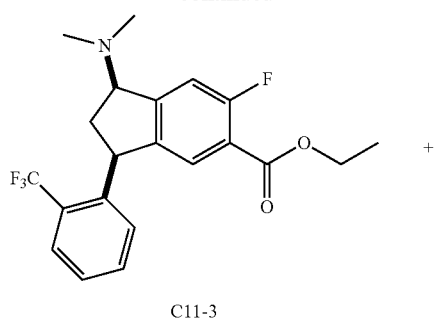

C11-3

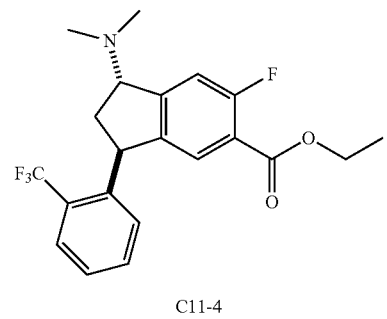

C11-4

K₂CO₃ (2.404 g, 17.39 mmol) was added to a mixture of compound C11-2 (1.5 g, 3.48 mmol), dimethylamine hydrochloride (0.851 g, 10.44 mmol) and tetrabutyl ammonium iodide (0.642 g, 1.739 mmol) in DMF (10 mL) at 0° C. and the mixture was stirred at 0° C. for 30 min. Then the reaction mixture was warmed to room temperature over 12 h., diluted with EtOAc (20 mL), washed with water, brine, dried over Na₂SO₄ and concentrated. The resulting residue was purified by chromatography over silica gel (eluting with PE:EtOAc=5:1) to give compounds C11-3 and C11-4.

Step D: trans-1-(dimethylamino)-6-fluoro-3-(2-(trifluoromethyl)phenyl)-2,3-dihydro-1H-inden-5-yl)methanol (C11-5)

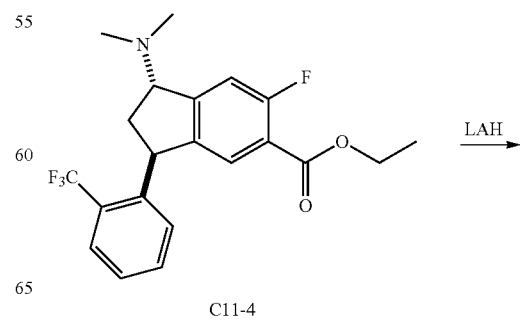

C11-4

-continued

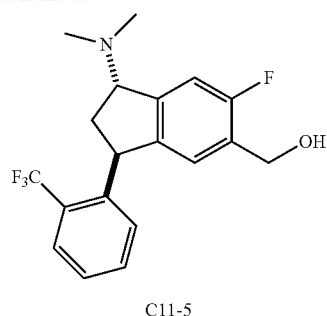

C11-5

LAH (202 mg, 5.31 mmol) was added to a mixture of compound C11-4 (700 mg, 1.770 mmol) in THF (20 mL) at 0° C. and the reaction was stirred for 4 hours. Then Na$_2$SO$_4$ (0.5 g) and water (2 ml) were added dropwise, and the resulting mixture was filtered. The filtrate was evaporated under reduced pressure to give a crude residue, which was purified by chromatography over silica gel (eluting with PE:EtOAc=99:1 to 70:30) to give compound C11-5.

Step E: (5aR,6S,6aS)-tert-butyl 3-((trans-1-(dimethylamino)-6-fluoro-3-(2-(trifluoromethyl)phenyl)-2,3-dihydro-1H-inden-5-yl)methoxy)-5,5a,6,6a-tetrahydrocyclopropa-[4,5]cyclopenta[1,2-c]pyridine-6-carboxylate (C11-6)

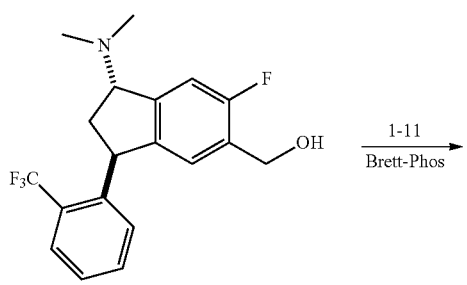

C11-5

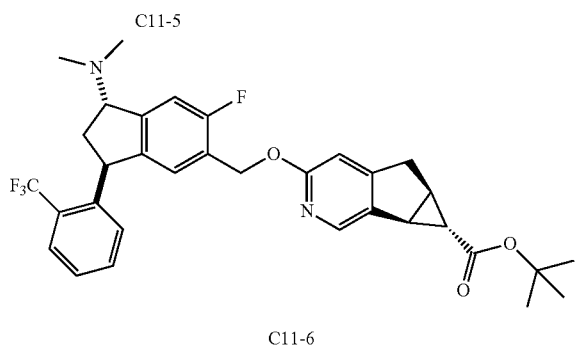

C11-6

A mixture of compound C11-5 (300 mg, 0.849 mmol), intermediate 1-11 (293 mg, 1.104 mmol), Brett-Phos Palladacycle (67.8 mg, 0.085 mmol) and Cs$_2$CO$_3$ (830 mg, 2.55 mmol) in toluene (10 mL) was heated to 100° C. for 16 h. Then the reaction was filtered and the filtrate was concentrated to give a residue that was purified by prep-HPLC (TFA condition) to give compound C11-6. MS(ESI) m/e (M+H$^+$): 583.0.

Step F: ((5aR,6S,6aS)-tert-butyl 3-(((1S,3S)-1-(dimethylamino)-6-fluoro-3-(2-(trifluoro-methyl)phenyl)-2,3-dihydro-1H-inden-5-yl)methoxy)-5,5a,6,6a-tetrahydrocyclopropa[4,5]-cyclopenta[1,2-c]pyridine-6-carboxylate and ((5aR,6S,6aS)-tert-butyl 3-(((1R,3R)-1-(dimethylamino)-6-fluoro-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylate, and ((5aR,6S,6aS)-tert-butyl 3-(((1R,3R)-1-(dimethylamino)-6-fluoro-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylate and (5aR,6S,6aS)-tert-butyl 3-(((1R,3R)-1-(dimethylamino)-6-fluoro-3-(2-(trifluoromethyl)phenyl)-2,3-dihydro-1H-inden-5-yl)methoxy)-5,5a,6,6a-tetrahydrocyclo-propa-[4,5]cyclopenta[1,2-c]pyridine-6-carboxylate (C11-7-1 and C11-7-2, structures unassigned)

C11-7-1

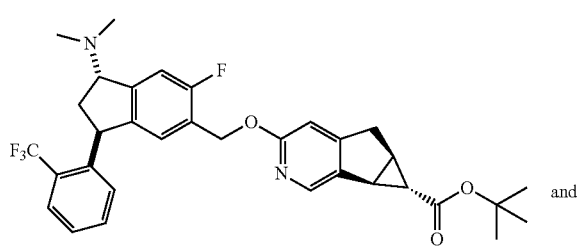

and

C11-7-2

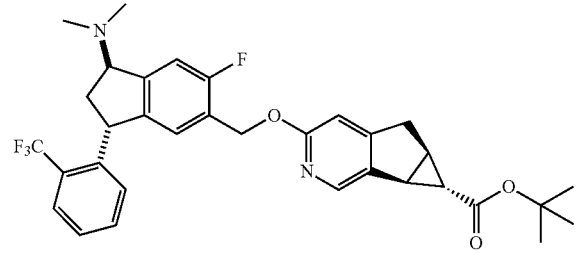

Compound C11-6 (200 mg. 326 mmol) was separated by SFC (Column: ChiralpakAD-H 250×4.6 mm I.D., 5 um Mobile phase: methanol (0.05% DEA) in CO$_2$ from 5% to 40% Flow rate: 2.5 mL/min Wavelength: 230 nm) to give the first eluting compound C11-7-1, followed by compound C11-7-2 (stereochemistry of (CH$_3$)$_2$N substituent and 2-CF3-phenyl substituent not assigned).

Step G: ((5aR,6S,6aS)-3-((((1S,3S)-1-(dimethyl-amino)-6-fluoro-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid, or ((5aR,6S,6aS)-3-((((1R,3R)-1-(dimethylamino)-6-fluoro-3-(2-(trifluoromethyl)phenyl)-2,3-dihydro-1H-inden-5-yl)methoxy)-5,5a,6,6a-tetrahydrocyclopropa[4,5]cyclopenta[1,2-c]pyridine-6-carboxylic acid (C11-8-1)

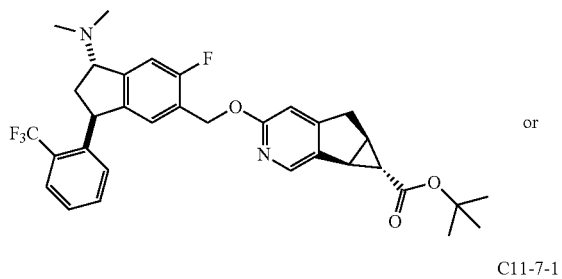

C11-7-1

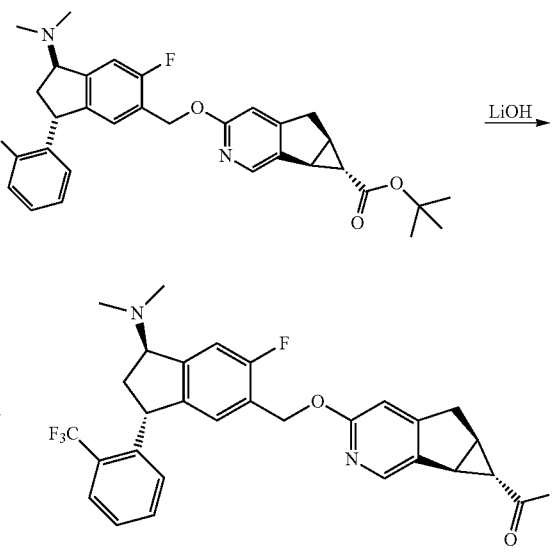

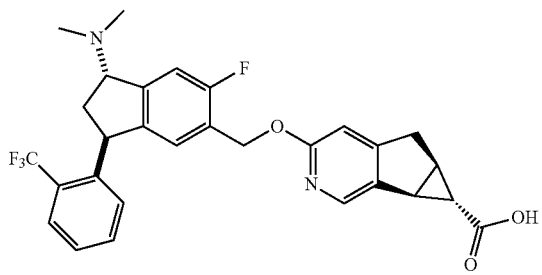

C11-8-1

Lithium hydroxide monohydrate (50.4 mg, 1.20 mmol) was added to a stirred mixture of the first eluting compound of Step F (C11-7-1, 70 mg, 0.120 mmol) in THF (1 mL), MeOH (1 mL) and water (1 mL). The reaction mixture was stirred at 25° C. for 20 h, and then filtered over Celite™. The filtrate was adjusted to pH=6-7, and the filtrate was concentrated to give a residue that was purified by reverse preparative HPLC (on an instrument fitted with a YMC-Actus Triart C18 150*30 mm*5 um using water and acetonitrile as the eluents. Mobile phase A: water (containing 0.1% TFA, v/v) mobile phase B: acetonitrile. Gradient: 44-74% B, 0-10 min; 100% B, 10.5-12.5 min; 5% B, 13-15 min) to give compound C11-8-1. $^1$HNMR (400 MHz, CD$_3$OD) δ 1.12 (br. s., 1H) 2.41-2.47 (m, 1H) 2.48-2.60 (m, 1H) 2.72-2.95 (m, 7H) 2.97-3.08 (m, 1H) 2.98-3.07 (m, 2H) 3.23 (d, J=6.26 Hz, 1H) 5.00-5.07 (m, 1H) 5.19 (d, J=7.83 Hz, 1H) 5.32-5.41 (m, 2H) 6.77 (s, 1H) 6.94 (d, J=7.43 Hz, 1H) 7.07 (d, J=6.26 Hz, 1H) 7.43-7.52 (m, 3H) 7.73 (d, J=7.43 Hz, 1H) 7.99 (s, 1H). MS(ESI) m/e (M+H$^+$): 527.0.

Example of a Pharmaceutical Composition

As a specific embodiment of an oral pharmaceutical composition, a 100 mg potency tablet is composed of 100 mg of any one of Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

Biological Assays

Generation of GPR40-Expressing Cells:

Human and mouse GPR40 stable cell-lines were generated in CHO cells stably expressing NFAT BLA (Beta-lactamase). A human GPR40 stable cell-line was generated in HER cells stably expressing the aequorin expressing reporter. The expression plasmids were transfected using lipofectamine (Life Technologies) following manufacturer's instructions. Stable cell-lines were generated following drug selection.

FLIPR Assays:

FLIPR (Fluorimetric Imaging Plate Reader, Molecular Devices) assays were performed to measure agonist-induced calcium mobilization of the stable clones. For the FLIPR assay, one day before assay, GPR40/CHO NFAT BLA cells were seeded into black-wall-clear-bottom 384-well plates (Costar) at 1.4×10e4 cells/20 µL medium/well. The cells were incubated with 20 µl/well of the assay buffer (HMS, 0.1% BSA, 20 mM HEPES, 2.5 mM probenecid, pH 7.4) containing 8 µM fluo-4, AM, 0.08% pluronic acid at room temperature for 100 minutes. Fluorescence output was measured using FLIPR. Compounds were dissolved in DMSO and diluted to desired concentrations with assay buffer. 13.3 µL/well of compound solution was added. The compounds in Examples 1-79 have EC$_{50}$ values less than 100 nanomolar (nM) in the FLIPR assay described above and are listed in Table I.

Inositol Phosphate Turnover (IP1) Assay

The assay is performed in 384-well format. HEK cells stably expressing human GPR40 are plated at 15,000 cells per well in growth medium (DMEM/10% fetal calf serum). Cell plates are then incubated 16 hours at 37 degrees in a 5% CO$_2$ incubator.

Measurement of Inositol Phosphate Turnover (IP1) is performed using the CisBio IP-One kit (Part number 62IPA-PEB). After the 16 hour incubation, the cells are washed with HEPES buffer and 10 ul of stimulation buffer (prepared as described in the kit) is added to each well. In a separate plate, compounds are diluted in DMSO (400-fold over the final concentration in the assay well) and 25 nl is acoustically transferred to the appropriate well in the assay cell plate. The plates are then incubated for 60 minutes at 37 degrees. 10 ul of detection buffer (also prepared as described in the IP-One kit) is added to each well and the plates are incubated for 60 minutes in the dark. The plates are then read in a Perkin Elmer EnVision or equivalent reader able to measure FRET. Fluorescent ratio of emission at 665 and 620 nm is then converted to IP1 concentration by back calculating from an IP1 standard curve prepared at the time of the assay. The compounds in Examples 1-79 have $EC_{50}$ values less than 1000 nanomolar (nM) in the Inositol Phosphate Turnover (IP1) Assay described above and are listed in Table I.

In Vivo Studies:

Male C57BL/6N mice (7-12 weeks of age) are housed 10 per cage and given access to normal diet rodent chow and water ad libitum. Mice are randomly assigned to treatment groups and fasted 4 to 6 h. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 min after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

TABLE I

Potency of Examples in Human GPR40 FLIPR and IP1 Assays

| Example Number | Human GPR40, FLIPR, EC50, nM | Human GPR40 IP1, EC50, nM |
|---|---|---|
| 1 | 32.59 | 11.43 |
| 2 | 50.5 | 47.36 |
| 3 | 9.28 | 768.8 |
| 4 | 13.72 | 17.98 |
| 5 | 20.79 | 21.58 |
| 6 | 22.91 | 22.58 |
| 7 | 32.94 | 35.34 |
| 8 | 12.25 | 21.13 |
| 9 | 16.95 | 22.38 |
| 10 | 4.90 | 38.93 |
| 11 | 17.8 | 35.11 |
| 12 | 19.37 | 70.42 |
| 13 | 22.56 | 40.57 |
| 14 | 11.63 | 21.78 |
| 15 | 8.604 | 7.767 |
| 16 | 7.293 | 27.71 |
| 17 | 21.74 | 43.66 |
| 18 | 13.15 | 24.61 |
| 19 | 15.52 | 17.47 |
| 20 | ND | 10.28 |
| 21 | 17.67 | 16.6 |
| 22 | 11.9 | 12.54 |
| 23 | 19.89 | 16.6 |
| 24 | ND | 52.97 |
| 25 | 6.918 | 6.912 |
| 26 | 14.09 | 20.79 |
| 27 | 7.217 | 15.56 |
| 28 | 6.903 | 41.17 |
| 29 | 6.493 | 16.83 |
| 30 | 33.02 | 35.02 |
| 31 | 51.89 | 214.3 |
| 32 | 8.944 | 9.958 |
| 33 | 15.29 | 26.18 |
| 34 | 33.87 | 23.24 |
| 35 | 53.39 | 167.9 |
| 36 | 26.88 | 47.57 |
| 37 | 42.51 | 91.53 |
| 38 | 5.347 | 11.85 |
| 39 | 13.88 | 15.41 |
| 40 | 16.69 | 430.8 |
| 41 | ND | 1.985 |
| 42 | 17.65 | 9.87 |
| 43 | 38.78 | 70.77 |
| 44 | 21.04 | 67.95 |
| 45 | ND | 222.7 |
| 46 | 8.745 | 79.62 |
| 47 | 11.43 | 236.2 |
| 48 | 77.78 | 36.15 |
| 49 | 84.99 | 96.1 |
| 50 | 43.17 | 15.04 |
| 52 | ND | 29.66 |
| 53 | 8.377 | 39.18 |
| 54 | 44.87 | 561.7 |
| 55 | 63.71 | 70.21 |
| 56 | ND | 43.84 |
| 57 | ND | 1.781 |
| 58 | ND | 818.5 |
| 59 | ND | 97.31 |
| 60 | ND | 10.78 |
| 61 | 40.54 | 653.4 |
| 62 | 14.64 | 42.91 |
| 63 | ND | 28.24 |
| 64 | ND | 154 |
| 65 | ND | 124.2 |
| 66 | 9.767 | 72.58 |
| 67 | 28.9 | 169.5 |
| 68 | 24.68 | 64.89 |
| 69 | 1.512 | 8.848 |
| 70 | 5.99 | 15.78 |
| 71 | 13.29 | 205.3 |
| 72 | 5.246 | 5.127 |
| 73 | 18.64 | 21.07 |
| 74 | 6.755 | 4.992 |
| 75 | ND | 157.4 |
| 76 | ND | 17.29 |
| 77 | ND | 7.085 |
| 78 | ND | 195.0 |
| 79 | ND | 15.39 |

ND is not determined

The scope of the claims should not be limited by the preferred embodiments set forth in the examples, but should be given the broadest interpretation consistent with the description as a whole.

While the invention has been described and illustrated with reference to certain particular embodiments thereof, those skilled in the art will appreciate that various adaptations, changes, modifications, substitutions, deletions, or additions of procedures and protocols may be made without departing from the scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention.

The invention claimed is:
1. A compound of structural formula A:

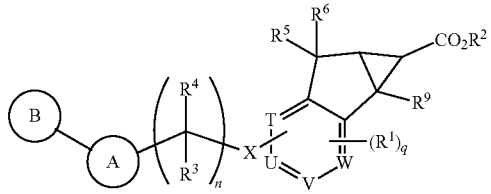

or a pharmaceutically acceptable salt thereof; wherein
X is selected from the group consisting of:
  (1) oxygen, and
  (2) $NR^7$;
T is CH;
U is CH;
V is N;
W is CH;
A is selected from the group consisting of:

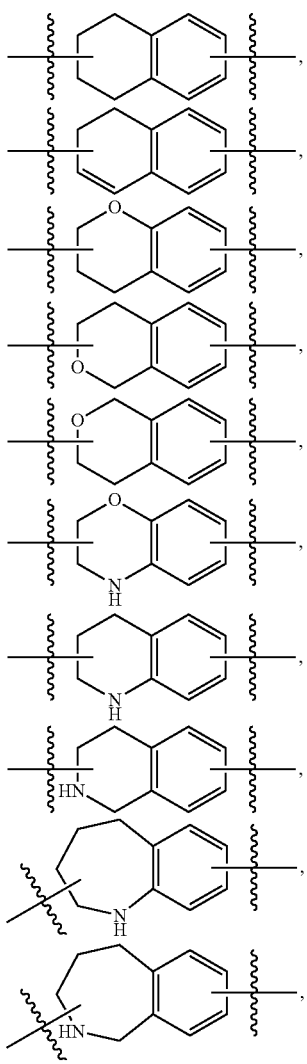

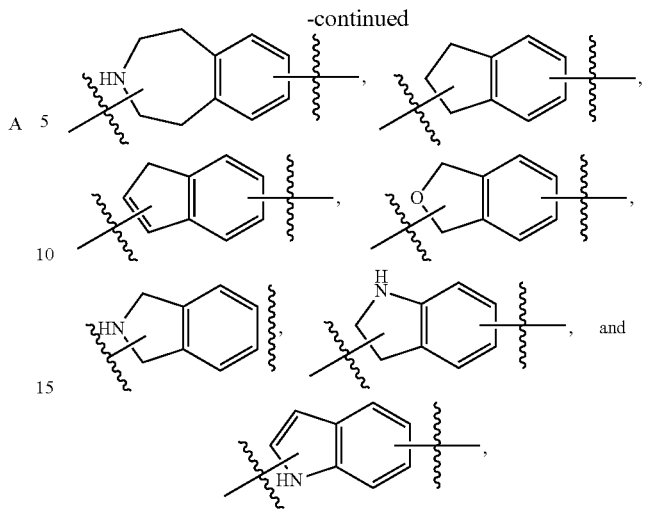

wherein A is unsubstituted or substituted with one to six substituents selected from $R^a$, and wherein two $R^a$ substituents together with the carbon atom to which they are attached may form a 3-6 membered cycloalkyl ring or a 3-6 membered cycloheteroalkyl ring containing 0 to 3 heteroatoms independently selected from oxygen, sulfur, and $NR^8$, and wherein each 3-6 membered cycloalkyl and each 3-6 membered cycloheteroalkyl ring is unsubstituted or substituted with 1 to 4 substituents selected from: —$C_{1-6}$alkyl, —O—$C_{1-6}$ alkyl, halogen and OH;
B is selected from the group consisting of:
  (1) $C_{1-6}$alkyl,
  (2) aryl,
  (3) aryl-O—,
  (4) $C_{3-6}$cycloalkyl-,
  (5) $C_{3-6}$cycloalkyl-$C_{1-10}$alkyl-,
  (6) $C_{3-6}$cycloalkyl-$C_{1-10}$alkyl-O—,
  (7) $C_{2-5}$cycloheteroalkyl-,
  (8) $C_{3-6}$cycloheteroalkyl-$C_{1-10}$alkyl-,
  (9) $C_{3-6}$cycloheteroalkyl-$C_{1-10}$alkyl-O—,
  (10) heteroaryl,
  (11) heteroaryl-O—,
  (12) aryl-$C_{1-10}$ alkyl-, and
  (13) heteroaryl-$C_{1-10}$ alkyl-;
wherein B is unsubstituted or substituted with one to six substituents selected from $R^b$;
each $R^1$ is independently selected from the group consisting of:
  (1) hydrogen,
  (2) halogen,
  (3) —$OR^e$,
  (4) —CN,
  (5) —$C_{1-6}$alkyl, and
  (6) —$C_{3-6}$cycloalkyl,
wherein each alkyl and cycloalkyl is unsubstituted or substituted with one to three substituents selected from $R^i$;
$R^2$ is selected from the group consisting of:
  (1) hydrogen,
  (2) —$C_{1-6}$alkyl, and
  (3) —$C_{3-6}$cycloalkyl,
wherein each alkyl and cycloalkyl is unsubstituted or substituted with one to three substituents selected from $R^j$;

each $R^3$ is independently selected from the group consisting of:
(1) hydrogen,
(2) halogen,
(3) —$OR^e$,
(4) —$C_{1-6}$alkyl,
(5) —$C_{2-6}$alkenyl,
(6) —$C_{2-6}$alkynyl,
(7) —$C_{3-6}$cycloalkyl, and
(8) —$C_{2-6}$cycloheteroalkyl,
wherein each alkyl, alkenyl, alkynyl, cycloalkyl and cycloheteroalkyl is unsubstituted or substituted with one to three substituents selected from $R^L$;
each $R^4$ is independently selected from the group consisting of:
(1) hydrogen,
(2) halogen,
(3) —$OR^e$,
(4) —$C_{1-6}$alkyl,
(5) —$C_{2-6}$alkenyl,
(6) —$C_{2-6}$alkynyl,
(7) —$C_{3-6}$cycloalkyl, and
(8) —$C_{2-6}$cycloheteroalkyl,
wherein each alkyl, alkenyl, alkynyl, and cycloalkyl is unsubstituted or substituted with one to three substituents selected from $R^L$;
$R^5$ is selected from the group consisting of:
(1) hydrogen,
(2) —$C_{1-3}$alkyl, and
(3) halogen;
$R^6$ is selected from the group consisting of:
(1) hydrogen,
(2) —$C_{1-3}$alkyl, and
(3) halogen, or
$R^5$ and $R^6$ can together form oxo;
$R^7$ is selected from the group consisting of:
(1) hydrogen,
(2) —$C(O)R^e$, and
(3) —$C_{1-10}$alkyl,
wherein —$C_{1-10}$alkyl is unsubstituted or substituted with one to five fluorines;
each $R^8$ is selected from the group consisting of:
(1) hydrogen,
(2) —$C(O)R^e$, and
(3) —$C_{1-10}$alkyl,
wherein —$C_{1-10}$alkyl is unsubstituted or substituted with one to five fluorines;
each $R^9$ is selected from the group consisting of:
(1) hydrogen, and
(2) —$C_{1-6}$alkyl,
wherein —$C_{1-6}$alkyl is unsubstituted or substituted with one to five fluorines;
each $R^a$ is independently selected from the group consisting of:
(1) —$C_{1-6}$alkyl,
(2) —O—$C_{1-6}$alkyl,
(3) halogen,
(4) oxo,
(5) —$OR^e$,
(6) —$N(R^c)S(O)_mR^e$,
(7) —$S(O)_mR^e$,
(8) —$S(O)_mNR^cR^d$,
(9) —$NR^cR^d$,
(10) —$C(O)R^e$,
(11) —$OC(O)R^e$,
(12) —$CO_2R^e$,
(13) —CN,
(14) —$C(O)NR^cR^d$,
(15) —$N(R^c)C(O)R^e$,
(16) —$N(R^c)C(O)OR^e$,
(17) —$N(R^c)C(O)NR^cR^d$,
(18) —$CF_3$,
(19) —$OCF_3$,
(20) —$OCHF_2$,
(21) —$(CH_2)_p$—$C_{3-6}$cycloalkyl,
(22) —$(CH_2)_p$—$C_{2-10}$cycloheteroalkyl,
(23) —$(CH_2)_p$-aryl, and
(24) —$(CH_2)_p$-heteroaryl,
wherein $R^a$ is unsubstituted or substituted with one to three substituents selected from $R^m$;
each $R^b$ is independently selected from the group consisting of:
(1) —$C_{1-10}$ alkyl,
(2) —O—$C_{1-10}$alkyl,
(3) —$C_{2-10}$ alkenyl,
(4) halogen,
(5) —OH,
(6) —$OC_{2-10}$ alkenyl,
(7) —$O(CH_2)pOC_{1-10}$alkyl,
(8) —$O(CH_2)pC_{3-6}$cycloalkyl,
(9) —$O(CH_2)pC_{2-10}$cycloheteroalkyl,
(10) —$O(CH_2)$p-aryl,
(11) —$O(CH_2)$p-heteroaryl,
(12) —$N(R^c)S(O)_mR^e$,
(13) —$S(O)_mR^e$,
(14) —$O(CH_2)$p-$S(O)_mR^e$,
(15) —$S(O)_mNR^cR^d$,
(16) —$NR^cR^d$,
(17) —$C(O)R^e$,
(18) —$OC(O)R^e$,
(19) —$CO_2R^e$,
(20) —CN,
(21) —$C(O)NR^cR^d$,
(22) —$N(R^c)C(O)R^e$,
(23) —$N(R^c)C(O)OR^e$,
(24) —$N(R^c)C(O)NR^cR^d$,
(25) —$O(CH_2)pO$-$C_{3-6}$cycloalkyl,
(26) —$O(CH_2)pO$-$C_{2-10}$cycloheteroalkyl,
(27) —$CF_3$,
(28) —$OCF_3$,
(29) —$OCHF_2$,
(30) —$(CH_2)p$-$C_{3-6}$cycloalkyl,
(31) —$(CH_2)p$-$C_{2-10}$cycloheteroalkyl,
(32) —$(CH_2)$p-aryl, and
(33) —$(CH_2)$p-heteroaryl,
wherein each $R^b$ is unsubstituted or substituted with one to five substituents selected from $R^k$;
each $R^c$ and $R^d$ is independently selected from the group consisting of:
(1) hydrogen,
(2) —$C_{1-10}$alkyl,
(3) —$C_{2-10}$alkenyl,
(4) —$C_{3-6}$cycloalkyl,
(5) $C_{3-6}$ cycloalkyl-$C_{1-10}$alkyl-,
(6) —$C_{2-6}$cycloheteroalkyl,
(7) $C_{2-6}$cycloheteroalkyl-$C_{1-10}$alkyl-,
(8) aryl,
(9) heteroaryl,
(10) aryl-$C_{1-10}$alkyl-, and
(11) heteroaryl-$C_{1-10}$alkyl-, or
$R^c$ and $R^d$ together with the atom(s) to which they are attached form a cycloheteroalkyl ring of 4 to 7 members containing 0-2 additional heteroatoms independently selected from oxygen, sulfur and N—$R^g$, and wherein each $R^c$ and $R^d$ is unsubstituted or substituted with one to three substituents independently selected from $R^f$;

each $R^e$ is independently selected from the group consisting of:
(1) hydrogen,
(2) —$C_{1-10}$alkyl,
(3) —$C_{2-10}$ alkenyl,
(4) —$C_{3-6}$ cycloalkyl,
(5) —$C_{3-6}$ cycloalkyl-$C_{1-10}$alkyl-,
(6) —$C_{2-5}$cycloheteroalkyl,
(7) —$C_{2-5}$cycloheteroalkyl-$C_{1-10}$alkyl-,
(8) aryl,
(9) heteroaryl,
(10) aryl-$C_{1-10}$alkyl-, and
(11) heteroaryl-$C_{1-10}$alkyl-, wherein each $R^e$ is unsubstituted or substituted with one to three substituents selected from $R^h$;

each $R^f$ is selected from the group consisting of:
(1) halogen,
(2) —$C_{1-10}$alkyl,
(3) —OH,
(4) —$OC_{1-6}$alkyl,
(5) —$S(O)_m$—$C_{1-4}$alkyl,
(6) —CN,
(7) —$CF_3$,
(8) —$OCHF_2$, and
(9) —$OCF_3$, wherein each alkyl is unsubstituted or substituted with one to three substituents independently selected from: —OH, halogen, cyano, and —$S(O)_2CH_3$;

each $R^g$ is selected from the group consisting of:
(1) hydrogen,
(2) —$C(O)R^e$, and
(3) —$C_{1-10}$alkyl, wherein alkyl is unsubstituted or substituted with one to five fluorines;

each $R^h$ is selected from the group consisting of:
(1) halogen,
(2) —$C_{1-10}$alkyl,
(3) —OH,
(4) —O—$C_{1-4}$alkyl,
(5) —$S(O)_m$—$C_{1-4}$alkyl,
(6) —CN,
(7) —$CF_3$,
(8) —$OCHF_2$, and
(9) —$OCF_3$, wherein each alkyl is unsubstituted or substituted with one to three substituents independently selected from: —OH, halogen, cyano, and —$S(O)_2CH_3$;

$R^i$ is independently selected from the group consisting of:
(1) —$C_{1-6}$alkyl,
(2) —$OR^e$,
(3) —$N(R^c)S(O)_mR^e$,
(4) halogen,
(5) —$S(O)_mR^e$,
(6) —$S(O)_mNR^cR^d$,
(7) —$NR^cR^d$,
(8) —$C(O)R^e$,
(9) —$OC(O)R^e$,
(10) —$CO_2R^e$,
(11) —CN,
(12) —$C(O)NR^cR^d$,
(13) —$N(R^c)C(O)R^e$,
(14) —$N(R^c)C(O)OR^e$,
(15) —$N(R^c)C(O)NR^cR^d$,
(16) —$CF_3$,
(17) —$OCF_3$,
(18) —$OCHF_2$,
(19) —$C_{3-6}$cycloalkyl, and
(20) —$C_{2-5}$cycloheteroalkyl;

$R^j$ is independently selected from the group consisting of:
(1) —$C_{1-6}$alkyl,
(2) —$OR^e$,
(3) —$N(R^c)S(O)_mR^e$,
(4) halogen,
(5) —$S(O)_mR^e$,
(6) —$S(O)_mNR^cR^d$,
(7) —$NR^cR^d$,
(8) —$C(O)R^e$,
(9) —$OC(O)R^e$,
(10) —$CO_2R^e$,
(11) —CN,
(12) —$C(O)NR^cR^d$,
(13) —$N(R^c)C(O)R^e$,
(14) —$N(R^c)C(O)OR^e$,
(15) —$N(R^c)C(O)NR^cR^d$,
(16) —$CF_3$,
(17) —$OCF_3$,
(18) —$OCHF_2$,
(19) —$C_{3-6}$cycloalkyl, and
(20) —$C_{2-5}$cycloheteroalkyl;

each $R^k$ is independently selected from the group consisting of:
(1) halogen,
(2) —$C_{1-6}$alkyl,
(3) —OH,
(4) oxo,
(5) —$OC_{1-6}$alkyl,
(6) —$SO_2$—$C_{1-6}$ alkyl,
(7) —$C_{1-6}$alkyl-$SO_2C_{1-6}$alkyl,
(8) —CN,
(9) —$CF_3$,
(10) —$OCHF_2$,
(11) —$OCF_3$,
(12) —$NH_2$,
(13) —$NHSO_2C_{1-6}$alkyl,
(14) —$NHC(O)C_{1-6}$alkyl,
(15) =$N(OCH_3)$,
(16) —$P(O)(OH)_2$, and
(17) —$P(O)(OC_{1-6}$alkyl$)_2$, wherein each alkyl is unsubstituted or substituted with one to three substituents independently selected from: —OH, —$OC_{1-6}$alkyl, halogen, cyano, and —$S(O)_2C_{1-6}$alkyl;

$R^L$ is selected from the group consisting of:
(1) —$C_{1-6}$alkyl,
(2) halogen,
(3) —$OR^e$,
(4) —$N(R^c)S(O)_mR^e$,
(5) —$S(O)_mR^e$,
(6) —$S(O)_mNR^cR^d$,
(7) —$NR^cR^d$,
(8) —$C(O)R^e$,
(9) —$OC(O)R^e$,
(10) —$CO_2R^e$,
(11) —CN,
(12) —$C(O)NR^cR^d$,
(13) —$N(R^c)C(O)R^e$,
(14) —$N(R^c)C(O)OR^e$,
(15) —$N(R^c)C(O)NR^cR^d$,
(16) —$CF_3$,
(17) —$OCF_3$,
(18) —$OCHF_2$,

(19) —C$_{3-6}$cycloalkyl, and
(20) —C$_{2-5}$cycloheteroalkyl;
each R$^m$ is independently selected from the group consisting of:
(1) halogen,
(2) —C$_{1-6}$ alkyl,
(3) —OH,
(4) oxo,
(5) —OC$_{1-6}$alkyl,
(6) —SO$_2$—C$_{1-6}$ alkyl,
(7) —C$_{1-6}$alkyl-SO$_2$C$_{1-6}$alkyl,
(8) —CN,
(9) —CF$_3$,
(10) —OCHF$_2$,
(11) —OCF$_3$,
(12) —NH$_2$,
(13) —NHSO$_2$C$_{1-6}$alkyl,
(14) —NHC(O)C$_{1-6}$alkyl,
(15) =N(OCH$_3$),
(16) —P(O)(OH)$_2$, and
(17) —P(O)(OC$_{1-6}$alkyl)$_2$,
wherein each C$_{1-10}$ alkyl is unsubstituted or substituted with one to three substituents independently selected from: —OH, —OC$_{1-6}$alkyl, halogen, cyano, and —S(O)$_2$C$_{1-6}$alkyl;
n is 1;
each m is independently 0, 1 or 2;
each p is independently selected from: 0, 1, 2, 3, 4, 5, 6, 7, 8, 9 or 10; and
q is independently selected from: 1, 2 or 3;
or a pharmaceutically acceptable salt thereof.

2. A compound of structural formula I:

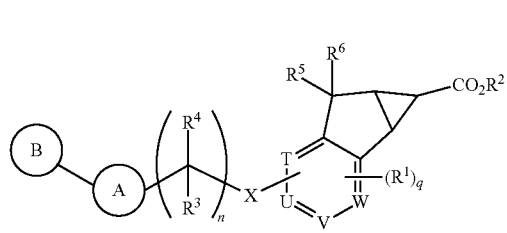

wherein
X is selected from the group consisting of:
(1) oxygen, and
(2) NR$^7$;
T is CH;
U is CH;
V is N;
W is CH;
A is selected from the group consisting of:

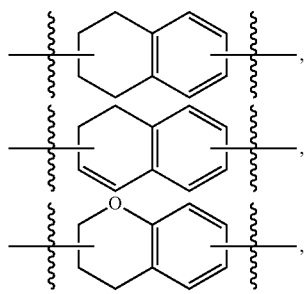

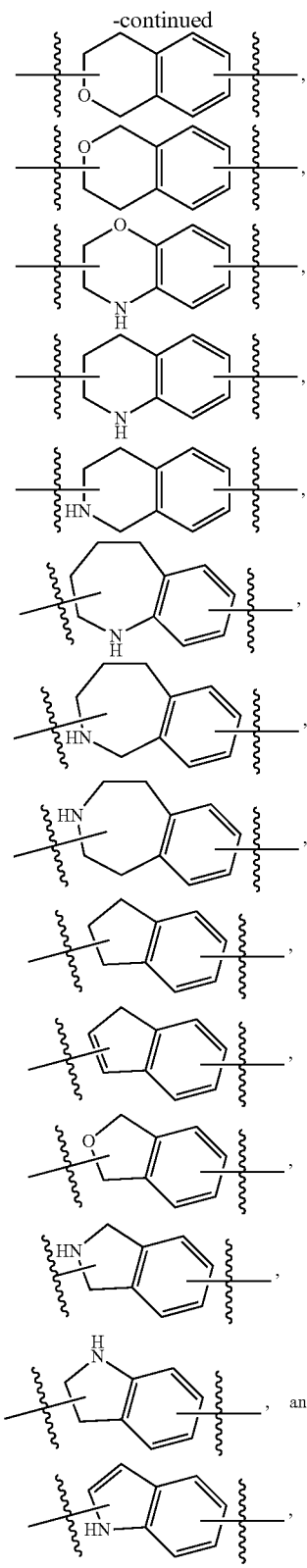

wherein A is unsubstituted or substituted with one to six substituents selected from R$^a$, and wherein two R$^a$ substituents together with the carbon atom to which they are attached may form a 3-6 membered cycloalkyl ring or a 3-6 membered cycloheteroalkyl ring containing 0 to 3 heteroatoms independently selected from oxygen, sulfur, and $NR^8$, and wherein each 3-6 membered cycloalkyl and each 3-6 membered cycloheteroalkyl ring is unsubstituted or substituted with 1 to 4 substituents selected from: $—C_{1-6}$alkyl, $—O—C_{1-6}$alkyl, halogen and OH B is selected from the group consisting of:
(1) aryl,
(2) aryl-O—,
(3) $C_{3-6}$cycloalkyl-,
(4) $C_{3-6}$cycloalkyl-$C_{1-10}$alkyl-,
(5) $C_{3-6}$cycloalkyl-$C_{1-10}$alkyl-O—,
(6) $C_{2-5}$cycloheteroalkyl-,
(7) $C_{3-6}$cycloheteroalkyl-$C_{1-10}$alkyl-,
(8) $C_{3-6}$cycloheteroalkyl-$C_{1-10}$alkyl-O—,
(9) heteroaryl,
(10) heteroaryl-O—,
(11) aryl-$C_{1-10}$ alkyl-, and
(12) heteroaryl-$C_{1-10}$ alkyl-;
wherein B is unsubstituted or substituted with one to six substituents selected from $R^b$;

each $R^1$ is independently selected from the group consisting of:
(1) hydrogen,
(2) halogen,
(3) $—OR^e$,
(4) —CN,
(5) $—C_{1-6}$alkyl, and
(6) $—C_{3-6}$cycloalkyl,
wherein each alkyl and cycloalkyl is unsubstituted or substituted with one to three substituents selected from $R^L$;

$R^2$ is selected from the group consisting of:
(1) hydrogen,
(2) $—C_{1-6}$alkyl, and
(3) $—C_{3-6}$cycloalkyl,
wherein each alkyl and cycloalkyl is unsubstituted or substituted with one to three substituents selected from $R^j$;

each $R^3$ is independently selected from the group consisting of:
(1) hydrogen,
(2) halogen,
(3) $—OR^e$,
(4) $—C_{1-6}$alkyl,
(5) $—C_{2-6}$alkenyl,
(6) $—C_{2-6}$alkynyl,
(7) $—C_{3-6}$cycloalkyl, and
(8) $—C_{2-6}$cycloheteroalkyl,
wherein each alkyl, alkenyl, alkynyl, cycloalkyl and cycloheteroalkyl is unsubstituted or substituted with one to three substituents selected from $R^L$;

each $R^4$ is independently selected from the group consisting of:
(1) hydrogen,
(2) halogen,
(3) $—OR^e$,
(4) $—C_{1-6}$alkyl,
(5) $—C_{2-6}$alkenyl,
(6) $—C_{2-6}$alkynyl,
(7) $—C_{3-6}$cycloalkyl, and
(8) $—C_{2-6}$cycloheteroalkyl,
wherein each alkyl, alkenyl, alkynyl, and cycloalkyl is unsubstituted or substituted with one to three substituents selected from $R^L$;

$R^5$ is selected from the group consisting of:
(1) hydrogen,
(2) $—C_{1-3}$alkyl, and
(3) halogen;

$R^6$ is selected from the group consisting of:
(1) hydrogen,
(2) $—C_{1-3}$alkyl, and
(3) halogen, or $R^5$ and $R^6$ can together form oxo;

$R^7$ is selected from the group consisting of:
(1) hydrogen,
(2) $—C(O)R^e$, and
(3) $—C_{1-10}$alkyl,
wherein $—C_{1-10}$alkyl is unsubstituted or substituted with one to five fluorines;

each $R^8$ is selected from the group consisting of:
(1) hydrogen,
(2) $—C(O)R^e$, and
(3) $—C_{1-10}$alkyl,
wherein $—C_{1-10}$alkyl is unsubstituted or substituted with one to five fluorines;

each $R^a$ is independently selected from the group consisting of:
(1) $—C_{1-6}$alkyl,
(2) $—O—C_{1-6}$alkyl,
(3) halogen,
(4) oxo,
(5) $—OR^e$,
(6) $—N(R^c)S(O)_mR^e$,
(7) $—S(O)_mR^e$,
(8) $—S(O)_mNR^cR^d$,
(9) $—NR^cR^d$,
(10) $—C(O)R^e$,
(11) $—OC(O)R^e$,
(12) $—CO_2R^e$,
(13) —CN,
(14) $—C(O)NR^cR^d$,
(15) $—N(R^c)C(O)R^e$,
(16) $—N(R^c)C(O)OR^e$,
(17) $—N(R^c)C(O)NR^cR^d$,
(18) $—CF_3$,
(19) $—OCF_3$,
(20) $—OCHF_2$,
(21) $—(CH_2)_p—C_{3-6}$cycloalkyl,
(22) $—(CH_2)_p—C_{2-10}$cycloheteroalkyl,
(23) $—(CH_2)_p$-aryl, and
(24) $—(CH_2)_p$-heteroaryl,
wherein $R^a$ is unsubstituted or substituted with one to three substituents selected from $R^m$;

each $R^b$ is independently selected from the group consisting of:
(1) $—C_{1-10}$ alkyl,
(2) $—O—C_{1-10}$alkyl,
(3) $—C_{2-10}$ alkenyl,
(4) halogen,
(5) —OH,
(6) $—OC_{2-10}$ alkenyl,
(7) $—O(CH_2)pOC_{1-10}$alkyl,
(8) $—O(CH_2)pC_{3-6}$cycloalkyl,
(9) $—O(CH_2)pC_{2-10}$cycloheteroalkyl,
(10) $—O(CH_2)p$-aryl,
(11) $—O(CH_2)p$-heteroaryl,
(12) $—N(R^c)S(O)_mR^e$,
(13) $—S(O)_mR^e$,
(14) $—O(CH_2)p-S(O)_mR^e$,
(15) $—S(O)_mNR^cR^d$,
(16) $—NR^cR^d$,

(17) —C(O)R$^e$,
(18) —OC(O)R$^e$,
(19) —CO$_2$R$^e$,
(20) —CN,
(21) —C(O)NR$^c$R$^d$,
(22) —N(R$^c$)C(O)R$^e$,
(23) —N(R$^c$)C(O)OR$^e$,
(24) —N(R$^c$)C(O)NR$^c$R$^d$,
(25) —O(CH$_2$)pO-C$_{3-6}$cycloalkyl,
(26) —O(CH$_2$)pO-C$_{2-10}$cycloheteroalkyl,
(27) —CF$_3$,
(28) —OCF$_3$,
(29) —OCHF$_2$,
(30) —(CH$_2$)p-C$_{3-6}$cycloalkyl,
(31) —(CH$_2$)p-C$_{2-10}$cycloheteroalkyl,
(32) —(CH$_2$)p-aryl, and
(33) —(CH$_2$)p-heteroaryl,
wherein each R$^b$ is unsubstituted or substituted with one to five substituents selected from R$^k$;
each R$^c$ and R$^d$ is independently selected from the group consisting of:
(1) hydrogen,
(2) —C$_{1-10}$alkyl,
(3) —C$_{2-10}$alkenyl,
(4) —C$_{3-6}$cycloalkyl,
(5) C$_{3-6}$ cycloalkyl-C$_{1-10}$alkyl-,
(6) —C$_{2-6}$cycloheteroalkyl,
(7) C$_{2-6}$cycloheteroalkyl-C$_{1-10}$alkyl-,
(8) aryl,
(9) heteroaryl,
(10) aryl-C$_{1-10}$alkyl-, and
(11) heteroaryl-C$_{1-10}$alkyl-, or
R$^c$ and R$^d$ together with the atom(s) to which they are attached form a cycloheteroalkyl ring of 4 to 7 members containing 0-2 additional heteroatoms independently selected from oxygen, sulfur and N—R$^g$, and wherein each R$^c$ and R$^d$ is unsubstituted or substituted with one to three substituents independently selected from R$^f$;
each R$^e$ is independently selected from the group consisting of:
(1) hydrogen,
(2) —C$_{1-10}$alkyl,
(3) —C$_{2-10}$ alkenyl,
(4) —C$_{3-6}$ cycloalkyl,
(5) —C$_{3-6}$ cycloalkyl-C$_{1-10}$alkyl-,
(6) —C$_{2-5}$cycloheteroalkyl,
(7) —C$_{2-5}$cycloheteroalkyl-C$_{1-10}$alkyl-,
(8) aryl,
(9) heteroaryl,
(10) aryl-C$_{1-10}$alkyl-, and
(11) heteroaryl-C$_{1-10}$alkyl-,
wherein each R$^e$ is unsubstituted or substituted with one to three substituents selected from R$^h$;
each R$^f$ is selected from the group consisting of:
(1) halogen,
(2) —C$_{1-10}$alkyl,
(3) —OH,
(4) —OC$_{1-6}$alkyl,
(5) —S(O)$_m$—C$_{1-4}$alkyl,
(6) —CN,
(7) —CF$_3$,
(8) —OCHF$_2$, and
(9) —OCF$_3$,
wherein each alkyl is unsubstituted or substituted with one to three substituents independently selected from:
—OH, halogen, cyano, and —S(O)$_2$CH$_3$;
each R$^g$ is selected from the group consisting of:
(1) hydrogen,
(2) —C(O)R$^e$, and
(3) —C$_{1-10}$alkyl,
wherein alkyl is unsubstituted or substituted with one to five fluorines;
each R$^h$ is selected from the group consisting of:
(1) halogen,
(2) —C$_{1-10}$alkyl,
(3) —OH,
(4) —O—C$_{1-4}$alkyl,
(5) —S(O)$_m$—C$_{1-4}$alkyl,
(6) —CN,
(7) —CF$_3$,
(8) —OCHF$_2$, and
(9) —OCF$_3$,
wherein each alkyl is unsubstituted or substituted with one to three substituents independently selected from:
—OH, halogen, cyano, and —S(O)$_2$CH$_3$;
R$^i$ is independently selected from the group consisting of:
(1) —C$_{1-6}$alkyl,
(2) —OR$^e$,
(3) —N(R$^c$)S(O)$_m$R$^e$,
(4) halogen,
(5) —S(O)$_m$R$^e$,
(6) —S(O)$_m$NR$^c$R$^d$,
(7) —NR$^c$R$^d$,
(8) —C(O)R$^e$,
(9) —OC(O)R$^e$,
(10) —CO$_2$R$^e$,
(11) —CN,
(12) —C(O)NR$^c$R$^d$,
(13) —N(R$^c$)C(O)R$^e$,
(14) —N(R$^c$)C(O)OR$^e$,
(15) —N(R$^c$)C(O)NR$^c$R$^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;
R$^j$ is independently selected from the group consisting of:
(1) —C$_{1-6}$alkyl,
(2) —OR$^e$,
(3) —N(R$^c$)S(O)$_m$R$^e$,
(4) halogen,
(5) —S(O)$_m$R$^e$,
(6) —S(O)$_m$NR$^c$R$^d$,
(7) —NR$^c$R$^d$,
(8) —C(O)R$^e$,
(9) —OC(O)R$^e$,
(10) —CO$_2$R$^e$,
(11) —CN,
(12) —C(O)NR$^c$R$^d$,
(13) —N(R$^c$)C(O)R$^e$,
(14) —N(R$^c$)C(O)OR$^e$,
(15) —N(R$^c$)C(O)NR$^c$R$^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;
each R$^k$ is independently selected from the group consisting of:
(1) halogen,
(2) —C$_{1-6}$alkyl,
(3) —OH,
(4) oxo, (5) —OC$_{1-6}$alkyl,
(6) —SO$_2$—C$_{1-6}$ alkyl,
(7) —C$_{1-6}$alkyl-SO$_2$C$_{1-6}$alkyl,
(8) —CN,
(9) —CF$_3$,
(10) —OCHF$_2$,
(11) —OCF$_3$,
(12) —NH$_2$,
(13) —NHSO$_2$C$_{1-6}$alkyl,
(14) —NHC(O)C$_{1-6}$alkyl,
(15) =N(OCH$_3$),
(16) —P(O)(OH)$_2$, and
(17) —P(O)(OC$_{1-6}$alkyl)$_2$,
wherein each alkyl is unsubstituted or substituted with one to three substituents independently selected from: —OH, —OC$_{1-6}$alkyl, halogen, cyano, and —S(O)$_2$C$_{1-6}$alkyl;
R$^L$ is selected from the group consisting of:
(1) —C$_{1-6}$alkyl,
(2) halogen,
(3) —OR$^e$,
(4) —N(R$^c$)S(O)$_m$R$^e$,
(5) —S(O)$_m$R$^e$,
(6) —S(O)$_m$NR$^c$R$^d$,
(7) —NR$^c$R$^d$,
(8) —C(O)R$^e$,
(9) —OC(O)R$^e$,
(10) —CO$_2$R$^e$,
(11) —CN,
(12) —C(O)NR$^c$R$^d$,
(13) —N(R$^c$)C(O)R$^e$,
(14) —N(R$^c$)C(O)OR$^e$,
(15) —N(R$^c$)C(O)NR$^c$R$^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;
each R$^m$ is independently selected from the group consisting of:
(1) halogen,
(2) —C$_{1-6}$ alkyl,
(3) —OH,
(4) oxo,
(5) —OC$_{1-6}$alkyl,
(6) —SO$_2$—C$_{1-6}$ alkyl,
(7) —C$_{1-6}$alkyl-SO$_2$C$_{1-6}$alkyl,
(8) —CN,
(9) —CF$_3$,
(10) —OCHF$_2$,
(11) —OCF$_3$,
(12) —NH$_2$,
(13) —NHSO$_2$C$_{1-6}$alkyl,
(14) —NHC(O)C$_{1-6}$alkyl,
(15) =N(OCH$_3$),
(16) —P(O)(OH)$_2$, and
(17) —P(O)(OC$_{1-6}$alkyl)$_2$,
wherein each C$_{1-10}$ alkyl is unsubstituted or substituted with one to three substituents independently selected from: —OH, —OC$_{1-6}$alkyl, halogen, cyano, and —S(O)$_2$C$_{1-6}$alkyl;
n is 1;
each m is independently 0, 1 or 2;
each p is independently selected from: 0, 1, 2, 3, 4, 5, 6, 7, 8, 9 or 10; and
q is independently selected from: 1, 2 or 3;
or a pharmaceutically acceptable salt thereof.

3. The compound according to claim 1 of structural formula Ia

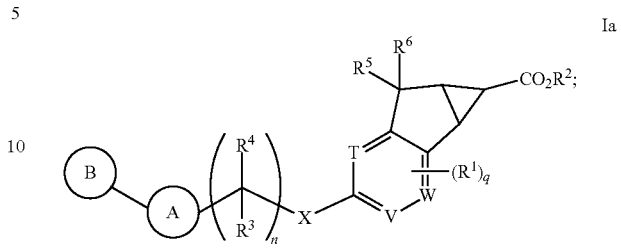

or a pharmaceutically acceptable salt thereof.

4. The compound according to claim 1 wherein R$^1$ is hydrogen; or a pharmaceutically acceptable salt thereof.

5. The compound according to claim 1 wherein X is oxygen; or a pharmaceutically acceptable salt thereof.

6. The compound according to claim 1 wherein A is selected from the group consisting of:

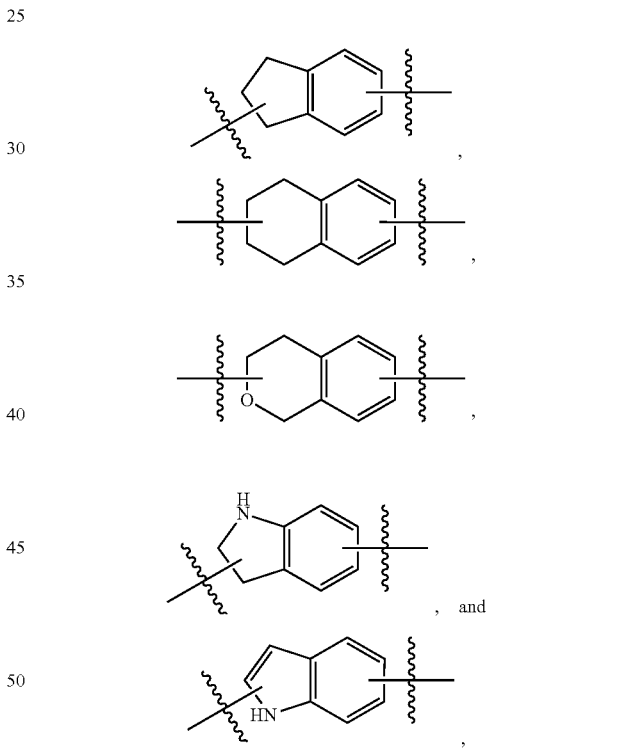

wherein A is unsubstituted or substituted with one to six substituents selected from R$^a$, and wherein two R$^a$ substituents together with the carbon atom to which they are attached may form a 3-6 membered cycloalkyl ring or a 3-6 membered cycloheteroalkyl ring containing 0 to 3 heteroatoms independently selected from oxygen, sulfur, and NR$^8$, and wherein each 3-6 membered cycloalkyl ring and each 3-6 membered cycloheteroalkyl ring is unsubstituted or substituted with 1 to 4 substituents selected from: —C$_{1-6}$alkyl, —O—C$_{1-6}$alkyl, halogen and OH;

or a pharmaceutically acceptable salt thereof.

7. The compound according to claim 1 wherein A is selected from the group consisting of:

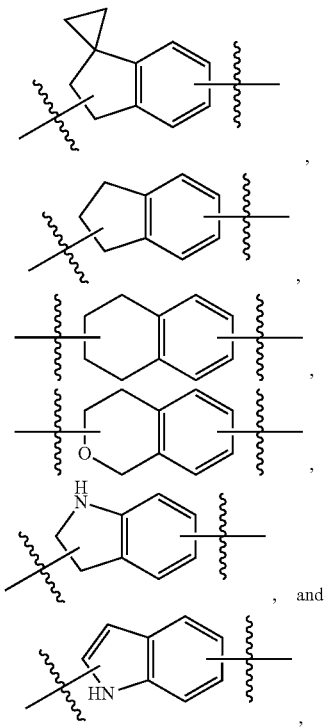

, and wherein A is unsubstituted or substituted with one to six substituents selected from $R^a$;
or a pharmaceutically acceptable salt thereof.

8. The compound according to claim 1 wherein B is selected from the group consisting of:
(1) aryl, and
(2) heteroaryl,
wherein each aryl and heteroaryl is unsubstituted or substituted with one to six substituents selected from $R^b$;
or a pharmaceutically acceptable salt thereof.

9. The compound according to claim 1 wherein B is selected from the group consisting of:
(1) phenyl,
(2) pyridine and
(3) benzimidazole,
wherein each phenyl, pyridine and benzimidazole is unsubstituted or substituted with one to six substituents selected from $R^b$;
or a pharmaceutically acceptable salt thereof.

10. The compound according to claim 1 wherein $R^3$ and $R^4$ are independently selected from the group consisting of:
(1) hydrogen,
(2) halogen, and
(3) —$C_{1-6}$alkyl,
wherein each alkyl is unsubstituted or substituted with one to three substituents selected from $R^L$; or a pharmaceutically acceptable salt thereof.

11. The compound according to claim 1 wherein $R^3$ and $R^4$ are hydrogen; or a pharmaceutically acceptable salt thereof.

12. The compound according to claim 1 wherein $R^2$ is hydrogen; or a pharmaceutically acceptable salt thereof.

13. The compound according to claim 1 wherein $R^5$ and $R^6$ are selected from the group consisting of:

(1) hydrogen, and
(2) halogen;
or a pharmaceutically acceptable salt thereof.

14. The compound according to claim 1 wherein $R^5$ and $R^6$ are hydrogen; or a pharmaceutically acceptable salt thereof.

15. The compound according to claim 1 wherein the absolute stereochemistry at the two stereogenic carbon centers is indicated below:

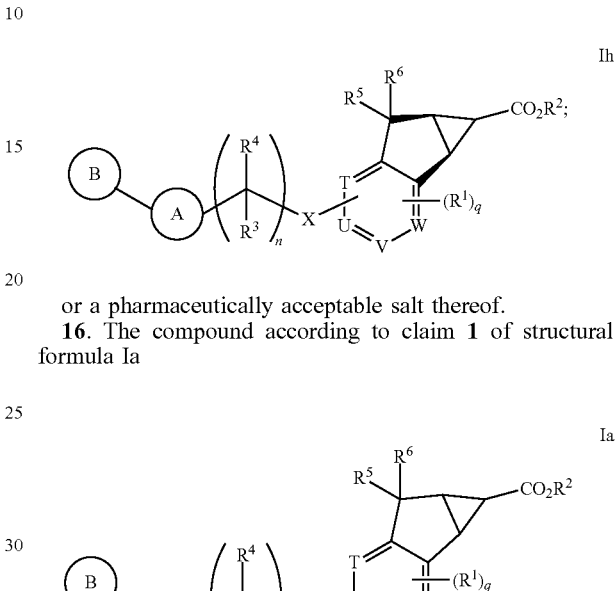

or a pharmaceutically acceptable salt thereof.

16. The compound according to claim 1 of structural formula Ia

Ia wherein:
X is oxygen;
T is CH;
U is CH;
V is N;
W is CH;
A is selected from the group consisting of:

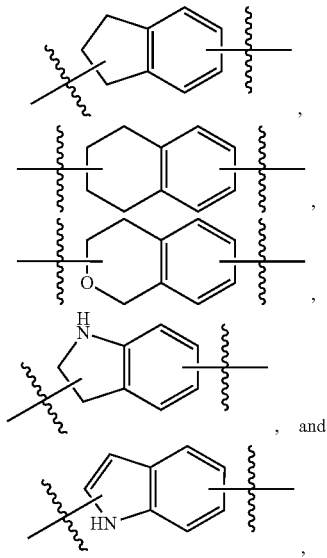

, and

, wherein A is unsubstituted or substituted with one to six substituents selected from R$^a$, and wherein two R$^a$ substituents together with the carbon atom to which they are attached may form a 3-6 membered cycloalkyl ring or a 3-6 membered cycloheteroalkyl ring containing 0 to 3 heteroatoms independently selected from oxygen, sulfur, and NR$^8$, and wherein each 3-6 membered cycloalkyl ring and each 3-6 membered cycloheteroalkyl ring is unsubstituted or substituted with 1 to 4 substituents selected from: —C$_{1-6}$alkyl, —O—C$_{1-6}$ alkyl, halogen and OH;

B is selected from the group consisting of:
  (1) aryl, and
  (2) heteroaryl,
wherein each aryl and heteroaryl is unsubstituted or substituted with one to six substituents selected from R$^b$;

R$^1$ and R$^2$ are hydrogen;
R$^3$ and R$^4$ are independently selected from the group consisting of:
  (1) hydrogen,
  (2) halogen, and
  (3) —C$_{1-6}$alkyl,
wherein each alkyl is unsubstituted or substituted with one to three substituents selected from R$^L$;
R$^5$ and R$^6$ are selected from the group consisting of:
  (1) hydrogen, and
  (2) halogen; and
n is 1;
or a pharmaceutically acceptable salt thereof.

17. The compound according to claim 1 of structural formula Ia wherein:
X is oxygen;
T is CH;
V is N;
W is CH;
A is selected from the group consisting of:

wherein A is unsubstituted or substituted with one to six substituents selected from R$^a$;

B is selected from the group consisting of:
  (1) phenyl,
  (2) pyridine, and
  (3) benzimidazole,
wherein each phenyl, pyridine and benzimidazole is unsubstituted or substituted with one to six substituents selected from R$^b$;

R$^1$, R$^2$, R$^3$, R$^4$, R$^5$ and R$^6$ are hydrogen; and
n is 1;
or a pharmaceutically acceptable salt thereof.

18. A compound selected from:

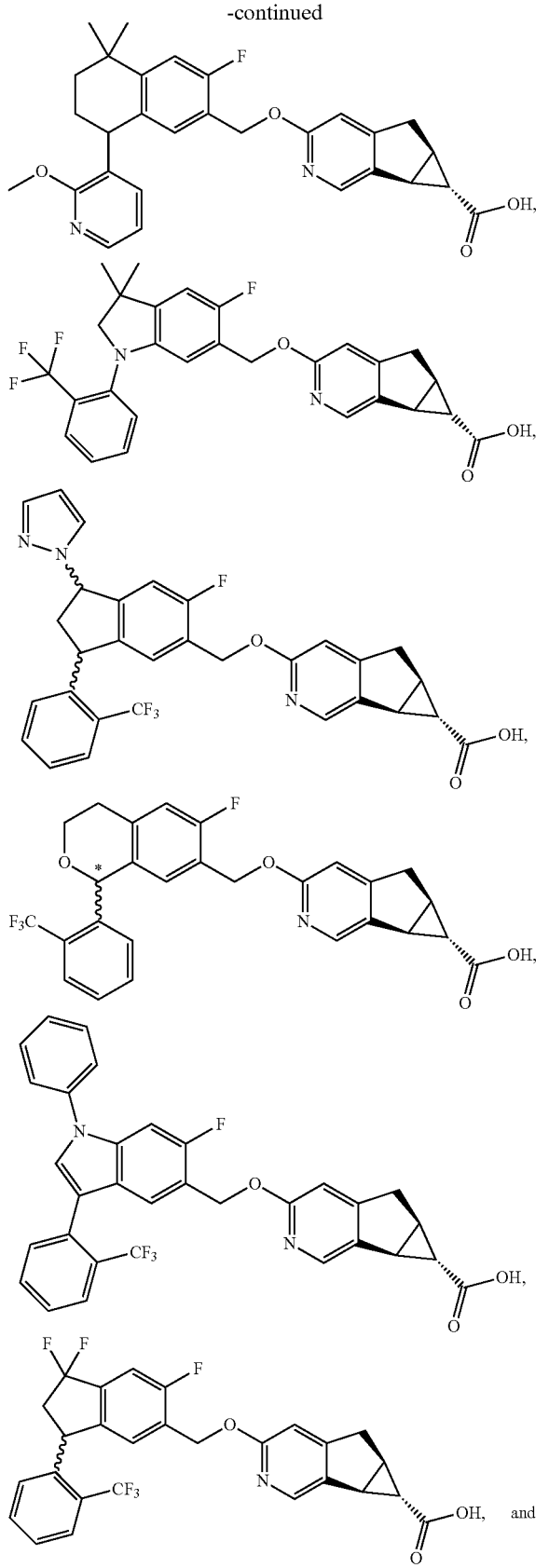

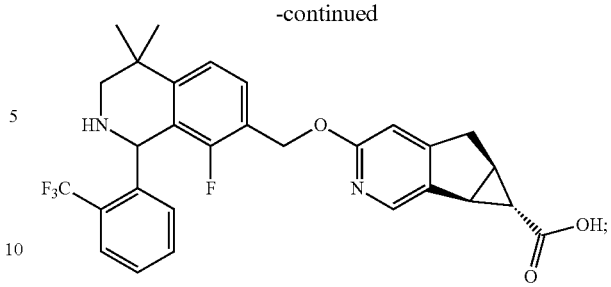

or a pharmaceutically acceptable salt thereof.

19. A pharmaceutical composition comprising a compound of claim 1, or a pharmaceutically acceptable salt thereof, and a pharmaceutically acceptable carrier.

20. A method of treating type 2 diabetes mellitus in a patient in need of treatment comprising the administration to the patient of a therapeutically effective amount of a compound of claim 1, or a pharmaceutically acceptable salt thereof.

21. A pharmaceutical composition comprising
   (1) a compound of claim 1 or a pharmaceutically acceptable salt thereof,
   (2) one or more compounds selected from the group consisting of:
      (a) PPAR gamma agonists and partial agonists;
      (b) biguanides;
      (c) protein tyrosine phosphatase-1B (PTP-1B) inhibitors;
      (d) dipeptidyl peptidase IV (DP-IV) inhibitors;
      (e) insulin or an insulin mimetic;
      (f) sulfonylureas;
      (g) α-glucosidase inhibitors;
      (h) agents which improve a patient's lipid profile, said agents being selected from the group consisting of (i) HMG-CoA reductase inhibitors, (ii) bile acid sequestrants, (iii) nicotinyl alcohol, nicotinic acid or a salt thereof, (iv) PPARα agonists, (v) cholesterol absorption inhibitors, (vi) acyl CoA: cholesterol acyltransferase (ACAT) inhibitors, (vii) CETP inhibitors, and (viii) phenolic anti-oxidants;
      (i) PPARα/γ dual agonists,
      (j) PPARδ agonists,
      (k) antiobesity compounds,
      (l) ileal bile acid transporter inhibitors;
      (m) anti-inflammatory agents;
      (n) glucagon receptor antagonists;
      (o) GLP-1;
      (p) GIP-1;
      (q) GLP-1 analogs;
      (r) HSD-1 inhibitors;
      (s) SGLT 1 inhibitors; and
      (t) SGLT 2 inhibitors; and
   (3) a pharmaceutically acceptable carrier.

22. A pharmaceutical composition comprising a compound according to claim 1, or a pharmaceutically acceptable salt thereof, and a compound selected from simvastatin, ezetimibe and sitagliptin; and a pharmaceutically acceptable carrier.

* * * * *